US012435127B2

(12) United States Patent
Patil et al.

(10) Patent No.: US 12,435,127 B2
(45) Date of Patent: Oct. 7, 2025

(54) THERAPEUTIC NEUTRALIZATION ANTIBODIES FOR THE TREATMENT OF PEANUT ALLERGY

(71) Applicants: The General Hospital Corporation, Boston, MA (US); Massachusetts Institute of Technology, Cambridge, MA (US)

(72) Inventors: Sarita U. Patil, Newton, MA (US); Wayne G. Shreffler, Beverly, MA (US); John Christopher Love, Somerville, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 782 days.

(21) Appl. No.: 17/762,902

(22) PCT Filed: Sep. 25, 2020

(86) PCT No.: PCT/US2020/052875
§ 371 (c)(1),
(2) Date: Mar. 23, 2022

(87) PCT Pub. No.: WO2021/062268
PCT Pub. Date: Apr. 1, 2021

(65) Prior Publication Data

US 2022/0348643 A1 Nov. 3, 2022

Related U.S. Application Data

(60) Provisional application No. 62/905,698, filed on Sep. 25, 2019.

(51) Int. Cl.

| | |
|---|---|
| ***C07K 16/16*** | (2006.01) |
| ***A61P 37/00*** | (2006.01) |
| ***G01N 33/68*** | (2006.01) |

(52) U.S. Cl.
CPC .............. *C07K 16/16* (2013.01); *A61P 37/00* (2018.01); *G01N 33/6854* (2013.01); *C07K 2317/21* (2013.01); *C07K 2317/30* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,868,786 | B2 | 1/2018 | Finkelman et al. |
| 2010/0080870 | A1 | 4/2010 | Ahmedna et al. |
| 2012/0283421 | A1 | 11/2012 | Caplan et al. |
| 2019/0144565 | A1 | 5/2019 | Adams et al. |

FOREIGN PATENT DOCUMENTS

| | | | |
|---|---|---|---|
| EP | 3244212 | A1 | 11/2017 |
| WO | WO-2001/039799 | A2 | 6/2001 |
| WO | WO-2016/209773 | A1 | 12/2016 |
| WO | WO-2017/187307 | A1 | 11/2017 |
| WO | WO-2018/144425 | A1 | 8/2018 |
| WO | WO-2018/234383 | A1 | 12/2018 |

OTHER PUBLICATIONS

Hoh et al., "Single B-cell deconvolution of peanut-specific antibody responses in allergic patients," available in PMC Jan. 1, 2017, published in final edited form as: J Allergy Clin Immunol. 137(1):157-167 (2016).
International Search Report and Written Opinion for International Patent Application No. PCT/US2020/052875, mailed Feb. 4, 2021 (14 pages).
Wilson, P., "Allergen specific antibody binding characteristics and longitudinal serological changes to purified peanut allergens," <https://citeseerx.ist.psu.edu/document?repid=rep1&type=pdf&doi=b76e5b4ac1fdcf092dbfafb67871e53e85756876>, retrieved Nov. 17, 2023, published Feb. 8, 2002 (44 pages).
Chen et al., "A Quantitative Method for Detecting Ara h 2 by Generation and Utilization of Monoclonal Antibodies," J Immunol Res. 2018:4894705 (May 2018) (10 pages).
Liao et al., "Human monoclonal antibodies to Ara h 2 inhibit allergen-induced, IgE-mediated cell activation," Clin Exp Allergy. 49(8):1154-7 (Aug. 2019).
Extended European Search Report for European Patent Application No. 20869296.2, dated Sep. 27, 2023 (9 pages).

*Primary Examiner* — Zachary S Skelding
(74) *Attorney, Agent, or Firm* — Clark & Elbing LLP

(57) ABSTRACT

The invention provides anti-Ara h 2 antibodies (e.g., an anti-Ara h 2 neutralizing antibody) and methods of using the same, e.g., for treating and/or preventing peanut allergy or sensitivity. Also provided herein are anti-Ara h 2 antibodies and methods of using the same, e.g., for diagnostics and methods of monitoring peanut oral immunotherapy.

19 Claims, No Drawings

Specification includes a Sequence Listing.

THERAPEUTIC NEUTRALIZATION ANTIBODIES FOR THE TREATMENT OF PEANUT ALLERGY

CROSS-REFERENCE TO RELATED APPLICATIONS

This application claims benefit of U.S. Provisional Application No. 62/905,698, filed Sep. 25, 2019, the contents of which are incorporated herein by reference in their entirety.

Statement as to Federally Funded Research

This invention was made with government support under AI121491 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Sep. 21, 2020, is named 51343-003WO2_Sequence_Listing_9_21_20_ST25 and is 569,497 bytes in size.

FIELD OF THE INVENTION

The present invention is related to human antibodies and antigen-binding fragments of human antibodies that specifically bind to a peanut allergen, therapeutic compositions comprising the antibodies and methods of using those antibodies including diagnostic uses.

BACKGROUND OF THE INVENTION

Peanut allergy is one of the most common causes of severe food allergy attacks. Peanut allergy symptoms can be life-threatening (anaphylaxis). For some people with peanut allergy, even miniscule amounts of peanuts can cause a serious reaction.

Rates of food allergy have nearly tripled in the past two decades, now affecting about 8% of children in the US, and incurring $25 billion in costs annually. There are over 3 million people in the US. More than 1% of children in the United States and Europe have peanut allergy caused by IgE, or allergy antibodies. They can have severe, even life-threatening allergic responses, known as anaphylaxis, to even tiny exposures to peanut. Peanut allergy tends to be persistent even after childhood in about 80% of affected patients. Currently, the only available treatment is avoidance and emergent use of epinephrine, which places our most vulnerable population at significant risk of mortality and morbidity. Recently, Palforzia, an oral immunotherapy (OIT) has been approved by the FDA as a treatment for food allergy.

OIT clinical trials conducted at Massachusetts General Hospital, like others, have consistently shown that less than one-third of patients develop lasting tolerance after cessation of peanut OIT, and the rate of reactions and anaphylaxis requiring epinephrine during OIT poses a serious and significant burden. Therefore, even with potential future implementation of OIT, a significant portion of patients with IgE-mediated food allergy will require treatment to prevent anaphylactic reactions on accidental encounters with peanut allergen.

A need therefore exists for compositions and methods for treating peanut allergy.

SUMMARY OF THE INVENTION

The invention provides antibodies and antigen-binding fragments thereof that bind specifically to the peanut allergen, Ara h 2. Such antibodies may be useful to bind the Ara h 2 allergen in vivo following exposure of a sensitized patient to a peanut allergen, and as such, may act to either promote clearance of Ara h 2, neutralization of the effects of Ara h 2 or to block the binding of the allergen to pre-formed IgE on the surface of mast cells or basophils. By doing so, the antibodies disclosed herein may prevent the release of histamine or other inflammatory mediators from mast cells or basophils, thereby preventing or diminishing the untoward effects observed in patients sensitized to a peanut allergen such as Ara h 2.

Peanut allergy occurs when an individual's immune system mistakenly identifies peanut proteins such as Ara h 2 as something harmful. Direct or indirect contact with peanuts causes the individual's immune system to release symptom-causing chemicals such as histamines into their bloodstream. Exposure to peanuts can trigger an allergic reaction and can occur in various ways including, without limitation, direct contact (e.g., eating peanuts or peanut-containing foods or through direct skin contact with peanuts); cross-contact (e.g., an unintended introduction of peanuts into a product) or inhalation (e.g., an allergic reaction may occur if an individual inhales dust or aerosols containing peanuts, from a source such as peanut flour or peanut oil cooking spray). In certain applications, the antibodies described herein may reduce, minimize, or prevent at least one symptom in a patient sensitive to the Ara h 2 peanut allergen, such as skin reactions such as hives, redness or swelling, itching or tingling in or around the mouth or throat, digestive problems such as diarrhea, stomach cramps, nausea, or vomiting, tightening of the throat, sneezing, congestion, nasal blockage, coughing, wheezing, bronchoconstriction, rhinitis, or shortness of breath. In other applications, the antibodies may be capable of preventing even more serious in vivo complications associated with exposure to the peanut allergen in sensitized individuals, such as asthmatic responses, swelling of the throat that makes it difficult to breath, a severe drop in blood pressure (shock), rapid pulse, dizziness, lightheadedness or loss of consciousness, anaphylaxis, or even death. Children and adults who have a severe peanut allergy are especially at risk of having this life-threatening reaction.

The anti-Ara h 2 antibody compositions and methods disclosed herein address an unmet need in the art.

Expert guidelines for treatment of peanut allergy recommend that, for example, patients are counseled to avoid the allergen and to use injectable epinephrine for treatment of anaphylaxis should exposure occur. However, up to 25% of pediatric visits to an emergency department are for treatment of IgE-mediated hypersensitivity, and there is growing recognition of the burden of the costs of this strategy, both in direct medical costs as well as indirect costs. The financial, social, and psychological burden of food allergy is considerable, and widely evident in our daily lives.

Passive protection using peanut-specific protective antibodies disclosed herein provide an extra margin of safety for patients with IgE-mediated food allergies, for example, by preventing allergic reactions to accidental ingestion or exposure. One of the most common reasons that patients and their families seek further therapy for food allergy is for the prevention of IgE-mediated food allergic reactions. Passive protection allows clinicians to provide a therapy with low risk for allergic reactions and which can provide long-lasting protection against reactions to accidental exposures.

Furthermore, patients who are not eligible for other treatments such as OIT, due to underlying eosinophilic esophagitis or extreme sensitivity to the allergen, would still be able to tolerate a strategy of passive protection. In clinical trials, the majority of patients experience side effects and even those who undergo OIT can still have episodes of treatment-related anaphylaxis. Passive protection offers the possibility of treatment without the side effects of allergen exposure. Lastly, passive immunization with peanut-specific antibodies may be an effective adjunctive therapy to immunotherapy as a strategy to decrease the high rate of adverse events known to occur with immunotherapy.

The development of peanut-specific antibodies that effectively neutralize the allergen further provide a useful diagnostic tool for monitoring clinical tolerance development during allergen-specific immunotherapy. In most forms of immunotherapy, both oral and sublingual, patients are subjected to repeated oral challenges to evaluate the development of tolerance. Suppression of effector cells and basophils has been shown to be effective biomarkers of tolerance in OIT, and that this suppression is mediated by antibodies in the serum.

Furthermore, a competitive assay using the antibodies described herein would be highly effective for monitoring tolerance during immunotherapy. In this assay, a comparison of individuals' OIT-induced allergen-specific antibodies with the pre-defined protective antibodies is utilized to determine whether their post-OIT antibody repertoire will effectively protect them against peanut exposures, without the need for repeated financially and medically intensive oral food challenges. As OIT is increasingly adopted outside of clinical trials, a robust methodology of monitoring tolerance is needed. The diagnostic test disclosed herein that relies on patient serum is superior as opposed to the methodology employed in previous clinical trials, which relies of a technically challenging and biologically variable assay that activates short-lived effector cells.

In one aspect, the invention features an isolated antibody that binds to Ara h 2 (conglutin-7), or an antigen-binding fragment thereof, wherein the antibody comprises the following six complementarity determining regions (CDRs): (a) an CDR-H1 comprising the amino acid sequence of GFTFRDYS (SEQ ID NO: 1); (b) an CDR-H2 comprising the amino acid sequence of IRFDGTTK (SEQ ID NO: 2); (c) an CDR-H3 comprising the amino acid sequence of X1KDNGWRAFDH (SEQ ID NO: 822), wherein X1 is V or A; (d) an CDR-L1 comprising the amino acid sequence of QSLLHRNGYIY (SEQ ID NO: 4); (e) an CDR-L2 comprising the amino acid sequence of FVS (SEQ ID NO: 5); and (f) an CDR-L3 comprising the amino acid sequence of MQX1 LEX2PWT (SEQ ID NO: 823), wherein X1 is S or A and X2 is N or T.

In another aspect, the invention features an isolated antibody that binds to Ara h 2 (conglutin-7), or an antigen-binding fragment thereof, wherein the antibody comprises the following six CDRs: (a) an CDR-H1 comprising the amino acid sequence of GFTFRDYS (SEQ ID NO: 1); (b) an CDR-H2 comprising the amino acid sequence of IRFDGTTK (SEQ ID NO: 2); (c) an CDR-H3 comprising the amino acid sequence of VKDNGWRAFDH (SEQ ID NO: 3); (d) an CDR-L1 comprising the amino acid sequence of QSLLHRNGYIY (SEQ ID NO: 4); (e) an CDR-L2 comprising the amino acid sequence of FVS (SEQ ID NO: 5); and (f) an CDR-L3 comprising the amino acid sequence of MQSLENPWT (SEQ ID NO: 6).

In some embodiments of either of the previous aspects, the antibody comprises (a) a heavy chain variable (VH) domain comprising an amino sequence having at least 90%, at least 95%, or at least 99% sequence identity to the amino acid sequence of SEQ ID NO: 7; (b) a light chain variable (VL) domain comprising an amino acid sequence having at least 90%, at least 95%, or at least 99% identity to the amino acid sequence of SEQ ID NO: 8; or (c) a VH domain as in (a) and a VL domain as in (b). In some embodiments, the antibody further comprises the following VH domain framework regions (FRs): (a) an FR-H1 comprising the amino acid sequence of VESGGGVVQPGASLRLSCVAS (SEQ ID NO: 9); (b) an FR-H2 comprising the amino acid sequence of MHWVRQAPGKGLEWMSF (SEQ ID NO: 10); (c) an FR-H3 comprising the amino acid sequence of DYRESVKGRFIISRDDSKNTLYLQMTSLRPED-TARYYC (SEQ ID NO: 11); and (d) an FR-H4 comprising the amino acid sequence of WGQGALVIVSS (SEQ ID NO: 12). In some embodiments, the VH domain comprises the amino acid sequence of SEQ ID NO: 7.

In some embodiments, the antibody further comprising the following VL domain FRs: (a) an FR-L1 comprising the amino acid sequence of EIVMTQSPLSLPVTPGEAASIS-CRSS (SEQ ID NO: 13); (b) an FR-L2 comprising the amino acid sequence of LDWYLQRPGQSPQLLIS (SEQ ID NO: 14); (c) an FR-L3 comprising the amino acid sequence of KRASGAPDRFSGSGSGTDFTLTISRVEAE-DFGVYFC (SEQ ID NO: 15); and (d) an FR-L4 comprising the amino acid sequence of FGP (SEQ ID NO: 16). In some embodiments, the VL domain comprises the amino acid sequence of SEQ ID NO: 8.

In another aspect, the invention features an isolated antibody that binds to Ara h 2, or an antigen-binding fragment thereof, wherein the antibody comprises (a) a VH domain comprising an amino acid sequence having at least 90%, at least 95%, or at least 99% sequence identity to the amino acid sequence of SEQ ID NO: 7 and (b) a VL domain comprising an amino acid sequence having at least 90%, at least 95%, or at least 99% sequence identity to the amino acid sequence of SEQ ID NO: 8.

In some embodiments, the antibody comprises a VH domain comprising the amino acid sequence of SEQ ID NO: 7 and a VL domain comprising the amino acid sequence of SEQ ID NO: 8.

In some embodiments of any of the previous aspects, the antibody comprises (a) a heavy chain comprising the amino acid sequence of SEQ ID NO: 17 and (b) a light chain comprising the amino acid sequence of SEQ ID NO: 18.

In some embodiments of any of the previous aspects, the antibody binds Ara h 2 with a $K_D$ of about 50 nM or less. In some embodiments, the $K_D$ is measured by a surface plasmon resonance assay. In some embodiments, the antibody binds Ara h 2 with a $K_D$ of between about 0.1 pM and about 40 nM. In some embodiments, the antibody binds Ara h 2 with a $K_D$ of between about 120 pM and about 20 nM. In some embodiments, the antibody binds Ara h 2 with a $K_D$ of between about 120 pM and about 10 nM.

In another aspect, the invention features an isolated antibody that binds to Ara h 2 (conglutin-7), or an antigen-binding fragment thereof, wherein the antibody comprises the following six CDRs: (a) an CDR-H1 comprising the amino acid sequence of GFTFRDYS (SEQ ID NO: 21); (b) an CDR-H2 comprising the amino acid sequence of IRFDGTTK (SEQ ID NO: 22); (c) an CDR-H3 comprising the amino acid sequence of AKDNGWRAFDH (SEQ ID NO: 23); (d) an CDR-L1 comprising the amino acid sequence of QSLLHRNGYIY (SEQ ID NO: 24); (e) an CDR-L2 comprising the amino acid sequence of FVS (SEQ ID NO: 25); and (f) an CDR-L3 comprising the amino acid sequence of MQALETPWT (SEQ ID NO: 26). In some embodiments, the antibody comprises (a) a VH domain comprising an amino sequence having at least 90%, at least 95%, or at least 99% sequence identity to the amino acid sequence of SEQ ID NO: 27; (b) a VL domain comprising an amino acid sequence having at least 90%, at least 95%, or at least 99% identity to the amino acid sequence of SEQ ID NO: 28; or (c) a VH domain as in (a) and a VL domain as in (b). In some embodiments, the antibody further comprises the following VH domain FRs: (a) an FR-H1 comprising the amino acid sequence of GGGVVQPGTSLRLSCVAS (SEQ ID NO: 29); (b) an FR-H2 comprising the amino acid sequence of MHWVRQAPGKGLEWVSF (SEQ ID NO: 30); (c) an FR-H3 comprising the amino acid sequence of DYRDSVKGRFIISRDDSKNTLYLQMTSLRVEDTALYYC (SEQ ID NO: 31); and (d) an FR-H4 comprising the amino acid sequence of WGQGALVTVSS (SEQ ID NO: 32). In some embodiments, the VH domain comprises the amino acid sequence of SEQ ID NO: 27. In some embodiments, the antibody further comprises the following VL domain FRs: (a) an FR-L1 comprising the amino acid sequence of VMTQSPLSLPVTPGEAASISCRSS (SEQ ID NO: 33); (b) an FR-L2 comprising the amino acid sequence of LDWYLQRPGQSPQLLIS (SEQ ID NO: 34); (c) an FR-L3 comprising the amino acid sequence of KRASGAPDRFSGSGSGTDFTLTISRVEAEDFGVYFC (SEQ ID NO: 35); and (d) an FR-L4 comprising the amino acid sequence of FGPGTKLEIK (SEQ ID NO: 36). In some embodiments, the VL domain comprises the amino acid sequence of SEQ ID NO: 28.

In another aspect, the invention features an isolated antibody that binds to Ara h 2, or an antigen-binding fragment thereof, wherein the antibody comprises: (a) a VH domain comprising an amino acid sequence having at least 90%, at least 95%, or at least 99% sequence identity to the amino acid sequence of SEQ ID NO: 27 and (b) a VL domain comprising an amino acid sequence having at least 90%, at least 95%, or at least 99% sequence identity to the amino acid sequence of SEQ ID NO: 28. In some embodiments, the antibody comprises a VH domain comprising the amino acid sequence of SEQ ID NO: 27 and a VL domain comprising the amino acid sequence of SEQ ID NO: 28. In some embodiments, the antibody comprises (a) a heavy chain comprising the amino acid sequence of SEQ ID NO: 37 and (b) a light chain comprising the amino acid sequence of SEQ ID NO: 38.

In some embodiments of any of the previous aspects, the antibody binds Ara h 2 with a $K_D$ of about 50 nM or less. In some embodiments, the $K_D$ is measured by a surface plasmon resonance assay. In some embodiments, the antibody binds Ara h 2 with a $K_D$ of between about 0.1 pM and about 40 nM. In some embodiments, the antibody binds Ara h 2 with a $K_D$ of between about 120 pM and about 20 nM. In some embodiments, the antibody binds Ara h 2 with a $K_D$ of between about 120 pM and about 10 nM.

In another aspect, the invention features an isolated antibody that binds to Ara h 2 (conglutin-7), or an antigen-binding fragment thereof, wherein the antibody comprises the following six CDRs: (a) an CDR-H1 comprising the amino acid sequence of GX1SX2SSYY (SEQ ID NO: 824), wherein X1 is D or G and X2 is I or M; (b) an CDR-H2 comprising the amino acid sequence of IFTX1GST (SEQ ID NO: 825), wherein X1 is S or T; (c) an CDR-H3 comprising the amino acid sequence of X1RDRRX2X3SX4DX5NWYWYFDL (SEQ ID NO: 826), wherein X1 is A or V, X2 is A or G, X3 is L or R, X4 is S or H, and X5 is G or S; (d) an CDR-L1 comprising the amino acid sequence of QTX1X2RN (SEQ ID NO: 827), wherein X1 is I or L and X2 is T or S; (e) an CDR-L2 comprising the amino acid sequence of GAS; and (f) an CDR-L3 comprising the amino acid sequence of QQSDNTPRT.

In another aspect, the invention features an isolated antibody that binds to Ara h 2 (conglutin-7), or an antigen-binding fragment thereof, wherein the antibody comprises the following six CDRs: (a) an CDR-H1 comprising the amino acid sequence of GDSISSYY (SEQ ID NO: 41); (b) an CDR-H2 comprising the amino acid sequence of IFTSGST (SEQ ID NO: 42); (c) an CDR-H3 comprising the amino acid sequence of ARDRRALSSDGNWYWYFDL (SEQ ID NO: 43); (d) an CDR-L1 comprising the amino acid sequence of QTITRN (SEQ ID NO: 44); (e) an CDR-L2 comprising the amino acid sequence of GAS (SEQ ID NO: 45); and (f) an CDR-L3 comprising the amino acid sequence of QQSDNTPRT (SEQ ID NO: 46). In some embodiments, the antibody comprises (a) a VH domain comprising an amino sequence having at least 90%, at least 95%, or at least 99% sequence identity to the amino acid sequence of SEQ ID NO: 47; (b) a VL domain comprising an amino acid sequence having at least 90%, at least 95%, or at least 99% identity to the amino acid sequence of SEQ ID NO: 48; or (c) a VH domain as in (a) and a VL domain as in (b). In some embodiments, the antibody further comprises the following VH domain FRs: (a) an FR-H1 comprising the amino acid sequence of ESGPRLVKPSETLSLTCIVS (SEQ ID NO: 49); (b) an FR-H2 comprising the amino acid sequence of WGWIRQPAGRGLEWIGR (SEQ ID NO: 50); (c) an FR-H3 comprising the amino acid sequence of TYNPSLKSRVSMSVETSKNQFSLTLTSVTAADTAVYFC (SEQ ID NO: 51); and (d) an FR-H4 comprising the amino acid sequence of WGRGTLVAVSS (SEQ ID NO: 52). In some embodiments, the VH domain comprises the amino acid sequence of SEQ ID NO: 47. In some embodiments, the antibody further comprises the following VL domain FRs: (a) an FR-L1 comprising the amino acid sequence of TQSPSSLSASVGDRVTITCRAS (SEQ ID NO: 53); (b) an FR-L2 comprising the amino acid sequence of LNWYQQKSGEAPKLLIY (SEQ ID NO: 54); (c) an FR-L3 comprising the amino acid sequence of ILQSGVPSRFTGSGSGTDFTLTISNLQPEDFASYSC (SEQ ID NO: 55); and (d) an FR-L4 comprising the amino acid sequence of GQGTKVEIK (SEQ ID NO: 56). In some embodiments, the VL domain comprises the amino acid sequence of SEQ ID NO: 48.

In another aspect, the invention features an isolated antibody that binds to Ara h 2, or an antigen-binding fragment thereof, wherein the antibody comprises (a) a VH domain comprising an amino acid sequence having at least 90%, at least 95%, or at least 99% sequence identity to the amino acid sequence of SEQ ID NO: 47 and (b) a VL domain comprising an amino acid sequence having at least 90%, at least 95%, or at least 99% sequence identity to the amino acid sequence of SEQ ID NO: 48. In some embodiments, the antibody comprises a VH domain comprising the amino acid sequence of SEQ ID NO: 47 and a VL domain comprising the amino acid sequence of SEQ ID NO: 48. In some embodiments, the antibody comprises (a) a heavy chain comprising the amino acid sequence of SEQ ID NO: 57 and (b) a light chain comprising the amino acid sequence of SEQ ID NO: 58.

In some embodiments of any of the previous aspects, the antibody binds Ara h 2 with a $K_D$ of about 50 nM or less. In some embodiments, the $K_D$ is measured by a surface plasmon resonance assay. In some embodiments, the antibody binds Ara h 2 with a $K_D$ of between about 0.1 pM and about 40 nM. In some embodiments, the antibody binds Ara h 2 with a $K_D$ of between about 120 pM and about 20 nM. In some embodiments, the antibody binds Ara h 2 with a $K_D$ of between about 120 pM and about 10 nM.

In another aspect, the invention features an isolated antibody that binds to Ara h 2 (conglutin-7), or an antigen-binding fragment thereof, wherein the antibody comprises the following six CDRs: (a) an CDR-H1 comprising the amino acid sequence of GGSMSSYY (SEQ ID NO: 61); (b) an CDR-H2 comprising the amino acid sequence of IFTTGST (SEQ ID NO: 62); (c) an CDR-H3 comprising the amino acid sequence of VRDRRGRSHDSNWYWYFDL (SEQ ID NO: 63); (d) an CDR-L1 comprising the amino acid sequence of QTLSRN (SEQ ID NO: 64); (e) an CDR-L2 comprising the amino acid sequence of GAS (SEQ ID NO: 65); and (f) an CDR-L3 comprising the amino acid sequence of QQSDNTPRT (SEQ ID NO: 66). In some embodiments, the antibody comprises (a) a VH domain comprising an amino sequence having at least 90%, at least 95%, or at least 99% sequence identity to the amino acid sequence of SEQ ID NO: 67; (b) a VL domain comprising an amino acid sequence having at least 90%, at least 95%, or at least 99% identity to the amino acid sequence of SEQ ID NO: 68; or (c) a VH domain as in (a) and a VL domain as in (b). In some embodiments, the antibody further comprises the following VH domain FRs: (a) an FR-H1 comprising the amino acid sequence of QVQLQESGPGLVKPSETLSLTCTVS (SEQ ID NO: 69); (b) an FR-H2 comprising the amino acid sequence of WGWIRQPAGRGLEWIGR (SEQ ID NO: 70); (c) an FR-H3 comprising the amino acid sequence of IYNASLNSRVSMSVDTSKNQFSLKLTSVTAADTALYFC (SEQ ID NO: 71); and (d) an FR-H4 comprising the amino acid sequence of WGRGTLVTVSS (SEQ ID NO: 72). In some embodiments, the VH domain comprises the amino acid sequence of SEQ ID NO: 67. In some embodiments, the antibody further comprises the following VL domain FRs: (a) an FR-L1 comprising the amino acid sequence of RVIITCRAS (SEQ ID NO: 73); (b) an FR-L2 comprising the amino acid sequence of LNWYQQKPGEAPKLLIY (SEQ ID NO: 74); (c) an FR-L3 comprising the amino acid sequence of TLQSGVPSRFTGSGSGTDFTLIISGLQPEDFATYYC (SEQ ID NO: 75); and (d) an FR-L4 comprising the amino acid sequence of FGQGT (SEQ ID NO: 76). In some embodiments, the VL domain comprises the amino acid sequence of SEQ ID NO: 68.

In another aspect, the invention features an isolated antibody that binds to Ara h 2, or an antigen-binding fragment thereof, wherein the antibody comprises (a) a VH domain comprising an amino acid sequence having at least 90%, at least 95%, or at least 99% sequence identity to the amino acid sequence of SEQ ID NO: 67 and (b) a VL domain comprising an amino acid sequence having at least 90%, at least 95%, or at least 99% sequence identity to the amino acid sequence of SEQ ID NO: 68. In some embodiments, the antibody comprises a VH domain comprising the amino acid sequence of SEQ ID NO: 67 and a VL domain comprising the amino acid sequence of SEQ ID NO: 68. In some embodiments, the antibody comprises (a) a heavy chain comprising the amino acid sequence of SEQ ID NO: 77 and (b) a light chain comprising the amino acid sequence of SEQ ID NO: 78.

In some embodiments of any of the previous aspects, the antibody binds Ara h 2 with a $K_D$ of about 50 nM or less. In some embodiments, the $K_D$ is measured by a surface plasmon resonance assay. In some embodiments, the antibody binds Ara h 2 with a $K_D$ of between about 0.1 pM and about 40 nM. In some embodiments, the antibody binds Ara h 2 with a $K_D$ of between about 120 pM and about 20 nM. In some embodiments, the antibody binds Ara h 2 with a $K_D$ of between about 120 pM and about 10 nM.

In some embodiments of any of the previous aspects, the antibody is capable of neutralizing Ara h 2.

In some embodiments of any of the previous aspects, the antibody is capable of blocking Ara h 2 binding with one or more binding partners.

In some embodiments of any of the previous aspects, the antibody is capable of blocking Ara h 2 binding with IgE.

In another aspect, the invention features an antibody that binds to the same epitope as the antibody of any one of the previous aspects. In some embodiments, whether the antibody binds to the same epitope or competes for binding to Ara h 2 is determined by an epitope binning assay.

In another aspect, the invention features an antibody that competes for binding to Ara h 2 with the antibody of any one of the previous aspects. In some embodiments, whether the antibody binds to the same epitope or competes for binding to Ara h 2 is determined by an epitope binning assay.

In some embodiments of any of the previous aspects, the antibody is monoclonal.

In some embodiments of any of the previous aspects, the antibody is humanized.

In some embodiments of any of the previous aspects, the antibody is an antibody fragment that binds Ara h 2. In some embodiments, the antibody fragment is selected from the group consisting of Fab, Fab'-SH, Fv, scFv, and $(Fab')_2$ fragments.

In some embodiments of any of the previous aspects, the antibody is a full-length antibody. In some embodiments, the antibody is an IgG antibody. In some embodiments, the antibody is an IgG1 antibody. In some embodiments, the antibody is an IgG4 antibody. In some embodiments, the IgG4 antibody comprises an S228P mutation (EU numbering).

In some embodiments of any of the previous aspects, the antibody is a monospecific antibody.

In some embodiments of any of the previous aspects, the antibody is a multispecific antibody. In some embodiments, the multispecific antibody binds two or more sites on Ara h 2. In some embodiments, the two or more sites on Ara h 2 are within one or more epitope bins. In some embodiments, the one or more epitope bins are Bin 1, Bin 2, and/or Bin 3. In some embodiments, epitope Bin 1 includes the epitope for anti-Ara h2 antibodies T1 and/or T3. In some embodiments, epitope Bin 2 includes the epitope for anti-Ara h2 antibodies T4 and/or T5. In some embodiments, epitope Bin 3 does not include the epitope for anti-Ara h2 antibodies T1, T3, T4, and T5. In some embodiments, the antibody is a bispecific antibody.

In another aspect, the invention features a polynucleotide encoding an isolated antibody of any one of the previous aspects.

In another aspect, the invention features a vector comprising a polynucleotide encoding an isolated antibody of any one of the previous aspects.

In another aspect, the invention features a host cell comprising a vector comprising a polynucleotide encoding an isolated antibody of any one of the previous aspects.

In another aspect, the invention features a composition comprising the antibody of any one of the previous aspects. In some embodiments, the composition further comprises a pharmaceutically acceptable carrier, excipient, or diluent. In some embodiments, the composition is a pharmaceutical composition.

In some embodiments of any of the previous aspects, the antibody of any one of the previous aspects or the composition of any one of the previous aspects is for use as a medicament.

In some embodiments of any of the previous aspects, the antibody of any one of the previous aspects or the composition of any one of the previous aspects is for use in treating or delaying a peanut sensitivity. In some embodiments, the peanut sensitivity is a peanut allergy.

In another aspect, the invention features a method of producing the antibody of any one of the previous aspects, the method comprising culturing a host cell that comprises a vector comprising a polynucleotide encoding an isolated antibody of any one of the previous aspects. In some embodiments, the host cell is prokaryotic. In some embodiments, the host cell is *Escherichia coli*. In some embodiments, the host cell is eukaryotic. In some embodiments, the host cell is a 293 cell, a CHO cell, a yeast cell, or a plant cell.

In another aspect, the invention features a method for treating a patient who demonstrates a sensitivity to, or an allergic reaction against, a nut or a portion thereof or an extract thereof, or to Ara h 2 protein, or for treating at least one symptom or complication associated with a sensitivity to, or allergic reaction against a nut or a portion thereof or an extract thereof, or to Ara h 2, comprising administering an effective amount of one or more isolated antibodies or antigen-binding fragments thereof that bind specifically to Ara h 2, according to the antibody of any one of the previous aspects. In some embodiments, the method further comprises administering an effective amount of a second therapeutic agent useful for diminishing an allergic reaction an allergic reaction against, a nut or a portion thereof or an extract thereof, or to Ara h 2 protein.

In another aspect, the invention features a method for detecting the presence of Ara h 2 neutralizing antibodies in a biological sample, comprising: (a) contacting a sample from a subject with a mixture comprising: (i) the antibody of any one of the previous aspects; and (ii) Ara h 2, or a fragment thereof; and (b) detecting the binding of antibodies present in the biological sample to Ara h 2, or a fragment thereof. In some embodiments, the antibody binding is detected using tandem biolayer interferometry. In some embodiments, the antibody from step (i) is bound to a solid support. In some embodiments, the Ara h 2, or a fragment thereof, is bound to a solid support. In some embodiments, antibody binding is detected using an enzyme-linked immunosorbent assay. In some embodiments, the subject is a human. In some embodiments, the subject has been diagnosed with a peanut sensitivity. In some embodiments, the subject has been diagnosed with a peanut allergy. In some embodiments, the subject has been previously treated or will be treated with peanut oral immunotherapy. In some embodiments, the sample is a blood or serum sample.

In another aspect, the invention features a method for detecting the presence of Ara h 2 neutralizing antibodies in a biological sample, comprising: (a) providing a sample from a subject; (b) contacting the sample with a mixture comprising: (i) the antibody of any one of the previous aspects; and (ii) Ara h 2, or a fragment thereof; and (c) detecting the binding of antibodies present in the biological sample to Ara h 2, or a fragment thereof. In some embodiments, the antibody binding is detected using tandem biolayer interferometry. In some embodiments, the antibody from step (i) is bound to a solid support. In some embodiments, the Ara h 2, or a fragment thereof, is bound to a solid support. In some embodiments, antibody binding is detected using an enzyme-linked immunosorbent assay. In some embodiments, the subject is a human. In some embodiments, the subject has been diagnosed with a peanut sensitivity. In some embodiments, the subject has been diagnosed with a peanut allergy. In some embodiments, the subject has been previously treated or will be treated with peanut oral immunotherapy. In some embodiments, the sample is a blood or serum sample.

In another aspect, the invention features a kit comprising the antibody or composition of any one of the previous aspects. In some embodiments, the kit further comprises instructions for use. In some embodiments, the kit further comprises one or more additional therapeutic agents (e.g., an antihistamine, epinephrine, a decongestant, or a corticosteroid).

Other features and advantages of the invention will be apparent from the following Detailed Description and the Claims.

DETAILED DESCRIPTION OF THE INVENTION

Peanut-specific IgG blocking antibodies as well as combinations of such antibodies are disclosed to prevent IgE-mediated allergic reactions in affected patients. Administered subcutaneously, these antibodies provide protection to peanut allergic patients (or patients having peanut hypersensitivity) as a preventive measure. While this therapy would not induce long-term tolerance, as OIT does, it would prevent allergic reactions, which carry mortality and morbidity, without the risks inherent to OIT. Moreover, the approach of using passive protection is particularly important in our most vulnerable population, young children, for whom food allergies can carry additional social and psychological burdens.

The use of peanut-specific protective antibodies would provide passive protection to pediatric or adult patients with IgE-mediated peanut hypersensitivity, diagnosed by a combination of skin prick testing, specific IgE measurement, component IgE measurement, or oral food challenge. The medication may be administered as a subcutaneous injection, able to be administered at home or in an outpatient office setting by an Allergist. The antibodies described herein may prevent allergic reactions to accidental peanut exposures, direct or indirect, by providing clinical tolerance to an exposure of about 50-300 mg of peanut protein, which is roughly equivalent to 1 peanut. In some instances, the antibodies described herein may provide a clinical tolerance to an exposure to at least about 50-300 mg (e.g., about 50 mg, about 60 mg, about 70 mg, about 80 mg, about 90 mg, about 100 mg, about 120 mg, about 140 mg, about 160 mg, about 180 mg, about 200 mg, about 220 mg, about 240 mg, about 260 mg, about 280 mg, about 300 mg, about 350 mg, about 400 mg, about 450 mg, about 500 mg, about 600 mg, about 700 mg, about 800 mg, about 900 mg, about 1 g, about 3 g, about 5 g, about 10 g, about 30 g, or more) of peanut protein.

The peanut-specific protective antibodies directed towards the immunodominant peanut antigen Ara h 2 as is disclosed herein were cloned from the circulation of pediatric patients who had sustained tolerance to peanut after OIT. From the same peanut OIT study, the suppression of basophil activation as a good biomarker of future tolerance is known. Furthermore, the suppression of basophils is mediated by IgG in the sera of tolerant patients, from whom the Ara h 2-specific antibodies described herein have been cloned. The protective antibodies were identified as those able to outcompete non-tolerant antibodies using biolayer light interferometry, as those have better antigen blocking capabilities.

Below we describe the invention as follows:

I. Definitions for understanding the specification;

II. Compositions and Methods including Therapy and Diagnostics; and

III. Examples.

I. DEFINITIONS

The term "about" as used herein refers to the usual error range for the respective value readily known to the skilled person in this technical field. Reference to "about" a value or parameter herein includes (and describes) embodiments that are directed to that value or parameter per se.

The term "peanut allergen" refers to Ara h 2, and isoforms thereof or a protein with an amino acid sequence of at least 90%, preferably of at least 92%, further preferably of at least 95%, and again further preferably of at least 98% amino acid sequence identity with such a peanut allergen and isoform thereof. Preferably, the peanut allergen is Ara h 2 with an amino acid sequence of at least, 90%, 92%, 93%, 94%, 95%, 96%, 97%, 98% or even 99% identity with Ara h 2:

```
                                    (SEQ ID NO: 821)
MAKLTILVALALFLLAAHASARQQWELQGDRRCQSQLERANLRPCEQHL

MQKIQRDEDSYGRDPYSPSQDPYSPSQDPDRRDPYSPSPYDRRGAGSSQ

HQERCCNELNEFENNQRCMCEALQQIMENQSDRLQGRQQEQQFKRELRN

LPQQCGLRAPQRCDLEVESGGRDRY
```

Signal sequence is amino acids 1-22. 4-hydroxyproline is located at positions 67, 74, and 86.

Allergenic fragments of Ara h 2 are also considered peanut allergens and may be identified according to standard methods.

The terms "anti-Ara h 2 antibody," "an antibody that binds to Ara h 2," and "an antibody that specifically binds to Ara h 2" refer to an antibody that is capable of binding Ara h 2 with sufficient affinity such that the antibody is useful as a preventative, diagnostic, and/or therapeutic agent in targeting Ara h 2. In one embodiment, the extent of binding of an anti-Ara h 2 antibody to an unrelated, non-Ara h 2 protein is less than about 10% of the binding of the antibody to Ara h 2 as measured, e.g., by a radioimmunoassay (RIA). In certain embodiments, an antibody that binds to Ara h 2 has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an antibody that binds to Ara h 2 has a $K_D$ of between about 0.0001 nM and about 100 nM. In certain embodiments, an anti-Ara h 2 antibody binds to an epitope of Ara h 2 that is conserved among Ara h 2 from different peanut species.

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "full-length antibody," "intact antibody," and "whole antibody" are used herein interchangeably to refer to an antibody having a structure substantially similar to a native antibody structure or having heavy chains that contain an Fc region as defined herein.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368(6474): 856-859); Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity, and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "antibody fragment" refers to a molecule other than an intact antibody that comprises a portion of an intact antibody that specifically binds to the antigen (e.g., an Ara h 2 protein described above to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$ is measured by a surface plasmon resonance assay," when used in the context of the claims, means that the $K_D$ is measured according the method described in Example 2 which measures kinetic parameters for binding of anti-Ara h 2 antibodies to Ara h 2 described in Patil et al., *J. Allergy Clin Immunol.* 136(1):125-134 (2015). Typically, the antibodies disclosed herein bind to Ara h 2 with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIACORE 3000 instrument using recombinant Ara h 2 as the analyte and the antibody as the ligand.

The term "EC50," as used herein, refers to the concentration of an antibody or an antigen-binding portion thereof, which induces a response, either in an in vivo or an in vitro assay, such as neutralization of Ara h 2 (e.g., blocking Ara h 2 binding with a binding partner (e.g., an IgE antibody)) as is described herein, which is 50% of the maximal response (i.e., halfway between the maximal response and the baseline).

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the allergic reaction and its complications in a patient already suffering from an allergic reaction to peanut exposure or at risk to being exposed to Ara h 2 or an allergenic fragment thereof. Amounts effective for this use will depend upon the severity of the allergic reaction being treated and the general state of the patient's own immune system.

The term "epitope" or "antigenic determinant" refers to a site on an antigen to which an immunoglobulin or antibody specifically binds on Ara h 2. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography, cryo-electron microscopy, and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., Ara h 2 or an allergic-inducing fragment thereof), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that specifically binds to Ara h 2 is substantially free of antibodies that specifically bind antigens other than Ara h 2). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to Ara h 2, is intended to refer to a nucleic acid molecule in which the nucleotide sequences encoding the antibody or antibody portion are free of other nucleotide sequences encoding antibodies that bind antigens other than Ara h 2, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program is registered under U.S. Copyright Registration No. TXU510087.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant Ara h 2 as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

A "subject," a "patient," or an "individual" is typically a human such as an adult, a child, or an infant.

As used herein, "administering" is meant a method of giving a dosage of a compound (e.g., an anti-Ara h 2 antibody or a nucleic acid encoding an anti-Ara h 2 antibody) or a composition (e.g., a pharmaceutical composition, e.g., a pharmaceutical composition including an anti-Ara h 2 antibody) to a subject. Preferably, the antibodies described herein are administered subcutaneously. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered, and the severity of the peanut allergy being treated). Preferably, the antibody or a combination of antibodies (for example, a combination of the T3 and T4 antibodies disclosed herein) are administered as a subcutaneous injection.

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dentrimer. Accordingly, one type of vector is a viral vector, wherein additional DNA segments (e.g., transgenes, e.g., transgenes encoding the heavy and/or light chain genes of an anti-Ara h 2 antibody) may be ligated into the viral genome, and the viral vector may then be administered (e.g., by electroporation, e.g., electroporation into muscle tissue) to the subject in order to allow for transgene expression in a manner analogous to gene therapy. Another type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

II. COMPOSITIONS AND METHODS

In one aspect, the invention is based, in part, on anti-Ara h 2 antibodies. Such antibodies are useful, for example, for treating a subject having, or at risk of developing, a peanut allergy following exposure, direct or indirect, to a peanut allergen such as Ara h 2.

A. Anti-Ara h 2 Antibodies

The invention provides isolated antibodies (e.g., any of the antibodies described herein) that bind to Ara h 2.

Accordingly, in one aspect, the invention provides isolated antibody that specifically binds to Ara h 2.

In another aspect, the antibody includes the following complementarity determining regions (CDRs): (a) a CDR-H1 comprising the amino acid sequence of GFTFRDYS; (b) a CDR-H2 comprising the amino acid sequence of IRFDGTTK; (c) a CDR-H3 comprising the amino acid sequence of $X_1$KDNGWRAFDH (SEQ ID NO: 822), wherein X1 is V or A; (d) a CDR-L1 comprising the amino acid sequence of QSLLHRNGYIY; (e) a CDR-L2 comprising the amino acid sequence of FVS; and (f) a CDR-L3 comprising the amino acid sequence of MQ$X_1$LE$X_2$PWT (SEQ ID NO: 823), wherein $X_1$ is S or A and $X_2$ is N or T, or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of the aforementioned sequences.

In another aspect, the invention provides isolated antibody that specifically binds to Ara h 2. In some instances, the antibody includes the following complementarity determining regions (CDRs): (a) a CDR-H1 comprising the amino acid sequence of G$X_1$S$X_2$SSYY (SEQ ID NO: 824), wherein $X_1$ is D or G and X2 is I or M; (b) a CDR-H2 comprising the amino acid sequence of IFTX1GST (SEQ ID NO: 825), wherein $X_1$ is S or T; (c) a CDR-H3 comprising the amino acid sequence of $X_1$RDRRX2$X_3$SX4DX5NWYWYFDL (SEQ ID NO: 826), wherein $X_1$ is A or V, $X_2$ is A or G, $X_3$ is L or R, $X_4$ is S or H, and $X_5$ is G or S; (d) a CDR-L1 comprising the amino acid sequence of QT$X_1$$X_2$RN (SEQ ID NO: 827), wherein $X_1$ is I or L and $X_2$ is T or S; (e) a CDR-L2 comprising the amino acid sequence of GAS; and (f) a CDR-L3 comprising the amino acid sequence of QQSDNTPRT, or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of the aforementioned sequences.

Examples of other antibodies include T1 (also referred to as V1), T3 (also referred to as V2), T4 (also referred to as V3), and T5 (also referred to as V4) as described herein, as well as the anti-Ara h 2 antibodies V5-V41 described herein.

T1

In some instances, the antibody includes one or more of the following six CDRs: (a) a CDR-H1 comprising the amino acid sequence of GFTFRDYS (SEQ ID NO: 1); (b) a CDR-H2 comprising the amino acid sequence of IRFDGTTK (SEQ ID NO: 2); (c) a CDR-H3 comprising the amino acid sequence of VKDNGWRAFDH (SEQ ID NO: 3); (d) a CDR-L1 comprising the amino acid sequence of QSLLHRNGYIY (SEQ ID NO: 4); (e) a CDR-L2 comprising the amino acid sequence of FVS (SEQ ID NO: 5); and (f) a CDR-L3 comprising the amino acid sequence of MQSLENPWT (SEQ ID NO: 6), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

In some instances, the antibody includes the following six CDRs: (a) a CDR-H1 comprising the amino acid sequence of GFTFRDYS (SEQ ID NO: 1); (b) a CDR-H2 comprising the amino acid sequence of IRFDGTTK (SEQ ID NO: 2); (c) a CDR-H3 comprising the amino acid sequence of VKDNGWRAFDH (SEQ ID NO: 3); (d) a CDR-L1 comprising the amino acid sequence of QSLLHRNGYIY (SEQ ID NO: 4); (e) a CDR-L2 comprising the amino acid sequence of FVS (SEQ ID NO: 5); and (f) a CDR-L3 comprising the amino acid sequence of MQSLENPWT (SEQ ID NO: 6).

In some instances, the antibody has a VH domain comprising an amino acid sequence having at least 90% sequence identity (e.g., at least 91%, 92%, 93%, 94%, 95%, 96%, 97%, 98%, or 99% sequence identity) to, or the sequence of, VESGGGVVQPGASLRLSCVASGFTFRDYSMHWVRQAPGKGLEWMSFIRFDGTTKDYRESVKGRFIISR DDSKNTLYLQMTSLRPEDTARYYCVKDNGWRAFDHWGQGALVIVSS (SEQ ID NO: 7); and/or a VL domain comprising an amino acid sequence having at least 90% sequence identity (e.g., at least 91%, 92%, 93%, 94%, 95%, 96%, 97%, 98%, or 99% sequence identity) to, or the sequence of, (SEQ ID NO: 8)
EIVMTQSPLSLPVTPGEAASISCRSSQSLLHRNGYIYLDWYLQRPGQSP

QLLISFVSKRASGAPDRFSGSGSGTDFTLTISRVEAEDFGVYFCMQSLE

NPWTFGP.

In some instances, the antibody comprises the following VH domain framework regions (FRs): (a) an FR-H1 comprising the amino acid sequence of VESGGGVVQPGASLRLSCVAS (SEQ ID NO: 9); (b) an FR-H2 comprising the amino acid sequence of MHWVRQAPGKGLEWMSF (SEQ ID NO: 10); (c) an FR-H3 comprising the amino acid sequence of DYRESVKGRFIISRDDSKNTLYLQMTSLRPEDTARYYC (SEQ ID NO: 11); and (d) an FR-H4 comprising the amino acid sequence of WGQGALVIVSS (SEQ ID NO: 12).

In some instances, the antibody comprises the following VL domain FRs: (a) an FR-L1 comprising the amino acid sequence of EIVMTQSPLSLPVTPGEAASISCRSS (SEQ ID NO: 13); (b) an FR-L2 comprising the amino acid sequence of LDWYLQRPGQSPQLLIS (SEQ ID NO: 14); (c) an FR-L3 comprising the amino acid sequence of KRASGAPDRFSGSGSGTDFTLTISRVEAEDFGVYFC (SEQ ID NO: 15); and (d) an FR-L4 comprising the amino acid sequence of FGP (SEQ ID NO: 16).

In some instances, the antibody includes a heavy chain and a light chain sequence, wherein: (a) the heavy chain comprises the amino acid sequence: VESGGGVVQPGASLRLSCVASGFTFRDYSMHWVRQAPGKGLEWMSFIRFDGTTKDYRESVKGRFIISR DDSKNTLYLQMTSLRPEDTARYYCVKDNGWRAFDH WGQGALVIVSSKGPSVFPLAPSSKSTSGGTAAL GXLVKDYFPEPVTVSWNSGALTSGVHTFPAVLQSSGLYSLSSVVTVPSSSLGTQTYICNVNHKPSNTKVD KXVEPKSCDKTHTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTL PPSRDEXTKNQVSLTCLVKGFYPSDIAVEWESNGQPENNYKTTPP VLDSDGSFFLYSKLTVDKSRWQQG NVFSCSVMHEALHNHYTQKSLSLSPGK (SEQ ID NO: 17); and (b) the light chain comprises the amino acid sequence:

(SEQ ID NO: 18)
EIVMTQSPLSLPVTPGEAASISCRSSQSLLHRNGYIYLDWYLQRPGQSP

QLLISFVSKRASGAPDRFSGSGSGTDFTLTISRVEAEDFGVYFCMQSLE

NPWTFGPAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC.

In some instances, the antibody includes a heavy chain comprising a nucleic acid sequence of SEQ ID NO: 19. In some instances, the antibody includes a light chain comprising a nucleic acid sequence of SEQ ID NO: 20.

T3

In some instances, the antibody includes one or more of the following six CDRs: (a) a CDR-H1 comprising the amino acid sequence of GFTFRDYS (SEQ ID NO: 21); (b) a CDR-H2 comprising the amino acid sequence of IRFDGTTK (SEQ ID NO: 22); (c) a CDR-H3 comprising the amino acid sequence of AKDNGWRAFDH (SEQ ID NO: 23); (d) a CDR-L1 comprising the amino acid sequence of QSLLHRNGYIY (SEQ ID NO: 24); (e) a CDR-L2 comprising the amino acid sequence of FVS (SEQ ID NO: 25); and (f) a CDR-L3 comprising the amino acid sequence of MQALETPWT (SEQ ID NO: 26), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21-26. In some instances, the antibody includes the following six CDRs: (a) a CDR-H1 comprising the amino acid sequence of GFTFRDYS (SEQ ID NO: 21); (b) a CDR-H2 comprising the amino acid sequence of IRFDGTTK (SEQ ID NO: 22); (c) a CDR-H3 comprising the amino acid sequence of AKDNGWRAFDH (SEQ ID NO: 23); (d) a CDR-L1 comprising the amino acid sequence of QSLLHRNGYIY (SEQ ID NO: 24); (e) a CDR-L2 comprising the amino acid sequence of FVS (SEQ ID NO: 25); and (f) a CDR-L3 comprising the amino acid sequence of MQALETPWT (SEQ ID NO: 26).

In some instances, the antibody has a VH domain comprising an amino acid sequence having at least 90% sequence identity (e.g., at least 91%, 92%, 93%, 94%, 95%, 96%, 97%, 98%, or 99% sequence identity) to, or the sequence of, GGGVVQPGTSLRLSCVASGFTFRDYSMHWVRQAPGKGLEWVSFIRFDGTTKDYRDSVKGRFIISRDDSK NTLYLQMTSLRVEDTALYYCAKDNGWRAFDHWGQGALVTVSS (SEQ ID NO: 27); and/or a VL domain comprising an amino acid sequence having at least 90% sequence identity (e.g., at least 91%, 92%, 93%, 94%, 95%, 96%, 97%, 98%, or 99% sequence identity) to, or the sequence of,

```
(SEQ ID NO: 28)
VMTQSPLSLPVTPGEAASISCRSSQSLLHRNGYIYLDWYLQRPGQSPQL
LISFVSKRASGAPDRFSGSGSGTDFTLTISRVEAEDFGVYFCMQALETP
WTFGPGTKLEIK.
```

In some instances, the antibody comprises the following VH domain FRs: (a) an FR-H1 comprising the amino acid sequence of GGGVVQPGTSLRLSCVAS (SEQ ID NO: 29); (b) an FR-H2 comprising the amino acid sequence of MHWVRQAPGKGLEWVSF (SEQ ID NO: 30); (c) an FR-H3 comprising the amino acid sequence of DYRDSVKGRFIISRDDSKNTLYLQMTSLRVEDTALYYC (SEQ ID NO: 31); and (d) an FR-H4 comprising the amino acid sequence of WGQGALVTVSS (SEQ ID NO: 32).

In some instances, the antibody comprises the following VL domain FRs: (a) an FR-L1 comprising the amino acid sequence of VMTQSPLSLPVTPGEAASISCRSS (SEQ ID NO: 33); (b) an FR-L2 comprising the amino acid sequence of LDWYLQRPGQSPQLLIS (SEQ ID NO: 34); (c) an FR-L3 comprising the amino acid sequence of KRASGAPDRFSGSGSGTDFTLTISRVEAEDFGVYFC (SEQ ID NO: 35); and (d) an FR-L4 comprising the amino acid sequence of FGPGTKLEIK (SEQ ID NO: 36).

In some instances, the antibody includes a heavy chain and a light chain sequence, wherein: (a) the heavy chain comprises the amino acid sequence: GGGVVQPGTSLRLSCVASGFTFRDYSMHWVRQAPGKGLEWVSFIRFDGTTKDYRDSVKGRFIISRDDSK NTLYLQMTSLRVEDTALYYCAKDNGWRAFDHWGQGALVTVSSKGPSVFPLAPSSKSTSGGTAALGXLV KDYFPEPVTVSWNSGALTSGVHTFPAVLQSSGLYSLSSVVTVPSSSLGTQTYCNVNHKPSNTKVDKXVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSR DEXTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 37); and (b) the light chain comprises the amino acid sequence:

```
(SEQ ID NO: 38)
VMTQSPLSLPVTPGEAASISCRSSQSLLHRNGYIYLDWYLQRPGQSPQL
LISFVSKRASGAPDRFSGSGSGTDFTLTISRVEAEDFGVYFCMQALETP
WTFGPGTKLEIKAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC.
```

In some instances, the antibody includes a heavy chain comprising a nucleic acid sequence of SEQ ID NO: 39. In some instances, the antibody includes a light chain comprising a nucleic acid sequence of SEQ ID NO: 40.

T4

In some instances, the antibody includes one or more of the following six CDRs: (a) a CDR-H1 comprising the amino acid sequence of GDSISSYY (SEQ ID NO: 41); (b) a CDR-H2 comprising the amino acid sequence of IFTSGST (SEQ ID NO: 42); (c) a CDR-H3 comprising the amino acid sequence of ARDRRALSSDGNWYWYFDL (SEQ ID NO: 43); (d) a CDR-L1 comprising the amino acid sequence of QTITRN (SEQ ID NO: 44); (e) a CDR-L2 comprising the amino acid sequence of GAS (SEQ ID NO: 45); and (f) a CDR-L3 comprising the amino acid sequence of QQSDNTPRT (SEQ ID NO: 46), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 41-46. In some instances, the antibody includes the following six CDRs: (a) a CDR-H1 comprising the amino acid sequence of GDSISSYY (SEQ ID NO: 41); (b) a CDR-H2 comprising the amino acid sequence of IFTSGST (SEQ ID NO: 42); (c) a CDR-H3 comprising the amino acid sequence of ARDRRALSSDGNWYWYFDL (SEQ ID NO: 43); (d) a CDR-L1 comprising the amino acid sequence of QTITRN (SEQ ID NO: 44); (e) a CDR-L2 comprising the amino acid sequence of GAS (SEQ ID NO: 45); and (f) a CDR-L3 comprising the amino acid sequence of QQSDNTPRT (SEQ ID NO: 46).

In some instances, the antibody has a VH domain comprising an amino acid sequence having at least 90% sequence identity (e.g., at least 91%, 92%, 93%, 94%, 95%, 96%, 97%, 98%, or 99% sequence identity) to, or the sequence of, ESGPRLVKPSETLSLTCIVSGDSISSYYWGWIRQPAGRGLEWIGRIFTSGSTTYNPSLKSRVSMSVETSK NQFSLTLTSVTAADTAVYFCARDRRALSSDGNWYWYFDLWGRGTLVAVSS (SEQ ID NO: 47); and/or a VL domain comprising an amino acid sequence having at least 90% sequence identity (e.g., at least 91%, 92%, 93%, 94%, 95%, 96%, 97%, 98%, or 99% sequence identity) to, or the sequence of,

```
                                        (SEQ ID NO: 48)
TQSPSSLSASVGDRVTITCRASQTITRNLNWYQQKSGEAPKLLIYGASI

LQSGVPSRFTGSGSGTDFTLTISNLQPEDFASYSCQQSDNTPRTFGQGT

KVEIK.
```

In some instances, the antibody comprises the following VH domain FRs: (a) an FR-H1 comprising the amino acid sequence of ESGPRLVKPSETLSLTCIVS (SEQ ID NO: 49); (b) an FR-H2 comprising the amino acid sequence of WGWIRQPAGRGLEWIGR (SEQ ID NO: 50); (c) an FR-H3 comprising the amino acid sequence of TYNPSLKSRVSMSVETSKNQFSLTLTSVTAAD-TAVYFC (SEQ ID NO: 51); and (d) an FR-H4 comprising the amino acid sequence of WGRGTLVAVSS (SEQ ID NO: 52).

In some instances, the antibody comprises the following VL domain FRs: (a) an FR-L1 comprising the amino acid sequence of TQSPSSLSASVGDRVTITCRAS (SEQ ID NO: 53); (b) an FR-L2 comprising the amino acid sequence of LNWYQQKSGEAPKLLIY (SEQ ID NO: 54); (c) an FR-L3 comprising the amino acid sequence of ILQSGVPSRFTGSGSGTDFTLTISNLQPEDFASYSC (SEQ ID NO: 55); and (d) an FR-L4 comprising the amino acid sequence of GQGTKVEIK (SEQ ID NO: 56).

In some instances, the antibody includes a heavy chain and a light chain sequence, wherein: (a) the heavy chain comprises the amino acid sequence: ESGPRLVKP-SETLSLTCIVSGDSISSYYWGWIRQPAGRGLEWIG-RIFTSGSTTYNPSLKSRVSMSVETSK NQFSLTLT-SVTAADTAVYFCARDRRALSSDGNWYW YFDLWGRGTLVAVSSKGPSVFPLAPSSKSTSGG TAALGXLVKDYFPEPVTVSWNSGALT-SGVHTFPAVLQSSGLYS-LSSVVTVPSSSLGTQTYICNVNHKPSN TKVDKXVE-PKSCDKTHTCPPCPAPELLGGPSVFLFPPKPKDTLMIS-RTPEVTCVVVDVSHEDPEVKFNWY VDGVEVHNAKTKPREEQYN-STYRVVSVLTVLHQDWLNGKEYKCKVSNKALPA-PIEKTISKAKGQPREPQ VYTLPPSRDEXTKNQVSLT-CLVKGFYPSDIAVEWESNGQPENNYK TTPPVLDSDGSFFLYSKLTVDKSR WQQGNVFSCSVMHEALHNHYTQKSLSLSPGK (SEQ ID NO: 57); and (b) the light chain comprises the amino acid sequence:

```
                                        (SEQ ID NO: 58)
TQSPSSLSASVGDRVTITCRASQTITRNLNWYQQKSGEAPKLLIYGASI

LQSGVPSRFTGSGSGTDFTLTISNLQPEDFASYSCQQSDNTPRTFGQGT

KVEIKAPSVFIFPPSDEQLKSGTASVVCLLNNFYPREAKVQWKVDNALQ

SGNSQESVTEQDSKDSTYSLSSTLTLSKADYEKHKVYACEVTHQGLSSP

VTKSFNRGEC.
```

In some instances, the antibody includes a heavy chain comprising a nucleic acid sequence of SEQ ID NO: 59. In some instances, the antibody includes a light chain comprising a nucleic acid sequence of SEQ ID NO: 60.

T5

In some instances, the antibody includes one or more of the following six CDRs: (a) a CDR-H1 comprising the amino acid sequence of GGSMSSYY (SEQ ID NO: 61); (b) a CDR-H2 comprising the amino acid sequence of IFTTGST (SEQ ID NO: 62); (c) a CDR-H3 comprising the amino acid sequence of VRDRRGRSHDSNWYWYFDL (SEQ ID NO: 63); (d) a CDR-L1 comprising the amino acid sequence of QTLSRN (SEQ ID NO: 64); (e) a CDR-L2 comprising the amino acid sequence of GAS (SEQ ID NO: 65); and (f) a CDR-L3 comprising the amino acid sequence of QQSDNTPRT (SEQ ID NO: 66), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 61-66. In some instances, the antibody includes the following six CDRs: (a) a CDR-H1 comprising the amino acid sequence of GGSMSSYY (SEQ ID NO: 61); (b) a CDR-H2 comprising the amino acid sequence of IFTTGST (SEQ ID NO: 62); (c) a CDR-H3 comprising the amino acid sequence of VRDRRGR-SHDSNWYWYFDL (SEQ ID NO: 63); (d) a CDR-L1 comprising the amino acid sequence of QTLSRN (SEQ ID NO: 64); (e) a CDR-L2 comprising the amino acid sequence of GAS (SEQ ID NO: 65); and (f) a CDR-L3 comprising the amino acid sequence of QQSDNTPRT (SEQ ID NO: 66).

In some instances, the antibody has a VH domain comprising an amino acid sequence having at least 90% sequence identity (e.g., at least 91%, 92%, 93%, 94%, 95%, 96%, 97%, 98%, or 99% sequence identity) to, or the sequence of, QVQLQESGPGLVKP-SETLSLTCTVSGGSMSSYYWGWIRQPAGRGLEWIG-RIFTTGSTIYNASLNSRVSM SVDTSKNQFSLKLT-SVTAADTALYFCVRDRRGRSHDSNWYWYFD LWGRGTLVTVSS (SEQ ID NO: 67); and/or a VL domain comprising an amino acid sequence having at least 90% sequence identity (e.g., at least 91%, 92%, 93%, 94%, 95%, 96%, 97%, 98%, or 99% sequence identity) to, or the sequence of, RVIIT-CRASQTLSRNLNWYQQKPGEAPKLLIY-GASTLQSGVPSRFTGSGSGTDFTLIISGLQPEDFA-TYYC QQSDNTPRTFGQGT (SEQ ID NO: 68).

In some instances, the antibody comprises the following VH domain FRs: (a) an FR-H1 comprising the amino acid sequence of QVQLQESGPGLVKPSETLSLTCTVS (SEQ ID NO: 69); (b) an FR-H2 comprising the amino acid sequence of WGWIRQPAGRGLEWIGR (SEQ ID NO: 70); (c) an FR-H3 comprising the amino acid sequence of IYNASLNSRVSMSVDTSKNQFSLKLTSVTAAD-TALYFC (SEQ ID NO: 71); and (d) an FR-H4 comprising the amino acid sequence of WGRGTLVTVSS (SEQ ID NO: 72).

In some instances, the antibody comprises the following VL domain FRs: (a) an FR-L1 comprising the amino acid sequence of RVIITCRAS (SEQ ID NO: 73); (b) an FR-L2 comprising the amino acid sequence of LNWYQQKPGEAPKLLIY (SEQ ID NO: 74); (c) an FR-L3 comprising the amino acid sequence of TLQSGVPSRFTGSGSGTDFTLIISGLQPEDFATYYC (SEQ ID NO: 75); and (d) an FR-L4 comprising the amino acid sequence of FGQGT (SEQ ID NO: 76).

In some instances, the antibody includes a heavy chain and a light chain sequence, wherein: (a) the heavy chain comprises the amino acid sequence: QVQLQESGPGLVKP-SETLSLTCTVSGGSMSSYYWGWIRQPAGRGLEWIG-RIFTTGSTIYNASLNSRVSM SVDTSKNQFSLKLT-SVTAADTALYFCVRDRRGRSHDSN WYWYFDLWGRGTLVTVSSKGPSVFPLAPSS KST-SGGTAALGXLVKDYFPEPVTVSWNSGALT-SGVHTFPAVLQSSGLYSLSSVVTVPSSSLGTQTYICNV NHKPSNTKVDKXVEPKSCDKTHTCPPCPA-PELLGGPSVFLFPPKPKDTLMISRTPE-VTCVVVDVSHEDPE VKFNWYVDGVEVHNAKTKPREEQYN-STYRVVSVLTVLHQDWLNGKEYKCKVSNKALPA-PIEKTISKAKG QPREPQVYTLPPSRDEXTKNQVSLT-CLVKGFYPSDIAVEWESNGQPENNYKT TPPVLDSDGSFFLYSKL TVDKSRWQQGNVFSCSVMHEALHNHYTQKSLSL-SPGK (SEQ ID NO: 77); and (b) the light chain comprises the amino acid sequence:

```
                                            (SEQ ID NO: 78)
RVIITCRASQTLSRNLNWYQQKPGEAPKLLIYGASTLQSGVPSRFTGSG

SGTDFTLIISGLQPEDFATYYCQQSDNTPRTFGQGTAPSVFIFPPSDEQ

LKSGTASVVCLLNNFYPREAKVQWKVDNALQSGNSQESVTEQDSKDSTY

SLSSTLTLSKADYEKHKVYACEVTHQGLSSPVTKSFNRGEC.
```

In some instances, the antibody includes a heavy chain comprising a nucleic acid sequence of SEQ ID NO: 79. In some instances, the antibody includes a light chain comprising a nucleic acid sequence of SEQ ID NO: 80.

V5-V41

In some instances, the antibody includes sequences corresponding to any one of the following antibodies: V5 (SEQ ID NOs: 81-100), V6 (SEQ ID NOs: 101-120), V7 (SEQ ID NOs: 121-140), V8 (SEQ ID NOs: 141-160), V9 (SEQ ID NOs: 161-180), V10 (SEQ ID NOs: 181-200), V11 (SEQ ID NOs: 201-120), V12 (SEQ ID NOs: 221-240), V13 (SEQ ID NOs: 241-260), V14 (SEQ ID NOs: 261-280), V15 (SEQ ID NOs: 281-300), V16 (SEQ ID NOs: 301-320), V17 (SEQ ID NOs: 321-340), V18 (SEQ ID NOs: 341-360), V19 (SEQ ID NOs: 361-380), V20 (SEQ ID NOs: 381-300), V21 (SEQ ID NOs: 401-420), V22 (SEQ ID NOs: 421-440), V23 (SEQ ID NOs: 441-460), V24 (SEQ ID NOs: 461-480), V25 (SEQ ID NOs: 481-500), V26 (SEQ ID NOs: 501-420), V27 (SEQ ID NOs: 521-540), V28 (SEQ ID NOs: 541-560), V29 (SEQ ID NOs: 561-580), V30 (SEQ ID NOs: 581-600), V31 (SEQ ID NOs: 601-620), V32 (SEQ ID NOs: 621-640), V33 (SEQ ID NOs: 641-660), V34 (SEQ ID NOs: 661-680), V35 (SEQ ID NOs: 681-700), V36 (SEQ ID NOs: 701-720), V37 (SEQ ID NOs: 721-740), V38 (SEQ ID NOs: 741-760), V39 (SEQ ID NOs: 761-780), V40 (SEQ ID NOs: 781-700), and V41 (SEQ ID NOs: 801-820).

In some instances, the antibody comprises a CDR-H1 comprising the amino acid sequence of SEQ ID NOs: 81, 101, 121, 141, 161, 181, 201, 221, 241, 261, 281, 301, 321, 341, 361, 381, 401, 421, 441, 461, 481, 501, 521, 541, 561, 581, 601, 621, 641, 661, 681, 701, 721, 741, 761, 781, or 801, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody comprises a CDR-H2 comprising the amino acid sequence of SEQ ID NOs: 82, 102, 122, 142, 162, 182, 202, 222, 242, 262, 282, 302, 322, 342, 362, 382, 402, 422, 442, 462, 482, 502, 522, 542, 562, 582, 602, 622, 642, 662, 682, 702, 722, 742, 762, 782, or 802, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody comprises a CDR-H3 comprising the amino acid sequence of SEQ ID NOs: 83, 103, 123, 143, 163, 183, 203, 223, 243, 263, 283, 303, 323, 343, 363, 383, 403, 423, 443, 463, 483, 503, 523, 543, 563, 583, 603, 623, 643, 663, 683, 703, 723, 743, 763, 783, or 803, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody comprises a CDR-L1 comprising the amino acid sequence of SEQ ID NOs: 84, 104, 124, 144, 164, 184, 204, 224, 244, 264, 284, 304, 324, 344, 364, 384, 404, 424, 444, 464, 484, 504, 524, 544, 564, 584, 604, 624, 644, 664, 684, 704, 724, 744, 764, 784, or 804, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody comprises a CDR-L2 comprising the amino acid sequence of SEQ ID NOs: 85, 105, 125, 145, 165, 185, 205, 225, 245, 265, 285, 305, 325, 345, 365, 385, 405, 425, 445, 465, 485, 505, 525, 545, 565, 585, 605, 625, 645, 665, 685, 705, 725, 745, 765, 785, or 805, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody comprises a CDR-L3 comprising the amino acid sequence of SEQ ID NOs: 86, 106, 126, 146, 166, 186, 206, 226, 246, 266, 286, 306, 326, 346, 366, 386, 406, 426, 446, 466, 486, 506, 526, 546, 566, 586, 606, 626, 646, 666, 686, 706, 726, 746, 766, 786, or 806, or variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity). In some instances, the antibody includes one or more of six CDRs, or a combination of one or more of the CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) of any of the following antibodies: V5-V41. In some instances, the antibody includes six CDRs from any one of the following antibodies: V5-V41.

In some instances, the antibody has a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NOs: 87, 107, 127, 147, 167, 187, 207, 227, 247, 267, 287, 307, 327, 347, 367, 387, 407, 427, 447, 467, 487, 507, 527, 547, 567, 587, 607, 627, 647, 667, 687, 707, 727, 747, 767, 787, or 807. In some instances, the antibody has a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NOs: 88, 108, 128, 148, 168, 188, 208, 228, 248, 268, 288, 308, 328, 348, 368, 388, 408, 428, 448, 468, 488, 508, 528, 548, 568, 588, 608, 628, 648, 668, 688, 708, 728, 748, 768, 788, or 808. In some instances, the antibody includes a VH and a VL sequence from any one of the following antibodies: V5-V41.

In some instances, the antibody includes an FR-H1 comprising an amino acid sequence any one of SEQ ID NOs: 89, 109, 129, 149, 169, 189, 209, 229, 249, 269, 289, 309, 329, 349, 369, 389, 409, 429, 449, 469, 489, 509, 529, 549, 569, 589, 609, 629, 649, 669, 689, 709, 729, 749, 769, 789, or 809. In some instances, the antibody includes an FR-H2 comprising an amino acid sequence any one of SEQ ID NOs: 90, 110, 130, 150, 170, 190, 210, 230, 250, 270, 290, 310, 330, 350, 370, 390, 410, 430, 450, 470, 490, 510, 530, 550, 570, 590, 610, 630, 650, 670, 690, 710, 730, 750, 770, 790, or 810. In some instances, the antibody includes an FR-H3 comprising an amino acid sequence any one of SEQ ID NOs: 91, 111, 131, 151, 171, 191, 211, 231, 251, 271, 291, 311, 331, 351, 371, 391, 411, 431, 451, 471, 491, 511, 531, 551, 571, 591, 611, 631, 651, 671, 691, 711, 731, 751, 771, 791, or 811. In some instances, the antibody includes an FR-H4 comprising an amino acid sequence any one of SEQ ID NOs: 92, 112, 132, 152, 172, 192, 212, 232, 252, 272, 292, 312, 332, 352, 372, 392, 412, 432, 452, 472, 492, 512, 532, 552, 572, 592, 612, 632, 652, 672, 692, 712, 732, 752, 772, 792, or 812.

In some instances, the antibody includes an FR-L1 comprising an amino acid sequence any one of SEQ ID NOs: 93, 113, 133, 153, 173, 193, 213, 233, 253, 273, 293, 313, 333, 353, 373, 393, 413, 433, 453, 473, 493, 513, 533, 553, 573, 593, 613, 633, 653, 673, 693, 713, 733, 753, 773, 793, 813. In some instances, the antibody includes an FR-L2 comprising an amino acid sequence any one of SEQ ID NOs: 94, 114, 134, 154, 174, 194, 214, 234, 254, 274, 294, 314, 334, 354, 374, 394, 414, 434, 454, 474, 494, 514, 534, 554, 574, 594, 614, 634, 654, 674, 694, 714, 734, 754, 774, 794, or 814. In some instances, the antibody includes an FR-L3 comprising an amino acid sequence any one of SEQ ID NOs: 95, 115, 135, 155, 175, 195, 215, 235, 255, 275, 295, 315, 335, 355, 375, 395, 415, 435, 455, 475, 495, 515, 535, 555, 575, 595, 615, 635, 655, 675, 695, 715, 735, 755, 775, 795, or 815. In some instances, the antibody includes an FR-L4 comprising an amino acid sequence any one of SEQ ID NOs: 96, 116, 136, 156, 176, 196, 216, 236, 256, 276, 296, 316, 336, 356, 376, 396, 416, 436, 456, 476, 496, 516, 536, 556, 576, 596, 616, 636, 656, 676, 696, 716, 736, 756, 776, 796, or 816.

In some instances, the antibody includes a heavy chain comprising an amino acid sequence any one of SEQ ID NOs: 97, 117, 137, 157, 177, 197, 217, 237, 257, 277, 297, 317, 337, 357, 377, 397, 417, 437, 457, 477, 497, 517, 537, 557, 577, 597, 617, 637, 657, 677, 697, 717, 737, 757, 777, 797, or 817. In some instances, the antibody includes a heavy chain comprising a nucleic acid sequence any one of SEQ ID NOs: 99, 119, 139, 159, 179, 199, 219, 239, 259, 279, 299, 319, 339, 359, 379, 399, 419, 439, 459, 479, 499, 519, 539, 559, 579, 599, 619, 639, 659, 679, 699, 719, 739, 759, 779, 799, or 819. In some instances, the antibody includes a light chain comprising an amino acid sequence any one of SEQ ID NOs: 98, 118, 138, 158, 178, 198, 218, 238, 258, 278, 298, 318, 338, 358, 378, 398, 418, 438, 458, 478, 498, 518, 538, 558, 578, 598, 618, 638, 658, 678, 698, 718, 738, 758, 778, 798, or 818. In some instances, the antibody includes a light chain comprising a nucleic acid sequence any one of SEQ ID NOs: 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, or 820. In some instances, the antibody includes a heavy chain and a light chain sequence from any one of the following antibodies: V5-V41.

Anti-Ara h 2 antibodies disclosed herein may be modified according to any standard methods such as those described herein. Accordingly, such modified antibodies are also useful in the compositions and methods described herein.

Furthermore, the invention further features any isolated antibody that binds to Ara h 2 (conglutin-7), or an antigen-binding fragment thereof, wherein the antibody comprises its respective components as described herein, for example, where the antibody includes following six complementarity determining regions (CDRs):

(a) an CDR-H1 comprising its respective amino acid sequence of SEQ ID NOs: 81, 101, 121, 141, 161, 181, 201, 221, 241, 261, 281, 301, 321, 341, 361, 381, 401, 421, 441, 461, 481, 501, 521, 541, 561, 581, 601, 621, 641, 661, 681, 701, 721, 741, 761, 781, or 801;

(b) an CDR-H2 comprising its respective amino acid sequence of SEQ ID NOs: 82, 102, 122, 142, 162,182, 202, 222, 242, 262, 282, 302, 322, 342, 362, 382, 402, 422, 442, 462, 482, 502, 522, 542, 562, 582, 602, 622, 642, 662, 682, 702, 722, 742, 762, 782, or 802;

(c) an CDR-H3 comprising its respective amino acid sequence of SEQ ID NOs: 83, 103, 123, 143, 163, 183, 203, 223, 243, 263, 283, 303, 323, 343, 363, 383, 403, 423, 443, 463, 483, 503, 523, 543, 563, 583, 603, 623, 643, 663, 683, 703, 723, 743, 763, 783, or 803;

(d) an CDR-L1 comprising its respective amino acid sequence of SEQ ID NOs: 84, 104, 124, 144, 164, 184, 204, 224, 244, 264, 284, 304, 324, 344, 364, 384, 404, 424, 444, 464, 484, 504, 524, 544, 564, 584, 604, 624, 644, 664, 684, 704, 724, 744, 764, 784, or 804;

(e) an CDR-L2 comprising its respective amino acid sequence of SEQ ID NOs: 85, 105, 125, 145, 165, 185, 205, 225, 245, 265, 285, 305, 325, 345, 365, 385, 405, 425, 445, 465, 485, 505, 525, 545, 565, 585, 605, 625, 645, 665, 685, 705, 725, 745, 765, 785, or 805; and (f) an CDR-L3 comprising its respective amino acid sequence 86, 106, 126, 146, 166, 186, 206, 226, 246, 266, 286, 306, 326, 346, 366, 386, 406, 426, 446, 466, 486, 506, 526, 546, 566, 586, 606, 626, 646, 666, 686, 706, 726, 746, 766, 786, or 806.

Antibodies of the invention may, for example, be monoclonal, human, humanized, or chimeric. The antibodies can be full-length antibodies or antibody fragments thereof (e.g., an antibody fragment that binds Ara h 2). The antibody fragment may be selected from the group consisting of Fab, Fab'-SH, Fv, scFv, and $(Fab')_2$ fragments. In some instances, the antibody is an IgG antibody (e.g., an IgG1 antibody). An antibody of the invention may have a half-life of 3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

In a further aspect, an anti-Ara h 2 antibody according to any of the above embodiments may incorporate any of the features, singly or in combination, as described in Sections 1-5 below.

1. Antibody Affinity

In certain embodiments, an antibody provided herein may have a dissociation constant ($K_D$) of ≤10 μM, ≤1 μM, ≤100 nM, ≤10 nM, ≤1 nM, ≤0.1 nM, or ≤0.01 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}I$)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}I$]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody (e.g., a human monoclonal antibody (HuMab), e.g., an anti-Ara h 2 HuMab). Human antibodies can be produced using various techniques known in the art.

In some instances, human antibodies are obtained by cloning the heavy and light chain genes directly from human B cells obtained from a human subject as is described herein in Example 1. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., Ara h 2).

In some instances, human antibodies may be prepared by administering an immunogen (e.g., Ara h 2) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Antibody Variants

In certain embodiments, amino acid sequence variants of the anti-Ara h 2 antibodies are contemplated.

For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in reduced antibody effector functions (e.g., complement-dependent cytotoxicity (CDC))

In certain instances, the invention contemplates an antibody, e.g., antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al. J. Immunol. Methods 202:163 (1996); Cragg, M. S. et al. *Blood.* 101:1045-1052 (2003); and Cragg, M. S. and M. J. Glennie Blood. 103:2738-2743 (2004)). FcRn binding and in vivo clearance/half-life determinations can also be performed using methods known in the art (see, e.g., Petkova, S. B. et al. Int'l. Immunol. 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain instances, the proline at position 329 of a wild-type human Fc region in the antibody is substituted with glycine or arginine or an amino acid residue large enough to destroy the proline sandwich within the Fc/Fc.gamma receptor interface that is formed between the proline 329 of the Fc and tryptophan residues Trp 87 and Trp 110 of FcgRIII (Sondermann et al.: Nature 406, 267-273 (20 Jul. 2000)). In certain instances, the antibody comprises at least one further amino acid substitution. In one instance, the further amino acid substitution is S228P, E233P, L234A, L235A, L235E, N297A, N297D, or P331S, and still in another instance the at least one further amino acid substitution is L234A and L235A of the human IgG1 Fc region or S228P and L235E of the human IgG4 Fc region (see e.g., US 2012/0251531), and still in another instance the at least one further amino acid substitution is L234A and L235A and P329G of the human IgG1 Fc region.

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

In other embodiments, Fc modifications are introduced to maximize dosing levels and to prevent anaphylaxis of peanut allergy.

In certain instances, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention are made in order to create antibody variants with certain improved properties.

In certain instances, it is desirable to create cysteine engineered anti-Ara h 2 antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues are substituted with cysteine: V205 (Kabat numbering) of the light chain; A118 (EU numbering) of the heavy chain;

and S400 (EU numbering) of the heavy chain Fc region. Cysteine engineered antibodies may be generated as described, for example, in U.S. Pat. No. 7,521,541.

In certain instances, an antibody of the invention provided herein are further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Isolation and Characterization of Human Antibodies to Ara h 2

An exemplary method for identifying anti-Ara h 2 antibodies is described in Example 1.

Sequence information for antibodies described herein can be ascertained using sequencing techniques which are well known in the art.

Similarly, affinity of the antibodies for anti-Ara h 2 antibodies can also be assessed using standard techniques. For example, Biacore 3000 can be used to determine the affinity of such antibodies. Antibodies are captured on the surface of a Biacore chip (GE healthcare), for example, via amine coupling (Sensor Chip CM5). The captured antibodies can be exposed to various concentrations of Ara h 2 in solution, and the $K_{on}$ and $K_{off}$ for an affinity ($K_D$) can be calculated, for example, by BIAevaluation software.

Antibodies can also be characterized for binding to Ara h 2 using a variety of known techniques, such as ELISA, Western blot, etc. Generally, the antibodies are initially characterized by ELISA. Briefly, microtiter plates can be coated with purified Ara h 2 in PBS, and then blocked with irrelevant proteins such as bovine serum albumin (BSA) diluted in PBS. Dilutions of plasma are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405.

In other instances, competition assays may be used to identify an antibody that competes with an anti-Ara h 2 antibody for binding to Ara h 2. In certain embodiments, such a competing antibody binds to the same epitope (e.g., a linear or a conformational epitope) that is bound by an anti-Ara h 2 antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized Ara h 2 is incubated in a solution comprising a first labeled antibody that binds to Ara h 2 and a second unlabeled antibody that is being tested for its ability to compete with the first antibody for binding to Ara h 2. The second antibody may be present in a hybridoma supernatant. As a control, immobilized Ara h 2 is incubated in a solution comprising the first labeled antibody but not the second unlabeled antibody. After incubation under conditions permissive for binding of the first antibody to Ara h 2, excess unbound antibody is removed, and the amount of label associated with immobilized Ara h 2 is measured. If the amount of label associated with immobilized Ara h 2 is substantially reduced in the test sample relative to the control sample, then that indicates that the second antibody is competing with the first antibody for binding to Ara h 2.

C. Compositions

In another aspect, the invention features a pharmaceutical composition comprising a therapeutically effective amount of one or more isolated human antibodies or antigen-binding fragments thereof that specifically bind Ara h 2, together with one or more pharmaceutically acceptable excipients. In one embodiment, the pharmaceutical composition comprises a therapeutically effective amount of two or more isolated human antibodies or antigen-binding fragments thereof that specifically bind Ara h 2 together with one or more pharmaceutically acceptable excipients.

In one embodiment, the invention features a composition, which is a combination of a therapeutically effective amount of one or more anti-Ara h 2 antibodies or antigen-binding fragments thereof of the invention, and a therapeutically effective amount of a second therapeutic agent. The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with an antibody or fragment thereof of the invention, for example, a second antibody other than those described herein that is capable of blocking the binding of Ara h 2 to IgE present on mast cells or basophils. A second therapeutic agent may also be any agent that is used as standard of care in treating an allergic response to any allergen. Such second therapeutic agent may be an antihistamine, epinephrine, a decongestant, or a corticosteroid.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

When multiple therapeutics are co-administered, dosages may be adjusted accordingly, as is recognized in the pertinent art.

Accordingly, the present invention provides a composition, e.g., a pharmaceutical composition, containing one or more (e.g., 1, 2, 3, or 4 or more) of the anti-Ara h 2 antibodies, or antibody fragments thereof, disclosed herein (e.g., antibodies V1-V41). The antibodies, if desired, may be modified according to any of the modifications outlined above. The pharmaceutical compositions may be formulated together with a pharmaceutically acceptable carrier, excipient, or diluent. In some instances, the pharmaceutical compositions include two or more of the anti-Ara h 2 antibodies. Preferably, each of the antibodies of the composition binds to a distinct epitope of Ara h 2.

A pharmaceutical composition described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Active ingredients of the pharmaceutical composition may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-Ara h 2 antibodies may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-HIV monoclonal antibodies (Balazs et al. *Nature.* 481: 81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10: 2253, 2013). Lentivirus vectors or other nucleic acids (e.g., RNA) capable of delivering transgenes could also be used to delivery antibody genes to establish serum antibody levels capable of prevention.

Also contemplated are kits including human anti-Ara h 2 antibodies and, optionally, instructions for use. The kits can further contain one or more additional reagents, such as a second, different anti-Ara h 2 antibody having a complementary activity that binds to an epitope on Ara h 2 that is distinct from the epitope to which the first anti-Ara h 2 antibody binds.

D. Therapy

Any of the anti-Ara h 2 antibodies described herein and compositions containing the antibodies can be used in a variety of in vitro and in vivo therapeutic applications. In some embodiments, an anti-Ara h 2 antibody may be used as a monotherapy. In some embodiments, an anti-Ara h 2 antibody may be used as a combination therapy.

The invention provides an anti-Ara h 2 antibody for use as a medicament. In further aspects, an anti-Ara h 2 antibody for use in treating a peanut allergy is provided. In certain embodiments, an anti-Ara h 2 antibody for use in a method of treatment is provided. In certain embodiments, the invention provides an anti-Ara h 2 antibody for use in a method of treating an individual having a peanut allergy comprising administering to the individual an effective amount of the anti-Ara h 2 antibody. In one such embodiment, the method further comprises administering to the individual an effective amount of at least one additional therapeutic agent, for example, as described below.

The invention provides an anti-Ara h 2 antibody in the manufacture or preparation of a medicament. In a further aspect, the invention provides for the use of an anti-Ara h 2 antibody in the manufacture or preparation of a medicament. In one embodiment, the medicament is for treatment of a peanut allergy. In a further embodiment, the medicament is for use in a method of treating a peanut allergy, e.g., comprising administering to an individual having a peanut allergy an effective amount of the medicament. In one such embodiment, the method further comprises administering to the individual an effective amount of at least one additional therapeutic agent, e.g., as described below.

In a further aspect, the invention provides a method for treating a peanut allergy. In some instances, the method comprises administering the individual having such a peanut allergy an effective amount of an anti-Ara h 2 antibody. In one embodiment, the method comprises administering to an individual having such peanut allergy an effective amount of an anti-Ara h 2 antibody (e.g., any anti-Ara h 2 antibody disclosed herein). In one such embodiment, the method further comprises administering to the individual an effective amount of at least one additional therapeutic agent, as described below.

In a further aspect, the invention provides pharmaceutical formulations comprising any of the anti-Ara h 2 antibodies provided herein, e.g., for use in any of the above therapeutic methods. In one embodiment, a pharmaceutical formulation comprises any of the anti-Ara h 2 antibodies provided herein and a pharmaceutically acceptable carrier.

In a further aspect, the invention features a method of treating a subject having a peanut allergy or who is sensitized to peanuts comprising administering a therapeutically effective amount of an antibody (e.g., a human monoclonal antibody) that specifically binds to Ara h 2 or a pharmaceutical composition thereof, thereby treating the subject.

Accordingly, the invention features method for treating a patient who demonstrates a sensitivity to a peanut allergen (e.g., Ara h 2), an allergic reaction against a peanut allergen, or to Ara h 2 protein, or for treating at least one symptom or complication associated with a sensitivity to, or allergic reaction against a peanut allergen, an allergic reaction against a peanut allergen, or to Ara h 2 protein, comprising administering an effective amount of one or more isolated human monoclonal antibodies or antigen-binding fragments thereof that bind specifically to Ara h 2, according to claims describe herein for T1 (also referred to as V1), T3 (also referred to as V2), T4 (also referred to as V3), or T5 (also referred to as V4) to a patient in need thereof, wherein the sensitivity to, or an allergic reaction against, to a peanut allergen, an allergic reaction against a peanut allergen, or to Ara h 2 protein, is lessened in severity and/or duration, or at least one symptom or complication associated with the sensitivity to, or allergic reaction against, to a peanut allergen, an allergic reaction against a peanut allergen, or to Ara h 2 protein is ameliorated, or that the frequency and/or duration of, or the severity of the sensitivity to or allergic reaction against, to a peanut allergen, an allergic reaction against a peanut allergen, or to Ara h 2 protein, is reduced following administration of one or more of the isolated human monoclonal antibodies or fragments thereof that bind specifically to Ara h 2.

Preferably, the method of treatment further comprises administering an effective amount of a second therapeutic agent useful for diminishing an allergic reaction to a peanut allergen, an allergic reaction against a peanut allergen, or to Ara h 2 protein. In some instances, the second therapeutic agent is selected from the group consisting of a corticosteroid, a bronchial dilator, an antihistamine, epinephrine, or a decongestant. Typically, treatment results in a reduction in allergic rhinitis, allergic conjunctivitis, allergic asthma, or an anaphylactic response following exposure, direct or indirect, of the patient to a peanut allergen, an allergic reaction against a peanut allergen, or to Ara h 2 protein.

Furthermore, as is discussed herein, antibodies of the invention can be used either alone or in combination with other agents in a therapy. For instance, an antibody of the invention may be co-administered with at least one additional therapeutic agent (e.g., a corticosteroid, a bronchial dilator, an antihistamine, epinephrine, and/or a decongestant). Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Ara h 2 antibody and administration of an additional therapeutic agent occur within about one month, or within about one, two or three weeks, or within about one, two, three, four, five, or six days, of each other.

Anti-Ara h 2 antibodies described herein may also be used in combination.

An antibody, such as modified antibodies disclosed herein such as T1 (also referred to as V1), T3 (also referred to as V2), T4 (also referred to as V3), T5 (also referred to as V4), or V5-V41 (and/or any additional therapeutic agent) can be administered by any suitable means, including parenteral, intrapulmonary, intranasal, oral, mucosal, intravenous, and, if desired for local treatment, intralesional administration. Parenteral infusions include intramuscular, intravenous, intraarterial, intraperitoneal, or subcutaneous administration. In some instances, an anti-Ara h 2 antibody (e.g., any anti-Ara h 2 antibody disclosed herein) may be administered orally, intrarectally, mucosally, intravenously, intramuscularly, intradermally, transdermally, subcutaneously, percutaneously, intraarterially, intraperitoneally, intravitreally, topically, intralesionally, intraarticularly, intraprostatically, intrapleurally, intratracheally, intrathecally, intranasally, intravaginally, intratumorally, intraperitoneally, peritoneally, intraventricularly, intracranially, subconjunctivally, intravesicularly, intrapericardially, intraumbilically, intraorbitally, ocularly, intraocularly, juxtasclerally, subtenonly, superchoroidally, by inhalation, by injection, by eye drop, by implantation, by infusion, by continuous infusion, by localized perfusion bathing target cells directly, by catheter, by lavage, in cremes, or in lipid compositions. In certain instances, antibody genes (e.g., genes encoding any one or more of the anti-Ara h 2 antibodies of the invention could be administered as a gene therapy to produce the one or more anti-Ara h 2 antibodies in the subject using either DNA vectors or viral vectors (e.g., rAAV vectors). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a peanut allergy or a subject who is hypersensitive to peanuts, the appropriate dosage of an antibody of the invention (when used alone or in combination with one or more other additional therapeutic agents) will depend on the severity of the allergic reaction to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending allergist. The antibody is suitably administered to the patient at one time or over a series of treatments. For repeated administrations over several days or longer, depending on the condition, the treatment would generally be sustained until a desired suppression of disease symptoms occurs. Doses may be administered intermittently, e.g. every week, every two weeks, every three weeks, every four weeks, every five weeks, every six weeks, every seven weeks, every eight weeks, every nine weeks, every ten weeks, every eleven weeks, or every twelve weeks (e.g., such that the patient receives from about two to about twenty, or e.g., about six doses of the antibody). For example, a dose may be administered once per month, once every two months, or once every three months (e.g., by subcutaneous injection) as an initial higher loading dose, followed by one or more lower doses may be administered. However, other dosage regimens may be useful. The progress of this therapy is easily monitored by conventional techniques and assays.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. An allergist having ordinary skill in the art can readily determine and prescribe the effective amount of the pharmaceutical composition required. For example, the allergist can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a human antibody of the invention) with another therapeutic agent which enhances or augments the therapeutic effect of the human antibodies.

E. Diagnostics

In certain embodiments, any of the anti-Ara h 2 antibodies of the invention are useful for in vitro or in vivo detection of peanut tolerance in allergic individuals. The term "detecting" as used herein encompasses quantitative or qualitative detection. In certain embodiments, a biological sample comprises a cell or tissue.

Current data suggests that there are three dominant conformational epitope bins where IgE binds to the Ara h 2 antigen and the recombinant IgG neutralizing anti Ara h 2 antibodies will compete for these sites and inhibit or displace IgE binding. With these neutralizing antibodies, the current tandem epitope binning by biolayer light interferometry assays can be used to assay whether a sample (e.g. a serum sample from a patient believed to have been exposed to a peanut allergen or a patient undergoing an OIT) contains antibodies that bind the same epitope bin, and whether those antibodies can effectively compete with the neutralizing antibodies. This test is useful to track the progress of therapy or to predict whether a patient will obtain the outcome of sustained unresponsiveness after OIT by assaying that patient's early OIT serum sample.

Accordingly, prior to the initiation of OIT, IgG antibodies isolated from patient serum will lack significant Ara h 2 neutralizing capacity and will be unable to compete with antibodies disclosed herein. During the course of treatment, patients that are responding to OIT will begin to produce IgG antibodies that are capable of competing with the anti-Ara h 2 antibodies while patients that are not responding to the therapy will maintain low levels of Ara h 2 neutralizing antibodies. The results of the competition assay can be used to predict whether an individual patient will attain a desired outcome of the treatment or can be used to adjust the duration of treatment to improve the likelihood of a desired outcome.

F. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. In some embodiments, the article of manufacture comprises an additional therapeutic agent (e.g., a corticosteroid, a bronchial dilator, an antihistamine, epinephrine, and/or a decongestant).

Other embodiments of the present invention are described in the following Examples. The present invention is further illustrated by the following examples which should not be construed as further limiting. The contents of all references, patents and published patent applications cited throughout this application are expressly incorporated herein by reference.

III. EXAMPLES

Example 1—Isolation of Genes Encoding Anti-Ara h 2 Antibodies from Patients Having Sustained Unresponsiveness to Peanut Allergen after One Month of Peanut Avoidance The peanut-specific protective antibodies directed towards the immunodominant peanut antigen Ara h 2 were cloned from the circulation of pediatric patients who had sustained tolerance to peanut after OIT. From the same peanut OIT study, suppression of basophil activation was identified as a good biomarker of future tolerance. Furthermore, the suppression of basophils is mediated by IgG in the sera of tolerant patients, from whom Ara h 2-specific antibodies were cloned. The protective antibodies were identified as those able to outcompete non-tolerant antibodies using biolayer light interferometry, as those have better antigen blocking capabilities.

Patient Selection

Peripheral blood was obtained after IRB-approved consent from peanut allergic participants of an open-label randomized trial of peanut OIT (NCT01324401). Study inclusion criteria included participants aged 7-21 years old with a diagnosis of peanut allergy based on a clinical history of reaction to peanut within one hour of ingestion and either an elevated skin prick test (>8 mm wheal) or elevated peanut-specific IgE (CAP FEIA>10 kU/L).

A total of 30 patients were enrolled, including 4 in an observational control arm, who were monitored for 1 year, after which they also received active OIT with premeasured peanut flour (Medium Roast, Golden Peanut Co., Alpharetta, GA). The protocol began with a 1 day modified rush before the build up phase to a 12 week maintenance phase with 4 grams of peanut protein, at the end of which desensitization was evaluated with an oral food challenge. After 4 weeks of peanut avoidance, subjects underwent a double blind oral food challenge to peanut.

Of the 22 subjects who were effectively desensitized, 9 subjects continued to have sustained unresponsiveness (SU) after a month of peanut avoidance and 13 subjects were found to have only transient desensitization (TD).

Specific Immunoglobulin E Measurement

Measurement of antigen-specific immunoglobulin levels in the serum or plasma from peripheral blood of subjects undergoing OIT was determined using the ImmunoCAP 1000 instrument (Phadia AB) according to the manufacturer's instructions.

Ara h 2 Specific B Cells Identification

Ara h 2 specific B cells from peripheral blood were identified by flow cytometry using a fluorescent tetramer created as described by Patil et al., *J. Allergy Clin Immunol.* 136(1):125-134 (2015). Briefly, peripheral blood mononuclear cells (PBMCs) isolated by density gradient centrifugation (Ficoll-Paque Plus; GE Healthcare) from peripheral blood of patients undergoing peanut OIT were then stained using CD3-APC (eBioscience clone OKT3), CD14-APC (eBioscience, clone 61D3), CD16-APC (eBioscience clone CB16), CD19-APC-Cy7 (BD Biosciences clone SJ25C1), CD27-PE (BD Pharmingen clone M-T271), CD38-Violet 421 (BD Biosciences clone HIT2), IgM-PE-Cy5 (BD Pharmingen clone G20-127), and AF488-Ara h 2 multimer. Data were analyzed using FlowJo 8.8.7 software (TreeStar).

Ara h 2 specific B cells, identified as tetramer$^+$CD19$^+$ cells were isolated 1-2 months after the start of OIT for single-cell indexed fluorescence-activated cell sorting (BD Aria II, BD Fusion SORP) into 96-well plates (Eppendorf)

for further single cell nested RT-PCR BCR amplification. Briefly, cells sorted into RNAsin containing single strand buffer were frozen at −80 C and subsequently underwent heat lysis with NP-40 and random hexamers. The RT reaction was followed by 2 nested PCR reactions for both heavy and light chains, as described by Patil et al., *J. Allergy Clin Immunol.* 136(1):125-134 (2015).

Successfully amplified products were Sanger sequenced (Genewiz Inc.) using second PCR primers. Consensus sequences combining both the forward and reverse sequences were determined using pairwise alignment in Geneious (Biomatters Ltd). These sequences were then analyzed using IMGT/V-BLAST to identify germline V, D, and J sequences with the highest identity, CDR3 regions, and nucleotide and amino acid changes from germline sequence.

Purified (Qiagen PCR purification kit) paired heavy and light chains subsequently underwent a third PCR reaction for the addition of restriction enzyme sites, followed by repeat PCR purification. For expression as recombinant antibodies on an $IgG_1$ backbone, digested heavy and light PCR amplicons were ligated into heavy and light chain vectors, respectively, as described by Patil et al., *J. Allergy Clin Immunol.* 136(1):125-134 (2015), and transformed in competent *E. coli* NEB5α bacteria (New England Biolabs) for ampicillin selection of plasmids with Sanger-sequence verified PCR amplicons. Plasmid DNA (25 ng) from selected heavy and light chains were transfected into HEK293 T cells using GenJet™ In Vitro DNA Transfection Reagent (SignaGen). Supernatants were harvested from cells after three days of culture at 37° C. with 5% CO2 in serum free HL-1 media (Lonza) supplemented with Pen-Strep and 8 mM Glutamax (Gibco). Antibodies were purified from supernatants using Protein G beads (ThermoFischer).

Recombinant Ara h 2 antibody specificity was verified by ImmunoCAP measurement for each antibody. Epitope binning was performed using SA-sensors (ForteBio) loaded with 0.5 uM concentration of biotinylated Ara h 2 (Indoor Technologies) by biolayer light interferometry (ForteBio Octet Red96). Epitope binning was performed using Octet Data Analysis Software.

In order to be expressed as monoclonal antibodies, restriction sites were added during cloning through the use of highly permissive, degenerate primers situated in the FR1 and FR4 regions, for subsequent cloning into a vector with an IgG1 constant region. As a result of both PCR error introduction rates as well as the primers required to add the requisite restriction enzyme cleavage sites, the original VDJ sequence cloned from RNA, rather than DNA, is now altered. The altered proteins are expressed as recombinant antibodies for further characterization. Furthermore, the original antibodies may have been an isotype other than IgG1 but are then artificially made into IgG1 (or any other) constant region containing antibody.

Example 2—Antibody Binding to Ara h 2 as Determined by Surface Plasmon Resonance Calculated equilibrium dissociative constants ($K_D$) for antigen binding to anti-Ara h 2 antibodies was determined using a real-time surface plasmon resonance biosensor (Biacore 3000) assay. Exemplary results are shown in Table 2.

TABLE 2

| ab | KD |
|---|---|
| T1 | 4.85E−09 |
| T3 | 1.93E−10 |
| T4 | 1.43E−12 |
| T5 | 1.12E−10 |

Example 3—Anti-Ara h 2 Antibody Epitope Characterization

The epitopes of antibodies T1 (also referred to as V1), T3 (also referred to as V2), T4 (also referred to as V3), and T5 (also referred to as V4) were characterized using biotinylated Ara h 2 by epitope binning by biolayer light interferometry (ForteBio, Octet). Experiments showed that antibodies T1 and T3 share the same epitope bin (Bin 1) and antibodies T4 and T5 share a different epitope bin (Bin 2).

OTHER EMBODIMENTS

Some embodiments of the technology described herein can be defined according to any of the following numbered embodiments:

T1:

1. An isolated antibody that binds to Ara h 2 (conglutin-7), or an antigen-binding fragment thereof, wherein the antibody comprises the following six complementarity determining regions (CDRs):
(a) an CDR-H1 comprising the amino acid sequence of GFTFRDYS (SEQ ID NO: 1);
(b) an CDR-H2 comprising the amino acid sequence of IRFDGTTK (SEQ ID NO: 2);
(c) an CDR-H3 comprising the amino acid sequence of VKDNGWRAFDH (SEQ ID NO: 3);
(d) an CDR-L1 comprising the amino acid sequence of QSLLHRNGYIY (SEQ ID NO: 4);
(e) an CDR-L2 comprising the amino acid sequence of FVS (SEQ ID NO: 5); and
(f) an CDR-L3 comprising the amino acid sequence of MQSLENPWT (SEQ ID NO: 6).

2. The antibody of embodiment 1, wherein the antibody comprises
(a) a heavy chain variable (VH) domain comprising an amino sequence having at least 90%, at least 95%, or at least 99% sequence identity to the amino acid sequence of SEQ ID NO: 7;
(b) a light chain variable (VL) domain comprising an amino acid sequence having at least 90%, at least 95%, or at least 99% identity to the amino acid sequence of SEQ ID NO: 8; or (c) a VH domain as in (a) and a VL domain as in (b).

3. The antibody of embodiment 1 or 2, further comprising the following VH domain framework regions (FRs):
(a) an FR-H1 comprising the amino acid sequence of VESGGGVVQPGASLRLSCVAS (SEQ ID NO: 9);
(b) an FR-H2 comprising the amino acid sequence of MHWVRQAPGKGLEWMSF (SEQ ID NO: 10);
(c) an FR-H3 comprising the amino acid sequence of DYRESVKGRFIISRDDSKNTLYLQMTSLRPEDTARYYC (SEQ ID NO: 11); and
(d) an FR-H4 comprising the amino acid sequence of WGQGALVIVSS (SEQ ID NO: 12).

4. The antibody of any one of embodiments 1-3, wherein the VH domain comprises the amino acid sequence of SEQ ID NO: 7.

5. The antibody of any one of embodiments 1-4, further comprising the following VL domain FRs:
(a) an FR-L1 comprising the amino acid sequence of EIVMTQSPLSLPVTPGEAASISCRSS (SEQ ID NO: 13);
(b) an FR-L2 comprising the amino acid sequence of LDWYLQRPGQSPQLLIS (SEQ ID NO: 14);
(c) an FR-L3 comprising the amino acid sequence of KRASGAPDRFSGSGSGTDFTLTISRVEAE-DFGVYFC (SEQ ID NO: 15); and
(d) an FR-L4 comprising the amino acid sequence of FGP (SEQ ID NO: 16).
6. The antibody of any one of embodiments 1-5, wherein the VL domain comprises the amino acid sequence of SEQ ID NO: 8.
7. An isolated antibody that binds to Ara h 2, or an antigen-binding fragment thereof, wherein the antibody comprises
(a) a VH domain comprising an amino acid sequence having at least 90%, at least 95%, or at least 99% sequence identity to the amino acid sequence of SEQ ID NO: 7 and
(b) a VL domain comprising an amino acid sequence having at least 90%, at least 95%, or at least 99% sequence identity to the amino acid sequence of SEQ ID NO: 8.
8. The antibody of embodiment 7, wherein the antibody comprises a VH domain comprising the amino acid sequence of SEQ ID NO: 7 and a VL domain comprising the amino acid sequence of SEQ ID NO: 8.
9. The antibody of any one of embodiments 1-8, wherein the antibody comprises (a) a heavy chain comprising the amino acid sequence of SEQ ID NO: 17 and (b) a light chain comprising the amino acid sequence of SEQ ID NO: 18.
10. The antibody of any one of embodiments 1-9, wherein the antibody binds Ara h 2 with a $K_D$ of about 50 nM or less.
11. The method of embodiment 10, wherein the $K_D$ is measured by a surface plasmon resonance assay.
12. The antibody of embodiment 11, wherein the antibody binds Ara h 2 with a $K_D$ of between about 0.1 pM and about 40 nM.
13. The antibody of embodiment 12, wherein the antibody binds Ara h 2 with a $K_D$ of between about 120 pM and about 20 nM.
14. The antibody of embodiment 13, wherein the antibody binds Ara h 2 with a $K_D$ of between about 120 pM and about 10 nM.
15. The antibody of any one of embodiments 1-14, wherein the antibody is capable neutralizing Ara h 2
16. An antibody that binds to the same epitope as the antibody of any one of embodiment 1-15.
17. An antibody that competes for binding to Ara h 2 with the antibody of any one of embodiments 1-16.
18. The antibody of embodiment 16 or 17, wherein whether the antibody binds to the same epitope or competes for binding to Ara h 2 is determined by an epitope binning assay.
19. The antibody of any one of embodiments 1-18, wherein the antibody is monoclonal.
20. The antibody of any one of embodiments 1-19, wherein the antibody is humanized.
21. The antibody of any one of embodiments 1-20, wherein the antibody is an antibody fragment that binds Ara h 2.
22. The antibody of embodiment 21, wherein the antibody fragment is selected from the group consisting of Fab, Fab'-SH, Fv, scFv, and $(Fab')_2$ fragments.
23. The antibody of any one of embodiments 1-20, wherein the antibody is a full-length antibody.
24. The antibody of embodiment 23, wherein the antibody is an IgG antibody.
25. The antibody of embodiment 24, wherein the IgG antibody is an IgG1 antibody.
26. The antibody of embodiment 24, wherein the IgG antibody is an IgG4 antibody.
27. The antibody of embodiment 26, wherein the IgG4 antibody comprises an S228P mutation (EU numbering).
28. The antibody of any one of embodiments 1-27, wherein the antibody is a monospecific antibody.
29. The antibody of any one of embodiments 1-27, wherein the antibody is a multispecific antibody.
30. The antibody of embodiment 29, wherein the antibody is a bispecific antibody.
31. A polynucleotide encoding an isolated antibody of any one of embodiments 1-30.
32. A vector comprising the polynucleotide of embodiment 31.
33. A host cell comprising the vector of embodiment 32.
34. A method of producing the antibody of any one of embodiments 1-33, the method comprising culturing a host cell that comprises the vector of embodiment 32 and recovering the antibody.
35. The method of embodiment 34, wherein the host cell is prokaryotic.
36. The method of embodiment 35, wherein the host cell is *Escherichia coli*.
37. The method of embodiment 34, wherein the host cell is eukaryotic.
38. The method of embodiment 37, wherein the host cell is a 293 cell, a CHO cell, a yeast cell, or a plant cell.
39. A method for treating a patient who demonstrates a sensitivity to, or an allergic reaction against, a nut or a portion thereof or an extract thereof, or to Ara h 2 protein, or for treating at least one symptom or complication associated with a sensitivity to, or allergic reaction against a nut or a portion thereof or an extract thereof, or to Ara h 2, comprising administering an effective amount of one or more isolated antibodies or antigen-binding fragments thereof that bind specifically to Ara h 2, according to any of embodiments 1-30.
40. The method of embodiment 39, further comprising administering an effective amount of a second therapeutic agent useful for diminishing an allergic reaction an allergic reaction against, a nut or a portion thereof or an extract thereof, or to Ara h 2 protein.
41. A method for detecting the presence of Ara h 2 neutralizing antibodies in a biological sample, comprising:
(a) providing a sample from a subject;
(b) contacting the sample with a mixture comprising:
(i) the antibody of any one of embodiments 1-30 and
(ii) Ara h 2, or a fragment thereof; and
(c) detecting the binding of antibodies present in the biological sample to Ara h 2, or a fragment thereof.
42. The method of embodiment 41, where antibody binding is detected using tandem biolayer interferometry.
43. The method of embodiments 41 or 42, where the antibody from step (b) is bound to a solid support.

44. The method of embodiments 41 or 42, where Ara h 2, or a fragment thereof, is bound to a solid support.
45. The method of embodiment 41, where antibody binding is detected using an enzyme-linked immunosorbent assay.

T3:

1. An isolated antibody that binds to Ara h 2 (conglutin-7), or an antigen-binding fragment thereof, wherein the antibody comprises the following six CDRs:
(a) an CDR-H1 comprising the amino acid sequence of GFTFRDYS (SEQ ID NO: 21);
(b) an CDR-H2 comprising the amino acid sequence of IRFDGTTK (SEQ ID NO: 22);
(c) an CDR-H3 comprising the amino acid sequence of AKDNGWRAFDH (SEQ ID NO: 23);
(d) an CDR-L1 comprising the amino acid sequence of QSLLHRNGYIY (SEQ ID NO: 24);
(e) an CDR-L2 comprising the amino acid sequence of FVS (SEQ ID NO: 25); and
(f) an CDR-L3 comprising the amino acid sequence of MQALETPWT (SEQ ID NO: 26).
2. The antibody of embodiment 1, wherein the antibody comprises
(a) a VH domain comprising an amino sequence having at least 90%, at least 95%, or at least 99% sequence identity to the amino acid sequence of SEQ ID NO: 27;
(b) a VL domain comprising an amino acid sequence having at least 90%, at least 95%, or at least 99% identity to the amino acid sequence of SEQ ID NO: 28; or (c) a VH domain as in (a) and a VL domain as in (b).
3. The antibody of embodiment 1 or 2, further comprising the following VH domain FRs:
(a) an FR-H1 comprising the amino acid sequence of GGGVVQPGTSLRLSCVAS (SEQ ID NO: 29);
(b) an FR-H2 comprising the amino acid sequence of MHWVRQAPGKGLEWVSF (SEQ ID NO: 30);
(c) an FR-H3 comprising the amino acid sequence of DYRDSVKGRFIISRDDSKNTLYLQMTSLRVEDTALYYC (SEQ ID NO: 31); and
(d) an FR-H4 comprising the amino acid sequence of WGQGALVTVSS (SEQ ID NO: 32).
4. The antibody of any one of embodiments 1-3, wherein the VH domain comprises the amino acid sequence of SEQ ID NO: 27.
5. The antibody of any one of embodiments 1-4, further comprising the following VL domain FRs:
(a) an FR-L1 comprising the amino acid sequence of VMTQSPLSLPVTPGEAASISCRSS (SEQ ID NO: 33);
(b) an FR-L2 comprising the amino acid sequence of LDWYLQRPGQSPQLLIS (SEQ ID NO: 34):
(c) an FR-L3 comprising the amino acid sequence of KRASGAPDRFSGSGSGTDFTLTISRVEAEDFGVYFC (SEQ ID NO: 35); and
(d) an FR-L4 comprising the amino acid sequence of FGPGTKLEIK (SEQ ID NO: 36).
6. The antibody of any one of embodiments 1-5, wherein the VL domain comprises the amino acid sequence of SEQ ID NO: 28.
7. An isolated antibody that binds to Ara h 2, or an antigen-binding fragment thereof, wherein the antibody comprises
(a) a VH domain comprising an amino acid sequence having at least 90%, at least 95%, or at least 99% sequence identity to the amino acid sequence of SEQ ID NO: 27 and
(b) a VL domain comprising an amino acid sequence having at least 90%, at least 95%, or at least 99% sequence identity to the amino acid sequence of SEQ ID NO: 28.
8. The antibody of embodiment 7, wherein the antibody comprises a VH domain comprising the amino acid sequence of SEQ ID NO: 27 and a VL domain comprising the amino acid sequence of SEQ ID NO: 28.
9. The antibody of any one of embodiments 1-8, wherein the antibody comprises (a) a heavy chain comprising the amino acid sequence of SEQ ID NO: 37 and (b) a light chain comprising the amino acid sequence of SEQ ID NO: 38.
10. The antibody of any one of embodiments 1-9, wherein the antibody binds Ara h 2 with a KD of about 50 nM or less.
11. The method of embodiment 10, wherein the KD is measured by a surface plasmon resonance assay.
12. The antibody of embodiment 11, wherein the antibody binds Ara h 2 with a KD of between about 0.1 pM and about 40 nM.
13. The antibody of embodiment 12, wherein the antibody binds Ara h 2 with a KD of between about 120 pM and about 20 nM.
14. The antibody of embodiment 13, wherein the antibody binds Ara h 2 with a KD of between about 120 pM and about 10 nM.
15. The antibody of any one of embodiments 1-14, wherein the antibody is capable neutralizing Ara h 2
16. An antibody that binds to the same epitope as the antibody of any one of embodiment 1-15.
17. An antibody that competes for binding to Ara h 2 with the antibody of any one of embodiments 1-16.
18. The antibody of embodiment 16 or 17, wherein whether the antibody binds to the same epitope or competes for binding to Ara h 2 is determined by an epitope binning assay.
19. The antibody of any one of embodiments 1-18, wherein the antibody is monoclonal.
20. The antibody of any one of embodiments 1-19, wherein the antibody is humanized.
21. The antibody of any one of embodiments 1-20, wherein the antibody is an antibody fragment that binds Ara h 2.
22. The antibody of embodiment 21, wherein the antibody fragment is selected from the group consisting of Fab, FabSH, Fv, scFv, and (Fab')2 fragments.
23. The antibody of any one of embodiments 1-20, wherein the antibody is a full-length antibody.
24. The antibody of embodiment 23, wherein the antibody is an IgG antibody.
25. The antibody of embodiment 24, wherein the IgG antibody is an IgG1 antibody.
26. The antibody of embodiment 24, wherein the IgG antibody is an IgG4 antibody.
27. The antibody of embodiment 26, wherein the IgG4 antibody comprises an S228P mutation (EU numbering).
28. The antibody of any one of embodiments 1-27, wherein the antibody is a monospecific antibody.
29. The antibody of any one of embodiments 1-27, wherein the antibody is a multispecific antibody.
30. The antibody of embodiment 29, wherein the antibody is a bispecific antibody.
31. A polynucleotide encoding an isolated antibody of any one of embodiments 1-30.

32. A vector comprising the polynucleotide of embodiment 31.
33. A host cell comprising the vector of embodiment 32.
34. A method of producing the antibody of any one of embodiments 1-33, the method comprising culturing a host cell that comprises the vector of embodiment 32 and recovering the antibody.
35. The method of embodiment 34, wherein the host cell is prokaryotic.
36. The method of embodiment 35, wherein the host cell is *Escherichia coli.*
37. The method of embodiment 34, wherein the host cell is eukaryotic.
38. The method of embodiment 37, wherein the host cell is a 293 cell, a CHO cell, a yeast cell, or a plant cell.
39. A method for treating a patient who demonstrates a sensitivity to, or an allergic reaction against, a nut or a portion thereof or an extract thereof, or to Ara h 2 protein, or for treating at least one symptom or complication associated with a sensitivity to, or allergic reaction against a nut or a portion thereof or an extract thereof, or to Ara h 2, comprising administering an effective amount of one or more isolated antibodies or antigen-binding fragments thereof that bind specifically to Ara h 2, according to any of embodiments 1-30.
40. The method of embodiment 39, further comprising administering an effective amount of a second therapeutic agent useful for diminishing an allergic reaction an allergic reaction against, a nut or a portion thereof or an extract thereof, or to Ara h 2 protein.
41. A method for detecting the presence of Ara h 2 neutralizing antibodies in a biological sample, comprising:
(a) providing a sample from a subject;
(b) contacting the sample with a mixture comprising:
(i) the antibody of any one of embodiments 1-30 and
(ii) Ara h 2, or a fragment thereof; and
(c) detecting the binding of antibodies present in the biological sample to Ara h 2, or a fragment thereof.
42. The method of embodiment 41, where antibody binding is detected using tandem biolayer interferometry.
43. The method of embodiments 41 or 42, where the antibody from step (b) is bound to a solid support.
44. The method of embodiments 41 or 42, where Ara h 2, or a fragment thereof, is bound to a solid support.
45. The method of embodiment 41, where antibody binding is detected using an enzyme-linked immunosorbent assay.

T4:

1. An isolated antibody that binds to Ara h 2 (conglutin-7), or an antigen-binding fragment thereof, wherein the antibody comprises the following six CDRs:
(a) an CDR-H1 comprising the amino acid sequence of GDSISSYY (SEQ ID NO: 41);
(b) an CDR-H2 comprising the amino acid sequence of IFTSGST (SEQ ID NO: 42):
(c) an CDR-H3 comprising the amino acid sequence of ARDRRALSSDGNWYVJYFDL (SEQ ID NO: 43);
(d) an CDR-L1 comprising the amino acid sequence of QTITRN (SEQ ID NO: 44);
(e) an CDR-L2 comprising the amino acid sequence of GAS (SEQ ID NO: 45); and
(f) an CDR-L3 comprising the amino acid sequence of QQSDNTPRT (SEQ ID NO: 46).
2. The antibody of embodiment 1, wherein the antibody comprises
(a) a VH domain comprising an amino sequence having at least 90%, at least 95%, or at least 99% sequence identity to the amino acid sequence of SEQ ID NO: 47;
(b) a VL domain comprising an amino acid sequence having at least 90%, at least 95%, or at least 99% identity to the amino acid sequence of SEQ ID NO: 48; or (c) a VH domain as in (a) and a VL domain as in (b).
3. The antibody of embodiment 1 or 2, further comprising the following VH domain FRs:
(a) an FR-H1 comprising the amino acid sequence of ESGPRLVKPSETLSLTCIVS (SEQ ID NO: 49);
(b) an FR-H2 comprising the amino acid sequence of WGWIRQPAGRGLEWIGR (SEQ ID NO: 50);
(c) an FR-H3 comprising the amino acid sequence of TYNPSLKSRVSMSVETSKNQFSLTLTSVTAAD-TAVYFC (SEQ ID NO: 51); and
(d) an FR-H4 comprising the amino acid sequence of WGRGTLVAVSS (SEQ ID NO: 52).
4. The antibody of any one of embodiments 1-3, wherein the VH domain comprises the amino acid sequence of SEQ ID NO: 47,
5. The antibody of any one of embodiments 1-4, further comprising the following VL domain FRs:
(a) an FR-L1 comprising the amino acid sequence of TQSPSSLSASVGDRVTITCRAS (SEQ ID NO: 53);
(b) an FR-L2 comprising the amino acid sequence of LNWYQQKSGEAPKLLIY (SEQ ID NO: 54);
(c) an FR-L3 comprising the amino acid sequence of ILQSGVPSRFTGSGSGTDFTLTISNLQPEDFA-SYSC (SEQ ID NO: 55); and
(d) an FR-L4 comprising the amino acid sequence of GQGTKVEIK (SEQ ID NO: 56).
6. The antibody of any one of embodiments 1-5, wherein the VL domain comprises the amino acid sequence of SEQ ID NO: 48.
7. An isolated antibody that binds to Ara h 2, or an antigen-binding fragment thereof, wherein the antibody comprises
(a) a VH domain comprising an amino acid sequence having at least 90%, at least 95%, or at least 99% sequence identity to the amino acid sequence of SEQ ID NO: 47 and
(b) a VL domain comprising an amino acid sequence having at least 90%, at least 95%, or at least 99% sequence identity to the amino acid sequence of SEQ ID NO: 48.
8. The antibody of embodiment 7, wherein the antibody comprises a VH domain comprising the amino acid sequence of SEQ ID NO: 47 and a VL domain comprising the amino acid sequence of SEQ ID NO: 48.
9. The antibody of any one of embodiments 1-8, wherein the antibody comprises (a) a heavy chain comprising the amino acid sequence of SEQ ID NO: 57 and (b) a light chain comprising the amino acid sequence of SEQ ID NO: 58.
10. The antibody of any one of embodiments 1-9, wherein the antibody binds Ara h 2 with a KD of about 50 nM or less.
11. The method of embodiment 10, wherein the KD is measured by a surface plasmon resonance assay.
12. The antibody of embodiment 11, wherein the antibody binds Ara h 2 with a KD of between about 0.1 pM and about 40 nM.
13. The antibody of embodiment 12, wherein the antibody binds Ara h 2 with a KD of between about 120 pM and about 20 nM.

14. The antibody of embodiment 13, wherein the antibody binds Ara h 2 with a KD of between about 120 pM and about 10 nM.

15. The antibody of any one of embodiments 1-14, wherein the antibody is capable neutralizing Ara h 2

18. An antibody that binds to the same epitope as the antibody of any one of embodiment 1-15.

17. An antibody that competes for binding to Ara h 2 with the antibody of any one of embodiments 1-16.

18. The antibody of embodiment 16 or 17, wherein whether the antibody binds to the same epitope or competes for binding to Ara h 2 is determined by an epitope binning assay.

19. The antibody of any one of embodiments 1-18, wherein the antibody is monoclonal, 20. The antibody of any one of embodiments 1-19, wherein the antibody is humanized.

21. The antibody of any one of embodiments 1-20, wherein the antibody is an antibody fragment that binds Ara h 2.

22. The antibody of embodiment 21, wherein the antibody fragment is selected from the group consisting of Fab, Fab'-SH, Fv, scFv, and (Fab')2 fragments.

23. The antibody of any one of embodiments 1-20, wherein the antibody is a full-length antibody.

24. The antibody of embodiment 23, wherein the antibody is an IgG antibody, 25. The antibody of embodiment 24, wherein the IgG antibody is an IgG1 antibody.

26. The antibody of embodiment 24, wherein the IgG antibody is an IgG4 antibody.

27. The antibody of embodiment 26, wherein the IgG4 antibody comprises an S228P mutation (EU numbering).

28. The antibody of any one of embodiments 1-27, wherein the antibody is a monospecific antibody.

29. The antibody of any one of embodiments 1-27, wherein the antibody is a multispecific antibody.

30. The antibody of embodiment 29, wherein the antibody is a bispecific antibody.

31. A polynucleotide encoding an isolated antibody of any one of embodiments 1-30.

32. A vector comprising the polynucleotide of embodiment 31,

33. A host cell comprising the vector of embodiment 32.

34. A method of producing the antibody of any one of embodiments 1-33, the method comprising culturing a host cell that comprises the vector of embodiment 32 and recovering the antibody.

35. The method of embodiment 34, wherein the host cell is prokaryotic.

36. The method of embodiment 35, wherein the host cell is *Escherichia coli.*

37. The method of embodiment 34, wherein the host cell is eukaryotic.

38. The method of embodiment 37, wherein the host cell is a 293 cell, a CHO cell, a yeast cell, or a plant cell.

39. A method for treating a patient who demonstrates a sensitivity to, or an allergic reaction against, a nut or a portion thereof or an extract thereof, or to Ara h 2 protein, or for treating at least one symptom or complication associated with a sensitivity to, or allergic reaction against a nut or a portion thereof or an extract thereof, or to Ara h 2, comprising administering an effective amount of one or more isolated antibodies or antigen-binding fragments thereof that bind specifically to Ara h 2, according to any of embodiments 1-30.

40. The method of embodiment 39, further comprising administering an effective amount of a second therapeutic agent useful for diminishing an allergic reaction an allergic reaction against, a nut or a portion thereof or an extract thereof, or to Ara h 2 protein.

41. A method for detecting the presence of Ara h 2 neutralizing antibodies in a biological sample, comprising:

(a) providing a sample from a subject;

(b) contacting the sample with a mixture comprising:

(i) the antibody of any one of embodiments 1-30 and (ii) Ara h 2, or a fragment thereof; and (c) detecting the binding of antibodies present in the biological sample to Ara h 2, or a fragment thereof.

42. The method of embodiment 41, where antibody binding is detected using tandem biolayer interferometry.

43. The method of embodiments 41 or 42, where the antibody from step (b) is bound to a solid support.

44. The method of embodiments 41 or 42, where Ara h 2, or a fragment thereof, is bound to a solid support, 45. The method of embodiment 41, where antibody binding is detected using an enzyme-linked immunosorbent assay.

T5:

1. An isolated antibody that binds to Ara h 2 (conglutin-7), or an antigen-binding fragment thereof, wherein the antibody comprises the following six CDRs:

(a) an CDR-H1 comprising the amino acid sequence of GGSMSSYY (SEQ ID NO: 61);

(b) an CDR-H2 comprising the amino acid sequence of IFTTGST (SEQ ID NO: 62);

(c) an CDR-H3 comprising the amino acid sequence of VRDRRGRSHDSNWYWYFDL (SEQ ID NO: 63);

(d) an CDR-L1 comprising the amino acid sequence of QTLSRN (SEQ ID NO: 64);

(e) an CDR-L2 comprising the amino acid sequence of GAS (SEQ ID NO: 65); and (f) an CDR-L3 comprising the amino acid sequence of QQSDNTPRT (SEQ ID NO: 66).

2. The antibody of embodiment 1, wherein the antibody comprises (a) a VH domain comprising an amino sequence having at least 90%, at least 95%, or at least 99% sequence identity to the amino acid sequence of SEQ ID NO: 67;

(b) a VL domain comprising an amino acid sequence having at least 90%, at least 95%, or at least 99% identity to the amino acid sequence of SEQ ID NO: 68; or (c) a VH domain as in (a) and a VL domain as in (b).

3. The antibody of embodiment 1 or 2, further comprising the following VH domain FRs:

(a) an FR-H1 comprising the amino acid sequence of QVQLQESGPGLVKPSETLSLTCTVS (SEQ ID NO: 69);

(b) an FR-H2 comprising the amino acid sequence of WGWIRQPAGRGLEWIGR (SEQ ID NO: 70);

(c) an FR-H3 comprising the amino acid sequence of IYNASLNSRVSMSVDTSKNQFSLKLTSVTAADTALYFC (SEQ ID NO: 71); and (d) an FR-H4 comprising the amino acid sequence of WGRGTLVTVSS (SEQ ID NO: 72).

4. The antibody of any one of embodiments 1-3, wherein the VH domain comprises the amino acid sequence of SEQ ID NO: 67.

5. The antibody of any one of embodiments 1-4, further comprising the following VL domain FRs:

(a) an FR-L1 comprising the amino acid sequence of RVIITCRAS (SEQ ID NO: 73);
(b) an FR-L2 comprising the amino acid sequence of LNWYQQKPGEAPKLLIY (SEQ ID NO: 74);
(c) an FR-L3 comprising the amino acid sequence of TLQSGVPSRFTGSGSGTDFTLIISGLQPEDFA-TYYC (SEQ ID NO: 75); and
(d) an FR-L4 comprising the amino acid sequence of FGQGT (SEQ ID NO: 76).

6. The antibody of any one of embodiments 1-5, wherein the VL domain comprises the amino acid sequence of SEQ ID NO: 68.

7. An isolated antibody that binds to Ara h 2, or an antigen-binding fragment thereof, wherein the antibody comprises
(a) a VH domain comprising an amino acid sequence having at least 90%, at least 95%, or at least 99% sequence identity to the amino acid sequence of SEQ ID NO: 67 and
(b) a VL domain comprising an amino acid sequence having at least 90%, at least 95%, or at least 99% sequence identity to the amino acid sequence of SEQ ID NO: 68.

8. The antibody of embodiment 7, wherein the antibody comprises a VH domain comprising the amino acid sequence of SEQ ID NO: 67 and a VL domain comprising the amino acid sequence of SEQ ID NO: 68.

9. The antibody of any one of embodiments 1-8, wherein the antibody comprises (a) a heavy chain comprising the amino acid sequence of SEQ ID NO: 77 and (b) a light chain comprising the amino acid sequence of SEQ ID NO: 78.

10. The antibody of any one of embodiments 1-9, wherein the antibody binds Ara h 2 with a KD of about 50 nM or less.

11. The method of embodiment 10, wherein the KD is measured by a surface plasmon resonance assay.

12. The antibody of embodiment 11, wherein the antibody binds Ara h 2 with a KD of between about 0.1 pM and about 40 nM.

13. The antibody of embodiment 12, wherein the antibody binds Ara h 2 with a KD of between about 120 pM and about 20 nM.

14. The antibody of embodiment 13, wherein the antibody binds Ara h 2 with a KD of between about 120 pM and about 10 nM.

15. The antibody of any one of embodiments 1-14, wherein the antibody is capable neutralizing Ara h 2

16. An antibody that binds to the same epitope as the antibody of any one of embodiment 1-15.

17. An antibody that competes for binding to Ara h 2 with the antibody of any one of embodiments 1-16.

18. The antibody of embodiment 16 or 17, wherein whether the antibody binds to the same epitope or competes for binding to Ara h 2 is determined by an epitope binning assay.

19. The antibody of any one of embodiments 1-18, wherein the antibody is monoclonal.

20. The antibody of any one of embodiments 1-19, wherein the antibody is humanized.

21. The antibody of any one of embodiments 1-20, wherein the antibody is an antibody fragment that binds Ara h 2.

22. The antibody of embodiment 21, wherein the antibody fragment is selected from the group consisting of Fab, Fab'-SH, Fv, scFv, and (Fab')2 fragments.

23. The antibody of any one of embodiments 1-20, wherein the antibody is a full-length antibody.

24. The antibody of embodiment 23, wherein the antibody is an IgG antibody.

25. The antibody of embodiment 24, wherein the IgG antibody is an IgG1 antibody.

26. The antibody of embodiment 24, wherein the IgG antibody is an IgG4 antibody.

27. The antibody of embodiment 26, wherein the IgG4 antibody comprises an S228P mutation (EU numbering).

28. The antibody of any one of embodiments 1-27, wherein the antibody is a monospecific antibody.

29. The antibody of any one of embodiments 1-27, wherein the antibody is a multispecific antibody.

30. The antibody of embodiment 29, wherein the antibody is a bispecific antibody.

31. A polynucleotide encoding an isolated antibody of any one of embodiments 1-30.

32. A vector comprising the polynucleotide of embodiment 31.

33. A host cell comprising the vector of embodiment 32.

34. A method of producing the antibody of any one of embodiments 1-33, the method comprising culturing a host cell that comprises the vector of embodiment 32 and recovering the antibody.

35. The method of embodiment 34, wherein the host cell is prokaryotic.

36. The method of embodiment 35, wherein the host cell is *Escherichia coli.*

37. The method of embodiment 34, wherein the host cell is eukaryotic.

38. The method of embodiment 37, wherein the host cell is a 293 cell, a CHO cell, a yeast cell, or a plant cell.

39. A method for treating a patient who demonstrates a sensitivity to, or an allergic reaction against, a nut or a portion thereof or an extract thereof, or to Ara h 2 protein, or for treating at least one symptom or complication associated with a sensitivity to, or allergic reaction against a nut or a portion thereof or an extract thereof, or to Ara h 2, comprising administering an effective amount of one or more isolated antibodies or antigen-binding fragments thereof that bind specifically to Ara h 2, according to any of embodiments 1-30.

40. The method of embodiment 39, further comprising administering an effective amount of a second therapeutic agent useful for diminishing an allergic reaction an allergic reaction against, a nut or a portion thereof or an extract thereof, or to Ara h 2 protein.

41. A method for detecting the presence of Ara h 2 neutralizing antibodies in a biological sample, comprising:
(a) providing a sample from a subject;
(b) contacting the sample with a mixture comprising:
(i) the antibody of any one of embodiments 1-30 and
(ii) Ara h 2, or a fragment thereof; and
(c) detecting the binding of antibodies present in the biological sample to Ara h 2, or a fragment thereof.

42. The method of embodiment 41, where antibody binding is detected using tandem biolayer interferometry.

43. The method of embodiments 41 or 42, where the antibody from step (b) is bound to a solid support.

44. The method of embodiments 41 or 42, where Ara h 2, or a fragment thereof, is bound to a solid support 45. The method of embodiment 41, where antibody binding is detected using an enzyme-linked immunosorbent assay.

Compositions and Methods

1. A pharmaceutical composition comprising a therapeutically effective amount of one or more isolated T1, T3, T4, or T5 antibodies, or antigen-binding fragments thereof, or of any of the V5-V41 antibodies, or antigen-binding fragments thereof, together with one or more pharmaceutically acceptable excipients.
2. A pharmaceutical composition comprising a combination of T3 and T4 antibodies.
3. A method for treating a patient who demonstrates a sensitivity to a peanut allergen, an allergic reaction against a peanut allergen, or to Ara h 2 protein, or for treating at least one symptom or complication associated with a sensitivity to, or allergic reaction against a peanut allergen, an allergic reaction against a peanut allergen, or to Ara h 2 protein, comprising administering an effective amount of one or more isolated human monoclonal antibodies or antigen-binding fragments thereof that bind specifically to Ara h 2, according to embodiments describe above for T1 (also referred to as V1), T3 (also referred to as V2), T4 (also referred to as V3), or T5 (also referred to as V4) to a patient in need thereof, wherein the sensitivity to, or an allergic reaction against, to a peanut allergen, an allergic reaction against a peanut allergen, or to Ara h 2 protein, is lessened in severity and/or duration, or at least one symptom or complication associated with the sensitivity to, or allergic reaction against, to a peanut allergen, an allergic reaction against a peanut allergen, or to Ara h 2 protein is ameliorated, or that the frequency and/or duration of, or the severity of the sensitivity to or allergic reaction against, to a peanut allergen, an allergic reaction against a peanut allergen, or to Ara h 2 protein, is reduced following administration of one or more of the isolated human monoclonal antibodies or fragments thereof that bind specifically to Ara h 2.
4. The method of embodiment 3, further comprising administering an effective amount of a second therapeutic agent useful for diminishing an allergic reaction to a peanut allergen, an allergic reaction against a peanut allergen, or to Ara h 2 protein.
5. The method of embodiment 4, wherein the second therapeutic agent is selected from the group consisting of a corticosteroid, a bronchial dilator, an antihistamine, epinephrine, or a decongestant.
6. The method of embodiment 3, wherein the treatment results in a reduction in allergic rhinitis, allergic conjunctivitis, allergic asthma, or an anaphylactic response following exposure, direct or indirect, of the patient to a peanut allergen, an allergic reaction against a peanut allergen, or to Ara h 2 protein.

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. An isolated antibody that binds to Ara h 2 (conglutin-7), or an antigen-binding fragment thereof, wherein the antibody comprises the following six CDRs:

(a) an CDR-H1 comprising the amino acid sequence of GFTFRDYS (SEQ ID NO: 21);

(b) an CDR-H2 comprising the amino acid sequence of IRFDGTTK (SEQ ID NO: 22);

(c) an CDR-H3 comprising the amino acid sequence of AKDNGWRAFDH (SEQ ID NO: 23);

(d) an CDR-L1 comprising the amino acid sequence of QSLLHRNGYIY (SEQ ID NO: 24);

(e) an CDR-L2 comprising the amino acid sequence of FVS (SEQ ID NO: 25); and (f) an CDR-L3 comprising the amino acid sequence of MQALETPWT (SEQ ID NO: 26).

2. The antibody of claim 1, wherein the antibody comprises (a) a VH domain comprising an amino sequence having at least 90%, at least 95%, or at least 99% sequence identity to the amino acid sequence of SEQ ID NO: 27;

(b) a VL domain comprising an amino acid sequence having at least 90%, at least 95%, or at least 99% identity to the amino acid sequence of SEQ ID NO: 28; or (c) a VH domain as in (a) and a VL domain as in (b).

3. The antibody of claim 1, further comprising the following VH domain FRs:

(a) an FR-H1 comprising the amino acid sequence of GGGVVQPGTSLRLSCVAS (SEQ ID NO: 29);

(b) an FR-H2 comprising the amino acid sequence of MHWVRQAPGKGLEWVSF (SEQ ID NO: 30);

(c) an FR-H3 comprising the amino acid sequence of DYRDSVKGRFIISRDDSKNTLYLQMTSLRVEDTALYYC (SEQ ID NO: 31); and (d) an FR-H4 comprising the amino acid sequence of WGQGALVTVSS (SEQ ID NO: 32).

4. The antibody of claim 1, wherein the VH domain comprises the amino acid sequence of SEQ ID NO: 27.

5. The antibody of claim 1, further comprising the following VL domain FRs:

(a) an FR-L1 comprising the amino acid sequence of VMTQSPLSLPVTPGEAASISCRSS (SEQ ID NO: 33);

(b) an FR-L2 comprising the amino acid sequence of LDWYLQRPGQSPQLLIS (SEQ ID NO: 34);

(c) an FR-L3 comprising the amino acid sequence of KRASGAPDRFSGSGSGTDFTLTISRVEAEDFGVYFC (SEQ ID NO: 35); and (d) an FR-L4 comprising the amino acid sequence of FGPGTKLEIK (SEQ ID NO: 36).

6. The antibody of claim 1, wherein the VL domain comprises the amino acid sequence of SEQ ID NO: 28.

7. An isolated antibody that binds to Ara h 2, or an antigen-binding fragment thereof, wherein the antibody comprises (a) a VH domain comprising an amino acid sequence of SEQ ID NO: 27 and (b) a VL domain comprising an amino acid sequence of SEQ ID NO: 28.

8. The antibody of claim 7, wherein the antibody comprises (a) a heavy chain comprising the amino acid sequence of SEQ ID NO: 37 and (b) a light chain comprising the amino acid sequence of SEQ ID NO: 38.

9. The antibody of claim 1, wherein the antibody binds Ara h 2 with a $K_D$ of about 50 nM or less.

10. The method of claim 9, wherein the $K_D$ is measured by a surface plasmon resonance assay.

11. The antibody of claim 10, wherein the antibody binds Ara h 2 with a $K_D$ of between about 0.1 pM and about 40 nM.

12. The antibody of claim 11, wherein the antibody binds Ara h 2 with a $K_D$ of between about 120 pM and about 20 nM.

13. The antibody of claim 12, wherein the antibody binds Ara h 2 with a $K_D$ of between about 120 PM and about 10 nM.

14. An isolated antibody that binds to Ara h 2 (conglutin-7), or an antigen-binding fragment thereof, wherein the antibody comprises the following six CDRs:

(a) an CDR-H1 comprising the amino acid sequence of GGSMSSYY (SEQ ID NO: 61);

(b) an CDR-H2 comprising the amino acid sequence of IFTTGST (SEQ ID NO: 62);

(c) an CDR-H3 comprising the amino acid sequence of VRDRRGRSHDSNWYWYFDL (SEQ ID NO: 63);

(d) an CDR-L1 comprising the amino acid sequence of QTLSRN (SEQ ID NO: 64);

(e) an CDR-L2 comprising the amino acid sequence of GAS (SEQ ID NO: 65); and (f) an CDR-L3 comprising the amino acid sequence of QQSDNTPRT (SEQ ID NO: 66).

15. The antibody of claim 14, wherein the antibody comprises (a) a VH domain comprising an amino sequence having at least 90%, at least 95%, or at least 99% sequence identity to the amino acid sequence of SEQ ID NO: 67;

(b) a VL domain comprising an amino acid sequence having at least 90%, at least 95%, or at least 99% identity to the amino acid sequence of SEQ ID NO: 68; or (c) a VH domain as in (a) and a VL domain as in (b).

16. The antibody of claim 14, further comprising the following VH domain FRs:

(a) an FR-H1 comprising the amino acid sequence of QVQLQESGPGLVKPSETLSLTCTVS (SEQ ID NO: 69);

(b) an FR-H2 comprising the amino acid sequence of WGWIRQPAGRGLEWIGR (SEQ ID NO: 70);

(c) an FR-H3 comprising the amino acid sequence of IYNASLNSRVSMSVDTSKNQFSLKLTSVTAAD-TALYFC (SEQ ID NO: 71); and (d) an FR-H4 comprising the amino acid sequence of WGRGTLVTVSS (SEQ ID NO: 72).

17. The antibody of claim 14, wherein the VH domain comprises the amino acid sequence of SEQ ID NO: 67.

18. The antibody of claim 14, further comprising the following VL domain FRs:

(a) an FR-L1 comprising the amino acid sequence of RVIITCRAS (SEQ ID NO: 73);

(b) an FR-L2 comprising the amino acid sequence of LNWYQQKPGEAPKLLIY (SEQ ID NO: 74);

(c) an FR-L3 comprising the amino acid sequence of TLQSGVPSRFTGSGSGTDFTLIISGLQPEDFA-TYYC (SEQ ID NO: 75); and (d) an FR-L4 comprising the amino acid sequence of FGQGT (SEQ ID NO: 76).

19. The antibody of claim 14, wherein the VL domain comprises the amino acid sequence of SEQ ID NO: 68.

* * * * *

SEQUENCE LISTING

```
<160> NUMBER OF SEQ ID NOS: 827

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Arg Asp Tyr Ser
1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Arg Phe Asp Gly Thr Thr Lys
1               5


<210> SEQ ID NO 3
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 3

Val Lys Asp Asn Gly Trp Arg Ala Phe Asp His
1 5 10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Gln Ser Leu Leu His Arg Asn Gly Tyr Ile Tyr
1 5 10

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Phe Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Met Gln Ser Leu Glu Asn Pro Trp Thr
1 5

<210> SEQ ID NO 7
<211> LENGTH: 114
<212> TYPE: PRT
<213> ORGANISM: Artificial Sequence
<220> FEATURE:
<223> OTHER INFORMATION: Synthetic Construct

<400> SEQUENCE: 7

Val Glu Ser Gly Gly Gly Val Val Gln Pro Gly Ala Ser Leu Arg Leu
1 5 10 15

Ser Cys Val Ala Ser Gly Phe Thr Phe Arg Asp Tyr Ser Met His Trp
20 25 30

Val Arg Gln Ala Pro Gly Lys Gly Leu Glu Trp Met Ser Phe Ile Arg
35 40 45

Phe Asp Gly Thr Thr Lys Asp Tyr Arg Glu Ser Val Lys Gly Arg Phe
50 55 60

Ile Ile Ser Arg Asp Asp Ser Lys Asn Thr Leu Tyr Leu Gln Met Thr
65 70 75 80

Ser Leu Arg Pro Glu Asp Thr Ala Arg Tyr Tyr Cys Val Lys Asp Asn
85 90 95

Gly Trp Arg Ala Phe Asp His Trp Gly Gln Gly Ala Leu Val Ile Val
100 105 110

Ser Ser

<210> SEQ ID NO 8
<211> LENGTH: 105
<212> TYPE: PRT
<213> ORGANISM: Artificial Sequence
<220> FEATURE:
<223> OTHER INFORMATION: Synthetic Construct

<400> SEQUENCE: 8

```
Glu Ile Val Met Thr Gln Ser Pro Leu Ser Leu Pro Val Thr Pro Gly
1               5                   10                  15

Glu Ala Ala Ser Ile Ser Cys Arg Ser Ser Gln Ser Leu Leu His Arg
            20                  25                  30

Asn Gly Tyr Ile Tyr Leu Asp Trp Tyr Leu Gln Arg Pro Gly Gln Ser
        35                  40                  45

Pro Gln Leu Leu Ile Ser Phe Val Ser Lys Arg Ala Ser Gly Ala Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Phe Gly Val Tyr Phe Cys Met Gln Ser
                85                  90                  95

Leu Glu Asn Pro Trp Thr Phe Gly Pro
            100                 105
```

<210> SEQ ID NO 9
<211> LENGTH: 21
<212> TYPE: PRT
<213> ORGANISM: Artificial Sequence
<220> FEATURE:
<223> OTHER INFORMATION: Synthetic Construct

<400> SEQUENCE: 9

```
Val Glu Ser Gly Gly Gly Val Val Gln Pro Gly Ala Ser Leu Arg Leu
1               5                   10                  15

Ser Cys Val Ala Ser
            20
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

```
Met His Trp Val Arg Gln Ala Pro Gly Lys Gly Leu Glu Trp Met Ser
1               5                   10                  15

Phe
```

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct

<400> SEQUENCE: 11

```
Asp Tyr Arg Glu Ser Val Lys Gly Arg Phe Ile Ile Ser Arg Asp Asp
1               5                   10                  15

Ser Lys Asn Thr Leu Tyr Leu Gln Met Thr Ser Leu Arg Pro Glu Asp
            20                  25                  30

Thr Ala Arg Tyr Tyr Cys
```

35

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Ala Leu Val Ile Val Ser Ser
1 5 10

<210> SEQ ID NO 13
<211> LENGTH: 26
<212> TYPE: PRT
<213> ORGANISM: Artificial Sequence
<220> FEATURE:
<223> OTHER INFORMATION: Synthetic Construct

<400> SEQUENCE: 13

Glu Ile Val Met Thr Gln Ser Pro Leu Ser Leu Pro Val Thr Pro Gly
1 5 10 15

Glu Ala Ala Ser Ile Ser Cys Arg Ser Ser
20 25

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Leu Asp Trp Tyr Leu Gln Arg Pro Gly Gln Ser Pro Gln Leu Leu Ile
1 5 10 15

Ser

<210> SEQ ID NO 15
<211> LENGTH: 36
<212> TYPE: PRT
<213> ORGANISM: Artificial Sequence
<220> FEATURE:
<223> OTHER INFORMATION: Synthetic Construct

<400> SEQUENCE: 15

Lys Arg Ala Ser Gly Ala Pro Asp Arg Phe Ser Gly Ser Gly Ser Gly
1 5 10 15

Thr Asp Phe Thr Leu Thr Ile Ser Arg Val Glu Ala Glu Asp Phe Gly
20 25 30

Val Tyr Phe Cys
35

<210> SEQ ID NO 16
<211> LENGTH: 3
<212> TYPE: PRT
<213> ORGANISM: Artificial Sequence
<220> FEATURE:
<223> OTHER INFORMATION: Synthetic Construct

<400> SEQUENCE: 16

Phe Gly Pro
1

<210> SEQ ID NO 17
<211> LENGTH: 441
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid

<400> SEQUENCE: 17

```
Val Glu Ser Gly Gly Gly Val Val Gln Pro Gly Ala Ser Leu Arg Leu
1               5                   10                  15

Ser Cys Val Ala Ser Gly Phe Thr Phe Arg Asp Tyr Ser Met His Trp
            20                  25                  30

Val Arg Gln Ala Pro Gly Lys Gly Leu Glu Trp Met Ser Phe Ile Arg
        35                  40                  45

Phe Asp Gly Thr Thr Lys Asp Tyr Arg Glu Ser Val Lys Gly Arg Phe
    50                  55                  60

Ile Ile Ser Arg Asp Asp Ser Lys Asn Thr Leu Tyr Leu Gln Met Thr
65                  70                  75                  80

Ser Leu Arg Pro Glu Asp Thr Ala Arg Tyr Tyr Cys Val Lys Asp Asn
                85                  90                  95

Gly Trp Arg Ala Phe Asp His Trp Gly Gln Gly Ala Leu Val Ile Val
            100                 105                 110

Ser Ser Lys Gly Pro Ser Val Phe Pro Leu Ala Pro Ser Ser Lys Ser
        115                 120                 125

Thr Ser Gly Gly Thr Ala Ala Leu Gly Xaa Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Xaa
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
```

```
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Xaa
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 18
<211> LENGTH: 209
<212> TYPE: PRT
<213> ORGANISM: Artificial Sequence
<220> FEATURE:
<223> OTHER INFORMATION: Synthetic Construct

<400> SEQUENCE: 18

Glu Ile Val Met Thr Gln Ser Pro Leu Ser Leu Pro Val Thr Pro Gly
1               5                   10                  15

Glu Ala Ala Ser Ile Ser Cys Arg Ser Ser Gln Ser Leu Leu His Arg
            20                  25                  30

Asn Gly Tyr Ile Tyr Leu Asp Trp Tyr Leu Gln Arg Pro Gly Gln Ser
        35                  40                  45

Pro Gln Leu Leu Ile Ser Phe Val Ser Lys Arg Ala Ser Gly Ala Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Phe Gly Val Tyr Phe Cys Met Gln Ser
                85                  90                  95

Leu Glu Asn Pro Trp Thr Phe Gly Pro Ala Pro Ser Val Phe Ile Phe
            100                 105                 110

Pro Pro Ser Asp Glu Gln Leu Lys Ser Gly Thr Ala Ser Val Val Cys
        115                 120                 125

Leu Leu Asn Asn Phe Tyr Pro Arg Glu Ala Lys Val Gln Trp Lys Val
    130                 135                 140

Asp Asn Ala Leu Gln Ser Gly Asn Ser Gln Glu Ser Val Thr Glu Gln
145                 150                 155                 160

Asp Ser Lys Asp Ser Thr Tyr Ser Leu Ser Ser Thr Leu Thr Leu Ser
                165                 170                 175

Lys Ala Asp Tyr Glu Lys His Lys Val Tyr Ala Cys Glu Val Thr His
            180                 185                 190

Gln Gly Leu Ser Ser Pro Val Thr Lys Ser Phe Asn Arg Gly Glu Cys
        195                 200                 205

Lys


<210> SEQ ID NO 19
```

<211> LENGTH: 344
<212> TYPE: DNA
<213> ORGANISM: Artificial Sequence
<220> FEATURE:
<223> OTHER INFORMATION: Synthetic Construct

<400> SEQUENCE: 19
ggtggagtcg gggggcggcg tggtccagcc tggggcgtcc ctgagactct cctgtgtggc 60
gtctggattc acctttcgtg actattccat gcactgggtc cgccaggctc caggcaaggg 120
gctggagtgg atgtcattta tacggtttga tgggaccact aaggactatc gagagtctgt 180
gaagggccga ttcatcattt ccagagacga ctccaagaac acactgtatc tgcaaatgac 240
gagcctgaga cctgaggaca cggctcgata ttactgtgtg aaagacaatg ggtggcgggc 300
ctttgaccac tggggccagg gagccctggt catcgtctcc tcag 344

<210> SEQ ID NO 20
<211> LENGTH: 316
<212> TYPE: DNA
<213> ORGANISM: Artificial Sequence
<220> FEATURE:
<223> OTHER INFORMATION: Synthetic Construct

<400> SEQUENCE: 20
gagattgtga tgactcagtc tccactctcc ctgcccgtca cccctggaga ggcggcctcc 60
atctcctgca ggtctagtca gagcctcctc catcgtaatg gatacatcta cttggactgg 120
tacctgcaga ggccagggca gtcaccacaa ctcctgatct ctttcgtttc taaacgggcc 180
tccggggccc ctgacaggtt cagtggctct ggttcaggca cagatttcac actgacaatt 240
agtagagtgg aggctgagga ctttggggtt tatttctgca tgcaatcgct agaaaacccc 300
tggacgttcg gcccag 316

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Gly Phe Thr Phe Arg Asp Tyr Ser
1 5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Ile Arg Phe Asp Gly Thr Thr Lys
1 5

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Ala Lys Asp Asn Gly Trp Arg Ala Phe Asp His 1 5 10

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Gln Ser Leu Leu His Arg Asn Gly Tyr Ile Tyr
1 5 10

<210> SEQ ID NO 25
<211> LENGTH: 3
<212> TYPE: PRT
<213> ORGANISM: Artificial Sequence
<220> FEATURE:
<223> OTHER INFORMATION: Synthetic Construct

<400> SEQUENCE: 25

Phe Val Ser
1

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Met Gln Ala Leu Glu Thr Pro Trp Thr
1 5

<210> SEQ ID NO 27
<211> LENGTH: 111
<212> TYPE: PRT
<213> ORGANISM: Artificial Sequence
<220> FEATURE:
<223> OTHER INFORMATION: Synthetic Construct

<400> SEQUENCE: 27

Gly Gly Gly Val Val Gln Pro Gly Thr Ser Leu Arg Leu Ser Cys Val
1 5 10 15

Ala Ser Gly Phe Thr Phe Arg Asp Tyr Ser Met His Trp Val Arg Gln
20 25 30

Ala Pro Gly Lys Gly Leu Glu Trp Val Ser Phe Ile Arg Phe Asp Gly
35 40 45

Thr Thr Lys Asp Tyr Arg Asp Ser Val Lys Gly Arg Phe Ile Ile Ser
50 55 60

Arg Asp Asp Ser Lys Asn Thr Leu Tyr Leu Gln Met Thr Ser Leu Arg
65 70 75 80

Val Glu Asp Thr Ala Leu Tyr Tyr Cys Ala Lys Asp Asn Gly Trp Arg
85 90 95

Ala Phe Asp His Trp Gly Gln Gly Ala Leu Val Thr Val Ser Ser
100 105 110

<210> SEQ ID NO 28
<211> LENGTH: 110
<212> TYPE: PRT
<213> ORGANISM: Artificial Sequence
<220> FEATURE:
<223> OTHER INFORMATION: Synthetic Construct

<400> SEQUENCE: 28

Val Met Thr Gln Ser Pro Leu Ser Leu Pro Val Thr Pro Gly Glu Ala
1 5 10 15

Ala Ser Ile Ser Cys Arg Ser Ser Gln Ser Leu Leu His Arg Asn Gly
20 25 30

Tyr Ile Tyr Leu Asp Trp Tyr Leu Gln Arg Pro Gly Gln Ser Pro Gln
35 40 45

Leu Leu Ile Ser Phe Val Ser Lys Arg Ala Ser Gly Ala Pro Asp Arg
50 55 60

Phe Ser Gly Ser Gly Ser Gly Thr Asp Phe Thr Leu Thr Ile Ser Arg
65 70 75 80

Val Glu Ala Glu Asp Phe Gly Val Tyr Phe Cys Met Gln Ala Leu Glu
85 90 95

Thr Pro Trp Thr Phe Gly Pro Gly Thr Lys Leu Glu Ile Lys
100 105 110

<210> SEQ ID NO 29
<211> LENGTH: 18
<212> TYPE: PRT
<213> ORGANISM: Artificial Sequence
<220> FEATURE:
<223> OTHER INFORMATION: Synthetic Construct

<400> SEQUENCE: 29

Gly Gly Gly Val Val Gln Pro Gly Thr Ser Leu Arg Leu Ser Cys Val
1 5 10 15

Ala Ser

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Met His Trp Val Arg Gln Ala Pro Gly Lys Gly Leu Glu Trp Val Ser
1 5 10 15

Phe

<210> SEQ ID NO 31
<211> LENGTH: 38
<212> TYPE: PRT
<213> ORGANISM: Artificial Sequence
<220> FEATURE:
<223> OTHER INFORMATION: Synthetic Construct

<400> SEQUENCE: 31

Asp Tyr Arg Asp Ser Val Lys Gly Arg Phe Ile Ile Ser Arg Asp Asp
1 5 10 15

Ser Lys Asn Thr Leu Tyr Leu Gln Met Thr Ser Leu Arg Val Glu Asp
20 25 30

Thr Ala Leu Tyr Tyr Cys
35

<210> SEQ ID NO 32
<211> LENGTH: 11
<212> TYPE: PRT
<213> ORGANISM: Artificial Sequence
<220> FEATURE:

<223> OTHER INFORMATION: Synthetic Construct

<400> SEQUENCE: 32

Trp Gly Gln Gly Ala Leu Val Thr Val Ser Ser
1 5 10

<210> SEQ ID NO 33
<211> LENGTH: 24
<212> TYPE: PRT
<213> ORGANISM: Artificial Sequence
<220> FEATURE:
<223> OTHER INFORMATION: Synthetic Construct

<400> SEQUENCE: 33

Val Met Thr Gln Ser Pro Leu Ser Leu Pro Val Thr Pro Gly Glu Ala
1 5 10 15

Ala Ser Ile Ser Cys Arg Ser Ser
20

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Leu Asp Trp Tyr Leu Gln Arg Pro Gly Gln Ser Pro Gln Leu Leu Ile
1 5 10 15

Ser

<210> SEQ ID NO 35
<211> LENGTH: 36
<212> TYPE: PRT
<213> ORGANISM: Artificial Sequence
<220> FEATURE:
<223> OTHER INFORMATION: Synthetic Construct

<400> SEQUENCE: 35

Lys Arg Ala Ser Gly Ala Pro Asp Arg Phe Ser Gly Ser Gly Ser Gly
1 5 10 15

Thr Asp Phe Thr Leu Thr Ile Ser Arg Val Glu Ala Glu Asp Phe Gly
20 25 30

Val Tyr Phe Cys
35

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Phe Gly Pro Gly Thr Lys Leu Glu Ile Lys
1 5 10

<210> SEQ ID NO 37
<211> LENGTH: 438
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid

<400> SEQUENCE: 37

```
Gly Gly Gly Val Val Gln Pro Gly Thr Ser Leu Arg Leu Ser Cys Val
1               5                   10                  15

Ala Ser Gly Phe Thr Phe Arg Asp Tyr Ser Met His Trp Val Arg Gln
            20                  25                  30

Ala Pro Gly Lys Gly Leu Glu Trp Val Ser Phe Ile Arg Phe Asp Gly
        35                  40                  45

Thr Thr Lys Asp Tyr Arg Asp Ser Val Lys Gly Arg Phe Ile Ile Ser
    50                  55                  60

Arg Asp Asp Ser Lys Asn Thr Leu Tyr Leu Gln Met Thr Ser Leu Arg
65                  70                  75                  80

Val Glu Asp Thr Ala Leu Tyr Tyr Cys Ala Lys Asp Asn Gly Trp Arg
                85                  90                  95

Ala Phe Asp His Trp Gly Gln Gly Ala Leu Val Thr Val Ser Ser Lys
            100                 105                 110

Gly Pro Ser Val Phe Pro Leu Ala Pro Ser Ser Lys Ser Thr Ser Gly
        115                 120                 125

Gly Thr Ala Ala Leu Gly Xaa Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Xaa Val Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Xaa Thr Lys Asn
            340                 345                 350
```

```
Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
        435


<210> SEQ ID NO 38
<211> LENGTH: 214
<212> TYPE: PRT
<213> ORGANISM: Artificial Sequence
<220> FEATURE:
<223> OTHER INFORMATION: Synthetic Construct

<400> SEQUENCE: 38

Val Met Thr Gln Ser Pro Leu Ser Leu Pro Val Thr Pro Gly Glu Ala
1               5                   10                  15

Ala Ser Ile Ser Cys Arg Ser Ser Gln Ser Leu Leu His Arg Asn Gly
            20                  25                  30

Tyr Ile Tyr Leu Asp Trp Tyr Leu Gln Arg Pro Gly Gln Ser Pro Gln
        35                  40                  45

Leu Leu Ile Ser Phe Val Ser Lys Arg Ala Ser Gly Ala Pro Asp Arg
    50                  55                  60

Phe Ser Gly Ser Gly Ser Gly Thr Asp Phe Thr Leu Thr Ile Ser Arg
65                  70                  75                  80

Val Glu Ala Glu Asp Phe Gly Val Tyr Phe Cys Met Gln Ala Leu Glu
                85                  90                  95

Thr Pro Trp Thr Phe Gly Pro Gly Thr Lys Leu Glu Ile Lys Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Lys
    210


<210> SEQ ID NO 39
<211> LENGTH: 336
<212> TYPE: DNA
<213> ORGANISM: Artificial Sequence
<220> FEATURE:
<223> OTHER INFORMATION: Synthetic Construct

<400> SEQUENCE: 39
```

cgggggggcgg cgtggtccag cctgggacgt ccctgagact ctcctgtgta gcgtctggat 60
tcaccttccg tgactattcc atgcactggg tccgccaggc tccaggcaag gggctggagt 120
gggtgtcatt tatacggttt gatgggacca ctaaggacta tcgagactct gtgaagggcc 180
gattcatcat ctccagagac gactccaaga acacactgta tctgcagatg acgagcctga 240
gagttgagga cacggcttta tattactgtg cgaaagacaa tgggtggcgg gcctttgacc 300
actggggcca gggagccctg gtcaccgtct cctcag 336

<210> SEQ ID NO 40
<211> LENGTH: 331
<212> TYPE: DNA
<213> ORGANISM: Artificial Sequence
<220> FEATURE:
<223> OTHER INFORMATION: Synthetic Construct

<400> SEQUENCE: 40
gtgatgactc agtctccact ctccctgccc gtcacccctg gagaggcggc ctccatctcc 60
tgcaggtcta gtcagagcct cctccatcgt aatggataca tctacttgga ttggtacctg 120
cagaggccag ggcagtctcc acaactcctg atctctttcg tttctaaacg ggcctccggg 180
gcccctgaca ggttcagtgg ctctggttca ggcacagatt ttacactgac aatcagcaga 240
gtggaggctg aggattttgg ggtttatttc tgcatgcaag cgctagaaac cccctggacg 300
ttcggcccag ggaccaaact ggagatcaaa c 331

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Gly Asp Ser Ile Ser Ser Tyr Tyr
1 5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct

<400> SEQUENCE: 42

Ile Phe Thr Ser Gly Ser Thr
1 5

<210> SEQ ID NO 43
<211> LENGTH: 19
<212> TYPE: PRT
<213> ORGANISM: Artificial Sequence
<220> FEATURE:
<223> OTHER INFORMATION: Synthetic Construct

<400> SEQUENCE: 43

Ala Arg Asp Arg Arg Ala Leu Ser Ser Asp Gly Asn Trp Tyr Trp Tyr
1 5 10 15

Phe Asp Leu

<210> SEQ ID NO 44
<211> LENGTH: 6

<212> TYPE: PRT
<213> ORGANISM: Artificial Sequence
<220> FEATURE:
<223> OTHER INFORMATION: Synthetic Construct

<400> SEQUENCE: 44

Gln Thr Ile Thr Arg Asn
1               5

<210> SEQ ID NO 45
<211> LENGTH: 3
<212> TYPE: PRT
<213> ORGANISM: Artificial Sequence
<220> FEATURE:
<223> OTHER INFORMATION: Synthetic Construct

<400> SEQUENCE: 45

Gly Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Gln Gln Ser Asp Asn Thr Pro Arg Thr
1               5

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

Glu Ser Gly Pro Arg Leu Val Lys Pro Ser Glu Thr Leu Ser Leu Thr
1               5                   10                  15

Cys Ile Val Ser Gly Asp Ser Ile Ser Ser Tyr Tyr Trp Gly Trp Ile
            20                  25                  30

Arg Gln Pro Ala Gly Arg Gly Leu Glu Trp Ile Gly Arg Ile Phe Thr
        35                  40                  45

Ser Gly Ser Thr Thr Tyr Asn Pro Ser Leu Lys Ser Arg Val Ser Met
    50                  55                  60

Ser Val Glu Thr Ser Lys Asn Gln Phe Ser Leu Thr Leu Thr Ser Val
65                  70                  75                  80

Thr Ala Ala Asp Thr Ala Val Tyr Phe Cys Ala Arg Asp Arg Arg Ala
                85                  90                  95

Leu Ser Ser Asp Gly Asn Trp Tyr Trp Tyr Phe Asp Leu Trp Gly Arg
            100                 105                 110

Gly Thr Leu Val Ala Val Ser Ser
        115                 120

<210> SEQ ID NO 48
<211> LENGTH: 103
<212> TYPE: PRT
<213> ORGANISM: Artificial Sequence
<220> FEATURE:
<223> OTHER INFORMATION: Synthetic Construct

<400> SEQUENCE: 48

```
Thr Gln Ser Pro Ser Ser Leu Ser Ala Ser Val Gly Asp Arg Val Thr
1               5                   10                  15

Ile Thr Cys Arg Ala Ser Gln Thr Ile Thr Arg Asn Leu Asn Trp Tyr
            20                  25                  30

Gln Gln Lys Ser Gly Glu Ala Pro Lys Leu Leu Ile Tyr Gly Ala Ser
        35                  40                  45

Ile Leu Gln Ser Gly Val Pro Ser Arg Phe Thr Gly Ser Gly Ser Gly
    50                  55                  60

Thr Asp Phe Thr Leu Thr Ile Ser Asn Leu Gln Pro Glu Asp Phe Ala
65                  70                  75                  80

Ser Tyr Ser Cys Gln Gln Ser Asp Asn Thr Pro Arg Thr Phe Gly Gln
                85                  90                  95

Gly Thr Lys Val Glu Ile Lys
            100


<210> SEQ ID NO 49
<211> LENGTH: 20
<212> TYPE: PRT
<213> ORGANISM: Artificial Sequence
<220> FEATURE:
<223> OTHER INFORMATION: Synthetic Construct

<400> SEQUENCE: 49

Glu Ser Gly Pro Arg Leu Val Lys Pro Ser Glu Thr Leu Ser Leu Thr
1               5                   10                  15

Cys Ile Val Ser
            20


<210> SEQ ID NO 50
<211> LENGTH: 17
<212> TYPE: PRT
<213> ORGANISM: Artificial Sequence
<220> FEATURE:
<223> OTHER INFORMATION: Synthetic Construct

<400> SEQUENCE: 50

Trp Gly Trp Ile Arg Gln Pro Ala Gly Arg Gly Leu Glu Trp Ile Gly
1               5                   10                  15

Arg


<210> SEQ ID NO 51
<211> LENGTH: 38
<212> TYPE: PRT
<213> ORGANISM: Artificial Sequence
<220> FEATURE:
<223> OTHER INFORMATION: Synthetic Construct

<400> SEQUENCE: 51

Thr Tyr Asn Pro Ser Leu Lys Ser Arg Val Ser Met Ser Val Glu Thr
1               5                   10                  15

Ser Lys Asn Gln Phe Ser Leu Thr Leu Thr Ser Val Thr Ala Ala Asp
            20                  25                  30

Thr Ala Val Tyr Phe Cys
        35


<210> SEQ ID NO 52
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 52

Trp Gly Arg Gly Thr Leu Val Ala Val Ser Ser
1 5 10

<210> SEQ ID NO 53
<211> LENGTH: 22
<212> TYPE: PRT
<213> ORGANISM: Artificial Sequence
<220> FEATURE:
<223> OTHER INFORMATION: Synthetic Construct

<400> SEQUENCE: 53

Thr Gln Ser Pro Ser Ser Leu Ser Ala Ser Val Gly Asp Arg Val Thr
1 5 10 15

Ile Thr Cys Arg Ala Ser
20

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Leu Asn Trp Tyr Gln Gln Lys Ser Gly Glu Ala Pro Lys Leu Leu Ile
1 5 10 15

Tyr

<210> SEQ ID NO 55
<211> LENGTH: 36
<212> TYPE: PRT
<213> ORGANISM: Artificial Sequence
<220> FEATURE:
<223> OTHER INFORMATION: Synthetic Construct

<400> SEQUENCE: 55

Ile Leu Gln Ser Gly Val Pro Ser Arg Phe Thr Gly Ser Gly Ser Gly
1 5 10 15

Thr Asp Phe Thr Leu Thr Ile Ser Asn Leu Gln Pro Glu Asp Phe Ala
20 25 30

Ser Tyr Ser Cys
35

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Phe Gly Gln Gly Thr Lys Val Glu Ile Lys
1 5 10

<210> SEQ ID NO 57
<211> LENGTH: 447
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (144)..(144)

```
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid

<400> SEQUENCE: 57

Glu Ser Gly Pro Arg Leu Val Lys Pro Ser Glu Thr Leu Ser Leu Thr
1               5                   10                  15

Cys Ile Val Ser Gly Asp Ser Ile Ser Ser Tyr Tyr Trp Gly Trp Ile
            20                  25                  30

Arg Gln Pro Ala Gly Arg Gly Leu Glu Trp Ile Gly Arg Ile Phe Thr
        35                  40                  45

Ser Gly Ser Thr Thr Tyr Asn Pro Ser Leu Lys Ser Arg Val Ser Met
    50                  55                  60

Ser Val Glu Thr Ser Lys Asn Gln Phe Ser Leu Thr Leu Thr Ser Val
65                  70                  75                  80

Thr Ala Ala Asp Thr Ala Val Tyr Phe Cys Ala Arg Asp Arg Arg Ala
                85                  90                  95

Leu Ser Ser Asp Gly Asn Trp Tyr Trp Tyr Phe Asp Leu Trp Gly Arg
            100                 105                 110

Gly Thr Leu Val Ala Val Ser Ser Lys Gly Pro Ser Val Phe Pro Leu
        115                 120                 125

Ala Pro Ser Ser Lys Ser Thr Ser Gly Gly Thr Ala Ala Leu Gly Xaa
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Xaa Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Xaa Thr Lys Asn Gln Val Ser Leu Thr Cys Leu
```

```
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 58
<211> LENGTH: 207
<212> TYPE: PRT
<213> ORGANISM: Artificial Sequence
<220> FEATURE:
<223> OTHER INFORMATION: Synthetic Construct

<400> SEQUENCE: 58

Thr Gln Ser Pro Ser Ser Leu Ser Ala Ser Val Gly Asp Arg Val Thr
1               5                   10                  15

Ile Thr Cys Arg Ala Ser Gln Thr Ile Thr Arg Asn Leu Asn Trp Tyr
            20                  25                  30

Gln Gln Lys Ser Gly Glu Ala Pro Lys Leu Leu Ile Tyr Gly Ala Ser
        35                  40                  45

Ile Leu Gln Ser Gly Val Pro Ser Arg Phe Thr Gly Ser Gly Ser Gly
    50                  55                  60

Thr Asp Phe Thr Leu Thr Ile Ser Asn Leu Gln Pro Glu Asp Phe Ala
65                  70                  75                  80

Ser Tyr Ser Cys Gln Gln Ser Asp Asn Thr Pro Arg Thr Phe Gly Gln
                85                  90                  95

Gly Thr Lys Val Glu Ile Lys Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln Trp Lys Val Asp Asn
    130                 135                 140

Ala Leu Gln Ser Gly Asn Ser Gln Glu Ser Val Thr Glu Gln Asp Ser
145                 150                 155                 160

Lys Asp Ser Thr Tyr Ser Leu Ser Ser Thr Leu Thr Leu Ser Lys Ala
                165                 170                 175

Asp Tyr Glu Lys His Lys Val Tyr Ala Cys Glu Val Thr His Gln Gly
            180                 185                 190

Leu Ser Ser Pro Val Thr Lys Ser Phe Asn Arg Gly Glu Cys Lys
        195                 200                 205


<210> SEQ ID NO 59
<211> LENGTH: 362
<212> TYPE: DNA
<213> ORGANISM: Artificial Sequence
<220> FEATURE:
<223> OTHER INFORMATION: Synthetic Construct

<400> SEQUENCE: 59

ggagtcgggc ccacgactgg tgaagccttc ggagaccctg tccctcacct gcattgtctc      60

tggtgactcc atcagtagtt attattgggg ctggatccgg cagcccgccg ggaggggact     120
```

ggagtggatt gggcggatct ttaccagcgg gagcaccacc tataatccct ccctcaagag 180
tcgagtctcc atgtcagtag agacatccaa gaaccagttc tccctgacac tgacctctgt 240
gaccgccgcg gacacggccg tttatttctg tgcgagagat cgaagggcac tttcgtctga 300
cggcaactgg tactggtact tcgatctctg ggccgtggc accctggtcg ctgtctcctc 360
gg 362

<210> SEQ ID NO 60
<211> LENGTH: 311
<212> TYPE: DNA
<213> ORGANISM: Artificial Sequence
<220> FEATURE:
<223> OTHER INFORMATION: Synthetic Construct

<400> SEQUENCE: 60
gacccagtct ccatcctccc tgtctgcatc tgtcggagac agagtcacca tcacttgccg 60
ggcaagtcag accattactc ggaatttaaa ttggtatcag cagaaatcag ggaagcccc 120 taagctcctg atctatggtg catccatttt gcaaagtggg gtcccatcaa ggttcactgg 180
cagtggatct gggacagatt tcactctcac catcagtaat ctgcaacctg aagattttgc 240
aagttactcc tgtcaacaga gtgacaatac cccgcggacg ttcggccaag ggaccaaggt 300
ggagatcaaa c 311

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Gly Gly Ser Met Ser Ser Tyr Tyr
1 5

<210> SEQ ID NO 62
<211> LENGTH: 7
<212> TYPE: PRT
<213> ORGANISM: Artificial Sequence
<220> FEATURE:
<223> OTHER INFORMATION: Synthetic Construct

<400> SEQUENCE: 62

Ile Phe Thr Thr Gly Ser Thr
1 5

<210> SEQ ID NO 63
<211> LENGTH: 19
<212> TYPE: PRT
<213> ORGANISM: Artificial Sequence
<220> FEATURE:
<223> OTHER INFORMATION: Synthetic Construct

<400> SEQUENCE: 63

Val Arg Asp Arg Arg Gly Arg Ser His Asp Ser Asn Trp Tyr Trp Tyr
1 5 10 15

Phe Asp Leu

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Gln Thr Leu Ser Arg Asn
1               5

<210> SEQ ID NO 65
<211> LENGTH: 3
<212> TYPE: PRT
<213> ORGANISM: Artificial Sequence
<220> FEATURE:
<223> OTHER INFORMATION: Synthetic Construct

<400> SEQUENCE: 65

Gly Ala Ser
1

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Ser Asp Asn Thr Pro Arg Thr
1               5

<210> SEQ ID NO 67
<211> LENGTH: 125
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Gly Trp Ile Arg Gln Pro Ala Gly Arg Gly Leu Glu Trp Ile
        35                  40                  45

Gly Arg Ile Phe Thr Thr Gly Ser Thr Ile Tyr Asn Ala Ser Leu Asn
    50                  55                  60

Ser Arg Val Ser Met Ser Val Asp Thr Ser Lys Asn Gln Phe Ser Leu
65                  70                  75                  80

Lys Leu Thr Ser Val Thr Ala Ala Asp Thr Ala Leu Tyr Phe Cys Val
                85                  90                  95

Arg Asp Arg Arg Gly Arg Ser His Asp Ser Asn Trp Tyr Trp Tyr Phe
            100                 105                 110

Asp Leu Trp Gly Arg Gly Thr Leu Val Thr Val Ser Ser
        115                 120                 125

<210> SEQ ID NO 68
<211> LENGTH: 85
<212> TYPE: PRT
<213> ORGANISM: Artificial Sequence
<220> FEATURE:
<223> OTHER INFORMATION: Synthetic Construct

<400> SEQUENCE: 68

Arg Val Ile Ile Thr Cys Arg Ala Ser Gln Thr Leu Ser Arg Asn Leu

```
1               5                   10                  15

Asn Trp Tyr Gln Gln Lys Pro Gly Glu Ala Pro Lys Leu Leu Ile Tyr
            20                  25                  30

Gly Ala Ser Thr Leu Gln Ser Gly Val Pro Ser Arg Phe Thr Gly Ser
        35                  40                  45

Gly Ser Gly Thr Asp Phe Thr Leu Ile Ile Ser Gly Leu Gln Pro Glu
    50                  55                  60

Asp Phe Ala Thr Tyr Tyr Cys Gln Gln Ser Asp Asn Thr Pro Arg Thr
65                  70                  75                  80

Phe Gly Gln Gly Thr
                85


<210> SEQ ID NO 69
<211> LENGTH: 25
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25


<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Trp Gly Trp Ile Arg Gln Pro Ala Gly Arg Gly Leu Glu Trp Ile Gly
1               5                   10                  15

Arg


<210> SEQ ID NO 71
<211> LENGTH: 38
<212> TYPE: PRT
<213> ORGANISM: Artificial Sequence
<220> FEATURE:
<223> OTHER INFORMATION: Synthetic Construct

<400> SEQUENCE: 71

Ile Tyr Asn Ala Ser Leu Asn Ser Arg Val Ser Met Ser Val Asp Thr
1               5                   10                  15

Ser Lys Asn Gln Phe Ser Leu Lys Leu Thr Ser Val Thr Ala Ala Asp
            20                  25                  30

Thr Ala Leu Tyr Phe Cys
        35


<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Trp Gly Arg Gly Thr Leu Val Thr Val Ser Ser
1               5                   10
```

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Arg Val Ile Ile Thr Cys Arg Ala Ser
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Leu Asn Trp Tyr Gln Gln Lys Pro Gly Glu Ala Pro Lys Leu Leu Ile
1               5                   10                  15

Tyr

<210> SEQ ID NO 75
<211> LENGTH: 36
<212> TYPE: PRT
<213> ORGANISM: Artificial Sequence
<220> FEATURE:
<223> OTHER INFORMATION: Synthetic Construct

<400> SEQUENCE: 75

Thr Leu Gln Ser Gly Val Pro Ser Arg Phe Thr Gly Ser Gly Ser Gly
1               5                   10                  15

Thr Asp Phe Thr Leu Ile Ile Ser Gly Leu Gln Pro Glu Asp Phe Ala
            20                  25                  30

Thr Tyr Tyr Cys
        35

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct

<400> SEQUENCE: 76

Phe Gly Gln Gly Thr
1               5

<210> SEQ ID NO 77
<211> LENGTH: 452
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (363)..(363)

<223> OTHER INFORMATION: Xaa can be any naturally occurring amino acid

<400> SEQUENCE: 77

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Gly Trp Ile Arg Gln Pro Ala Gly Arg Gly Leu Glu Trp Ile
        35                  40                  45

Gly Arg Ile Phe Thr Thr Gly Ser Thr Ile Tyr Asn Ala Ser Leu Asn
    50                  55                  60

Ser Arg Val Ser Met Ser Val Asp Thr Ser Lys Asn Gln Phe Ser Leu
65                  70                  75                  80

Lys Leu Thr Ser Val Thr Ala Ala Asp Thr Ala Leu Tyr Phe Cys Val
                85                  90                  95

Arg Asp Arg Arg Gly Arg Ser His Asp Ser Asn Trp Tyr Trp Tyr Phe
            100                 105                 110

Asp Leu Trp Gly Arg Gly Thr Leu Val Thr Val Ser Ser Lys Gly Pro
        115                 120                 125

Ser Val Phe Pro Leu Ala Pro Ser Ser Lys Ser Thr Ser Gly Gly Thr
    130                 135                 140

Ala Ala Leu Gly Xaa Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Xaa Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Xaa Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 78
<211> LENGTH: 189
<212> TYPE: PRT
<213> ORGANISM: Artificial Sequence
<220> FEATURE:
<223> OTHER INFORMATION: Synthetic Construct

<400> SEQUENCE: 78

```
Arg Val Ile Ile Thr Cys Arg Ala Ser Gln Thr Leu Ser Arg Asn Leu
1               5                   10                  15

Asn Trp Tyr Gln Gln Lys Pro Gly Glu Ala Pro Lys Leu Leu Ile Tyr
            20                  25                  30

Gly Ala Ser Thr Leu Gln Ser Gly Val Pro Ser Arg Phe Thr Gly Ser
        35                  40                  45

Gly Ser Gly Thr Asp Phe Thr Leu Ile Ile Ser Gly Leu Gln Pro Glu
    50                  55                  60

Asp Phe Ala Thr Tyr Tyr Cys Gln Gln Ser Asp Asn Thr Pro Arg Thr
65                  70                  75                  80

Phe Gly Gln Gly Thr Ala Pro Ser Val Phe Ile Phe Pro Pro Ser Asp
                85                  90                  95

Glu Gln Leu Lys Ser Gly Thr Ala Ser Val Val Cys Leu Leu Asn Asn
            100                 105                 110

Phe Tyr Pro Arg Glu Ala Lys Val Gln Trp Lys Val Asp Asn Ala Leu
        115                 120                 125

Gln Ser Gly Asn Ser Gln Glu Ser Val Thr Glu Gln Asp Ser Lys Asp
    130                 135                 140

Ser Thr Tyr Ser Leu Ser Ser Thr Leu Thr Leu Ser Lys Ala Asp Tyr
145                 150                 155                 160

Glu Lys His Lys Val Tyr Ala Cys Glu Val Thr His Gln Gly Leu Ser
                165                 170                 175

Ser Pro Val Thr Lys Ser Phe Asn Arg Gly Glu Cys Lys
            180                 185
```

<210> SEQ ID NO 79
<211> LENGTH: 376
<212> TYPE: DNA
<213> ORGANISM: Artificial Sequence
<220> FEATURE:
<223> OTHER INFORMATION: Synthetic Construct

<400> SEQUENCE: 79

```
caggtgcagc tgcaggagtc gggcccagga ctggtgaagc cttcggagac cctgtccctc     60

acctgcactg tctctggtgg ctccatgagt agttactact ggggctggat ccggcagccc    120

gccgggaggg gactggagtg gattgggcga atcttcacca ctgggagcac catctacaac    180

gcctccctca acagtcgagt ctccatgtca gtagacacgt ccaagaatca gttctccctg    240

aaactgacct ctgtgaccgc cgcggacacg gccttgtatt tctgtgtgag agatcgaaga    300

gggcgatcgc atgacagcaa ctggtactgg tacttcgatc tctggggccg tggcaccctg    360
```

gtcactgtct cctcgg 376

<210> SEQ ID NO 80
<211> LENGTH: 258
<212> TYPE: DNA
<213> ORGANISM: Artificial Sequence
<220> FEATURE:
<223> OTHER INFORMATION: Synthetic Construct

<400> SEQUENCE: 80
cagagtcatc atcacttgcc gggcaagtca gacccttagc cgcaatttaa attggtatca 60
gcagaaacca ggggaagccc ctaaactcct gatctatggt gcatccactt tacaaagtgg 120
ggtcccatca aggttcactg gcagtgggtc tgggacagat ttcactctca tcattagtgg 180
tctgcaacct gaagattttg caacttacta ctgtcagcag agtgacaata ccccgcggac 240
gttcggccaa gggaccaa 258

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Phe Thr Phe Ser Thr Phe Ser
1 5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Ile Lys Pro Asn Gly Asn Asp Lys
1 5

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

Ala Arg Pro Arg Gly Tyr Ser Ser Thr Leu Tyr Arg Tyr Phe Asp Tyr
1 5 10 15

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Gln Ser Val Ile Ser Thr Tyr
1 5

<210> SEQ ID NO 85
<211> LENGTH: 3
<212> TYPE: PRT

<213> ORGANISM: Artificial Sequence
<220> FEATURE:
<223> OTHER INFORMATION: Synthetic Construct

<400> SEQUENCE: 85

Gly Ala Ser
1

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct

<400> SEQUENCE: 86

Gln Gln Tyr Gly Ser Ser His Phe Thr
1               5

<210> SEQ ID NO 87
<211> LENGTH: 122
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 87

Cys Xaa Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Thr Phe Ser
            20                  25                  30

Met Ser Trp Val Arg Gln Ala Pro Gly Lys Gly Leu Glu Trp Leu Ala
        35                  40                  45

Asn Ile Lys Pro Asn Gly Asn Asp Lys Asp Tyr Val Asp Ser Val Arg
    50                  55                  60

Gly Gln Phe Thr Ile Ser Arg Asp Asn Ala Lys Asn Ser Leu Phe Leu
65                  70                  75                  80

Gln Met Asn Asn Leu Arg Ala Glu Asp Thr Ala Val Tyr Tyr Cys Ala
                85                  90                  95

Arg Pro Arg Gly Tyr Ser Ser Thr Leu Tyr Arg Tyr Phe Asp Tyr Trp
            100                 105                 110

Gly Gln Gly Thr Leu Val Thr Val Ser Ser
        115                 120

<210> SEQ ID NO 88
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: Xaa can be any naturally occurring amino acid

<400> SEQUENCE: 88

Lys Leu Gly Xaa Xaa Gln Ser Pro Gly Thr Leu Ser Leu Ser Pro Gly
1               5                   10                  15

Glu Arg Val Thr Leu Ser Cys Arg Ala Ser Gln Ser Val Ile Ser Thr
            20                  25                  30

```
Tyr Leu Ala Trp Tyr Gln Gln Lys Pro Gly Gln Ser Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser His
                85                  90                  95

Phe Thr Phe Gly Pro Gly Thr Lys Val Asp Ile Arg
            100                 105


<210> SEQ ID NO 89
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 89

Cys Xaa Leu Val Glu Ser Gly Gly Gly Leu Val Gln Pro Gly Gly Ser
1               5                   10                  15

Leu Arg Leu Ser Cys Ala Ala Ser
            20


<210> SEQ ID NO 90
<211> LENGTH: 17
<212> TYPE: PRT
<213> ORGANISM: Artificial Sequence
<220> FEATURE:
<223> OTHER INFORMATION: Synthetic Construct

<400> SEQUENCE: 90

Met Ser Trp Val Arg Gln Ala Pro Gly Lys Gly Leu Glu Trp Leu Ala
1               5                   10                  15

Asn


<210> SEQ ID NO 91
<211> LENGTH: 38
<212> TYPE: PRT
<213> ORGANISM: Artificial Sequence
<220> FEATURE:
<223> OTHER INFORMATION: Synthetic Construct

<400> SEQUENCE: 91

Asp Tyr Val Asp Ser Val Arg Gly Gln Phe Thr Ile Ser Arg Asp Asn
1               5                   10                  15

Ala Lys Asn Ser Leu Phe Leu Gln Met Asn Asn Leu Arg Ala Glu Asp
            20                  25                  30

Thr Ala Val Tyr Tyr Cys
        35


<210> SEQ ID NO 92
<211> LENGTH: 11
<212> TYPE: PRT
<213> ORGANISM: Artificial Sequence
<220> FEATURE:
<223> OTHER INFORMATION: Synthetic Construct

<400> SEQUENCE: 92
```

Trp Gly Gln Gly Thr Leu Val Thr Val Ser Ser
1 5 10

<210> SEQ ID NO 93
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: Xaa can be any naturally occurring amino acid

<400> SEQUENCE: 93

Lys Leu Gly Xaa Xaa Gln Ser Pro Gly Thr Leu Ser Leu Ser Pro Gly
1 5 10 15

Glu Arg Val Thr Leu Ser Cys Arg Ala Ser
20 25

<210> SEQ ID NO 94
<211> LENGTH: 17
<212> TYPE: PRT
<213> ORGANISM: Artificial Sequence
<220> FEATURE:
<223> OTHER INFORMATION: Synthetic Construct

<400> SEQUENCE: 94

Leu Ala Trp Tyr Gln Gln Lys Pro Gly Gln Ser Pro Arg Leu Leu Ile
1 5 10 15

Tyr

<210> SEQ ID NO 95
<211> LENGTH: 36
<212> TYPE: PRT
<213> ORGANISM: Artificial Sequence
<220> FEATURE:
<223> OTHER INFORMATION: Synthetic Construct

<400> SEQUENCE: 95

Ser Arg Ala Thr Gly Ile Pro Asp Arg Phe Ser Gly Ser Gly Ser Gly
1 5 10 15

Thr Asp Phe Thr Leu Thr Ile Ser Arg Leu Glu Pro Glu Asp Phe Ala
20 25 30

Val Tyr Tyr Cys
35

<210> SEQ ID NO 96
<211> LENGTH: 10
<212> TYPE: PRT
<213> ORGANISM: Artificial Sequence
<220> FEATURE:
<223> OTHER INFORMATION: Synthetic Construct

<400> SEQUENCE: 96

Phe Gly Pro Gly Thr Lys Val Asp Ile Arg
1 5 10

<210> SEQ ID NO 97
<211> LENGTH: 449
<212> TYPE: PRT
<213> ORGANISM: Artificial Sequence
<220> FEATURE:
<223> OTHER INFORMATION: Synthetic Construct
<220> FEATURE:

<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid

<400> SEQUENCE: 97

```
Cys Xaa Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Thr Phe Ser
            20                  25                  30

Met Ser Trp Val Arg Gln Ala Pro Gly Lys Gly Leu Glu Trp Leu Ala
        35                  40                  45

Asn Ile Lys Pro Asn Gly Asn Asp Lys Asp Tyr Val Asp Ser Val Arg
    50                  55                  60

Gly Gln Phe Thr Ile Ser Arg Asp Asn Ala Lys Asn Ser Leu Phe Leu
65                  70                  75                  80

Gln Met Asn Asn Leu Arg Ala Glu Asp Thr Ala Val Tyr Tyr Cys Ala
                85                  90                  95

Arg Pro Arg Gly Tyr Ser Ser Thr Leu Tyr Arg Tyr Phe Asp Tyr Trp
            100                 105                 110

Gly Gln Gly Thr Leu Val Thr Val Ser Ser Lys Gly Pro Ser Val Phe
        115                 120                 125

Pro Leu Ala Pro Ser Ser Lys Ser Thr Ser Gly Gly Thr Ala Ala Leu
    130                 135                 140

Gly Xaa Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Xaa Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Xaa Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 98
<211> LENGTH: 212
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: Xaa can be any naturally occurring amino acid

<400> SEQUENCE: 98

Lys Leu Gly Xaa Xaa Gln Ser Pro Gly Thr Leu Ser Leu Ser Pro Gly
1               5                   10                  15

Glu Arg Val Thr Leu Ser Cys Arg Ala Ser Gln Ser Val Ile Ser Thr
            20                  25                  30

Tyr Leu Ala Trp Tyr Gln Gln Lys Pro Gly Gln Ser Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser His
                85                  90                  95

Phe Thr Phe Gly Pro Gly Thr Lys Val Asp Ile Arg Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys Lys
```

210

<210> SEQ ID NO 99
<211> LENGTH: 367
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: n is a, c, g, or t

<400> SEQUENCE: 99
tgcannctgg tggagtctgg gggaggcttg gtccagcctg gggggatccct gagactctcc 60 tgtgcagcct ctggattcac ctttagtacc ttttcaatga gctgggtccg ccaggctcca 120
gggaaggggc tggagtggct ggccaacata aagccaaatg gaaatgacaa agactatgtg 180
gactctgtga ggggccaatt caccatctcc agagacaacg ccaagaactc actgtttctg 240
caaatgaaca acctgagagc cgaggacacg gccgtatatt actgtgcgag accgcgtggt 300
tatagcagca ccttgtaccg ttactttgac tactggggcc agggaaccct ggtcaccgtc 360
tcctcag 367

<210> SEQ ID NO 100
<211> LENGTH: 325
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 100
aaattgggnn nnangcagtc tccaggcacc ctgtctttgt ctccagggga aagagtcacc 60
ctctcctgca gggccagtca gagtgttatc agcacttatt tagcctggta ccagcagaaa 120
cctggccagt ctcccaggct cctcatctat ggtgcatcta gtagggccac tggcatccca 180
gacaggttca gtggcagtgg gtctgggaca gacttcactc tcaccatcag cagactggag 240
cctgaagatt ttgcagtata ttactgtcag cagtatggta gctcacactt cactttcggc 300
cctgggacca aagtggatat cagac 325

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Gly Phe Thr Phe Ser Ser Tyr Ser
1               5

<210> SEQ ID NO 102
<211> LENGTH: 8
<212> TYPE: PRT
<213> ORGANISM: Artificial Sequence
<220> FEATURE:

<223> OTHER INFORMATION: Synthetic Construct

<400> SEQUENCE: 102

Ile Ser Ser Ser Ser Ser Thr Ile
1 5

<210> SEQ ID NO 103
<211> LENGTH: 17
<212> TYPE: PRT
<213> ORGANISM: Artificial Sequence
<220> FEATURE:
<223> OTHER INFORMATION: Synthetic Construct

<400> SEQUENCE: 103

Ala Arg Glu Asp Ser Gly Arg Phe Gly Asp Ile Tyr Tyr Gly Met Asp
1 5 10 15

Val

<210> SEQ ID NO 104
<211> LENGTH: 6
<212> TYPE: PRT
<213> ORGANISM: Artificial Sequence
<220> FEATURE:
<223> OTHER INFORMATION: Synthetic Construct

<400> SEQUENCE: 104

Gln Asp Ile Ser Asn Tyr
1 5

<210> SEQ ID NO 105
<211> LENGTH: 3
<212> TYPE: PRT
<213> ORGANISM: Artificial Sequence
<220> FEATURE:
<223> OTHER INFORMATION: Synthetic Construct

<400> SEQUENCE: 105

Asp Ala Ser
1

<210> SEQ ID NO 106
<211> LENGTH: 9
<212> TYPE: PRT
<213> ORGANISM: Artificial Sequence
<220> FEATURE:
<223> OTHER INFORMATION: Synthetic Construct

<400> SEQUENCE: 106

Gln Gln Tyr Asp Asn Leu Pro Tyr Thr
1 5

<210> SEQ ID NO 107
<211> LENGTH: 123
<212> TYPE: PRT
<213> ORGANISM: Artificial Sequence
<220> FEATURE:
<223> OTHER INFORMATION: Synthetic Construct

<400> SEQUENCE: 107

Cys Arg Leu Val Glu Ser Gly Gly Gly Leu Val Gln Pro Gly Gly Ser
1 5 10 15

Leu Arg Leu Ser Cys Ala Ala Ser Gly Phe Thr Phe Ser Ser Tyr Ser
20 25 30

Met Asn Trp Val Arg Gln Ala Pro Gly Lys Gly Leu Glu Trp Val Ser
35 40 45

```
Tyr Ile Ser Ser Ser Ser Ser Thr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Asp Glu Asp Thr Ala Val Tyr Tyr Cys Ala
                85                  90                  95

Arg Glu Asp Ser Gly Arg Phe Gly Asp Ile Tyr Tyr Gly Met Asp Val
            100                 105                 110

Trp Gly Gln Gly Thr Thr Val Thr Val Ser Ser
        115                 120


<210> SEQ ID NO 108
<211> LENGTH: 102
<212> TYPE: PRT
<213> ORGANISM: Artificial Sequence
<220> FEATURE:
<223> OTHER INFORMATION: Synthetic Construct

<400> SEQUENCE: 108

Gln Ser Pro Ser Ser Leu Ser Ala Ser Val Gly Asp Arg Val Thr Ile
1               5                   10                  15

Thr Cys Gln Ala Ser Gln Asp Ile Ser Asn Tyr Leu Asn Trp Tyr Gln
            20                  25                  30

Gln Lys Pro Gly Lys Ala Pro Lys Leu Leu Ile Tyr Asp Ala Ser Asn
        35                  40                  45

Leu Glu Thr Gly Val Pro Ser Arg Phe Ser Gly Ser Gly Ser Gly Thr
    50                  55                  60

Asp Phe Thr Phe Thr Ile Ser Ser Leu Gln Pro Glu Asp Ile Ala Thr
65                  70                  75                  80

Tyr Tyr Cys Gln Gln Tyr Asp Asn Leu Pro Tyr Thr Phe Gly Gln Gly
                85                  90                  95

Thr Lys Leu Glu Ile Lys
            100


<210> SEQ ID NO 109
<211> LENGTH: 24
<212> TYPE: PRT
<213> ORGANISM: Artificial Sequence
<220> FEATURE:
<223> OTHER INFORMATION: Synthetic Construct

<400> SEQUENCE: 109

Cys Arg Leu Val Glu Ser Gly Gly Gly Leu Val Gln Pro Gly Gly Ser
1               5                   10                  15

Leu Arg Leu Ser Cys Ala Ala Ser
            20


<210> SEQ ID NO 110
<211> LENGTH: 17
<212> TYPE: PRT
<213> ORGANISM: Artificial Sequence
<220> FEATURE:
<223> OTHER INFORMATION: Synthetic Construct

<400> SEQUENCE: 110

Met Asn Trp Val Arg Gln Ala Pro Gly Lys Gly Leu Glu Trp Val Ser
1               5                   10                  15

Tyr
```

<210> SEQ ID NO 111
<211> LENGTH: 38
<212> TYPE: PRT
<213> ORGANISM: Artificial Sequence
<220> FEATURE:
<223> OTHER INFORMATION: Synthetic Construct

<400> SEQUENCE: 111

Tyr Tyr Ala Asp Ser Val Lys Gly Arg Phe Thr Ile Ser Arg Asp Asn
1 5 10 15

Ala Lys Asn Ser Leu Tyr Leu Gln Met Asn Ser Leu Arg Asp Glu Asp
20 25 30

Thr Ala Val Tyr Tyr Cys
35

<210> SEQ ID NO 112
<211> LENGTH: 11
<212> TYPE: PRT
<213> ORGANISM: Artificial Sequence
<220> FEATURE:
<223> OTHER INFORMATION: Synthetic Construct

<400> SEQUENCE: 112

Trp Gly Gln Gly Thr Thr Val Thr Val Ser Ser
1 5 10

<210> SEQ ID NO 113
<211> LENGTH: 21
<212> TYPE: PRT
<213> ORGANISM: Artificial Sequence
<220> FEATURE:
<223> OTHER INFORMATION: Synthetic Construct

<400> SEQUENCE: 113

Gln Ser Pro Ser Ser Leu Ser Ala Ser Val Gly Asp Arg Val Thr Ile
1 5 10 15

Thr Cys Gln Ala Ser
20

<210> SEQ ID NO 114
<211> LENGTH: 17
<212> TYPE: PRT
<213> ORGANISM: Artificial Sequence
<220> FEATURE:
<223> OTHER INFORMATION: Synthetic Construct

<400> SEQUENCE: 114

Leu Asn Trp Tyr Gln Gln Lys Pro Gly Lys Ala Pro Lys Leu Leu Ile
1 5 10 15

Tyr

<210> SEQ ID NO 115
<211> LENGTH: 36
<212> TYPE: PRT
<213> ORGANISM: Artificial Sequence
<220> FEATURE:
<223> OTHER INFORMATION: Synthetic Construct

<400> SEQUENCE: 115

Asn Leu Glu Thr Gly Val Pro Ser Arg Phe Ser Gly Ser Gly Ser Gly
1 5 10 15

Thr Asp Phe Thr Phe Thr Ile Ser Ser Leu Gln Pro Glu Asp Ile Ala
20 25 30

Thr Tyr Tyr Cys

35

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Phe Gly Gln Gly Thr Lys Leu Glu Ile Lys
1               5                   10

<210> SEQ ID NO 117
<211> LENGTH: 450
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 117

Cys Arg Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ser
            20                  25                  30

Met Asn Trp Val Arg Gln Ala Pro Gly Lys Gly Leu Glu Trp Val Ser
        35                  40                  45

Tyr Ile Ser Ser Ser Ser Ser Thr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Asp Glu Asp Thr Ala Val Tyr Tyr Cys Ala
                85                  90                  95

Arg Glu Asp Ser Gly Arg Phe Gly Asp Ile Tyr Tyr Gly Met Asp Val
            100                 105                 110

Trp Gly Gln Gly Thr Thr Val Thr Val Ser Ser Lys Gly Pro Ser Val
        115                 120                 125

Phe Pro Leu Ala Pro Ser Ser Lys Ser Thr Ser Gly Gly Thr Ala Ala
    130                 135                 140

Leu Gly Xaa Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Xaa Val Glu Pro Lys Ser Cys Asp
    210                 215                 220

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Xaa Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 118
<211> LENGTH: 206
<212> TYPE: PRT
<213> ORGANISM: Artificial Sequence
<220> FEATURE:
<223> OTHER INFORMATION: Synthetic Construct

<400> SEQUENCE: 118

Gln Ser Pro Ser Ser Leu Ser Ala Ser Val Gly Asp Arg Val Thr Ile
1               5                   10                  15

Thr Cys Gln Ala Ser Gln Asp Ile Ser Asn Tyr Leu Asn Trp Tyr Gln
            20                  25                  30

Gln Lys Pro Gly Lys Ala Pro Lys Leu Leu Ile Tyr Asp Ala Ser Asn
        35                  40                  45

Leu Glu Thr Gly Val Pro Ser Arg Phe Ser Gly Ser Gly Ser Gly Thr
    50                  55                  60

Asp Phe Thr Phe Thr Ile Ser Ser Leu Gln Pro Glu Asp Ile Ala Thr
65                  70                  75                  80

Tyr Tyr Cys Gln Gln Tyr Asp Asn Leu Pro Tyr Thr Phe Gly Gln Gly
                85                  90                  95

Thr Lys Leu Glu Ile Lys Ala Pro Ser Val Phe Ile Phe Pro Pro Ser
            100                 105                 110

Asp Glu Gln Leu Lys Ser Gly Thr Ala Ser Val Val Cys Leu Leu Asn
        115                 120                 125
```

```
Asn Phe Tyr Pro Arg Glu Ala Lys Val Gln Trp Lys Val Asp Asn Ala
    130                 135                 140

Leu Gln Ser Gly Asn Ser Gln Glu Ser Val Thr Glu Gln Asp Ser Lys
145                 150                 155                 160

Asp Ser Thr Tyr Ser Leu Ser Ser Thr Leu Thr Leu Ser Lys Ala Asp
                165                 170                 175

Tyr Glu Lys His Lys Val Tyr Ala Cys Glu Val Thr His Gln Gly Leu
            180                 185                 190

Ser Ser Pro Val Thr Lys Ser Phe Asn Arg Gly Glu Cys Lys
        195                 200                 205


<210> SEQ ID NO 119
<211> LENGTH: 370
<212> TYPE: DNA
<213> ORGANISM: Artificial Sequence
<220> FEATURE:
<223> OTHER INFORMATION: Synthetic Construct

<400> SEQUENCE: 119

gtgcaggctg gtggagtctg ggggaggctt ggtacagcct ggggggtccc tgagactctc     60

ctgtgcagcc tctggattca ccttcagtag ctatagcatg aactgggtcc gccaggctcc    120

agggaagggg ctggagtggg tttcatacat tagtagtagt agtagtacca tatactacgc    180

agactctgtg aagggccgat tcaccatctc cagagacaat gccaagaact cactgtatct    240

gcaaatgaac agcctgagag acgaggacac ggctgtgtat tactgtgcga gagaggatag    300

cggtaggttc ggggatatat actacggtat ggacgtctgg ggccaaggga ccacggtcac    360

cgtctcctca                                                           370


<210> SEQ ID NO 120
<211> LENGTH: 308
<212> TYPE: DNA
<213> ORGANISM: Artificial Sequence
<220> FEATURE:
<223> OTHER INFORMATION: Synthetic Construct

<400> SEQUENCE: 120

ccagtctcca tcctccctgt ctgcatctgt aggagacaga gtcaccatca cttgccaggc     60

gagtcaggac attagcaact atttaaattg gtatcagcag aaaccaggga aagcccctaa    120

gctcctgatc tacgatgcat ccaatttgga aacaggggtc ccatcaaggt tcagtggaag    180

tggatctggg acagatttta ctttcaccat cagcagcctg cagcctgaag atattgcaac    240

atattactgt caacagtatg ataatctccc gtacactttt ggccagggga ccaagctgga    300

gatcaaac                                                             308


<210> SEQ ID NO 121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 121

Gly Asp Ser Ile Ser Ser Tyr Tyr
1               5


<210> SEQ ID NO 122
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 122

Ile Phe Thr Thr Gly Ser Thr
1 5

<210> SEQ ID NO 123
<211> LENGTH: 19
<212> TYPE: PRT
<213> ORGANISM: Artificial Sequence
<220> FEATURE:
<223> OTHER INFORMATION: Synthetic Construct

<400> SEQUENCE: 123

Ala Arg Asp Arg Arg Gly Leu Ser His Gly Thr Asn Trp His Trp Phe
1 5 10 15

Phe Asp Leu

<210> SEQ ID NO 124
<211> LENGTH: 6
<212> TYPE: PRT
<213> ORGANISM: Artificial Sequence
<220> FEATURE:
<223> OTHER INFORMATION: Synthetic Construct

<400> SEQUENCE: 124

Gln Thr Ile Ser Ser Ser
1 5

<210> SEQ ID NO 125
<211> LENGTH: 3
<212> TYPE: PRT
<213> ORGANISM: Artificial Sequence
<220> FEATURE:
<223> OTHER INFORMATION: Synthetic Construct

<400> SEQUENCE: 125

Gly Val Ser
1

<210> SEQ ID NO 126
<211> LENGTH: 9
<212> TYPE: PRT
<213> ORGANISM: Artificial Sequence
<220> FEATURE:
<223> OTHER INFORMATION: Synthetic Construct

<400> SEQUENCE: 126

Gln Gln Thr Phe Ser Pro Pro Arg Thr
1 5

<210> SEQ ID NO 127
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 127

```
Val Xaa Xaa Gln Xaa Xaa Gly Pro Gly Leu Val Lys Pro Ser Glu Ala
1               5                   10                  15

Leu Ser Leu Thr Cys Ser Val Ser Gly Asp Ser Ile Ser Ser Tyr Tyr
            20                  25                  30

Trp Ser Trp Ile Arg Gln Ser Ala Gly Lys Gly Pro Glu Trp Ile Gly
        35                  40                  45

Arg Ile Phe Thr Thr Gly Ser Thr Ile Tyr Asn Pro Ser Leu Lys Thr
    50                  55                  60

Arg Val Ser Met Ser Ile Asp Thr Ser Lys Asn Arg Phe Ser Leu Gln
65                  70                  75                  80

Leu Ser Ser Val Thr Ala Ala Asp Thr Ala Val Tyr Tyr Cys Ala Arg
                85                  90                  95

Asp Arg Arg Gly Leu Ser His Gly Thr Asn Trp His Trp Phe Phe Asp
            100                 105                 110

Leu Trp Gly Arg Gly Thr Leu Val Thr Val Ser Ser
        115                 120


<210> SEQ ID NO 128
<211> LENGTH: 103
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 128

Xaa Gln Ser Pro Ser Ser Leu Ser Ala Ser Val Gly Asp Arg Val Thr
1               5                   10                  15

Ile Thr Cys Arg Ala Ser Gln Thr Ile Ser Ser Ser Leu Asn Trp Tyr
            20                  25                  30

Gln Gln Thr Pro Gly Lys Pro Pro Lys Leu Leu Ile Tyr Gly Val Ser
        35                  40                  45

Thr Leu Gln Thr Gly Val Pro Ser Arg Phe Thr Gly Gly Gly Ser Gly
    50                  55                  60

Thr Asn Phe Asn Leu Thr Ile Ser Ser Val Gln Pro Glu Asp Phe Thr
65                  70                  75                  80

Thr Tyr Tyr Cys Gln Gln Thr Phe Ser Pro Pro Arg Thr Phe Gly Gln
                85                  90                  95

Gly Thr Lys Val Glu Met Lys
            100


<210> SEQ ID NO 129
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 129

Val Xaa Xaa Gln Xaa Xaa Gly Pro Gly Leu Val Lys Pro Ser Glu Ala
```

1 5 10 15

Leu Ser Leu Thr Cys Ser Val Ser
20

<210> SEQ ID NO 130
<211> LENGTH: 17
<212> TYPE: PRT
<213> ORGANISM: Artificial Sequence
<220> FEATURE:
<223> OTHER INFORMATION: Synthetic Construct

<400> SEQUENCE: 130

Trp Ser Trp Ile Arg Gln Ser Ala Gly Lys Gly Pro Glu Trp Ile Gly
1 5 10 15

Arg

<210> SEQ ID NO 131
<211> LENGTH: 38
<212> TYPE: PRT
<213> ORGANISM: Artificial Sequence
<220> FEATURE:
<223> OTHER INFORMATION: Synthetic Construct

<400> SEQUENCE: 131

Ile Tyr Asn Pro Ser Leu Lys Thr Arg Val Ser Met Ser Ile Asp Thr
1 5 10 15

Ser Lys Asn Arg Phe Ser Leu Gln Leu Ser Ser Val Thr Ala Ala Asp
20 25 30

Thr Ala Val Tyr Tyr Cys
35

<210> SEQ ID NO 132
<211> LENGTH: 11
<212> TYPE: PRT
<213> ORGANISM: Artificial Sequence
<220> FEATURE:
<223> OTHER INFORMATION: Synthetic Construct

<400> SEQUENCE: 132

Trp Gly Arg Gly Thr Leu Val Thr Val Ser Ser
1 5 10

<210> SEQ ID NO 133
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 133

Xaa Gln Ser Pro Ser Ser Leu Ser Ala Ser Val Gly Asp Arg Val Thr
1 5 10 15

Ile Thr Cys Arg Ala Ser
20

<210> SEQ ID NO 134
<211> LENGTH: 17
<212> TYPE: PRT
<213> ORGANISM: Artificial Sequence
<220> FEATURE:
<223> OTHER INFORMATION: Synthetic Construct

<400> SEQUENCE: 134

Leu Asn Trp Tyr Gln Gln Thr Pro Gly Lys Pro Pro Lys Leu Leu Ile
1               5                   10                  15

Tyr

<210> SEQ ID NO 135
<211> LENGTH: 36
<212> TYPE: PRT
<213> ORGANISM: Artificial Sequence
<220> FEATURE:
<223> OTHER INFORMATION: Synthetic Construct

<400> SEQUENCE: 135

Thr Leu Gln Thr Gly Val Pro Ser Arg Phe Thr Gly Gly Gly Ser Gly
1               5                   10                  15

Thr Asn Phe Asn Leu Thr Ile Ser Ser Val Gln Pro Glu Asp Phe Thr
            20                  25                  30

Thr Tyr Tyr Cys
        35

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Phe Gly Gln Gly Thr Lys Val Glu Met Lys
1               5                   10

<210> SEQ ID NO 137
<211> LENGTH: 451
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid

<400> SEQUENCE: 137

Val Xaa Xaa Gln Xaa Xaa Gly Pro Gly Leu Val Lys Pro Ser Glu Ala
1               5                   10                  15

Leu Ser Leu Thr Cys Ser Val Ser Gly Asp Ser Ile Ser Ser Tyr Tyr
            20                  25                  30

Trp Ser Trp Ile Arg Gln Ser Ala Gly Lys Gly Pro Glu Trp Ile Gly
        35                  40                  45

```
Arg Ile Phe Thr Thr Gly Ser Thr Ile Tyr Asn Pro Ser Leu Lys Thr
    50                  55                  60

Arg Val Ser Met Ser Ile Asp Thr Ser Lys Asn Arg Phe Ser Leu Gln
65                  70                  75                  80

Leu Ser Ser Val Thr Ala Ala Asp Thr Ala Val Tyr Tyr Cys Ala Arg
                85                  90                  95

Asp Arg Arg Gly Leu Ser His Gly Thr Asn Trp His Trp Phe Phe Asp
            100                 105                 110

Leu Trp Gly Arg Gly Thr Leu Val Thr Val Ser Ser Lys Gly Pro Ser
        115                 120                 125

Val Phe Pro Leu Ala Pro Ser Ser Lys Ser Thr Ser Gly Gly Thr Ala
    130                 135                 140

Ala Leu Gly Xaa Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Xaa Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Xaa Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 138
<211> LENGTH: 207
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 138

```
Xaa Gln Ser Pro Ser Ser Leu Ser Ala Ser Val Gly Asp Arg Val Thr
1               5                   10                  15

Ile Thr Cys Arg Ala Ser Gln Thr Ile Ser Ser Ser Leu Asn Trp Tyr
            20                  25                  30

Gln Gln Thr Pro Gly Lys Pro Pro Lys Leu Leu Ile Tyr Gly Val Ser
        35                  40                  45

Thr Leu Gln Thr Gly Val Pro Ser Arg Phe Thr Gly Gly Gly Ser Gly
    50                  55                  60

Thr Asn Phe Asn Leu Thr Ile Ser Ser Val Gln Pro Glu Asp Phe Thr
65                  70                  75                  80

Thr Tyr Tyr Cys Gln Gln Thr Phe Ser Pro Pro Arg Thr Phe Gly Gln
                85                  90                  95

Gly Thr Lys Val Glu Met Lys Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln Trp Lys Val Asp Asn
    130                 135                 140

Ala Leu Gln Ser Gly Asn Ser Gln Glu Ser Val Thr Glu Gln Asp Ser
145                 150                 155                 160

Lys Asp Ser Thr Tyr Ser Leu Ser Ser Thr Leu Thr Leu Ser Lys Ala
                165                 170                 175

Asp Tyr Glu Lys His Lys Val Tyr Ala Cys Glu Val Thr His Gln Gly
            180                 185                 190

Leu Ser Ser Pro Val Thr Lys Ser Phe Asn Arg Gly Glu Cys Lys
        195                 200                 205
```

<210> SEQ ID NO 139
<211> LENGTH: 374
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 139

```
ggtgcannnn caggantngg gcccaggact ggtgaagcct tcggaggccc tgtccctcac     60

ctgcagtgtc tctggtgact ccatcagtag ttactattgg agttggatcc ggcagtccgc    120

cgggaaggga ccggagtgga ttggccgtat ctttaccact gggagcacca tctacaatcc    180
```

atccctcaag actcgagtca gcatgtcgat agacacgtcc aagaaccggt tttccctgca 240
gttgagttct gtgaccgccg cggacacggc cgtatattat tgtgcgagag atcgaagggg 300
gctttcgcat ggcaccaatt ggcattggtt cttcgattta tggggccgcg gcaccctggt 360
cactgtctcc tcag 374

<210> SEQ ID NO 140
<211> LENGTH: 310
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n is a, c, g, or t

<400> SEQUENCE: 140
anccagtctc catcgtccct gtctgcatct gtaggagaca gagtcaccat cacttgtcgg 60
gcaagtcaga ccattagcag cagtttaaat tggtatcagc agacaccagg gaaacccccct 120 aaactcctga tctatggtgt atccactttg caaactgggg tcccatcaag gttcactggc 180
ggtggatctg ggacaaattt caatctcacc atcagtagtg tgcaacctga agattttaca 240
acttactact gtcaacagac tttttctccc ccgcggactt ttggccaagg gaccaaggtg 300
gaaatgaaac 310

<210> SEQ ID NO 141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 141

Gly Asp Ser Ile Ser Ser Tyr Tyr
1 5

<210> SEQ ID NO 142
<211> LENGTH: 7
<212> TYPE: PRT
<213> ORGANISM: Artificial Sequence
<220> FEATURE:
<223> OTHER INFORMATION: Synthetic Construct

<400> SEQUENCE: 142

Ile Phe Thr Ser Gly Ser Thr
1 5

<210> SEQ ID NO 143
<211> LENGTH: 19
<212> TYPE: PRT
<213> ORGANISM: Artificial Sequence
<220> FEATURE:
<223> OTHER INFORMATION: Synthetic Construct

<400> SEQUENCE: 143

Ala Arg Asp Arg Arg Gly Arg Ser His Asp Ser Asn Trp Tyr Trp Tyr
1 5 10 15

Phe Asp Leu

<210> SEQ ID NO 144
<211> LENGTH: 6

<212> TYPE: PRT
<213> ORGANISM: Artificial Sequence
<220> FEATURE:
<223> OTHER INFORMATION: Synthetic Construct

<400> SEQUENCE: 144

Gln Ser Ile Ser Thr Asn
1               5

<210> SEQ ID NO 145
<211> LENGTH: 3
<212> TYPE: PRT
<213> ORGANISM: Artificial Sequence
<220> FEATURE:
<223> OTHER INFORMATION: Synthetic Construct

<400> SEQUENCE: 145

Gly Ala Ser
1

<210> SEQ ID NO 146
<211> LENGTH: 9
<212> TYPE: PRT
<213> ORGANISM: Artificial Sequence
<220> FEATURE:
<223> OTHER INFORMATION: Synthetic Construct

<400> SEQUENCE: 146

Gln Gln Ser Asp Asn Thr Pro Arg Thr
1               5

<210> SEQ ID NO 147
<211> LENGTH: 121
<212> TYPE: PRT
<213> ORGANISM: Artificial Sequence
<220> FEATURE:
<223> OTHER INFORMATION: Synthetic Construct

<400> SEQUENCE: 147

Gln Glu Ser Gly Pro Gly Leu Val Lys Pro Ser Glu Thr Leu Ser Leu
1               5                   10                  15

Thr Cys Thr Val Ser Gly Asp Ser Ile Ser Ser Tyr Tyr Trp Gly Trp
            20                  25                  30

Ile Arg Gln Pro Ala Gly Gly Gly Leu Glu Trp Ile Gly Arg Ile Phe
        35                  40                  45

Thr Ser Gly Ser Thr Asn Tyr Asn Pro Ser Leu Lys Ser Arg Leu Thr
    50                  55                  60

Met Ser Val Asp Thr Ser Lys Asn Gln Phe Ser Leu Thr Leu Asn Ser
65                  70                  75                  80

Leu Thr Ala Ala Asp Thr Ala Val Tyr Phe Cys Ala Arg Asp Arg Arg
                85                  90                  95

Gly Arg Ser His Asp Ser Asn Trp Tyr Trp Tyr Phe Asp Leu Trp Gly
            100                 105                 110

Arg Gly Ala Leu Val Thr Val Ser Ser
        115                 120

<210> SEQ ID NO 148
<211> LENGTH: 102
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (55)..(55)
<223> OTHER INFORMATION: Xaa can be any naturally occurring amino acid

<400> SEQUENCE: 148

Gln Ser Pro Ser Ser Leu Ser Ala Ser Val Gly Asp Arg Val Thr Ile
1 5 10 15

Thr Cys Arg Pro Ser Gln Ser Ile Ser Thr Asn Leu Asn Trp Tyr Gln
20 25 30

Gln Lys Pro Gly Lys Ala Pro Lys Leu Leu Ile Tyr Gly Ala Ser Ile
35 40 45

Leu Gln Ser Gly Asp Pro Xaa Arg Phe Thr Gly Ser Arg Ser Gly Ser
50 55 60

Asp Phe Thr Leu Thr Ile Ser Gly Leu Gln Pro Glu Asp Phe Ala Thr
65 70 75 80

Tyr Tyr Cys Gln Gln Ser Asp Asn Thr Pro Arg Thr Phe Gly Gln Gly
85 90 95

Thr Lys Val Glu Thr Lys
100

<210> SEQ ID NO 149
<211> LENGTH: 21
<212> TYPE: PRT
<213> ORGANISM: Artificial Sequence
<220> FEATURE:
<223> OTHER INFORMATION: Synthetic Construct

<400> SEQUENCE: 149

Gln Glu Ser Gly Pro Gly Leu Val Lys Pro Ser Glu Thr Leu Ser Leu
1 5 10 15

Thr Cys Thr Val Ser
20

<210> SEQ ID NO 150
<211> LENGTH: 17
<212> TYPE: PRT
<213> ORGANISM: Artificial Sequence
<220> FEATURE:
<223> OTHER INFORMATION: Synthetic Construct

<400> SEQUENCE: 150

Trp Gly Trp Ile Arg Gln Pro Ala Gly Gly Gly Leu Glu Trp Ile Gly
1 5 10 15

Arg

<210> SEQ ID NO 151
<211> LENGTH: 38
<212> TYPE: PRT
<213> ORGANISM: Artificial Sequence
<220> FEATURE:
<223> OTHER INFORMATION: Synthetic Construct

<400> SEQUENCE: 151

Asn Tyr Asn Pro Ser Leu Lys Ser Arg Leu Thr Met Ser Val Asp Thr
1 5 10 15

Ser Lys Asn Gln Phe Ser Leu Thr Leu Asn Ser Leu Thr Ala Ala Asp
20 25 30

Thr Ala Val Tyr Phe Cys
35

<210> SEQ ID NO 152
<211> LENGTH: 11

<212> TYPE: PRT
<213> ORGANISM: Artificial Sequence
<220> FEATURE:
<223> OTHER INFORMATION: Synthetic Construct

<400> SEQUENCE: 152

Trp Gly Arg Gly Ala Leu Val Thr Val Ser Ser
1               5                   10

<210> SEQ ID NO 153
<211> LENGTH: 21
<212> TYPE: PRT
<213> ORGANISM: Artificial Sequence
<220> FEATURE:
<223> OTHER INFORMATION: Synthetic Construct

<400> SEQUENCE: 153

Gln Ser Pro Ser Ser Leu Ser Ala Ser Val Gly Asp Arg Val Thr Ile
1               5                   10                  15

Thr Cys Arg Pro Ser
            20

<210> SEQ ID NO 154
<211> LENGTH: 17
<212> TYPE: PRT
<213> ORGANISM: Artificial Sequence
<220> FEATURE:
<223> OTHER INFORMATION: Synthetic Construct

<400> SEQUENCE: 154

Leu Asn Trp Tyr Gln Gln Lys Pro Gly Lys Ala Pro Lys Leu Leu Ile
1               5                   10                  15

Tyr

<210> SEQ ID NO 155
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 155

Ile Leu Gln Ser Gly Asp Pro Xaa Arg Phe Thr Gly Ser Arg Ser Gly
1               5                   10                  15

Ser Asp Phe Thr Leu Thr Ile Ser Gly Leu Gln Pro Glu Asp Phe Ala
            20                  25                  30

Thr Tyr Tyr Cys
        35

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Phe Gly Gln Gly Thr Lys Val Glu Thr Lys
1               5                   10

<210> SEQ ID NO 157

```
<211> LENGTH: 448
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 157

Gln Glu Ser Gly Pro Gly Leu Val Lys Pro Ser Glu Thr Leu Ser Leu
1               5                   10                  15

Thr Cys Thr Val Ser Gly Asp Ser Ile Ser Ser Tyr Tyr Trp Gly Trp
            20                  25                  30

Ile Arg Gln Pro Ala Gly Gly Gly Leu Glu Trp Ile Gly Arg Ile Phe
        35                  40                  45

Thr Ser Gly Ser Thr Asn Tyr Asn Pro Ser Leu Lys Ser Arg Leu Thr
    50                  55                  60

Met Ser Val Asp Thr Ser Lys Asn Gln Phe Ser Leu Thr Leu Asn Ser
65                  70                  75                  80

Leu Thr Ala Ala Asp Thr Ala Val Tyr Phe Cys Ala Arg Asp Arg Arg
                85                  90                  95

Gly Arg Ser His Asp Ser Asn Trp Tyr Trp Tyr Phe Asp Leu Trp Gly
            100                 105                 110

Arg Gly Ala Leu Val Thr Val Ser Ser Lys Gly Pro Ser Val Phe Pro
        115                 120                 125

Leu Ala Pro Ser Ser Lys Ser Thr Ser Gly Gly Thr Ala Ala Leu Gly
    130                 135                 140

Xaa Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Xaa Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Xaa Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 158
<211> LENGTH: 206
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (55)..(55)
<223> OTHER INFORMATION: Xaa can be any naturally occurring amino acid

<400> SEQUENCE: 158

Gln Ser Pro Ser Ser Leu Ser Ala Ser Val Gly Asp Arg Val Thr Ile
1 5 10 15

Thr Cys Arg Pro Ser Gln Ser Ile Ser Thr Asn Leu Asn Trp Tyr Gln
20 25 30

Gln Lys Pro Gly Lys Ala Pro Lys Leu Leu Ile Tyr Gly Ala Ser Ile
35 40 45

Leu Gln Ser Gly Asp Pro Xaa Arg Phe Thr Gly Ser Arg Ser Gly Ser
50 55 60

Asp Phe Thr Leu Thr Ile Ser Gly Leu Gln Pro Glu Asp Phe Ala Thr
65 70 75 80

Tyr Tyr Cys Gln Gln Ser Asp Asn Thr Pro Arg Thr Phe Gly Gln Gly
85 90 95

Thr Lys Val Glu Thr Lys Ala Pro Ser Val Phe Ile Phe Pro Pro Ser
100 105 110

Asp Glu Gln Leu Lys Ser Gly Thr Ala Ser Val Val Cys Leu Leu Asn
115 120 125

Asn Phe Tyr Pro Arg Glu Ala Lys Val Gln Trp Lys Val Asp Asn Ala
130 135 140

Leu Gln Ser Gly Asn Ser Gln Glu Ser Val Thr Glu Gln Asp Ser Lys
145 150 155 160

Asp Ser Thr Tyr Ser Leu Ser Ser Thr Leu Thr Leu Ser Lys Ala Asp
165 170 175

Tyr Glu Lys His Lys Val Tyr Ala Cys Glu Val Thr His Gln Gly Leu
180 185 190

Ser Ser Pro Val Thr Lys Ser Phe Asn Arg Gly Glu Cys Lys
195 200 205

<210> SEQ ID NO 159
<211> LENGTH: 365
<212> TYPE: DNA
<213> ORGANISM: Artificial Sequence
<220> FEATURE:
<223> OTHER INFORMATION: Synthetic Construct

<400> SEQUENCE: 159
gcaggagtcg ggcccaggac tggtgaagcc ctcggagacc ctgtccctca cctgcactgt 60
ctctggtgac tccatcagta gttactattg gggctggatc cggcagcccg ccgggggggg 120
actggagtgg attgggcgga tctttaccag tgggagcacc aactacaatc cctccctcaa 180
gagtcggctc accatgtcag tcgacacgtc caagaaccag ttctccctga cactcaactc 240
actgaccgcc gcggacacgg ccgtgtattt ctgtgcgaga gatcgcaggg ggcgttcgca 300
tgacagcaac tggtactggt acttcgatct ctggggccgt ggcgccctgg tcactgtctc 360
ctcgg 365

<210> SEQ ID NO 160
<211> LENGTH: 309
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (166)..(166)
<223> OTHER INFORMATION: n is a, c, g, or t

<400> SEQUENCE: 160
cccagtctcc atcctccctg tctgcatctg tgggagacag agtcaccatc acttgccggc 60
caagtcagag cattagcacc aatttaaatt ggtatcagca gaagcctggg aaagccccta 120
agctcctgat ctatggtgca tccattttac agagtggtga cccacntaga ttcactggca 180
gtagatctgg gtcagatttc actctcacca tcagtggttt gcaacctgaa gattttgcaa 240
cttactactg tcaacagagt gacaatactc cgcggacctt cggccaaggg accaaggtgg 300
aaaccaaac 309

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Gly Gly Ser Ile Ser Ser Tyr Tyr
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic Construct

<400> SEQUENCE: 162

Ile Phe Thr Ser Gly Ser Thr
1               5

<210> SEQ ID NO 163
<211> LENGTH: 19
<212> TYPE: PRT

<213> ORGANISM: Artificial Sequence
<220> FEATURE:
<223> OTHER INFORMATION: Synthetic Construct

<400> SEQUENCE: 163

Val Arg Asp Arg Arg Gly Leu Leu Tyr Ser Asn Ile Trp Tyr Trp Ser
1               5                   10                  15

Phe Asp Leu

<210> SEQ ID NO 164
<211> LENGTH: 6
<212> TYPE: PRT
<213> ORGANISM: Artificial Sequence
<220> FEATURE:
<223> OTHER INFORMATION: Synthetic Construct

<400> SEQUENCE: 164

Gln Ser Ile Thr Asn Tyr
1               5

<210> SEQ ID NO 165
<211> LENGTH: 3
<212> TYPE: PRT
<213> ORGANISM: Artificial Sequence
<220> FEATURE:
<223> OTHER INFORMATION: Synthetic Construct

<400> SEQUENCE: 165

Ala Ala Ser
1

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Gln Gln Ser Tyr Ser Thr Pro Trp Thr
1               5

<210> SEQ ID NO 167
<211> LENGTH: 125
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 167

Gln Val Gln Leu Xaa Xaa Xaa Gly Pro Gly Xaa Val Lys Pro Ser Glu
1               5                   10                  15

Thr Leu Ser Leu Thr Cys Ser Val Ser Gly Gly Ser Ile Ser Ser Tyr
            20                  25                  30

Tyr Trp Gly Trp Ile Arg Gln Pro Pro Gly Lys Gly Leu Glu Trp Ile
        35                  40                  45

Gly Arg Ile Phe Thr Ser Gly Ser Thr Asn Tyr Asn Pro Ser Leu Glu
    50                  55                  60

Ser Arg Val Thr Met Ser Val Asp Met Ser Lys Asn Gln Phe Ser Leu
65 70 75 80

Ser Leu Ser Ser Val Thr Ala Ala Asp Thr Ala Val Tyr Tyr Cys Val
85 90 95

Arg Asp Arg Arg Gly Leu Leu Tyr Ser Asn Ile Trp Tyr Trp Ser Phe
100 105 110

Asp Leu Trp Gly Arg Gly Thr Leu Val Thr Val Ser Ser
115 120 125

<210> SEQ ID NO 168
<211> LENGTH: 102
<212> TYPE: PRT
<213> ORGANISM: Artificial Sequence
<220> FEATURE:
<223> OTHER INFORMATION: Synthetic Construct

<400> SEQUENCE: 168

Gln Ser Pro Ser Ser Leu Ser Ala Ser Ala Gly Asp Arg Val Thr Ile
1 5 10 15

Thr Cys Arg Ala Ser Gln Ser Ile Thr Asn Tyr Leu Asn Trp Tyr Gln
20 25 30

Gln Lys Pro Met Arg Ala Pro Lys Leu Leu Ile Tyr Ala Ala Ser Thr
35 40 45

Leu Gln Ser Gly Val Pro Ser Arg Phe Ser Gly Ser Gly Ser Gly Thr
50 55 60

Asp Phe Thr Leu Thr Ile Ser Ser Leu Gln Pro Glu Asp Phe Ala Thr
65 70 75 80

Tyr Tyr Cys Gln Gln Ser Tyr Ser Thr Pro Trp Thr Phe Gly Gln Gly
85 90 95

Thr Lys Val Glu Ile Arg
100

<210> SEQ ID NO 169
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 169

Gln Val Gln Leu Xaa Xaa Xaa Gly Pro Gly Xaa Val Lys Pro Ser Glu
1 5 10 15

Thr Leu Ser Leu Thr Cys Ser Val Ser
20 25

<210> SEQ ID NO 170
<211> LENGTH: 17
<212> TYPE: PRT
<213> ORGANISM: Artificial Sequence
<220> FEATURE:
<223> OTHER INFORMATION: Synthetic Construct

<400> SEQUENCE: 170

Trp Gly Trp Ile Arg Gln Pro Pro Gly Lys Gly Leu Glu Trp Ile Gly 1 5 10 15

Arg

<210> SEQ ID NO 171
<211> LENGTH: 38
<212> TYPE: PRT
<213> ORGANISM: Artificial Sequence
<220> FEATURE:
<223> OTHER INFORMATION: Synthetic Construct

<400> SEQUENCE: 171

Asn Tyr Asn Pro Ser Leu Glu Ser Arg Val Thr Met Ser Val Asp Met
1 5 10 15

Ser Lys Asn Gln Phe Ser Leu Ser Leu Ser Ser Val Thr Ala Ala Asp
20 25 30

Thr Ala Val Tyr Tyr Cys
35

<210> SEQ ID NO 172
<211> LENGTH: 11
<212> TYPE: PRT
<213> ORGANISM: Artificial Sequence
<220> FEATURE:
<223> OTHER INFORMATION: Synthetic Construct

<400> SEQUENCE: 172

Trp Gly Arg Gly Thr Leu Val Thr Val Ser Ser
1 5 10

<210> SEQ ID NO 173
<211> LENGTH: 21
<212> TYPE: PRT
<213> ORGANISM: Artificial Sequence
<220> FEATURE:
<223> OTHER INFORMATION: Synthetic Construct

<400> SEQUENCE: 173

Gln Ser Pro Ser Ser Leu Ser Ala Ser Ala Gly Asp Arg Val Thr Ile
1 5 10 15

Thr Cys Arg Ala Ser
20

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Leu Asn Trp Tyr Gln Gln Lys Pro Met Arg Ala Pro Lys Leu Leu Ile
1 5 10 15

Tyr

<210> SEQ ID NO 175
<211> LENGTH: 36
<212> TYPE: PRT
<213> ORGANISM: Artificial Sequence
<220> FEATURE:
<223> OTHER INFORMATION: Synthetic Construct

<400> SEQUENCE: 175

Thr Leu Gln Ser Gly Val Pro Ser Arg Phe Ser Gly Ser Gly Ser Gly
1 5 10 15

```
Thr Asp Phe Thr Leu Thr Ile Ser Ser Leu Gln Pro Glu Asp Phe Ala
            20                  25                  30

Thr Tyr Tyr Cys
        35


<210> SEQ ID NO 176
<211> LENGTH: 10
<212> TYPE: PRT
<213> ORGANISM: Artificial Sequence
<220> FEATURE:
<223> OTHER INFORMATION: Synthetic Construct

<400> SEQUENCE: 176

Phe Gly Gln Gly Thr Lys Val Glu Ile Arg
1               5                   10


<210> SEQ ID NO 177
<211> LENGTH: 452
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (363)..(363)
<223> OTHER INFORMATION: Xaa can be any naturally occurring amino acid

<400> SEQUENCE: 177

Gln Val Gln Leu Xaa Xaa Xaa Gly Pro Gly Xaa Val Lys Pro Ser Glu
1               5                   10                  15

Thr Leu Ser Leu Thr Cys Ser Val Ser Gly Gly Ser Ile Ser Ser Tyr
            20                  25                  30

Tyr Trp Gly Trp Ile Arg Gln Pro Pro Gly Lys Gly Leu Glu Trp Ile
        35                  40                  45

Gly Arg Ile Phe Thr Ser Gly Ser Thr Asn Tyr Asn Pro Ser Leu Glu
    50                  55                  60

Ser Arg Val Thr Met Ser Val Asp Met Ser Lys Asn Gln Phe Ser Leu
65                  70                  75                  80

Ser Leu Ser Ser Val Thr Ala Ala Asp Thr Ala Val Tyr Tyr Cys Val
                85                  90                  95

Arg Asp Arg Arg Gly Leu Leu Tyr Ser Asn Ile Trp Tyr Trp Ser Phe
            100                 105                 110

Asp Leu Trp Gly Arg Gly Thr Leu Val Thr Val Ser Ser Lys Gly Pro
        115                 120                 125

Ser Val Phe Pro Leu Ala Pro Ser Ser Lys Ser Thr Ser Gly Gly Thr
    130                 135                 140

Ala Ala Leu Gly Xaa Leu Val Lys Asp Tyr Phe Pro Glu Pro Val Thr
145                 150                 155                 160
```

```
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Xaa Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Xaa Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 178
<211> LENGTH: 206
<212> TYPE: PRT
<213> ORGANISM: Artificial Sequence
<220> FEATURE:
<223> OTHER INFORMATION: Synthetic Construct

<400> SEQUENCE: 178

```
Gln Ser Pro Ser Ser Leu Ser Ala Ser Ala Gly Asp Arg Val Thr Ile
1               5                   10                  15

Thr Cys Arg Ala Ser Gln Ser Ile Thr Asn Tyr Leu Asn Trp Tyr Gln
            20                  25                  30

Gln Lys Pro Met Arg Ala Pro Lys Leu Leu Ile Tyr Ala Ala Ser Thr
        35                  40                  45

Leu Gln Ser Gly Val Pro Ser Arg Phe Ser Gly Ser Gly Ser Gly Thr
    50                  55                  60
```

```
Asp Phe Thr Leu Thr Ile Ser Ser Leu Gln Pro Glu Asp Phe Ala Thr
65                  70                  75                  80

Tyr Tyr Cys Gln Gln Ser Tyr Ser Thr Pro Trp Thr Phe Gly Gln Gly
                85                  90                  95

Thr Lys Val Glu Ile Arg Ala Pro Ser Val Phe Ile Phe Pro Pro Ser
            100                 105                 110

Asp Glu Gln Leu Lys Ser Gly Thr Ala Ser Val Val Cys Leu Leu Asn
        115                 120                 125

Asn Phe Tyr Pro Arg Glu Ala Lys Val Gln Trp Lys Val Asp Asn Ala
    130                 135                 140

Leu Gln Ser Gly Asn Ser Gln Glu Ser Val Thr Glu Gln Asp Ser Lys
145                 150                 155                 160

Asp Ser Thr Tyr Ser Leu Ser Ser Thr Leu Thr Leu Ser Lys Ala Asp
                165                 170                 175

Tyr Glu Lys His Lys Val Tyr Ala Cys Glu Val Thr His Gln Gly Leu
            180                 185                 190

Ser Ser Pro Val Thr Lys Ser Phe Asn Arg Gly Glu Cys Lys
        195                 200                 205
```

<210> SEQ ID NO 179
<211> LENGTH: 376
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 179

```
caggtgcagc tgcannnntn gggcccagga ntggtgaagc cttcggagac cctgtccctc     60

acctgcagtg tctctggtgg ctccatcagt agttactact ggggctggat ccggcagccc    120

cccgggaagg gactggagtg gattgggcgt atttttacca gtgggagcac caactataac    180

ccctccctcg agagtcgcgt caccatgtca gtagacatgt ccaagaacca gttctccctg    240

agcctgagct ctgtgaccgc cgcggacacg gccgtatatt actgtgtgag agatcggagg    300

ggacttttgt atagcaacat ctggtactgg tccttcgatc tctggggccg tggcaccctg    360

gtcactgtct cctcag                                                    376
```

<210> SEQ ID NO 180
<211> LENGTH: 308
<212> TYPE: DNA
<213> ORGANISM: Artificial Sequence
<220> FEATURE:
<223> OTHER INFORMATION: Synthetic Construct

<400> SEQUENCE: 180

```
ccagtctcca tcctccctgt ctgcatctgc aggagacaga gtcaccatca cttgccgggc     60

aagtcagagc attactaact atttaaattg gtatcaacag aaaccaatga gagcccctaa    120

gctcctgatc tatgctgcat ccactttgca aagtggggtc ccatcaaggt tcagtggcag    180
```

tggctctggg acagatttca ctctcaccat cagcagtctg caacctgaag attttgcaac 240
ttactactgt caacagagtt acagtacccc gtggacgttc ggccaaggga ccaaggtgga 300
gatcagac 308

<210> SEQ ID NO 181
<211> LENGTH: 8
<212> TYPE: PRT
<213> ORGANISM: Artificial Sequence
<220> FEATURE:
<223> OTHER INFORMATION: Synthetic Construct

<400> SEQUENCE: 181

Gly Phe Pro Phe Glu Lys Phe Ala
1 5

<210> SEQ ID NO 182
<211> LENGTH: 8
<212> TYPE: PRT
<213> ORGANISM: Artificial Sequence
<220> FEATURE:
<223> OTHER INFORMATION: Synthetic Construct

<400> SEQUENCE: 182

Ile Ser Gly Thr Gly Ala Val Thr
1 5

<210> SEQ ID NO 183
<211> LENGTH: 15
<212> TYPE: PRT
<213> ORGANISM: Artificial Sequence
<220> FEATURE:
<223> OTHER INFORMATION: Synthetic Construct

<400> SEQUENCE: 183

Ala Lys Asp Arg Thr Pro Val Thr Asn Tyr Tyr Gly Met Asp Val
1 5 10 15

<210> SEQ ID NO 184
<211> LENGTH: 6
<212> TYPE: PRT
<213> ORGANISM: Artificial Sequence
<220> FEATURE:
<223> OTHER INFORMATION: Synthetic Construct

<400> SEQUENCE: 184

Gln Thr Ile Asp Asn Tyr
1 5

<210> SEQ ID NO 185
<211> LENGTH: 3
<212> TYPE: PRT
<213> ORGANISM: Artificial Sequence
<220> FEATURE:
<223> OTHER INFORMATION: Synthetic Construct

<400> SEQUENCE: 185

Gly Ala Phe
1

<210> SEQ ID NO 186
<211> LENGTH: 9
<212> TYPE: PRT
<213> ORGANISM: Artificial Sequence
<220> FEATURE:
<223> OTHER INFORMATION: Synthetic Construct

<400> SEQUENCE: 186

Gln Gln Thr Tyr Ser Thr Pro Tyr Thr
1 5

<210> SEQ ID NO 187
<211> LENGTH: 119
<212> TYPE: PRT
<213> ORGANISM: Artificial Sequence
<220> FEATURE:
<223> OTHER INFORMATION: Synthetic Construct

<400> SEQUENCE: 187

Leu Val Glu Ser Gly Gly Asn Leu Gly Gln Pro Gly Gly Ser Leu Arg
1 5 10 15

Leu Ser Cys Ala Ala Ser Gly Phe Pro Phe Glu Lys Phe Ala Ile Asn
20 25 30

Trp Val Arg Gln Ala Pro Gly Lys Gly Leu Glu Trp Val Ser Ala Ile
35 40 45

Ser Gly Thr Gly Ala Val Thr Tyr Tyr Ala Asp Ser Val Glu Gly Arg
50 55 60

Phe Ser Ile Ser Arg Asp Asn Ser Lys Asn Thr Val Phe Leu Glu Met
65 70 75 80

Asn Ser Leu Arg Val Glu Asp Thr Ala Val Tyr Phe Cys Ala Lys Asp
85 90 95

Arg Thr Pro Val Thr Asn Tyr Tyr Gly Met Asp Val Trp Gly Gln Gly
100 105 110

Thr Thr Val Thr Val Ser Ser
115

<210> SEQ ID NO 188
<211> LENGTH: 102
<212> TYPE: PRT
<213> ORGANISM: Artificial Sequence
<220> FEATURE:
<223> OTHER INFORMATION: Synthetic Construct

<400> SEQUENCE: 188

Gln Ser Pro Ala Ser Leu Ser Ala Ser Val Gly Asp Arg Val Thr Ile
1 5 10 15

Thr Cys Arg Gly Ser Gln Thr Ile Asp Asn Tyr Leu Asn Trp Tyr Gln
20 25 30

His Lys Pro Gly Lys Ala Pro Lys Leu Leu Ile Tyr Gly Ala Phe Ser
35 40 45

Leu Gln Gly Gly Val Pro Ser Arg Phe Ser Gly Ser Gly Tyr Gly Thr
50 55 60

Asp Phe Thr Leu Thr Ile Ser Ser Leu Gln Pro Glu Asp Phe Ala Thr
65 70 75 80

Tyr Tyr Cys Gln Gln Thr Tyr Ser Thr Pro Tyr Thr Phe Gly Gln Gly
85 90 95

Thr Lys Leu Glu Thr Asn
100

<210> SEQ ID NO 189
<211> LENGTH: 22
<212> TYPE: PRT
<213> ORGANISM: Artificial Sequence
<220> FEATURE:
<223> OTHER INFORMATION: Synthetic Construct

<400> SEQUENCE: 189

Leu Val Glu Ser Gly Gly Asn Leu Gly Gln Pro Gly Gly Ser Leu Arg
1 5 10 15

Leu Ser Cys Ala Ala Ser
20

<210> SEQ ID NO 190
<211> LENGTH: 17
<212> TYPE: PRT
<213> ORGANISM: Artificial Sequence
<220> FEATURE:
<223> OTHER INFORMATION: Synthetic Construct

<400> SEQUENCE: 190

Ile Asn Trp Val Arg Gln Ala Pro Gly Lys Gly Leu Glu Trp Val Ser
1 5 10 15

Ala

<210> SEQ ID NO 191
<211> LENGTH: 38
<212> TYPE: PRT
<213> ORGANISM: Artificial Sequence
<220> FEATURE:
<223> OTHER INFORMATION: Synthetic Construct

<400> SEQUENCE: 191

Tyr Tyr Ala Asp Ser Val Glu Gly Arg Phe Ser Ile Ser Arg Asp Asn
1 5 10 15

Ser Lys Asn Thr Val Phe Leu Glu Met Asn Ser Leu Arg Val Glu Asp
20 25 30

Thr Ala Val Tyr Phe Cys
35

<210> SEQ ID NO 192
<211> LENGTH: 11
<212> TYPE: PRT
<213> ORGANISM: Artificial Sequence
<220> FEATURE:
<223> OTHER INFORMATION: Synthetic Construct

<400> SEQUENCE: 192

Trp Gly Gln Gly Thr Thr Val Thr Val Ser Ser
1 5 10

<210> SEQ ID NO 193
<211> LENGTH: 21
<212> TYPE: PRT
<213> ORGANISM: Artificial Sequence
<220> FEATURE:
<223> OTHER INFORMATION: Synthetic Construct

<400> SEQUENCE: 193

Gln Ser Pro Ala Ser Leu Ser Ala Ser Val Gly Asp Arg Val Thr Ile
1 5 10 15

Thr Cys Arg Gly Ser
20

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Leu Asn Trp Tyr Gln His Lys Pro Gly Lys Ala Pro Lys Leu Leu Ile
1 5 10 15

Tyr

<210> SEQ ID NO 195
<211> LENGTH: 36
<212> TYPE: PRT
<213> ORGANISM: Artificial Sequence
<220> FEATURE:
<223> OTHER INFORMATION: Synthetic Construct

<400> SEQUENCE: 195

Ser Leu Gln Gly Gly Val Pro Ser Arg Phe Ser Gly Ser Gly Tyr Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 196
<211> LENGTH: 10
<212> TYPE: PRT
<213> ORGANISM: Artificial Sequence
<220> FEATURE:
<223> OTHER INFORMATION: Synthetic Construct

<400> SEQUENCE: 196

Phe Gly Gln Gly Thr Lys Leu Glu Thr Asn
1 5 10

<210> SEQ ID NO 197
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 197

Leu Val Glu Ser Gly Gly Asn Leu Gly Gln Pro Gly Gly Ser Leu Arg
1 5 10 15

Leu Ser Cys Ala Ala Ser Gly Phe Pro Phe Glu Lys Phe Ala Ile Asn
20 25 30

Trp Val Arg Gln Ala Pro Gly Lys Gly Leu Glu Trp Val Ser Ala Ile
35 40 45

Ser Gly Thr Gly Ala Val Thr Tyr Tyr Ala Asp Ser Val Glu Gly Arg
50 55 60

Phe Ser Ile Ser Arg Asp Asn Ser Lys Asn Thr Val Phe Leu Glu Met
65 70 75 80

Asn Ser Leu Arg Val Glu Asp Thr Ala Val Tyr Phe Cys Ala Lys Asp
85 90 95

```
Arg Thr Pro Val Thr Asn Tyr Tyr Gly Met Asp Val Trp Gly Gln Gly
            100                 105                 110

Thr Thr Val Thr Val Ser Ser Lys Gly Pro Ser Val Phe Pro Leu Ala
        115                 120                 125

Pro Ser Ser Lys Ser Thr Ser Gly Gly Thr Ala Ala Leu Gly Xaa Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Xaa Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Xaa Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 198
<211> LENGTH: 206
<212> TYPE: PRT
<213> ORGANISM: Artificial Sequence
<220> FEATURE:
<223> OTHER INFORMATION: Synthetic Construct

<400> SEQUENCE: 198

```
Gln Ser Pro Ala Ser Leu Ser Ala Ser Val Gly Asp Arg Val Thr Ile
1               5                   10                  15
```

```
Thr Cys Arg Gly Ser Gln Thr Ile Asp Asn Tyr Leu Asn Trp Tyr Gln
            20                  25                  30

His Lys Pro Gly Lys Ala Pro Lys Leu Leu Ile Tyr Gly Ala Phe Ser
        35                  40                  45

Leu Gln Gly Gly Val Pro Ser Arg Phe Ser Gly Ser Gly Tyr Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Thr Tyr Ser Thr Pro Tyr Thr Phe Gly Gln Gly
                85                  90                  95

Thr Lys Leu Glu Thr Asn Ala Pro Ser Val Phe Ile Phe Pro Pro Ser
            100                 105                 110

Asp Glu Gln Leu Lys Ser Gly Thr Ala Ser Val Val Cys Leu Leu Asn
        115                 120                 125

Asn Phe Tyr Pro Arg Glu Ala Lys Val Gln Trp Lys Val Asp Asn Ala
    130                 135                 140

Leu Gln Ser Gly Asn Ser Gln Glu Ser Val Thr Glu Gln Asp Ser Lys
145                 150                 155                 160

Asp Ser Thr Tyr Ser Leu Ser Ser Thr Leu Thr Leu Ser Lys Ala Asp
                165                 170                 175

Tyr Glu Lys His Lys Val Tyr Ala Cys Glu Val Thr His Gln Gly Leu
            180                 185                 190

Ser Ser Pro Val Thr Lys Ser Phe Asn Arg Gly Glu Cys Lys
        195                 200                 205


<210> SEQ ID NO 199
<211> LENGTH: 359
<212> TYPE: DNA
<213> ORGANISM: Artificial Sequence
<220> FEATURE:
<223> OTHER INFORMATION: Synthetic Construct

<400> SEQUENCE: 199

agctggtgga gtctgggggga aacttgggac agccgggggg gtccctgaga ctgtcctgtg      60

cagcctctgg attccccttt gagaagtttg ccatcaactg ggtccgccag gctccaggga     120

aggggctgga gtgggtctcg gctattagtg gtactggtgc tgtcacatac tacgcagact     180

ccgtggaggg ccggttctcc atctccagag acaattccaa gaacacggtg tttctggaga     240

tgaacagcct gagagtcgag gacacggccg tgtatttctg tgcgaaagat cggactccgg     300

tgacaaacta ctacggcatg gacgtctggg gccaagggac cacggtcacc gtctcctca      359


<210> SEQ ID NO 200
<211> LENGTH: 309
<212> TYPE: DNA
<213> ORGANISM: Artificial Sequence
<220> FEATURE:
<223> OTHER INFORMATION: Synthetic Construct

<400> SEQUENCE: 200

cccagtcgcc agcgtccctg tccgcatctg taggagacag agtcaccatc acttgccggg      60

gaagtcagac cattgacaat tatttaaatt ggtatcagca caaacctggg aaagccccta     120

aactcctgat ctatggggct ttcagtttgc agggtggggt cccatcaagg ttcagtggca     180

gtggatatgg gacagatttc actctcacca tcagcagtct gcaacctgaa gactttgcaa     240

cttactactg tcagcagact tacagtaccc cgtacacttt tggccagggg accaagctgg     300

agaccaatc                                                             309
```

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 201

Gly Phe Thr Phe Asn Arg Phe Ala
1               5

<210> SEQ ID NO 202
<211> LENGTH: 8
<212> TYPE: PRT
<213> ORGANISM: Artificial Sequence
<220> FEATURE:
<223> OTHER INFORMATION: Synthetic Construct

<400> SEQUENCE: 202

Ile Ser Gly Thr Gly Ala Val Thr
1               5

<210> SEQ ID NO 203
<211> LENGTH: 15
<212> TYPE: PRT
<213> ORGANISM: Artificial Sequence
<220> FEATURE:
<223> OTHER INFORMATION: Synthetic Construct

<400> SEQUENCE: 203

Ala Lys Asp Arg Thr Pro Val Thr Asn Tyr Tyr Gly Met Asp Val
1               5                   10                  15

<210> SEQ ID NO 204
<211> LENGTH: 6
<212> TYPE: PRT
<213> ORGANISM: Artificial Sequence
<220> FEATURE:
<223> OTHER INFORMATION: Synthetic Construct

<400> SEQUENCE: 204

Gln Thr Ile Asp Asn Tyr
1               5

<210> SEQ ID NO 205
<211> LENGTH: 3
<212> TYPE: PRT
<213> ORGANISM: Artificial Sequence
<220> FEATURE:
<223> OTHER INFORMATION: Synthetic Construct

<400> SEQUENCE: 205

Ala Ala Ser
1

<210> SEQ ID NO 206
<211> LENGTH: 9
<212> TYPE: PRT
<213> ORGANISM: Artificial Sequence
<220> FEATURE:
<223> OTHER INFORMATION: Synthetic Construct

<400> SEQUENCE: 206

Gln Gln Thr Ser Ser Thr Pro Tyr Thr
1               5

<210> SEQ ID NO 207
<211> LENGTH: 121
<212> TYPE: PRT
<213> ORGANISM: Artificial Sequence
<220> FEATURE:
<223> OTHER INFORMATION: Synthetic Construct

<400> SEQUENCE: 207

Val Gln Leu Val Glu Ser Gly Gly Thr Leu Gly Gln Pro Gly Gly Ser
1 5 10 15

Leu Arg Leu Ser Cys Thr Ala Ser Gly Phe Thr Phe Asn Arg Phe Ala
20 25 30

Ile Asn Trp Val Arg Gln Ala Pro Gly Lys Gly Leu Glu Trp Val Ala
35 40 45

Ala Ile Ser Gly Thr Gly Ala Val Thr Tyr Tyr Ala Asp Ser Val Glu
50 55 60

Gly Arg Phe Ser Ile Ser Arg Glu Asn Ser Asn Asn Thr Val Phe Leu
65 70 75 80

Glu Met Asn Asn Leu Arg Gly Glu Asp Thr Ala Val Tyr Phe Cys Ala
85 90 95

Lys Asp Arg Thr Pro Val Thr Asn Tyr Tyr Gly Met Asp Val Trp Gly
100 105 110

Gln Gly Thr Thr Val Thr Val Ser Ser
115 120

<210> SEQ ID NO 208
<211> LENGTH: 103
<212> TYPE: PRT
<213> ORGANISM: Artificial Sequence
<220> FEATURE:
<223> OTHER INFORMATION: Synthetic Construct

<400> SEQUENCE: 208

Thr Gln Ser Pro Ser Ser Leu Ser Ala Ser Val Gly Asp Arg Val Ile
1 5 10 15

Ile Thr Cys Arg Gly Ser Gln Thr Ile Asp Asn Tyr Leu Asn Trp Tyr
20 25 30

Gln Gln Lys Pro Gly Lys Ala Pro Arg Leu Leu Ile Ser Ala Ala Ser
35 40 45

Ser Leu Gln Gly Gly Val Pro Ser Arg Phe Ser Gly Ser Gly Tyr Gly
50 55 60

Thr Asp Phe Thr Leu Thr Ile Ser Ser Leu Gln Pro Glu Asp Phe Ala
65 70 75 80

Thr Tyr Tyr Cys Gln Gln Thr Ser Ser Thr Pro Tyr Thr Phe Gly Gln
85 90 95

Gly Thr Lys Val Glu Ile Lys
100

<210> SEQ ID NO 209
<211> LENGTH: 24
<212> TYPE: PRT
<213> ORGANISM: Artificial Sequence
<220> FEATURE:
<223> OTHER INFORMATION: Synthetic Construct

<400> SEQUENCE: 209

Val Gln Leu Val Glu Ser Gly Gly Thr Leu Gly Gln Pro Gly Gly Ser
1 5 10 15

Leu Arg Leu Ser Cys Thr Ala Ser

20

<210> SEQ ID NO 210
<211> LENGTH: 17
<212> TYPE: PRT
<213> ORGANISM: Artificial Sequence
<220> FEATURE:
<223> OTHER INFORMATION: Synthetic Construct

<400> SEQUENCE: 210

Ile Asn Trp Val Arg Gln Ala Pro Gly Lys Gly Leu Glu Trp Val Ala
1 5 10 15

Ala

<210> SEQ ID NO 211
<211> LENGTH: 38
<212> TYPE: PRT
<213> ORGANISM: Artificial Sequence
<220> FEATURE:
<223> OTHER INFORMATION: Synthetic Construct

<400> SEQUENCE: 211

Tyr Tyr Ala Asp Ser Val Glu Gly Arg Phe Ser Ile Ser Arg Glu Asn
1 5 10 15

Ser Asn Asn Thr Val Phe Leu Glu Met Asn Asn Leu Arg Gly Glu Asp
20 25 30

Thr Ala Val Tyr Phe Cys
35

<210> SEQ ID NO 212
<211> LENGTH: 11
<212> TYPE: PRT
<213> ORGANISM: Artificial Sequence
<220> FEATURE:
<223> OTHER INFORMATION: Synthetic Construct

<400> SEQUENCE: 212

Trp Gly Gln Gly Thr Thr Val Thr Val Ser Ser
1 5 10

<210> SEQ ID NO 213
<211> LENGTH: 22
<212> TYPE: PRT
<213> ORGANISM: Artificial Sequence
<220> FEATURE:
<223> OTHER INFORMATION: Synthetic Construct

<400> SEQUENCE: 213

Thr Gln Ser Pro Ser Ser Leu Ser Ala Ser Val Gly Asp Arg Val Ile
1 5 10 15

Ile Thr Cys Arg Gly Ser
20

<210> SEQ ID NO 214
<211> LENGTH: 17
<212> TYPE: PRT
<213> ORGANISM: Artificial Sequence
<220> FEATURE:
<223> OTHER INFORMATION: Synthetic Construct

<400> SEQUENCE: 214

Leu Asn Trp Tyr Gln Gln Lys Pro Gly Lys Ala Pro Arg Leu Leu Ile
1 5 10 15

Ser

<210> SEQ ID NO 215
<211> LENGTH: 36
<212> TYPE: PRT
<213> ORGANISM: Artificial Sequence
<220> FEATURE:
<223> OTHER INFORMATION: Synthetic Construct

<400> SEQUENCE: 215

Ser Leu Gln Gly Gly Val Pro Ser Arg Phe Ser Gly Ser Gly Tyr Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Phe Gly Gln Gly Thr Lys Val Glu Ile Lys
1 5 10

<210> SEQ ID NO 217
<211> LENGTH: 448
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 217

Val Gln Leu Val Glu Ser Gly Gly Thr Leu Gly Gln Pro Gly Gly Ser
1 5 10 15

Leu Arg Leu Ser Cys Thr Ala Ser Gly Phe Thr Phe Asn Arg Phe Ala
20 25 30

Ile Asn Trp Val Arg Gln Ala Pro Gly Lys Gly Leu Glu Trp Val Ala
35 40 45

Ala Ile Ser Gly Thr Gly Ala Val Thr Tyr Tyr Ala Asp Ser Val Glu
50 55 60

Gly Arg Phe Ser Ile Ser Arg Glu Asn Ser Asn Asn Thr Val Phe Leu
65 70 75 80

Glu Met Asn Asn Leu Arg Gly Glu Asp Thr Ala Val Tyr Phe Cys Ala
85 90 95

Lys Asp Arg Thr Pro Val Thr Asn Tyr Tyr Gly Met Asp Val Trp Gly
100 105 110

Gln Gly Thr Thr Val Thr Val Ser Ser Lys Gly Pro Ser Val Phe Pro
115 120 125

```
Leu Ala Pro Ser Ser Lys Ser Thr Ser Gly Gly Thr Ala Ala Leu Gly
    130                 135                 140

Xaa Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Xaa Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Xaa Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 218
<211> LENGTH: 207
<212> TYPE: PRT
<213> ORGANISM: Artificial Sequence
<220> FEATURE:
<223> OTHER INFORMATION: Synthetic Construct

<400> SEQUENCE: 218

Thr Gln Ser Pro Ser Ser Leu Ser Ala Ser Val Gly Asp Arg Val Ile
1               5                   10                  15

Ile Thr Cys Arg Gly Ser Gln Thr Ile Asp Asn Tyr Leu Asn Trp Tyr
            20                  25                  30

Gln Gln Lys Pro Gly Lys Ala Pro Arg Leu Leu Ile Ser Ala Ala Ser
        35                  40                  45
```

```
Ser Leu Gln Gly Gly Val Pro Ser Arg Phe Ser Gly Ser Gly Tyr Gly
    50                  55                  60

Thr Asp Phe Thr Leu Thr Ile Ser Ser Leu Gln Pro Glu Asp Phe Ala
65                  70                  75                  80

Thr Tyr Tyr Cys Gln Gln Thr Ser Ser Thr Pro Tyr Thr Phe Gly Gln
                85                  90                  95

Gly Thr Lys Val Glu Ile Lys Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln Trp Lys Val Asp Asn
    130                 135                 140

Ala Leu Gln Ser Gly Asn Ser Gln Glu Ser Val Thr Glu Gln Asp Ser
145                 150                 155                 160

Lys Asp Ser Thr Tyr Ser Leu Ser Ser Thr Leu Thr Leu Ser Lys Ala
                165                 170                 175

Asp Tyr Glu Lys His Lys Val Tyr Ala Cys Glu Val Thr His Gln Gly
            180                 185                 190

Leu Ser Ser Pro Val Thr Lys Ser Phe Asn Arg Gly Glu Cys Lys
        195                 200                 205


<210> SEQ ID NO 219
<211> LENGTH: 363
<212> TYPE: DNA
<213> ORGANISM: Artificial Sequence
<220> FEATURE:
<223> OTHER INFORMATION: Synthetic Construct

<400> SEQUENCE: 219

gtgcagctgg tggagtctgg gggaaccctg ggacagccgg gggggtccct gagactctcc     60

tgtacagcct ctggattcac ctttaataga tttgccatca actgggtccg ccaggctcca    120

gggaaggggc tggaatgggt cgccgctatt agtggcactg gtgctgtcac atactacgca    180

gactccgtgg agggtcggtt ctccatctcc agagagaatt ccaacaacac ggtttttctg    240

gaaatgaaca acctgagagg cgaagacacg gccgtatatt tctgtgcgaa agatcggact    300

ccggtgacaa actattacgg catggacgtc tggggccaag ggaccacggt caccgtctcc    360

tca                                                                  363


<210> SEQ ID NO 220
<211> LENGTH: 312
<212> TYPE: DNA
<213> ORGANISM: Artificial Sequence
<220> FEATURE:
<223> OTHER INFORMATION: Synthetic Construct

<400> SEQUENCE: 220

agacccagtc tccatcgtcc ctgtctgcat ctgtgggaga cagagtcatc atcacttgcc     60

ggggaagtca gaccattgac aattatttaa attggtatca gcagaaacct gggaaagccc    120

ccaggctcct tatctctgcg gcatccagct tgcaaggggg ggtcccttca aggttcagtg    180

gcagtggata tgggacggat ttcaccctca ccatcagcag tctgcaacct gaagattttg    240

caacttacta ctgtcagcag acttccagta ccccgtacac ttttggccag gggaccaagg    300

tggagatcaa ac                                                        312


<210> SEQ ID NO 221
<211> LENGTH: 8
```

<212> TYPE: PRT
<213> ORGANISM: Artificial Sequence
<220> FEATURE:
<223> OTHER INFORMATION: Synthetic Construct

<400> SEQUENCE: 221

Gly Phe Thr Phe Ser Ile Phe Gly
1 5

<210> SEQ ID NO 222
<211> LENGTH: 8
<212> TYPE: PRT
<213> ORGANISM: Artificial Sequence
<220> FEATURE:
<223> OTHER INFORMATION: Synthetic Construct

<400> SEQUENCE: 222

Ile Ser Gly Thr Gly Glu Ile Thr
1 5

<210> SEQ ID NO 223
<211> LENGTH: 15
<212> TYPE: PRT
<213> ORGANISM: Artificial Sequence
<220> FEATURE:
<223> OTHER INFORMATION: Synthetic Construct

<400> SEQUENCE: 223

Ala Lys Glu Arg Thr Lys Tyr Gln Leu Ala Tyr Pro Phe Asp Tyr
1 5 10 15

<210> SEQ ID NO 224
<211> LENGTH: 6
<212> TYPE: PRT
<213> ORGANISM: Artificial Sequence
<220> FEATURE:
<223> OTHER INFORMATION: Synthetic Construct

<400> SEQUENCE: 224

Gln Asp Ile Thr Thr Tyr
1 5

<210> SEQ ID NO 225
<211> LENGTH: 3
<212> TYPE: PRT
<213> ORGANISM: Artificial Sequence
<220> FEATURE:
<223> OTHER INFORMATION: Synthetic Construct

<400> SEQUENCE: 225

Asp Ala Ser
1

<210> SEQ ID NO 226
<211> LENGTH: 9
<212> TYPE: PRT
<213> ORGANISM: Artificial Sequence
<220> FEATURE:
<223> OTHER INFORMATION: Synthetic Construct

<400> SEQUENCE: 226

Gln Gln Tyr Glu Asn Phe Pro Arg Thr
1 5

<210> SEQ ID NO 227
<211> LENGTH: 121
<212> TYPE: PRT

<213> ORGANISM: Artificial Sequence
<220> FEATURE:
<223> OTHER INFORMATION: Synthetic Construct

<400> SEQUENCE: 227

```
Val Gln Leu Val Glu Ser Gly Gly Gly Leu Val Gln Pro Gly Gly Ser
1               5                   10                  15

Leu Arg Leu Ser Cys Thr Ala Ser Gly Phe Thr Phe Ser Ile Phe Gly
            20                  25                  30

Met Ser Trp Val Arg Gln Ala Pro Gly Lys Gly Leu Glu Trp Val Ser
        35                  40                  45

Ser Ile Ser Gly Thr Gly Glu Ile Thr Lys Tyr Thr Asp Ser Val Lys
    50                  55                  60

Gly Arg Phe Thr Ile Ser Arg Asp Asn Ser Lys Thr Thr Val Tyr Leu
65                  70                  75                  80

Gln Met Lys Ser Leu Arg Ala Glu Asp Thr Ala Phe Tyr Phe Cys Ala
                85                  90                  95

Lys Glu Arg Thr Lys Tyr Gln Leu Ala Tyr Pro Phe Asp Tyr Trp Gly
            100                 105                 110

Gln Gly Thr Leu Val Thr Val Ser Ser
        115                 120
```

<210> SEQ ID NO 228
<211> LENGTH: 103
<212> TYPE: PRT
<213> ORGANISM: Artificial Sequence
<220> FEATURE:
<223> OTHER INFORMATION: Synthetic Construct

<400> SEQUENCE: 228

```
Thr Gln Ser Pro Ser Ser Leu Ser Ala Ser Val Gly Asp Arg Val Thr
1               5                   10                  15

Ile Thr Cys Gln Ala Ser Gln Asp Ile Thr Thr Tyr Leu Ser Trp Tyr
            20                  25                  30

Gln Gln Ile Pro Gly Lys Ala Pro Lys Leu Leu Ile Ser Asp Ala Ser
        35                  40                  45

Phe Leu Gln Ala Gly Val Pro Ser Arg Phe Ser Gly Ser Gly Ser Gly
    50                  55                  60

Thr Asp Phe Thr Phe Thr Ile Thr Asn Leu Gln Pro Glu Asp Val Ala
65                  70                  75                  80

Thr Tyr Tyr Cys Gln Gln Tyr Glu Asn Phe Pro Arg Thr Phe Gly Gly
                85                  90                  95

Gly Thr Lys Val Glu Ile Arg
            100
```

<210> SEQ ID NO 229
<211> LENGTH: 24
<212> TYPE: PRT
<213> ORGANISM: Artificial Sequence
<220> FEATURE:
<223> OTHER INFORMATION: Synthetic Construct

<400> SEQUENCE: 229

```
Val Gln Leu Val Glu Ser Gly Gly Gly Leu Val Gln Pro Gly Gly Ser
1               5                   10                  15

Leu Arg Leu Ser Cys Thr Ala Ser
            20
```

<210> SEQ ID NO 230

<211> LENGTH: 17
<212> TYPE: PRT
<213> ORGANISM: Artificial Sequence
<220> FEATURE:
<223> OTHER INFORMATION: Synthetic Construct

<400> SEQUENCE: 230

Met Ser Trp Val Arg Gln Ala Pro Gly Lys Gly Leu Glu Trp Val Ser
1 5 10 15

Ser

<210> SEQ ID NO 231
<211> LENGTH: 38
<212> TYPE: PRT
<213> ORGANISM: Artificial Sequence
<220> FEATURE:
<223> OTHER INFORMATION: Synthetic Construct

<400> SEQUENCE: 231

Lys Tyr Thr Asp Ser Val Lys Gly Arg Phe Thr Ile Ser Arg Asp Asn
1 5 10 15

Ser Lys Thr Thr Val Tyr Leu Gln Met Lys Ser Leu Arg Ala Glu Asp
20 25 30

Thr Ala Phe Tyr Phe Cys
35

<210> SEQ ID NO 232
<211> LENGTH: 11
<212> TYPE: PRT
<213> ORGANISM: Artificial Sequence
<220> FEATURE:
<223> OTHER INFORMATION: Synthetic Construct

<400> SEQUENCE: 232

Trp Gly Gln Gly Thr Leu Val Thr Val Ser Ser
1 5 10

<210> SEQ ID NO 233
<211> LENGTH: 22
<212> TYPE: PRT
<213> ORGANISM: Artificial Sequence
<220> FEATURE:
<223> OTHER INFORMATION: Synthetic Construct

<400> SEQUENCE: 233

Thr Gln Ser Pro Ser Ser Leu Ser Ala Ser Val Gly Asp Arg Val Thr
1 5 10 15

Ile Thr Cys Gln Ala Ser
20

<210> SEQ ID NO 234
<211> LENGTH: 17
<212> TYPE: PRT
<213> ORGANISM: Artificial Sequence
<220> FEATURE:
<223> OTHER INFORMATION: Synthetic Construct

<400> SEQUENCE: 234

Leu Ser Trp Tyr Gln Gln Ile Pro Gly Lys Ala Pro Lys Leu Leu Ile
1 5 10 15

Ser

<210> SEQ ID NO 235
<211> LENGTH: 36

<212> TYPE: PRT
<213> ORGANISM: Artificial Sequence
<220> FEATURE:
<223> OTHER INFORMATION: Synthetic Construct

<400> SEQUENCE: 235

```
Phe Leu Gln Ala Gly Val Pro Ser Arg Phe Ser Gly Ser Gly Ser Gly
1               5                   10                  15

Thr Asp Phe Thr Phe Thr Ile Thr Asn Leu Gln Pro Glu Asp Val Ala
            20                  25                  30

Thr Tyr Tyr Cys
        35
```

<210> SEQ ID NO 236
<211> LENGTH: 10
<212> TYPE: PRT
<213> ORGANISM: Artificial Sequence
<220> FEATURE:
<223> OTHER INFORMATION: Synthetic Construct

<400> SEQUENCE: 236

```
Phe Gly Gly Gly Thr Lys Val Glu Ile Arg
1               5                   10
```

<210> SEQ ID NO 237
<211> LENGTH: 448
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 237

```
Val Gln Leu Val Glu Ser Gly Gly Gly Leu Val Gln Pro Gly Gly Ser
1               5                   10                  15

Leu Arg Leu Ser Cys Thr Ala Ser Gly Phe Thr Phe Ser Ile Phe Gly
            20                  25                  30

Met Ser Trp Val Arg Gln Ala Pro Gly Lys Gly Leu Glu Trp Val Ser
        35                  40                  45

Ser Ile Ser Gly Thr Gly Glu Ile Thr Lys Tyr Thr Asp Ser Val Lys
    50                  55                  60

Gly Arg Phe Thr Ile Ser Arg Asp Asn Ser Lys Thr Thr Val Tyr Leu
65                  70                  75                  80

Gln Met Lys Ser Leu Arg Ala Glu Asp Thr Ala Phe Tyr Phe Cys Ala
                85                  90                  95

Lys Glu Arg Thr Lys Tyr Gln Leu Ala Tyr Pro Phe Asp Tyr Trp Gly
            100                 105                 110

Gln Gly Thr Leu Val Thr Val Ser Ser Lys Gly Pro Ser Val Phe Pro
        115                 120                 125

Leu Ala Pro Ser Ser Lys Ser Thr Ser Gly Gly Thr Ala Ala Leu Gly
    130                 135                 140

Xaa Leu Val Lys Asp Tyr Phe Pro Glu Pro Val Thr Val Ser Trp Asn
```

```
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Xaa Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Xaa Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 238
<211> LENGTH: 207
<212> TYPE: PRT
<213> ORGANISM: Artificial Sequence
<220> FEATURE:
<223> OTHER INFORMATION: Synthetic Construct

<400> SEQUENCE: 238

Thr Gln Ser Pro Ser Ser Leu Ser Ala Ser Val Gly Asp Arg Val Thr
1               5                   10                  15

Ile Thr Cys Gln Ala Ser Gln Asp Ile Thr Thr Tyr Leu Ser Trp Tyr
            20                  25                  30

Gln Gln Ile Pro Gly Lys Ala Pro Lys Leu Leu Ile Ser Asp Ala Ser
        35                  40                  45

Phe Leu Gln Ala Gly Val Pro Ser Arg Phe Ser Gly Ser Gly Ser Gly
    50                  55                  60

Thr Asp Phe Thr Phe Thr Ile Thr Asn Leu Gln Pro Glu Asp Val Ala
```

```
65                  70                  75                  80

Thr Tyr Tyr Cys Gln Gln Tyr Glu Asn Phe Pro Arg Thr Phe Gly Gly
                85                  90                  95

Gly Thr Lys Val Glu Ile Arg Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln Trp Lys Val Asp Asn
    130                 135                 140

Ala Leu Gln Ser Gly Asn Ser Gln Glu Ser Val Thr Glu Gln Asp Ser
145                 150                 155                 160

Lys Asp Ser Thr Tyr Ser Leu Ser Ser Thr Leu Thr Leu Ser Lys Ala
                165                 170                 175

Asp Tyr Glu Lys His Lys Val Tyr Ala Cys Glu Val Thr His Gln Gly
            180                 185                 190

Leu Ser Ser Pro Val Thr Lys Ser Phe Asn Arg Gly Glu Cys Lys
        195                 200                 205
```

<210> SEQ ID NO 239
<211> LENGTH: 364
<212> TYPE: DNA
<213> ORGANISM: Artificial Sequence
<220> FEATURE:
<223> OTHER INFORMATION: Synthetic Construct

<400> SEQUENCE: 239

```
gtgcagctgg tggagtctgg gggaggcttg gtacagcctg gggggtccct gagactctcg     60

tgtactgcct ctggcttcac ttttagcatc tttggcatga gttgggtccg ccaggctcca    120

gggaaggggc tggagtgggt ctcaagtatc agtggtactg gtgaaattac gaaatacaca    180

gactccgtga agggccggtt caccatctcc agagacaatt ccaagactac cgtgtatctg    240

cagatgaaga gcctgagagc cgaggacacg gccttttatt tctgtgcaaa agaaagaacg    300

aagtatcaat tggcataccc ctttgactac tggggccagg gaaccctggt caccgtctcc    360

tcgg                                                                 364
```

<210> SEQ ID NO 240
<211> LENGTH: 310
<212> TYPE: DNA
<213> ORGANISM: Artificial Sequence
<220> FEATURE:
<223> OTHER INFORMATION: Synthetic Construct

<400> SEQUENCE: 240

```
acccagtctc catcctccct gtctgcttct gttggagaca gagtcaccat cacttgccag     60

gcgagtcaag acattaccac ttatttgagt tggtatcagc agataccagg gaaagcccct    120

aaactcctga tctccgatgc atcctttttg caagcagggg tcccttcaag attcagtgga    180

agtgggtctg ggacagattt tactttcacc atcaccaacc tgcagcctga ggatgttgca    240

acatactact gtcaacagta tgagaatttc ccgcgaactt tcggcggagg gaccaaggtg    300

gagatcagac                                                           310
```

<210> SEQ ID NO 241
<211> LENGTH: 8
<212> TYPE: PRT
<213> ORGANISM: Artificial Sequence
<220> FEATURE:
<223> OTHER INFORMATION: Synthetic Construct

<400> SEQUENCE: 241

Gly Asp Ser Ile Ser Ser Tyr Tyr
1 5

<210> SEQ ID NO 242
<211> LENGTH: 7
<212> TYPE: PRT
<213> ORGANISM: Artificial Sequence
<220> FEATURE:
<223> OTHER INFORMATION: Synthetic Construct

<400> SEQUENCE: 242

Ile Phe Thr Ser Gly Ser Thr
1 5

<210> SEQ ID NO 243
<211> LENGTH: 20
<212> TYPE: PRT
<213> ORGANISM: Artificial Sequence
<220> FEATURE:
<223> OTHER INFORMATION: Synthetic Construct

<400> SEQUENCE: 243

Ala Lys His Thr Arg Asp Phe Trp Ser Asp Asp Ser Arg Val His Trp
1 5 10 15

Tyr Phe Asn Leu
20

<210> SEQ ID NO 244
<211> LENGTH: 7
<212> TYPE: PRT
<213> ORGANISM: Artificial Sequence
<220> FEATURE:
<223> OTHER INFORMATION: Synthetic Construct

<400> SEQUENCE: 244

Gln Ser Val Ser Asn Asn Phe
1 5

<210> SEQ ID NO 245
<211> LENGTH: 3
<212> TYPE: PRT
<213> ORGANISM: Artificial Sequence
<220> FEATURE:
<223> OTHER INFORMATION: Synthetic Construct

<400> SEQUENCE: 245

Gly Ala Ser
1

<210> SEQ ID NO 246
<211> LENGTH: 9
<212> TYPE: PRT
<213> ORGANISM: Artificial Sequence
<220> FEATURE:
<223> OTHER INFORMATION: Synthetic Construct

<400> SEQUENCE: 246

Gln Gln Tyr Asp Ser Ser Pro Tyr Thr
1 5

<210> SEQ ID NO 247
<211> LENGTH: 121
<212> TYPE: PRT
<213> ORGANISM: Artificial Sequence
<220> FEATURE:
<223> OTHER INFORMATION: Synthetic Construct

<400> SEQUENCE: 247

Glu Ser Gly Pro Gly Leu Val Lys Pro Ser Glu Thr Leu Ser Leu Thr
1               5                   10                  15

Cys Thr Val Ser Gly Asp Ser Ile Ser Ser Tyr Tyr Trp Ser Trp Ile
            20                  25                  30

Arg Gln Pro Ala Gly Lys Gly Leu Glu Trp Ile Gly Arg Ile Phe Thr
        35                  40                  45

Ser Gly Ser Thr Asn Ile Asn Pro Ser Leu Lys Ser Arg Val Thr Met
    50                  55                  60

Ser Val Asp Thr Ser Lys Asn Gln Phe Ser Leu Gln Leu Gly Ser Val
65                  70                  75                  80

Thr Ala Ala Asp Thr Ala Ile Tyr Tyr Cys Ala Lys His Thr Arg Asp
                85                  90                  95

Phe Trp Ser Asp Asp Ser Arg Val His Trp Tyr Phe Asn Leu Trp Gly
            100                 105                 110

Arg Gly Thr Leu Val Thr Val Ser Ser
        115                 120

<210> SEQ ID NO 248
<211> LENGTH: 103
<212> TYPE: PRT
<213> ORGANISM: Artificial Sequence
<220> FEATURE:
<223> OTHER INFORMATION: Synthetic Construct

<400> SEQUENCE: 248

Gln Ser Pro Gly Thr Leu Ser Leu Ser Pro Gly Glu Arg Ala Thr Leu
1               5                   10                  15

Ser Cys Arg Ala Ser Gln Ser Val Ser Asn Asn Phe Leu Ala Trp Tyr
            20                  25                  30

Gln Gln Gln Pro Gly Gln Ala Pro Ser Leu Leu Ile Tyr Gly Ala Ser
        35                  40                  45

Thr Arg Ala Thr Gly Ile Pro Asp Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80

Val Tyr Phe Cys Gln Gln Tyr Asp Ser Ser Pro Tyr Thr Phe Gly Gln
                85                  90                  95

Gly Thr Lys Leu Glu Ile Lys
            100

<210> SEQ ID NO 249
<211> LENGTH: 20
<212> TYPE: PRT
<213> ORGANISM: Artificial Sequence
<220> FEATURE:
<223> OTHER INFORMATION: Synthetic Construct

<400> SEQUENCE: 249

Glu Ser Gly Pro Gly Leu Val Lys Pro Ser Glu Thr Leu Ser Leu Thr
1               5                   10                  15

Cys Thr Val Ser
            20

<210> SEQ ID NO 250
<211> LENGTH: 17

<212> TYPE: PRT
<213> ORGANISM: Artificial Sequence
<220> FEATURE:
<223> OTHER INFORMATION: Synthetic Construct

<400> SEQUENCE: 250

Trp Ser Trp Ile Arg Gln Pro Ala Gly Lys Gly Leu Glu Trp Ile Gly
1 5 10 15

Arg

<210> SEQ ID NO 251
<211> LENGTH: 38
<212> TYPE: PRT
<213> ORGANISM: Artificial Sequence
<220> FEATURE:
<223> OTHER INFORMATION: Synthetic Construct

<400> SEQUENCE: 251

Asn Ile Asn Pro Ser Leu Lys Ser Arg Val Thr Met Ser Val Asp Thr
1 5 10 15

Ser Lys Asn Gln Phe Ser Leu Gln Leu Gly Ser Val Thr Ala Ala Asp
20 25 30

Thr Ala Ile Tyr Tyr Cys
35

<210> SEQ ID NO 252
<211> LENGTH: 11
<212> TYPE: PRT
<213> ORGANISM: Artificial Sequence
<220> FEATURE:
<223> OTHER INFORMATION: Synthetic Construct

<400> SEQUENCE: 252

Trp Gly Arg Gly Thr Leu Val Thr Val Ser Ser
1 5 10

<210> SEQ ID NO 253
<211> LENGTH: 21
<212> TYPE: PRT
<213> ORGANISM: Artificial Sequence
<220> FEATURE:
<223> OTHER INFORMATION: Synthetic Construct

<400> SEQUENCE: 253

Gln Ser Pro Gly Thr Leu Ser Leu Ser Pro Gly Glu Arg Ala Thr Leu
1 5 10 15

Ser Cys Arg Ala Ser
20

<210> SEQ ID NO 254
<211> LENGTH: 17
<212> TYPE: PRT
<213> ORGANISM: Artificial Sequence
<220> FEATURE:
<223> OTHER INFORMATION: Synthetic Construct

<400> SEQUENCE: 254

Leu Ala Trp Tyr Gln Gln Gln Pro Gly Gln Ala Pro Ser Leu Leu Ile
1 5 10 15

Tyr

<210> SEQ ID NO 255
<211> LENGTH: 36
<212> TYPE: PRT

<213> ORGANISM: Artificial Sequence
<220> FEATURE:
<223> OTHER INFORMATION: Synthetic Construct

<400> SEQUENCE: 255

Thr Arg Ala Thr Gly Ile Pro Asp Arg Phe Ser Gly Ser Gly Ser Gly
1 5 10 15

Thr Asp Phe Thr Leu Thr Ile Ser Arg Leu Glu Pro Glu Asp Phe Ala
20 25 30

Val Tyr Phe Cys
35

<210> SEQ ID NO 256
<211> LENGTH: 10
<212> TYPE: PRT
<213> ORGANISM: Artificial Sequence
<220> FEATURE:
<223> OTHER INFORMATION: Synthetic Construct

<400> SEQUENCE: 256

Phe Gly Gln Gly Thr Lys Leu Glu Ile Lys
1 5 10

<210> SEQ ID NO 257
<211> LENGTH: 448
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 257

Glu Ser Gly Pro Gly Leu Val Lys Pro Ser Glu Thr Leu Ser Leu Thr
1 5 10 15

Cys Thr Val Ser Gly Asp Ser Ile Ser Ser Tyr Tyr Trp Ser Trp Ile
20 25 30

Arg Gln Pro Ala Gly Lys Gly Leu Glu Trp Ile Gly Arg Ile Phe Thr
35 40 45

Ser Gly Ser Thr Asn Ile Asn Pro Ser Leu Lys Ser Arg Val Thr Met
50 55 60

Ser Val Asp Thr Ser Lys Asn Gln Phe Ser Leu Gln Leu Gly Ser Val
65 70 75 80

Thr Ala Ala Asp Thr Ala Ile Tyr Tyr Cys Ala Lys His Thr Arg Asp
85 90 95

Phe Trp Ser Asp Asp Ser Arg Val His Trp Tyr Phe Asn Leu Trp Gly
100 105 110

Arg Gly Thr Leu Val Thr Val Ser Ser Lys Gly Pro Ser Val Phe Pro
115 120 125

Leu Ala Pro Ser Ser Lys Ser Thr Ser Gly Gly Thr Ala Ala Leu Gly
130 135 140

Xaa Leu Val Lys Asp Tyr Phe Pro Glu Pro Val Thr Val Ser Trp Asn
145 150 155 160

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Xaa Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Xaa Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 258
<211> LENGTH: 207
<212> TYPE: PRT
<213> ORGANISM: Artificial Sequence
<220> FEATURE:
<223> OTHER INFORMATION: Synthetic Construct

<400> SEQUENCE: 258

Gln Ser Pro Gly Thr Leu Ser Leu Ser Pro Gly Glu Arg Ala Thr Leu
1               5                   10                  15

Ser Cys Arg Ala Ser Gln Ser Val Ser Asn Asn Phe Leu Ala Trp Tyr
            20                  25                  30

Gln Gln Gln Pro Gly Gln Ala Pro Ser Leu Leu Ile Tyr Gly Ala Ser
        35                  40                  45

Thr Arg Ala Thr Gly Ile Pro Asp Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80
```

```
Val Tyr Phe Cys Gln Gln Tyr Asp Ser Ser Pro Tyr Thr Phe Gly Gln
                85                  90                  95

Gly Thr Lys Leu Glu Ile Lys Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln Trp Lys Val Asp Asn
    130                 135                 140

Ala Leu Gln Ser Gly Asn Ser Gln Glu Ser Val Thr Glu Gln Asp Ser
145                 150                 155                 160

Lys Asp Ser Thr Tyr Ser Leu Ser Ser Thr Leu Thr Leu Ser Lys Ala
                165                 170                 175

Asp Tyr Glu Lys His Lys Val Tyr Ala Cys Glu Val Thr His Gln Gly
            180                 185                 190

Leu Ser Ser Pro Val Thr Lys Ser Phe Asn Arg Gly Glu Cys Lys
        195                 200                 205


<210> SEQ ID NO 259
<211> LENGTH: 365
<212> TYPE: DNA
<213> ORGANISM: Artificial Sequence
<220> FEATURE:
<223> OTHER INFORMATION: Synthetic Construct

<400> SEQUENCE: 259

ggagtcgggc ccaggactgg tgaagccttc ggagaccctg tccctcacct gcactgtctc      60

tggtgactcc atcagtagtt attattggag ctggatccgg cagcccgccg ggaagggact     120

ggagtggatc gggcgtatct tcaccagtgg gagcaccaac atcaacccct ccctcaagag     180

tcgagtcacc atgtcagtag acacgtccaa aaatcagttc tccctgcagc tgggttcggt     240

gaccgccgcg gacacggcca tctattattg tgcgaaacat acccgcgatt tttggagtga     300

tgactctcgg gtccactggt acttcaatct ctggggccgt ggcaccctgg tcactgtctc     360

ctcag                                                                 365


<210> SEQ ID NO 260
<211> LENGTH: 310
<212> TYPE: DNA
<213> ORGANISM: Artificial Sequence
<220> FEATURE:
<223> OTHER INFORMATION: Synthetic Construct

<400> SEQUENCE: 260

cagtctccag gcaccctgtc tttgtctcca ggggaaagag ccaccctctc ctgcagggcc      60

agtcagagtg ttagcaacaa cttcttagcc tggtaccagc agcaacctgg ccaggctccc     120

agtctcctca tctatggtgc ttccactagg gccactggca tcccagacag gttcagtggc     180

agtgggtctg ggacagactt cactctcacc atcagcagac tggagcctga agattttgca     240

gtgtatttct gtcagcaata tgatagctca ccgtacactt ttggccaggg gaccaagctg     300

gagatcaaac                                                            310


<210> SEQ ID NO 261
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 261

Gly Phe Asn Phe Asp Asp Tyr Thr
1               5

<210> SEQ ID NO 262
<211> LENGTH: 8
<212> TYPE: PRT
<213> ORGANISM: Artificial Sequence
<220> FEATURE:
<223> OTHER INFORMATION: Synthetic Construct

<400> SEQUENCE: 262

Ile Lys Trp Asn Ser Asn Asn Ile
1               5

<210> SEQ ID NO 263
<211> LENGTH: 11
<212> TYPE: PRT
<213> ORGANISM: Artificial Sequence
<220> FEATURE:
<223> OTHER INFORMATION: Synthetic Construct

<400> SEQUENCE: 263

Val Lys Asp Asn Gly Phe Arg Gly Phe His Ile
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Synthetic Construct

<400> SEQUENCE: 264

Gln Ser Leu Leu His Arg Asn Gly Tyr Asn Tyr
1               5                   10

<210> SEQ ID NO 265
<211> LENGTH: 3
<212> TYPE: PRT
<213> ORGANISM: Artificial Sequence
<220> FEATURE:
<223> OTHER INFORMATION: Synthetic Construct

<400> SEQUENCE: 265

Leu Gly Ser
1

<210> SEQ ID NO 266
<211> LENGTH: 8
<212> TYPE: PRT
<213> ORGANISM: Artificial Sequence
<220> FEATURE:
<223> OTHER INFORMATION: Synthetic Construct

<400> SEQUENCE: 266

Met Gln Ala Leu Glu Ser Trp Thr
1               5

<210> SEQ ID NO 267
<211> LENGTH: 117
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 267

```
Val Xaa Xaa Val Glu Ser Gly Gly Gly Phe Val Gln Pro Gly Gly Ser
1               5                   10                  15

Leu Arg Leu Ser Cys Val Ala Ser Gly Phe Asn Phe Asp Asp Tyr Thr
            20                  25                  30

Met His Trp Val Arg Gln Val Ala Gly Thr Gly Leu Glu Trp Val Ser
        35                  40                  45

Ser Ile Lys Trp Asn Ser Asn Asn Ile Asp Tyr Ala Asp Ser Val Lys
    50                  55                  60

Gly Arg Phe Thr Ile Ser Arg Asp Asn Ala Lys Asn Ser Leu Phe Leu
65                  70                  75                  80

Gln Met Asp Ser Leu Arg Val Glu Asp Thr Ala Phe Tyr Tyr Cys Val
                85                  90                  95

Lys Asp Asn Gly Phe Arg Gly Phe His Ile Trp Gly Gln Gly Thr Met
            100                 105                 110

Val Thr Val Ser Ser
        115
```

<210> SEQ ID NO 268
<211> LENGTH: 107
<212> TYPE: PRT
<213> ORGANISM: Artificial Sequence
<220> FEATURE:
<223> OTHER INFORMATION: Synthetic Construct

<400> SEQUENCE: 268

```
Thr Gln Ser Pro Leu Ser Leu Ser Val Thr Pro Gly Glu Ser Ala Ser
1               5                   10                  15

Ile Ser Cys Arg Ser Ser Gln Ser Leu Leu His Arg Asn Gly Tyr Asn
            20                  25                  30

Tyr Leu Asp Trp Tyr Leu Gln Lys Pro Gly Gln Ser Pro Gln Leu Leu
        35                  40                  45

Ile His Leu Gly Ser Lys Arg Ala Ser Gly Val Pro Asp Arg Phe Ser
    50                  55                  60

Gly Ser Gly Ser Gly Thr Asp Phe Thr Leu Lys Ile Ser Arg Val Glu
65                  70                  75                  80

Ala Glu Asp Val Gly Val Tyr Tyr Cys Met Gln Ala Leu Glu Ser Trp
                85                  90                  95

Thr Phe Gly Gln Gly Thr Lys Val Glu Ile Lys
            100                 105
```

<210> SEQ ID NO 269
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 269

```
Val Xaa Xaa Val Glu Ser Gly Gly Gly Phe Val Gln Pro Gly Gly Ser
1               5                   10                  15

Leu Arg Leu Ser Cys Val Ala Ser
            20
```

<210> SEQ ID NO 270
<211> LENGTH: 17
<212> TYPE: PRT
<213> ORGANISM: Artificial Sequence
<220> FEATURE:
<223> OTHER INFORMATION: Synthetic Construct

<400> SEQUENCE: 270

Met His Trp Val Arg Gln Val Ala Gly Thr Gly Leu Glu Trp Val Ser
1 5 10 15

Ser

<210> SEQ ID NO 271
<211> LENGTH: 38
<212> TYPE: PRT
<213> ORGANISM: Artificial Sequence
<220> FEATURE:
<223> OTHER INFORMATION: Synthetic Construct

<400> SEQUENCE: 271

Asp Tyr Ala Asp Ser Val Lys Gly Arg Phe Thr Ile Ser Arg Asp Asn
1 5 10 15

Ala Lys Asn Ser Leu Phe Leu Gln Met Asp Ser Leu Arg Val Glu Asp
20 25 30

Thr Ala Phe Tyr Tyr Cys
35

<210> SEQ ID NO 272
<211> LENGTH: 11
<212> TYPE: PRT
<213> ORGANISM: Artificial Sequence
<220> FEATURE:
<223> OTHER INFORMATION: Synthetic Construct

<400> SEQUENCE: 272

Trp Gly Gln Gly Thr Met Val Thr Val Ser Ser
1 5 10

<210> SEQ ID NO 273
<211> LENGTH: 22
<212> TYPE: PRT
<213> ORGANISM: Artificial Sequence
<220> FEATURE:
<223> OTHER INFORMATION: Synthetic Construct

<400> SEQUENCE: 273

Thr Gln Ser Pro Leu Ser Leu Ser Val Thr Pro Gly Glu Ser Ala Ser
1 5 10 15

Ile Ser Cys Arg Ser Ser
20

<210> SEQ ID NO 274
<211> LENGTH: 17
<212> TYPE: PRT
<213> ORGANISM: Artificial Sequence
<220> FEATURE:
<223> OTHER INFORMATION: Synthetic Construct

<400> SEQUENCE: 274

Leu Asp Trp Tyr Leu Gln Lys Pro Gly Gln Ser Pro Gln Leu Leu Ile
1 5 10 15

His

<210> SEQ ID NO 275
<211> LENGTH: 36
<212> TYPE: PRT
<213> ORGANISM: Artificial Sequence
<220> FEATURE:
<223> OTHER INFORMATION: Synthetic Construct

<400> SEQUENCE: 275

Lys Arg Ala Ser Gly Val Pro Asp Arg Phe Ser Gly Ser Gly Ser Gly
1 5 10 15

Thr Asp Phe Thr Leu Lys Ile Ser Arg Val Glu Ala Glu Asp Val Gly
20 25 30

Val Tyr Tyr Cys
35

<210> SEQ ID NO 276
<211> LENGTH: 10
<212> TYPE: PRT
<213> ORGANISM: Artificial Sequence
<220> FEATURE:
<223> OTHER INFORMATION: Synthetic Construct

<400> SEQUENCE: 276

Phe Gly Gln Gly Thr Lys Val Glu Ile Lys
1 5 10

<210> SEQ ID NO 277
<211> LENGTH: 444
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

<400> SEQUENCE: 277

Val Xaa Xaa Val Glu Ser Gly Gly Gly Phe Val Gln Pro Gly Gly Ser
1 5 10 15

Leu Arg Leu Ser Cys Val Ala Ser Gly Phe Asn Phe Asp Asp Tyr Thr
20 25 30

Met His Trp Val Arg Gln Val Ala Gly Thr Gly Leu Glu Trp Val Ser
35 40 45

Ser Ile Lys Trp Asn Ser Asn Asn Ile Asp Tyr Ala Asp Ser Val Lys
50 55 60

Gly Arg Phe Thr Ile Ser Arg Asp Asn Ala Lys Asn Ser Leu Phe Leu
65 70 75 80

Gln Met Asp Ser Leu Arg Val Glu Asp Thr Ala Phe Tyr Tyr Cys Val
85 90 95

Lys Asp Asn Gly Phe Arg Gly Phe His Ile Trp Gly Gln Gly Thr Met
100 105 110

```
Val Thr Val Ser Ser Lys Gly Pro Ser Val Phe Pro Leu Ala Pro Ser
        115                 120                 125

Ser Lys Ser Thr Ser Gly Gly Thr Ala Ala Leu Gly Xaa Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Xaa Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Xaa Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 278
<211> LENGTH: 211
<212> TYPE: PRT
<213> ORGANISM: Artificial Sequence
<220> FEATURE:
<223> OTHER INFORMATION: Synthetic Construct

<400> SEQUENCE: 278

Thr Gln Ser Pro Leu Ser Leu Ser Val Thr Pro Gly Glu Ser Ala Ser
1               5                   10                  15

Ile Ser Cys Arg Ser Ser Gln Ser Leu Leu His Arg Asn Gly Tyr Asn
            20                  25                  30
```

```
Tyr Leu Asp Trp Tyr Leu Gln Lys Pro Gly Gln Ser Pro Gln Leu Leu
        35                  40                  45

Ile His Leu Gly Ser Lys Arg Ala Ser Gly Val Pro Asp Arg Phe Ser
    50                  55                  60

Gly Ser Gly Ser Gly Thr Asp Phe Thr Leu Lys Ile Ser Arg Val Glu
65                  70                  75                  80

Ala Glu Asp Val Gly Val Tyr Tyr Cys Met Gln Ala Leu Glu Ser Trp
                85                  90                  95

Thr Phe Gly Gln Gly Thr Lys Val Glu Ile Lys Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210
```

<210> SEQ ID NO 279
<211> LENGTH: 354
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 279

```
aggtgncagn ggtggagtct gggggaggct tcgtacagcc tggcgggtcc ctgagactct     60

cctgtgtagc ctctggattc aactttgatg attataccat gcactgggtc cgacaagttg    120

cagggacggg cctggagtgg gtctcaagta ttaaatggaa ctctaataac atagactatg    180

cggactctgt gaagggccgg ttcaccatct ccagagacaa cgccaagaat tccctgtttc    240

tgcagatgga tagtctcaga gttgaagaca cggccttcta ttactgtgta aaagataatg    300

gcttccgtgg ttttcatata tggggccaag ggacaatggt caccgtctct tcag          354
```

<210> SEQ ID NO 280
<211> LENGTH: 323
<212> TYPE: DNA
<213> ORGANISM: Artificial Sequence
<220> FEATURE:
<223> OTHER INFORMATION: Synthetic Construct

<400> SEQUENCE: 280

```
gactcagtct ccactctccc tgtccgtcac ccctggagag tcggcctcca tctcctgcag     60

gtctagtcag agcctcctgc atcgtaatgg atacaactat ttggattggt acctgcagaa    120
```

gccagggcag tctccacaac tcctgatcca tttgggttct aagcgggcct ccggggtccc 180
tgacaggttc agtggcagtg gatcaggcac agattttaca ctgaaaatca gcagagtgga 240
ggctgaggat gttggggttt attactgcat gcaagctcta gaaagctgga cgttcggcca 300
agggaccaag gtggaaatca aac 323

<210> SEQ ID NO 281
<211> LENGTH: 8
<212> TYPE: PRT
<213> ORGANISM: Artificial Sequence
<220> FEATURE:
<223> OTHER INFORMATION: Synthetic Construct

<400> SEQUENCE: 281

Gly Tyr Thr Phe Thr Thr Tyr Ala
1 5

<210> SEQ ID NO 282
<211> LENGTH: 8
<212> TYPE: PRT
<213> ORGANISM: Artificial Sequence
<220> FEATURE:
<223> OTHER INFORMATION: Synthetic Construct

<400> SEQUENCE: 282

Ile Asn Ala Gly Asn Gly Asn Pro
1 5

<210> SEQ ID NO 283
<211> LENGTH: 14
<212> TYPE: PRT
<213> ORGANISM: Artificial Sequence
<220> FEATURE:
<223> OTHER INFORMATION: Synthetic Construct

<400> SEQUENCE: 283

Ala Arg Asp Ala Ala Gly Thr Arg Gly Asn Trp Leu Asp Pro
1 5 10

<210> SEQ ID NO 284
<211> LENGTH: 12
<212> TYPE: PRT
<213> ORGANISM: Artificial Sequence
<220> FEATURE:
<223> OTHER INFORMATION: Synthetic Construct

<400> SEQUENCE: 284

Gln Ser Val Leu Tyr Ser Ser Asn Asn Lys Asn Tyr
1 5 10

<210> SEQ ID NO 285
<211> LENGTH: 3
<212> TYPE: PRT
<213> ORGANISM: Artificial Sequence
<220> FEATURE:
<223> OTHER INFORMATION: Synthetic Construct

<400> SEQUENCE: 285

Trp Ala Ser
1

<210> SEQ ID NO 286
<211> LENGTH: 9
<212> TYPE: PRT
<213> ORGANISM: Artificial Sequence
<220> FEATURE:
<223> OTHER INFORMATION: Synthetic Construct

<400> SEQUENCE: 286

Gln Gln Tyr Tyr Ser Thr Pro Leu Thr
1 5

<210> SEQ ID NO 287
<211> LENGTH: 116
<212> TYPE: PRT
<213> ORGANISM: Artificial Sequence
<220> FEATURE:
<223> OTHER INFORMATION: Synthetic Construct

<400> SEQUENCE: 287

Gln Ser Gly Ala Glu Val Lys Lys Pro Gly Ala Ser Val Lys Ile Ser
1 5 10 15

Cys Lys Ala Ser Gly Tyr Thr Phe Thr Thr Tyr Ala Met His Trp Val
20 25 30

Arg Gln Ala Pro Gly Gln Arg Leu Glu Trp Met Gly Gly Ile Asn Ala
35 40 45

Gly Asn Gly Asn Pro Lys Tyr Ser Glu Lys Phe Gln Asp Arg Val Thr
50 55 60

Ile Thr Arg Asp Thr Ser Ala Thr Thr Ala Tyr Met Glu Leu Ser Ser
65 70 75 80

Leu Arg Ser Glu Asp Thr Ala Val Tyr Tyr Cys Ala Arg Asp Ala Ala
85 90 95

Gly Thr Arg Gly Asn Trp Leu Asp Pro Trp Gly Gln Gly Thr Leu Val
100 105 110

Thr Val Ser Ser
115

<210> SEQ ID NO 288
<211> LENGTH: 108
<212> TYPE: PRT
<213> ORGANISM: Artificial Sequence
<220> FEATURE:
<223> OTHER INFORMATION: Synthetic Construct

<400> SEQUENCE: 288

Gln Ser Pro Asp Ser Leu Ala Val Ser Leu Gly Glu Arg Ala Thr Ile
1 5 10 15

Asn Cys Lys Ser Ser Gln Ser Val Leu Tyr Ser Ser Asn Asn Lys Asn
20 25 30

Tyr Leu Ala Trp Tyr Gln Gln Lys Pro Gly Gln Pro Pro Lys Leu Leu
35 40 45

Ile Tyr Trp Ala Ser Thr Arg Glu Ser Gly Val Pro Asp Arg Phe Ser
50 55 60

Gly Ser Gly Ser Gly Thr Asp Phe Thr Leu Thr Ile Ser Ser Leu Gln
65 70 75 80

Ala Glu Asp Val Ala Val Tyr Tyr Cys Gln Gln Tyr Tyr Ser Thr Pro
85 90 95

Leu Thr Phe Gly Gly Gly Thr Lys Val Glu Ile Lys
100 105

<210> SEQ ID NO 289
<211> LENGTH: 20
<212> TYPE: PRT
<213> ORGANISM: Artificial Sequence
<220> FEATURE:

<223> OTHER INFORMATION: Synthetic Construct

<400> SEQUENCE: 289

Gln Ser Gly Ala Glu Val Lys Lys Pro Gly Ala Ser Val Lys Ile Ser
1               5                   10                  15

Cys Lys Ala Ser
            20

<210> SEQ ID NO 290
<211> LENGTH: 17
<212> TYPE: PRT
<213> ORGANISM: Artificial Sequence
<220> FEATURE:
<223> OTHER INFORMATION: Synthetic Construct

<400> SEQUENCE: 290

Met His Trp Val Arg Gln Ala Pro Gly Gln Arg Leu Glu Trp Met Gly
1               5                   10                  15

Gly

<210> SEQ ID NO 291
<211> LENGTH: 38
<212> TYPE: PRT
<213> ORGANISM: Artificial Sequence
<220> FEATURE:
<223> OTHER INFORMATION: Synthetic Construct

<400> SEQUENCE: 291

Lys Tyr Ser Glu Lys Phe Gln Asp Arg Val Thr Ile Thr Arg Asp Thr
1               5                   10                  15

Ser Ala Thr Thr Ala Tyr Met Glu Leu Ser Ser Leu Arg Ser Glu Asp
            20                  25                  30

Thr Ala Val Tyr Tyr Cys
        35

<210> SEQ ID NO 292
<211> LENGTH: 11
<212> TYPE: PRT
<213> ORGANISM: Artificial Sequence
<220> FEATURE:
<223> OTHER INFORMATION: Synthetic Construct

<400> SEQUENCE: 292

Trp Gly Gln Gly Thr Leu Val Thr Val Ser Ser
1               5                   10

<210> SEQ ID NO 293
<211> LENGTH: 21
<212> TYPE: PRT
<213> ORGANISM: Artificial Sequence
<220> FEATURE:
<223> OTHER INFORMATION: Synthetic Construct

<400> SEQUENCE: 293

Gln Ser Pro Asp Ser Leu Ala Val Ser Leu Gly Glu Arg Ala Thr Ile
1               5                   10                  15

Asn Cys Lys Ser Ser
            20

<210> SEQ ID NO 294
<211> LENGTH: 17
<212> TYPE: PRT
<213> ORGANISM: Artificial Sequence
<220> FEATURE:

<223> OTHER INFORMATION: Synthetic Construct

<400> SEQUENCE: 294

Leu Ala Trp Tyr Gln Gln Lys Pro Gly Gln Pro Pro Lys Leu Leu Ile
1 5 10 15

Tyr

<210> SEQ ID NO 295
<211> LENGTH: 36
<212> TYPE: PRT
<213> ORGANISM: Artificial Sequence
<220> FEATURE:
<223> OTHER INFORMATION: Synthetic Construct

<400> SEQUENCE: 295

Thr Arg Glu Ser Gly Val Pro Asp Arg Phe Ser Gly Ser Gly Ser Gly
1 5 10 15

Thr Asp Phe Thr Leu Thr Ile Ser Ser Leu Gln Ala Glu Asp Val Ala
20 25 30

Val Tyr Tyr Cys
35

<210> SEQ ID NO 296
<211> LENGTH: 10
<212> TYPE: PRT
<213> ORGANISM: Artificial Sequence
<220> FEATURE:
<223> OTHER INFORMATION: Synthetic Construct

<400> SEQUENCE: 296

Phe Gly Gly Gly Thr Lys Val Glu Ile Lys
1 5 10

<210> SEQ ID NO 297
<211> LENGTH: 443
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (354)..(354)
<223> OTHER INFORMATION: Xaa can be any naturally occurring amino acid

<400> SEQUENCE: 297

Gln Ser Gly Ala Glu Val Lys Lys Pro Gly Ala Ser Val Lys Ile Ser
1 5 10 15

Cys Lys Ala Ser Gly Tyr Thr Phe Thr Thr Tyr Ala Met His Trp Val
20 25 30

Arg Gln Ala Pro Gly Gln Arg Leu Glu Trp Met Gly Gly Ile Asn Ala
35 40 45

Gly Asn Gly Asn Pro Lys Tyr Ser Glu Lys Phe Gln Asp Arg Val Thr
50 55 60

Ile Thr Arg Asp Thr Ser Ala Thr Thr Ala Tyr Met Glu Leu Ser Ser
65 70 75 80

Leu Arg Ser Glu Asp Thr Ala Val Tyr Tyr Cys Ala Arg Asp Ala Ala

```
                85                  90                  95

Gly Thr Arg Gly Asn Trp Leu Asp Pro Trp Gly Gln Gly Thr Leu Val
            100                 105                 110

Thr Val Ser Ser Lys Gly Pro Ser Val Phe Pro Leu Ala Pro Ser Ser
        115                 120                 125

Lys Ser Thr Ser Gly Gly Thr Ala Ala Leu Gly Xaa Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Xaa Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Xaa Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 298
<211> LENGTH: 212
<212> TYPE: PRT
<213> ORGANISM: Artificial Sequence
<220> FEATURE:
<223> OTHER INFORMATION: Synthetic Construct

<400> SEQUENCE: 298

Gln Ser Pro Asp Ser Leu Ala Val Ser Leu Gly Glu Arg Ala Thr Ile
```

-continued 1 5 10 15

Asn Cys Lys Ser Ser Gln Ser Val Leu Tyr Ser Ser Asn Asn Lys Asn
20 25 30

Tyr Leu Ala Trp Tyr Gln Gln Lys Pro Gly Gln Pro Pro Lys Leu Leu
35 40 45

Ile Tyr Trp Ala Ser Thr Arg Glu Ser Gly Val Pro Asp Arg Phe Ser
50 55 60

Gly Ser Gly Ser Gly Thr Asp Phe Thr Leu Thr Ile Ser Ser Leu Gln
65 70 75 80

Ala Glu Asp Val Ala Val Tyr Tyr Cys Gln Gln Tyr Tyr Ser Thr Pro
85 90 95

Leu Thr Phe Gly Gly Gly Thr Lys Val Glu Ile Lys Ala Pro Ser Val
100 105 110

Phe Ile Phe Pro Pro Ser Asp Glu Gln Leu Lys Ser Gly Thr Ala Ser
115 120 125

Val Val Cys Leu Leu Asn Asn Phe Tyr Pro Arg Glu Ala Lys Val Gln
130 135 140

Trp Lys Val Asp Asn Ala Leu Gln Ser Gly Asn Ser Gln Glu Ser Val
145 150 155 160

Thr Glu Gln Asp Ser Lys Asp Ser Thr Tyr Ser Leu Ser Ser Thr Leu
165 170 175

Thr Leu Ser Lys Ala Asp Tyr Glu Lys His Lys Val Tyr Ala Cys Glu
180 185 190

Val Thr His Gln Gly Leu Ser Ser Pro Val Thr Lys Ser Phe Asn Arg
195 200 205

Gly Glu Cys Lys
210

<210> SEQ ID NO 299
<211> LENGTH: 350
<212> TYPE: DNA
<213> ORGANISM: Artificial Sequence
<220> FEATURE:
<223> OTHER INFORMATION: Synthetic Construct

<400> SEQUENCE: 299
gcagtccggg gctgaggtga agaagcctgg ggcctcagtg aagatttcct gcaaggcttc 60
tggatacacc ttcactactt atgctatgca ttgggtgcgc caggcccccg gacaaaggct 120
tgagtggatg ggagggatca acgctggcaa tggtaatcca aaatattcag agaagttcca 180
ggacagagtc accattacca gggacacatc cgcgaccaca gcctacatgg agctgagcag 240
cctgagatct gaggacacgg ctgtgtatta ctgtgcgaga gatgcggccg gcactcgagg 300
aaactggctc gacccctggg gccagggtac cctggtcacc gtctcctcag 350

<210> SEQ ID NO 300
<211> LENGTH: 326
<212> TYPE: DNA
<213> ORGANISM: Artificial Sequence
<220> FEATURE:
<223> OTHER INFORMATION: Synthetic Construct

<400> SEQUENCE: 300
ccagtctcca gactccctgg ctgtgtctct gggcgagagg gccaccatca actgcaagtc 60
cagccagagt gttttataca gctccaacaa taagaactac ttagcttggt accagcagaa 120
accaggacag cctcctaagc tgctcattta ctgggcatct actcgggaat ccggggtccc 180
tgaccgattc agtggcagcg ggtctgggac agatttcact ctcaccatca gcagcctgca 240
ggctgaagat gtggcagttt attactgtca gcaatattat agtactcctc tcactttcgg 300
cggagggacc aaggtggaga tcaaac 326

<210> SEQ ID NO 301
<211> LENGTH: 8
<212> TYPE: PRT
<213> ORGANISM: Artificial Sequence
<220> FEATURE:
<223> OTHER INFORMATION: Synthetic Construct

<400> SEQUENCE: 301

Gly Phe Thr Phe Thr Thr Tyr Ala
1 5

<210> SEQ ID NO 302
<211> LENGTH: 8
<212> TYPE: PRT
<213> ORGANISM: Artificial Sequence
<220> FEATURE:
<223> OTHER INFORMATION: Synthetic Construct

<400> SEQUENCE: 302

Ile Ser Gly Ser Gly Gly Ser Thr
1 5

<210> SEQ ID NO 303
<211> LENGTH: 14
<212> TYPE: PRT
<213> ORGANISM: Artificial Sequence
<220> FEATURE:
<223> OTHER INFORMATION: Synthetic Construct

<400> SEQUENCE: 303

Ala Lys Asp Trp Ser Ser Gly Tyr Leu Gly Tyr Phe Asp Tyr
1 5 10

<210> SEQ ID NO 304
<211> LENGTH: 12
<212> TYPE: PRT
<213> ORGANISM: Artificial Sequence
<220> FEATURE:
<223> OTHER INFORMATION: Synthetic Construct

<400> SEQUENCE: 304

Gln Ser Val Leu Tyr Ser Ser Asn Asn Lys Asn Tyr
1 5 10

<210> SEQ ID NO 305
<211> LENGTH: 3
<212> TYPE: PRT
<213> ORGANISM: Artificial Sequence
<220> FEATURE:
<223> OTHER INFORMATION: Synthetic Construct

<400> SEQUENCE: 305

Trp Ala Ser
1

<210> SEQ ID NO 306
<211> LENGTH: 9
<212> TYPE: PRT
<213> ORGANISM: Artificial Sequence
<220> FEATURE:
<223> OTHER INFORMATION: Synthetic Construct

<400> SEQUENCE: 306

Gln Gln Tyr Tyr Ser Thr Pro Leu Thr
1 5

<210> SEQ ID NO 307
<211> LENGTH: 117
<212> TYPE: PRT
<213> ORGANISM: Artificial Sequence
<220> FEATURE:
<223> OTHER INFORMATION: Synthetic Construct

<400> SEQUENCE: 307

Val Glu Ser Gly Gly Gly Leu Val Gln Pro Gly Gly Ser Leu Arg Leu
1 5 10 15

Ser Cys Ala Ala Ser Gly Phe Thr Phe Thr Thr Tyr Ala Met Thr Trp
20 25 30

Val Arg Gln Ala Pro Gly Lys Gly Leu Glu Trp Val Ser Ala Ile Ser
35 40 45

Gly Ser Gly Gly Ser Thr Tyr Tyr Ala Asp Ser Val Lys Gly Arg Phe
50 55 60

Thr Ile Ser Arg Asp Asn Ser Lys Asn Thr Leu Tyr Leu Gln Met Asn
65 70 75 80

Ser Leu Arg Ala Glu Asp Thr Ala Val Tyr Tyr Cys Ala Lys Asp Trp
85 90 95

Ser Ser Gly Tyr Leu Gly Tyr Phe Asp Tyr Trp Gly Gln Gly Thr Leu
100 105 110

Val Thr Val Ser Ser
115

<210> SEQ ID NO 308
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (99)..(99)
<223> OTHER INFORMATION: Xaa can be any naturally occurring amino acid

<400> SEQUENCE: 308

Gln Ser Pro Asp Ser Leu Ala Val Ser Leu Gly Glu Arg Ala Thr Ile
1 5 10 15

Asn Cys Lys Ser Ser Gln Ser Val Leu Tyr Ser Ser Asn Asn Lys Asn
20 25 30

Tyr Leu Ala Trp Tyr Gln Gln Lys Pro Gly Gln Pro Pro Lys Leu Leu
35 40 45

Ile Tyr Trp Ala Ser Thr Arg Glu Ser Gly Val Pro Asp Arg Phe Ser
50 55 60

Gly Ser Gly Ser Gly Thr Asp Phe Thr Leu Thr Ile Ser Ser Leu Gln
65 70 75 80

Ala Glu Asp Val Ala Val Tyr Tyr Cys Gln Gln Tyr Tyr Ser Thr Pro
85 90 95

Leu Thr Xaa Gly Gly Gly Thr Lys Val Glu Ile Lys
100 105

<210> SEQ ID NO 309
<211> LENGTH: 21
<212> TYPE: PRT
<213> ORGANISM: Artificial Sequence
<220> FEATURE:
<223> OTHER INFORMATION: Synthetic Construct

<400> SEQUENCE: 309

Val Glu Ser Gly Gly Gly Leu Val Gln Pro Gly Gly Ser Leu Arg Leu
1               5                   10                  15

Ser Cys Ala Ala Ser
            20

<210> SEQ ID NO 310
<211> LENGTH: 17
<212> TYPE: PRT
<213> ORGANISM: Artificial Sequence
<220> FEATURE:
<223> OTHER INFORMATION: Synthetic Construct

<400> SEQUENCE: 310

Met Thr Trp Val Arg Gln Ala Pro Gly Lys Gly Leu Glu Trp Val Ser
1               5                   10                  15

Ala

<210> SEQ ID NO 311
<211> LENGTH: 38
<212> TYPE: PRT
<213> ORGANISM: Artificial Sequence
<220> FEATURE:
<223> OTHER INFORMATION: Synthetic Construct

<400> SEQUENCE: 311

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 312
<211> LENGTH: 11
<212> TYPE: PRT
<213> ORGANISM: Artificial Sequence
<220> FEATURE:
<223> OTHER INFORMATION: Synthetic Construct

<400> SEQUENCE: 312

Trp Gly Gln Gly Thr Leu Val Thr Val Ser Ser
1               5                   10

<210> SEQ ID NO 313
<211> LENGTH: 21
<212> TYPE: PRT
<213> ORGANISM: Artificial Sequence
<220> FEATURE:
<223> OTHER INFORMATION: Synthetic Construct

<400> SEQUENCE: 313

Gln Ser Pro Asp Ser Leu Ala Val Ser Leu Gly Glu Arg Ala Thr Ile
1               5                   10                  15

Asn Cys Lys Ser Ser
            20

<210> SEQ ID NO 314
<211> LENGTH: 17
<212> TYPE: PRT
<213> ORGANISM: Artificial Sequence
<220> FEATURE:
<223> OTHER INFORMATION: Synthetic Construct

<400> SEQUENCE: 314

Leu Ala Trp Tyr Gln Gln Lys Pro Gly Gln Pro Pro Lys Leu Leu Ile
1 5 10 15

Tyr

<210> SEQ ID NO 315
<211> LENGTH: 36
<212> TYPE: PRT
<213> ORGANISM: Artificial Sequence
<220> FEATURE:
<223> OTHER INFORMATION: Synthetic Construct

<400> SEQUENCE: 315

Thr Arg Glu Ser Gly Val Pro Asp Arg Phe Ser Gly Ser Gly Ser Gly
1 5 10 15

Thr Asp Phe Thr Leu Thr Ile Ser Ser Leu Gln Ala Glu Asp Val Ala
20 25 30

Val Tyr Tyr Cys
35

<210> SEQ ID NO 316
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 316

Xaa Gly Gly Gly Thr Lys Val Glu Ile Lys
1 5 10

<210> SEQ ID NO 317
<211> LENGTH: 444
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

<400> SEQUENCE: 317

Val Glu Ser Gly Gly Gly Leu Val Gln Pro Gly Gly Ser Leu Arg Leu
1 5 10 15

Ser Cys Ala Ala Ser Gly Phe Thr Phe Thr Thr Tyr Ala Met Thr Trp
20 25 30

Val Arg Gln Ala Pro Gly Lys Gly Leu Glu Trp Val Ser Ala Ile Ser
35 40 45

Gly Ser Gly Gly Ser Thr Tyr Tyr Ala Asp Ser Val Lys Gly Arg Phe
50 55 60

```
Thr Ile Ser Arg Asp Asn Ser Lys Asn Thr Leu Tyr Leu Gln Met Asn
65                  70                  75                  80

Ser Leu Arg Ala Glu Asp Thr Ala Val Tyr Tyr Cys Ala Lys Asp Trp
                85                  90                  95

Ser Ser Gly Tyr Leu Gly Tyr Phe Asp Tyr Trp Gly Gln Gly Thr Leu
            100                 105                 110

Val Thr Val Ser Ser Lys Gly Pro Ser Val Phe Pro Leu Ala Pro Ser
        115                 120                 125

Ser Lys Ser Thr Ser Gly Gly Thr Ala Ala Leu Gly Xaa Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Xaa Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Xaa Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 318
<211> LENGTH: 212
<212> TYPE: PRT
<213> ORGANISM: Artificial Sequence
<220> FEATURE:

<223> OTHER INFORMATION: Synthetic Construct
<220> FEATURE:
<221> NAME/KEY: misc_feature
<222> LOCATION: (99)..(99)
<223> OTHER INFORMATION: Xaa can be any naturally occurring amino acid

<400> SEQUENCE: 318

Gln Ser Pro Asp Ser Leu Ala Val Ser Leu Gly Glu Arg Ala Thr Ile
1 5 10 15

Asn Cys Lys Ser Ser Gln Ser Val Leu Tyr Ser Ser Asn Asn Lys Asn
20 25 30

Tyr Leu Ala Trp Tyr Gln Gln Lys Pro Gly Gln Pro Pro Lys Leu Leu
35 40 45

Ile Tyr Trp Ala Ser Thr Arg Glu Ser Gly Val Pro Asp Arg Phe Ser
50 55 60

Gly Ser Gly Ser Gly Thr Asp Phe Thr Leu Thr Ile Ser Ser Leu Gln
65 70 75 80

Ala Glu Asp Val Ala Val Tyr Tyr Cys Gln Gln Tyr Tyr Ser Thr Pro
85 90 95

Leu Thr Xaa Gly Gly Gly Thr Lys Val Glu Ile Lys Ala Pro Ser Val
100 105 110

Phe Ile Phe Pro Pro Ser Asp Glu Gln Leu Lys Ser Gly Thr Ala Ser
115 120 125

Val Val Cys Leu Leu Asn Asn Phe Tyr Pro Arg Glu Ala Lys Val Gln
130 135 140

Trp Lys Val Asp Asn Ala Leu Gln Ser Gly Asn Ser Gln Glu Ser Val
145 150 155 160

Thr Glu Gln Asp Ser Lys Asp Ser Thr Tyr Ser Leu Ser Ser Thr Leu
165 170 175

Thr Leu Ser Lys Ala Asp Tyr Glu Lys His Lys Val Tyr Ala Cys Glu
180 185 190

Val Thr His Gln Gly Leu Ser Ser Pro Val Thr Lys Ser Phe Asn Arg
195 200 205

Gly Glu Cys Lys
210

<210> SEQ ID NO 319
<211> LENGTH: 353
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: n is a, c, g, or t

<400> SEQUENCE: 319
ggtngagtct gggggaggct tggtacagcc tggggggtcc ctgagactct cctgtgcagc 60
ctctggattc acctttacca cctatgccat gacctgggtc cgccaggctc cagggaaggg 120
gctggagtgg gtctcagcta ttagtggtag tggtggtagc acatactacg cagactccgt 180
gaagggccgg ttcaccatct ccagagacaa ttccaagaac acgctgtatc tgcaaatgaa 240
cagcctgaga gccgaggaca cggccgtata ttactgtgcg aaagattgga gtagtggtta 300
tttgggctac tttgactact ggggccaggg aaccctggtc accgtctcct cag 353

<210> SEQ ID NO 320
<211> LENGTH: 326

<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (297)..(297)
<223> OTHER INFORMATION: n is a, c, g, or t

<400> SEQUENCE: 320
ccagtctcca gactccctgg ctgtgtctct gggcgagagg gccaccatca actgcaagtc 60
cagccagagt gttttataca gctccaacaa taagaactac ttagcttggt accagcagaa 120
accaggacag cctcctaagc tgctcattta ctgggcatct acccgggaat ccggggtccc 180
tgaccgattc agtggcagcg ggtctgggac agatttcact ctcaccatca gcagcctgca 240
ggctgaagat gtggcagttt attactgtca gcaatattat agtactcctc tcacttncgg 300
cggagggacc aaggtggaga tcaaac 326

<210> SEQ ID NO 321
<211> LENGTH: 8
<212> TYPE: PRT
<213> ORGANISM: Artificial Sequence
<220> FEATURE:
<223> OTHER INFORMATION: Synthetic Construct

<400> SEQUENCE: 321

Gly Phe Val Phe Asp Asp Tyr Ser
1 5

<210> SEQ ID NO 322
<211> LENGTH: 8
<212> TYPE: PRT
<213> ORGANISM: Artificial Sequence
<220> FEATURE:
<223> OTHER INFORMATION: Synthetic Construct

<400> SEQUENCE: 322

Ile Ser Trp Asp Gly Gly Arg Thr
1 5

<210> SEQ ID NO 323
<211> LENGTH: 11
<212> TYPE: PRT
<213> ORGANISM: Artificial Sequence
<220> FEATURE:
<223> OTHER INFORMATION: Synthetic Construct

<400> SEQUENCE: 323

Val Lys Asp Thr Gly Leu Arg Ser Phe Asp Ser
1 5 10

<210> SEQ ID NO 324
<211> LENGTH: 11
<212> TYPE: PRT
<213> ORGANISM: Artificial Sequence
<220> FEATURE:
<223> OTHER INFORMATION: Synthetic Construct

<400> SEQUENCE: 324

Gln Ser Leu Met His Thr Asn Gly Tyr Ile Tyr
1 5 10

<210> SEQ ID NO 325
<211> LENGTH: 3
<212> TYPE: PRT

<213> ORGANISM: Artificial Sequence
<220> FEATURE:
<223> OTHER INFORMATION: Synthetic Construct

<400> SEQUENCE: 325

Leu Gly Ser
1

<210> SEQ ID NO 326
<211> LENGTH: 8
<212> TYPE: PRT
<213> ORGANISM: Artificial Sequence
<220> FEATURE:
<223> OTHER INFORMATION: Synthetic Construct

<400> SEQUENCE: 326

Met Gln Ala Leu Gln Ser Trp Thr
1 5

<210> SEQ ID NO 327
<211> LENGTH: 113
<212> TYPE: PRT
<213> ORGANISM: Artificial Sequence
<220> FEATURE:
<223> OTHER INFORMATION: Synthetic Construct

<400> SEQUENCE: 327

Glu Ser Gly Gly Glu Val Val Gln Pro Gly Arg Ser Leu Arg Leu Ser
1 5 10 15

Cys Ala Ala Ser Gly Phe Val Phe Asp Asp Tyr Ser Met His Trp Val
20 25 30

Arg Gln Val Pro Gly Lys Gly Leu Glu Trp Val Ala Leu Ile Ser Trp
35 40 45

Asp Gly Gly Arg Thr Ser Tyr Gly His Ser Val Lys Gly Arg Phe Thr
50 55 60

Ile Ser Arg Asp Asn Thr Lys Asp Ser Leu Phe Leu Gln Met Asn Ser
65 70 75 80

Leu Arg Pro Glu Asp Thr Ala Leu Tyr Tyr Cys Val Lys Asp Thr Gly
85 90 95

Leu Arg Ser Phe Asp Ser Trp Gly Gln Gly Ile Leu Val Thr Val Ser
100 105 110

Ser

<210> SEQ ID NO 328
<211> LENGTH: 111
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 328

Met Xaa Xaa Xaa Thr Gln Ser Pro Leu Ser Leu Pro Val Thr Pro Gly
1 5 10 15

Glu Pro Ala Ser Ile Ser Cys Arg Ser Ser Gln Ser Leu Met His Thr
20 25 30

Asn Gly Tyr Ile Tyr Leu Asp Trp Tyr Leu Gln Lys Pro Gly Gln Ser
35 40 45

Pro Gln Leu Leu Ile Tyr Leu Gly Ser Lys Arg Ala Pro Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Gln Gly Thr Lys Val Glu Ile Lys
            100                 105                 110


<210> SEQ ID NO 329
<211> LENGTH: 20
<212> TYPE: PRT
<213> ORGANISM: Artificial Sequence
<220> FEATURE:
<223> OTHER INFORMATION: Synthetic Construct

<400> SEQUENCE: 329

Glu Ser Gly Gly Glu Val Val Gln Pro Gly Arg Ser Leu Arg Leu Ser
1               5                   10                  15

Cys Ala Ala Ser
            20


<210> SEQ ID NO 330
<211> LENGTH: 17
<212> TYPE: PRT
<213> ORGANISM: Artificial Sequence
<220> FEATURE:
<223> OTHER INFORMATION: Synthetic Construct

<400> SEQUENCE: 330

Met His Trp Val Arg Gln Val Pro Gly Lys Gly Leu Glu Trp Val Ala
1               5                   10                  15

Leu


<210> SEQ ID NO 331
<211> LENGTH: 38
<212> TYPE: PRT
<213> ORGANISM: Artificial Sequence
<220> FEATURE:
<223> OTHER INFORMATION: Synthetic Construct

<400> SEQUENCE: 331

Ser Tyr Gly His Ser Val Lys Gly Arg Phe Thr Ile Ser Arg Asp Asn
1               5                   10                  15

Thr Lys Asp Ser Leu Phe Leu Gln Met Asn Ser Leu Arg Pro Glu Asp
            20                  25                  30

Thr Ala Leu Tyr Tyr Cys
        35


<210> SEQ ID NO 332
<211> LENGTH: 11
<212> TYPE: PRT
<213> ORGANISM: Artificial Sequence
<220> FEATURE:
<223> OTHER INFORMATION: Synthetic Construct

<400> SEQUENCE: 332

Trp Gly Gln Gly Ile Leu Val Thr Val Ser Ser
1               5                   10


<210> SEQ ID NO 333
<211> LENGTH: 26
<212> TYPE: PRT
<213> ORGANISM: Artificial Sequence
```

<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 333

```
Met Xaa Xaa Xaa Thr Gln Ser Pro Leu Ser Leu Pro Val Thr Pro Gly
1               5                   10                  15

Glu Pro Ala Ser Ile Ser Cys Arg Ser Ser
            20                  25
```

<210> SEQ ID NO 334
<211> LENGTH: 17
<212> TYPE: PRT
<213> ORGANISM: Artificial Sequence
<220> FEATURE:
<223> OTHER INFORMATION: Synthetic Construct

<400> SEQUENCE: 334

```
Leu Asp Trp Tyr Leu Gln Lys Pro Gly Gln Ser Pro Gln Leu Leu Ile
1               5                   10                  15

Tyr
```

<210> SEQ ID NO 335
<211> LENGTH: 36
<212> TYPE: PRT
<213> ORGANISM: Artificial Sequence
<220> FEATURE:
<223> OTHER INFORMATION: Synthetic Construct

<400> SEQUENCE: 335

```
Lys Arg Ala Pro Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35
```

<210> SEQ ID NO 336
<211> LENGTH: 10
<212> TYPE: PRT
<213> ORGANISM: Artificial Sequence
<220> FEATURE:
<223> OTHER INFORMATION: Synthetic Construct

<400> SEQUENCE: 336

```
Phe Gly Gln Gly Thr Lys Val Glu Ile Lys
1               5                   10
```

<210> SEQ ID NO 337
<211> LENGTH: 440
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid

<400> SEQUENCE: 337

Glu Ser Gly Gly Glu Val Val Gln Pro Gly Arg Ser Leu Arg Leu Ser
1 5 10 15

Cys Ala Ala Ser Gly Phe Val Phe Asp Asp Tyr Ser Met His Trp Val
20 25 30

Arg Gln Val Pro Gly Lys Gly Leu Glu Trp Val Ala Leu Ile Ser Trp
35 40 45

Asp Gly Gly Arg Thr Ser Tyr Gly His Ser Val Lys Gly Arg Phe Thr
50 55 60

Ile Ser Arg Asp Asn Thr Lys Asp Ser Leu Phe Leu Gln Met Asn Ser
65 70 75 80

Leu Arg Pro Glu Asp Thr Ala Leu Tyr Tyr Cys Val Lys Asp Thr Gly
85 90 95

Leu Arg Ser Phe Asp Ser Trp Gly Gln Gly Ile Leu Val Thr Val Ser
100 105 110

Ser Lys Gly Pro Ser Val Phe Pro Leu Ala Pro Ser Ser Lys Ser Thr
115 120 125

Ser Gly Gly Thr Ala Ala Leu Gly Xaa Leu Val Lys Asp Tyr Phe Pro
130 135 140

Glu Pro Val Thr Val Ser Trp Asn Ser Gly Ala Leu Thr Ser Gly Val
145 150 155 160

His Thr Phe Pro Ala Val Leu Gln Ser Ser Gly Leu Tyr Ser Leu Ser
165 170 175

Ser Val Val Thr Val Pro Ser Ser Ser Leu Gly Thr Gln Thr Tyr Ile
180 185 190

Cys Asn Val Asn His Lys Pro Ser Asn Thr Lys Val Asp Lys Xaa Val
195 200 205

Glu Pro Lys Ser Cys Asp Lys Thr His Thr Cys Pro Pro Cys Pro Ala
210 215 220

Pro Glu Leu Leu Gly Gly Pro Ser Val Phe Leu Phe Pro Pro Lys Pro
225 230 235 240

Lys Asp Thr Leu Met Ile Ser Arg Thr Pro Glu Val Thr Cys Val Val
245 250 255

Val Asp Val Ser His Glu Asp Pro Glu Val Lys Phe Asn Trp Tyr Val
260 265 270

Asp Gly Val Glu Val His Asn Ala Lys Thr Lys Pro Arg Glu Glu Gln
275 280 285

Tyr Asn Ser Thr Tyr Arg Val Val Ser Val Leu Thr Val Leu His Gln
290 295 300

Asp Trp Leu Asn Gly Lys Glu Tyr Lys Cys Lys Val Ser Asn Lys Ala
305 310 315 320

Leu Pro Ala Pro Ile Glu Lys Thr Ile Ser Lys Ala Lys Gly Gln Pro
325 330 335

Arg Glu Pro Gln Val Tyr Thr Leu Pro Pro Ser Arg Asp Glu Xaa Thr
340 345 350

Lys Asn Gln Val Ser Leu Thr Cys Leu Val Lys Gly Phe Tyr Pro Ser
355 360 365

Asp Ile Ala Val Glu Trp Glu Ser Asn Gly Gln Pro Glu Asn Asn Tyr
370 375 380

Lys Thr Thr Pro Pro Val Leu Asp Ser Asp Gly Ser Phe Phe Leu Tyr
385 390 395 400

Ser Lys Leu Thr Val Asp Lys Ser Arg Trp Gln Gln Gly Asn Val Phe
405 410 415

Ser Cys Ser Val Met His Glu Ala Leu His Asn His Tyr Thr Gln Lys
420 425 430

Ser Leu Ser Leu Ser Pro Gly Lys
435 440

<210> SEQ ID NO 338
<211> LENGTH: 215
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 338

Met Xaa Xaa Xaa Thr Gln Ser Pro Leu Ser Leu Pro Val Thr Pro Gly
1 5 10 15

Glu Pro Ala Ser Ile Ser Cys Arg Ser Ser Gln Ser Leu Met His Thr
20 25 30

Asn Gly Tyr Ile Tyr Leu Asp Trp Tyr Leu Gln Lys Pro Gly Gln Ser
35 40 45

Pro Gln Leu Leu Ile Tyr Leu Gly Ser Lys Arg Ala Pro Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Ser Trp Thr Phe Gly Gln Gly Thr Lys Val Glu Ile Lys Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Lys
210 215

<210> SEQ ID NO 339
<211> LENGTH: 342
<212> TYPE: DNA
<213> ORGANISM: Artificial Sequence
<220> FEATURE:
<223> OTHER INFORMATION: Synthetic Construct

<400> SEQUENCE: 339
tggagtctgg cggagaggtc gtacagccgg ggaggtccct gaggctgtcc tgtgcagcct 60
ctggattcgt ctttgatgat tattccatgc actgggtccg tcaagtcccg gggaagggcc 120
ttgagtgggt cgctctaatt agttgggatg gtggtcgcac atcctatgga cactctgtga 180
agggccgatt caccatctcc agagacaaca ccaaggactc cctgtttctg caaatgaaca 240
gtctgagacc cgaggacacc gccctttatt actgtgtaaa agatactgga cttcgaagct 300
ttgactcttg gggccaggga attctggtca ccgtctcgtc ag 342

<210> SEQ ID NO 340
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 340
atgttngnnn agactcagtc tccactctcc ctgcccgtca ctcctggaga gccggcctcc 60
atctcctgca ggtctagtca gagcctcatg catactaatg gatacatcta tttggattgg 120
tacctgcaga agcctgggca gtctccacag ctcctgatct atctgggttc taagcgggcc 180
cccggggtcc ccgacaggtt cagtggcagt ggatcaggca cagattttac actgaaaatc 240
agcagagtgg aggctgagga tgttggggtt tattactgca tgcaagctct acaaagttgg 300
acgttcggcc aagggaccaa ggtggaaatc aaac 334

<210> SEQ ID NO 341
<211> LENGTH: 8
<212> TYPE: PRT
<213> ORGANISM: Artificial Sequence
<220> FEATURE:
<223> OTHER INFORMATION: Synthetic Construct

<400> SEQUENCE: 341

Gly Phe Thr Phe Ser His Ala Ser
1 5

<210> SEQ ID NO 342
<211> LENGTH: 10
<212> TYPE: PRT
<213> ORGANISM: Artificial Sequence
<220> FEATURE:
<223> OTHER INFORMATION: Synthetic Construct

<400> SEQUENCE: 342

Ile Arg Ser Lys Thr Asp Gly Gly Thr Thr
1 5 10

<210> SEQ ID NO 343
<211> LENGTH: 15
<212> TYPE: PRT
<213> ORGANISM: Artificial Sequence
<220> FEATURE:
<223> OTHER INFORMATION: Synthetic Construct

<400> SEQUENCE: 343

Asn Thr His Phe Tyr Cys Asn Arg Ser Met Cys Tyr Gly Asp Tyr
1 5 10 15

<210> SEQ ID NO 344
<211> LENGTH: 12
<212> TYPE: PRT
<213> ORGANISM: Artificial Sequence
<220> FEATURE:
<223> OTHER INFORMATION: Synthetic Construct

<400> SEQUENCE: 344

```
Gln Ser Val Leu Tyr Ser Ser Asn Asn Lys Asn Tyr
1               5                   10
```

<210> SEQ ID NO 345
<211> LENGTH: 3
<212> TYPE: PRT
<213> ORGANISM: Artificial Sequence
<220> FEATURE:
<223> OTHER INFORMATION: Synthetic Construct

<400> SEQUENCE: 345

```
Trp Ala Ser
1
```

<210> SEQ ID NO 346
<211> LENGTH: 8
<212> TYPE: PRT
<213> ORGANISM: Artificial Sequence
<220> FEATURE:
<223> OTHER INFORMATION: Synthetic Construct

<400> SEQUENCE: 346

```
Gln Gln Tyr Tyr Ser Gly Arg Thr
1               5
```

<210> SEQ ID NO 347
<211> LENGTH: 119
<212> TYPE: PRT
<213> ORGANISM: Artificial Sequence
<220> FEATURE:
<223> OTHER INFORMATION: Synthetic Construct

<400> SEQUENCE: 347

```
Glu Ser Gly Gly Gly Leu Val Lys Pro Gly Gly Ser Leu Arg Leu Ser
1               5                   10                  15

Cys Ala Ala Ser Gly Phe Thr Phe Ser His Ala Ser Met Ser Trp Val
            20                  25                  30

Arg Gln Ala Pro Gly Lys Gly Leu Glu Trp Val Gly Arg Ile Arg Ser
        35                  40                  45

Lys Thr Asp Gly Gly Thr Thr Asp Tyr Ala Ala Pro Val Lys Gly Arg
    50                  55                  60

Phe Thr Ile Ser Arg Asp Asp Ser Lys Asn Thr Leu Tyr Leu Gln Met
65                  70                  75                  80

Asn Ser Leu Lys Thr Glu Asp Thr Ala Val Tyr Tyr Cys Asn Thr His
                85                  90                  95

Phe Tyr Cys Asn Arg Ser Met Cys Tyr Gly Asp Tyr Trp Gly Gln Gly
            100                 105                 110

Thr Leu Val Thr Val Ser Ser
        115
```

<210> SEQ ID NO 348
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 348

Asp Ile Xaa Xaa Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Arg Gly Ser Gly Ser Gly Thr Asp Phe Ser Leu Thr
65 70 75 80

Ile Ser Ser Leu Gln Ala Glu Asp Val Ala Val Tyr Tyr Cys Gln Gln
85 90 95

Tyr Tyr Ser Gly Arg Thr Phe Gly Pro Gly Thr Lys Val Asp Phe Lys
100 105 110

<210> SEQ ID NO 349
<211> LENGTH: 20
<212> TYPE: PRT
<213> ORGANISM: Artificial Sequence
<220> FEATURE:
<223> OTHER INFORMATION: Synthetic Construct

<400> SEQUENCE: 349

Glu Ser Gly Gly Gly Leu Val Lys Pro Gly Gly Ser Leu Arg Leu Ser
1 5 10 15

Cys Ala Ala Ser
20

<210> SEQ ID NO 350
<211> LENGTH: 17
<212> TYPE: PRT
<213> ORGANISM: Artificial Sequence
<220> FEATURE:
<223> OTHER INFORMATION: Synthetic Construct

<400> SEQUENCE: 350

Met Ser Trp Val Arg Gln Ala Pro Gly Lys Gly Leu Glu Trp Val Gly
1 5 10 15

Arg

<210> SEQ ID NO 351
<211> LENGTH: 38
<212> TYPE: PRT
<213> ORGANISM: Artificial Sequence
<220> FEATURE:
<223> OTHER INFORMATION: Synthetic Construct

<400> SEQUENCE: 351

Asp Tyr Ala Ala Pro Val Lys Gly Arg Phe Thr Ile Ser Arg Asp Asp
1 5 10 15

Ser Lys Asn Thr Leu Tyr Leu Gln Met Asn Ser Leu Lys Thr Glu Asp
20 25 30

Thr Ala Val Tyr Tyr Cys
35

<210> SEQ ID NO 352
<211> LENGTH: 11
<212> TYPE: PRT
<213> ORGANISM: Artificial Sequence
<220> FEATURE:
<223> OTHER INFORMATION: Synthetic Construct

<400> SEQUENCE: 352

Trp Gly Gln Gly Thr Leu Val Thr Val Ser Ser
1 5 10

<210> SEQ ID NO 353
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 353

Asp Ile Xaa Xaa Thr Gln Ser Pro Asp Ser Leu Ala Val Ser Leu Gly
1 5 10 15

Glu Arg Ala Thr Ile Asn Cys Lys Ser Ser
20 25

<210> SEQ ID NO 354
<211> LENGTH: 17
<212> TYPE: PRT
<213> ORGANISM: Artificial Sequence
<220> FEATURE:
<223> OTHER INFORMATION: Synthetic Construct

<400> SEQUENCE: 354

Leu Ala Trp Tyr Gln Gln Lys Pro Gly Gln Pro Pro Lys Leu Leu Ile
1 5 10 15

Tyr

<210> SEQ ID NO 355
<211> LENGTH: 36
<212> TYPE: PRT
<213> ORGANISM: Artificial Sequence
<220> FEATURE:
<223> OTHER INFORMATION: Synthetic Construct

<400> SEQUENCE: 355

Thr Arg Glu Ser Gly Val Pro Asp Arg Phe Arg Gly Ser Gly Ser Gly
1 5 10 15

Thr Asp Phe Ser Leu Thr Ile Ser Ser Leu Gln Ala Glu Asp Val Ala
20 25 30

Val Tyr Tyr Cys
35

<210> SEQ ID NO 356
<211> LENGTH: 10
<212> TYPE: PRT
<213> ORGANISM: Artificial Sequence
<220> FEATURE:
<223> OTHER INFORMATION: Synthetic Construct

<400> SEQUENCE: 356

Phe Gly Pro Gly Thr Lys Val Asp Phe Lys
1 5 10

<210> SEQ ID NO 357
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 357

```
Glu Ser Gly Gly Gly Leu Val Lys Pro Gly Gly Ser Leu Arg Leu Ser
1               5                   10                  15

Cys Ala Ala Ser Gly Phe Thr Phe Ser His Ala Ser Met Ser Trp Val
            20                  25                  30

Arg Gln Ala Pro Gly Lys Gly Leu Glu Trp Val Gly Arg Ile Arg Ser
        35                  40                  45

Lys Thr Asp Gly Gly Thr Thr Asp Tyr Ala Ala Pro Val Lys Gly Arg
    50                  55                  60

Phe Thr Ile Ser Arg Asp Asp Ser Lys Asn Thr Leu Tyr Leu Gln Met
65                  70                  75                  80

Asn Ser Leu Lys Thr Glu Asp Thr Ala Val Tyr Tyr Cys Asn Thr His
                85                  90                  95

Phe Tyr Cys Asn Arg Ser Met Cys Tyr Gly Asp Tyr Trp Gly Gln Gly
            100                 105                 110

Thr Leu Val Thr Val Ser Ser Lys Gly Pro Ser Val Phe Pro Leu Ala
        115                 120                 125

Pro Ser Ser Lys Ser Thr Ser Gly Gly Thr Ala Ala Leu Gly Xaa Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Xaa Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Xaa Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 358
<211> LENGTH: 216
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 358

Asp Ile Xaa Xaa Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Arg Gly Ser Gly Ser Gly Thr Asp Phe Ser Leu Thr
65 70 75 80

Ile Ser Ser Leu Gln Ala Glu Asp Val Ala Val Tyr Tyr Cys Gln Gln
85 90 95

Tyr Tyr Ser Gly Arg Thr Phe Gly Pro Gly Thr Lys Val Asp Phe Lys
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys Lys
210 215

<210> SEQ ID NO 359
<211> LENGTH: 360
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n is a, c, g, or t

<400> SEQUENCE: 359
tngagtctgg gggaggcttg gtaaagcctg gggggtccct tagactctcc tgtgcagcct 60
ctggattcac tttcagtcac gcctcgatga gctgggtccg ccaggctcca gggaaggggc 120
tggagtgggt tggccgtatt agaagcaaaa ctgatggcgg gacaacagac tacgctgcac 180
ccgtgaaagg cagattcacc atctcaagag atgattcaaa aaacacactg tatctgcaaa 240
tgaacagcct gaaaaccgag gacacagccg tgtattactg taatacccac ttctattgca 300
atagaagcat gtgctatggt gactactggg gccagggaac cctggtcacc gtctcctcag 360

<210> SEQ ID NO 360
<211> LENGTH: 337
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(10)
<223> OTHER INFORMATION: n is a, c, g, or t

<400> SEQUENCE: 360
gacatcgnnn agacccagtc tccagactcc ctggctgtgt ctctgggcga gagggccacc 60
atcaactgca agtccagcca gagtgtttta tacagctcca ataataagaa ttacttagct 120
tggtaccagc agaaaccagg gcagcctcct aagttgctca tttactgggc atctacccgg 180
gaatccgggg tccctgaccg attcagaggc agcgggtctg ggacagattt ctctctcacc 240
atcagcagcc tgcaggctga agatgtggca gtttattact gtcagcaata ttatagtggt 300
cgcactttcg gccctgggac caaagtggat ttcaaac 337

<210> SEQ ID NO 361
<211> LENGTH: 8
<212> TYPE: PRT
<213> ORGANISM: Artificial Sequence
<220> FEATURE:
<223> OTHER INFORMATION: Synthetic Construct

<400> SEQUENCE: 361

Gly Phe Thr Phe Glu Asp Tyr Ser
1 5

<210> SEQ ID NO 362
<211> LENGTH: 8
<212> TYPE: PRT
<213> ORGANISM: Artificial Sequence
<220> FEATURE:
<223> OTHER INFORMATION: Synthetic Construct

<400> SEQUENCE: 362

Ile Ser Trp Asp Gly Gly Arg Thr
1               5

<210> SEQ ID NO 363
<211> LENGTH: 11
<212> TYPE: PRT
<213> ORGANISM: Artificial Sequence
<220> FEATURE:
<223> OTHER INFORMATION: Synthetic Construct

<400> SEQUENCE: 363

Val Lys Asp Thr Gly Leu Arg Ser Phe Asp Ser
1               5                   10

<210> SEQ ID NO 364
<211> LENGTH: 11
<212> TYPE: PRT
<213> ORGANISM: Artificial Sequence
<220> FEATURE:
<223> OTHER INFORMATION: Synthetic Construct

<400> SEQUENCE: 364

Gln Ser Leu Val His Ser Asn Gly Ile Asn Tyr
1               5                   10

<210> SEQ ID NO 365
<211> LENGTH: 3
<212> TYPE: PRT
<213> ORGANISM: Artificial Sequence
<220> FEATURE:
<223> OTHER INFORMATION: Synthetic Construct

<400> SEQUENCE: 365

Met Gly Phe
1

<210> SEQ ID NO 366
<211> LENGTH: 8
<212> TYPE: PRT
<213> ORGANISM: Artificial Sequence
<220> FEATURE:
<223> OTHER INFORMATION: Synthetic Construct

<400> SEQUENCE: 366

Met Gln Ala Leu Gln Ser Trp Thr
1               5

<210> SEQ ID NO 367
<211> LENGTH: 114
<212> TYPE: PRT
<213> ORGANISM: Artificial Sequence
<220> FEATURE:
<223> OTHER INFORMATION: Synthetic Construct

<400> SEQUENCE: 367

Val Glu Ser Gly Gly Val Val Val Gln Arg Gly Gly Ser Leu Arg Leu
1               5                   10                  15

Ser Cys Ala Gly Ser Gly Phe Thr Phe Glu Asp Tyr Ser Met His Trp
            20                  25                  30

Val Arg Gln Ser Pro Gly Lys Gly Leu Glu Trp Val Ser Leu Ile Ser
        35                  40                  45

Trp Asp Gly Gly Arg Thr Ser Tyr Gly Asp Ser Val Lys Gly Arg Phe
    50                  55                  60

Thr Ile Ser Arg Asp Asn Ser Lys Lys Ser Leu Phe Leu Gln Met Thr
65                  70                  75                  80

```
Asn Leu Arg Pro Glu Asp Thr Ala Leu Tyr Tyr Cys Val Lys Asp Thr
                85                  90                  95

Gly Leu Arg Ser Phe Asp Ser Trp Gly Gln Gly Thr Leu Val Thr Val
            100                 105                 110

Ser Ser


<210> SEQ ID NO 368
<211> LENGTH: 111
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 368

Met Xaa Xaa Xaa Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Ile Asn Tyr Leu Asp Trp Tyr Ile Gln Lys Pro Gly Gln Ser
        35                  40                  45

Pro Gln Leu Leu Ile Tyr Met Gly Phe Lys Arg Ala Ala Gly Val Pro
    50                  55                  60

Asp Arg Phe Ser Gly Ser Val Ser Gly Thr Asp Phe Thr Leu Met Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Gln Gly Thr Arg Val Glu Ile Lys
            100                 105                 110


<210> SEQ ID NO 369
<211> LENGTH: 21
<212> TYPE: PRT
<213> ORGANISM: Artificial Sequence
<220> FEATURE:
<223> OTHER INFORMATION: Synthetic Construct

<400> SEQUENCE: 369

Val Glu Ser Gly Gly Val Val Val Gln Arg Gly Gly Ser Leu Arg Leu
1               5                   10                  15

Ser Cys Ala Gly Ser
            20


<210> SEQ ID NO 370
<211> LENGTH: 17
<212> TYPE: PRT
<213> ORGANISM: Artificial Sequence
<220> FEATURE:
<223> OTHER INFORMATION: Synthetic Construct

<400> SEQUENCE: 370

Met His Trp Val Arg Gln Ser Pro Gly Lys Gly Leu Glu Trp Val Ser
1               5                   10                  15

Leu


<210> SEQ ID NO 371
<211> LENGTH: 38
<212> TYPE: PRT
```

<213> ORGANISM: Artificial Sequence
<220> FEATURE:
<223> OTHER INFORMATION: Synthetic Construct

<400> SEQUENCE: 371

Ser Tyr Gly Asp Ser Val Lys Gly Arg Phe Thr Ile Ser Arg Asp Asn
1 5 10 15

Ser Lys Lys Ser Leu Phe Leu Gln Met Thr Asn Leu Arg Pro Glu Asp
20 25 30

Thr Ala Leu Tyr Tyr Cys
35

<210> SEQ ID NO 372
<211> LENGTH: 11
<212> TYPE: PRT
<213> ORGANISM: Artificial Sequence
<220> FEATURE:
<223> OTHER INFORMATION: Synthetic Construct

<400> SEQUENCE: 372

Trp Gly Gln Gly Thr Leu Val Thr Val Ser Ser
1 5 10

<210> SEQ ID NO 373
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 373

Met Xaa Xaa Xaa Thr Gln Ser Pro Leu Ser Leu Pro Val Thr Pro Gly
1 5 10 15

Glu Pro Ala Ser Ile Ser Cys Arg Ser Ser
20 25

<210> SEQ ID NO 374
<211> LENGTH: 17
<212> TYPE: PRT
<213> ORGANISM: Artificial Sequence
<220> FEATURE:
<223> OTHER INFORMATION: Synthetic Construct

<400> SEQUENCE: 374

Leu Asp Trp Tyr Ile Gln Lys Pro Gly Gln Ser Pro Gln Leu Leu Ile
1 5 10 15

Tyr

<210> SEQ ID NO 375
<211> LENGTH: 36
<212> TYPE: PRT
<213> ORGANISM: Artificial Sequence
<220> FEATURE:
<223> OTHER INFORMATION: Synthetic Construct

<400> SEQUENCE: 375

Lys Arg Ala Ala Gly Val Pro Asp Arg Phe Ser Gly Ser Val Ser Gly
1 5 10 15

Thr Asp Phe Thr Leu Met Ile Ser Arg Val Glu Ala Glu Asp Val Gly
20 25 30

Val Tyr Tyr Cys
35

<210> SEQ ID NO 376
<211> LENGTH: 10
<212> TYPE: PRT
<213> ORGANISM: Artificial Sequence
<220> FEATURE:
<223> OTHER INFORMATION: Synthetic Construct

<400> SEQUENCE: 376

Phe Gly Gln Gly Thr Arg Val Glu Ile Lys
1 5 10

<210> SEQ ID NO 377
<211> LENGTH: 441
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid

<400> SEQUENCE: 377

Val Glu Ser Gly Gly Val Val Val Gln Arg Gly Gly Ser Leu Arg Leu
1 5 10 15

Ser Cys Ala Gly Ser Gly Phe Thr Phe Glu Asp Tyr Ser Met His Trp
20 25 30

Val Arg Gln Ser Pro Gly Lys Gly Leu Glu Trp Val Ser Leu Ile Ser
35 40 45

Trp Asp Gly Gly Arg Thr Ser Tyr Gly Asp Ser Val Lys Gly Arg Phe
50 55 60

Thr Ile Ser Arg Asp Asn Ser Lys Lys Ser Leu Phe Leu Gln Met Thr
65 70 75 80

Asn Leu Arg Pro Glu Asp Thr Ala Leu Tyr Tyr Cys Val Lys Asp Thr
85 90 95

Gly Leu Arg Ser Phe Asp Ser Trp Gly Gln Gly Thr Leu Val Thr Val
100 105 110

Ser Ser Lys Gly Pro Ser Val Phe Pro Leu Ala Pro Ser Ser Lys Ser
115 120 125

Thr Ser Gly Gly Thr Ala Ala Leu Gly Xaa Leu Val Lys Asp Tyr Phe
130 135 140

Pro Glu Pro Val Thr Val Ser Trp Asn Ser Gly Ala Leu Thr Ser Gly
145 150 155 160

Val His Thr Phe Pro Ala Val Leu Gln Ser Ser Gly Leu Tyr Ser Leu
165 170 175

Ser Ser Val Val Thr Val Pro Ser Ser Ser Leu Gly Thr Gln Thr Tyr
180 185 190

Ile Cys Asn Val Asn His Lys Pro Ser Asn Thr Lys Val Asp Lys Xaa
195 200 205

Val Glu Pro Lys Ser Cys Asp Lys Thr His Thr Cys Pro Pro Cys Pro
210 215 220

```
Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Xaa
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 378
<211> LENGTH: 215
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 378

Met Xaa Xaa Xaa Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Ile Asn Tyr Leu Asp Trp Tyr Ile Gln Lys Pro Gly Gln Ser
        35                  40                  45

Pro Gln Leu Leu Ile Tyr Met Gly Phe Lys Arg Ala Ala Gly Val Pro
    50                  55                  60

Asp Arg Phe Ser Gly Ser Val Ser Gly Thr Asp Phe Thr Leu Met Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Gln Gly Thr Arg Val Glu Ile Lys Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Lys
    210                 215


<210> SEQ ID NO 379
<211> LENGTH: 343
<212> TYPE: DNA
<213> ORGANISM: Artificial Sequence
<220> FEATURE:
<223> OTHER INFORMATION: Synthetic Construct

<400> SEQUENCE: 379

gtggagtctg gcggagtcgt ggtacagcgg ggggggtccc tgagactctc ctgtgcaggc     60

tctggattca cctttgagga ttattccatg cactgggtcc gtcaatctcc ggggaagggt    120

cttgagtggg tctctcttat tagttgggat ggtggccgga catcctatgg agactctgtg    180

aaggggcggt tcaccatctc cagagacaac agcaagaagt ccctgtttct gcaaatgacc    240

aatctgagac ccgaagacac cgccctctat tattgtgtaa aagatactgg actccgaagt    300

tttgactctt ggggccaggg aaccctggtc accgtctcct cag                      343


<210> SEQ ID NO 380
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 380

atgttngnng ngactcagtc tcctctctcc ctgcccgtca cccctggaga gccggcctcc     60

atctcctgtc ggtctagtca gagcctcgtg catagtaatg gaatcaacta tttggactgg    120

tacatccaga agccagggca gtctccacaa ctcctgatct atatgggttt taagcgggcc    180

gccggggtcc ctgacaggtt cagtggcagt gtctcaggca cagattttac actgatgatc    240

agcagagtgg aggctgagga tgttggggtc tattactgca tgcaagctct acaaagttgg    300

acgttcggcc aagggaccag ggtggaaatc aaac                                334


<210> SEQ ID NO 381
<211> LENGTH: 8
```

<212> TYPE: PRT
<213> ORGANISM: Artificial Sequence
<220> FEATURE:
<223> OTHER INFORMATION: Synthetic Construct

<400> SEQUENCE: 381

Gly Phe Ile Phe Asp Asp Tyr Ser
1 5

<210> SEQ ID NO 382
<211> LENGTH: 8
<212> TYPE: PRT
<213> ORGANISM: Artificial Sequence
<220> FEATURE:
<223> OTHER INFORMATION: Synthetic Construct

<400> SEQUENCE: 382

Ile Ser Trp Asp Gly Gly Arg Thr
1 5

<210> SEQ ID NO 383
<211> LENGTH: 11
<212> TYPE: PRT
<213> ORGANISM: Artificial Sequence
<220> FEATURE:
<223> OTHER INFORMATION: Synthetic Construct

<400> SEQUENCE: 383

Val Lys Asp Thr Gly Leu Arg Ser Phe Asp Ser
1 5 10

<210> SEQ ID NO 384
<211> LENGTH: 11
<212> TYPE: PRT
<213> ORGANISM: Artificial Sequence
<220> FEATURE:
<223> OTHER INFORMATION: Synthetic Construct

<400> SEQUENCE: 384

Gln Ser Leu Val His Ser Asn Gly Tyr Thr Tyr
1 5 10

<210> SEQ ID NO 385
<211> LENGTH: 3
<212> TYPE: PRT
<213> ORGANISM: Artificial Sequence
<220> FEATURE:
<223> OTHER INFORMATION: Synthetic Construct

<400> SEQUENCE: 385

Met Gly Ser
1

<210> SEQ ID NO 386
<211> LENGTH: 8
<212> TYPE: PRT
<213> ORGANISM: Artificial Sequence
<220> FEATURE:
<223> OTHER INFORMATION: Synthetic Construct

<400> SEQUENCE: 386

Met Gln Ala Leu Gln Ser Trp Thr
1 5

<210> SEQ ID NO 387
<211> LENGTH: 113
<212> TYPE: PRT

<213> ORGANISM: Artificial Sequence
<220> FEATURE:
<223> OTHER INFORMATION: Synthetic Construct

<400> SEQUENCE: 387

Glu Ser Gly Gly Glu Val Val Gln Pro Gly Gly Ser Leu Arg Leu Ser
1 5 10 15

Cys Val Ala Ser Gly Phe Ile Phe Asp Asp Tyr Ser Met His Trp Val
20 25 30

Arg Gln Val Pro Gly Lys Gly Leu Glu Trp Val Ser Leu Ile Ser Trp
35 40 45

Asp Gly Gly Arg Thr Ser Tyr Gly Asp Ser Val Lys Gly Arg Phe Thr
50 55 60

Ile Ser Arg Asp Asn Asn Lys Lys Thr Leu Phe Leu Gln Met Asn Ser
65 70 75 80

Leu Arg Pro Glu Asp Thr Ala Leu Tyr Tyr Cys Val Lys Asp Thr Gly
85 90 95

Leu Arg Ser Phe Asp Ser Trp Gly Gln Gly Ile Leu Val Thr Val Ser
100 105 110

Ser

<210> SEQ ID NO 388
<211> LENGTH: 111
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 388

Asp Val Xaa Glu Thr Gln Ser Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Gly Tyr Thr Tyr Leu Asp Trp Tyr Leu Gln Arg Pro Gly Gln Ser
35 40 45

Pro Gln Leu Leu Ile Tyr Met Gly Ser Lys Arg Ala Ser Gly Val Pro
50 55 60

Asp Arg Phe Ser Gly Ser Phe Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Ser Trp Thr Phe Gly Leu Gly Thr Lys Val Glu Ile Lys
100 105 110

<210> SEQ ID NO 389
<211> LENGTH: 20
<212> TYPE: PRT
<213> ORGANISM: Artificial Sequence
<220> FEATURE:
<223> OTHER INFORMATION: Synthetic Construct

<400> SEQUENCE: 389

Glu Ser Gly Gly Glu Val Val Gln Pro Gly Gly Ser Leu Arg Leu Ser
1 5 10 15

Cys Val Ala Ser
20

<210> SEQ ID NO 390
<211> LENGTH: 17
<212> TYPE: PRT
<213> ORGANISM: Artificial Sequence
<220> FEATURE:
<223> OTHER INFORMATION: Synthetic Construct

<400> SEQUENCE: 390

Met His Trp Val Arg Gln Val Pro Gly Lys Gly Leu Glu Trp Val Ser
1 5 10 15

Leu

<210> SEQ ID NO 391
<211> LENGTH: 38
<212> TYPE: PRT
<213> ORGANISM: Artificial Sequence
<220> FEATURE:
<223> OTHER INFORMATION: Synthetic Construct

<400> SEQUENCE: 391

Ser Tyr Gly Asp Ser Val Lys Gly Arg Phe Thr Ile Ser Arg Asp Asn
1 5 10 15

Asn Lys Lys Thr Leu Phe Leu Gln Met Asn Ser Leu Arg Pro Glu Asp
20 25 30

Thr Ala Leu Tyr Tyr Cys
35

<210> SEQ ID NO 392
<211> LENGTH: 11
<212> TYPE: PRT
<213> ORGANISM: Artificial Sequence
<220> FEATURE:
<223> OTHER INFORMATION: Synthetic Construct

<400> SEQUENCE: 392

Trp Gly Gln Gly Ile Leu Val Thr Val Ser Ser
1 5 10

<210> SEQ ID NO 393
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 393

Asp Val Xaa Glu Thr Gln Ser Pro Leu Ser Leu Pro Val Thr Pro Gly
1 5 10 15

Glu Pro Ala Ser Ile Ser Cys Arg Ser Ser
20 25

<210> SEQ ID NO 394
<211> LENGTH: 17
<212> TYPE: PRT
<213> ORGANISM: Artificial Sequence
<220> FEATURE:
<223> OTHER INFORMATION: Synthetic Construct

<400> SEQUENCE: 394

Leu Asp Trp Tyr Leu Gln Arg Pro Gly Gln Ser Pro Gln Leu Leu Ile 1 5 10 15

Tyr

<210> SEQ ID NO 395
<211> LENGTH: 36
<212> TYPE: PRT
<213> ORGANISM: Artificial Sequence
<220> FEATURE:
<223> OTHER INFORMATION: Synthetic Construct

<400> SEQUENCE: 395

Lys Arg Ala Ser Gly Val Pro Asp Arg Phe Ser Gly Ser Phe Ser Gly
1 5 10 15

Thr Asp Phe Thr Leu Lys Ile Ser Arg Val Glu Ala Glu Asp Val Gly
20 25 30

Val Tyr Tyr Cys
35

<210> SEQ ID NO 396
<211> LENGTH: 10
<212> TYPE: PRT
<213> ORGANISM: Artificial Sequence
<220> FEATURE:
<223> OTHER INFORMATION: Synthetic Construct

<400> SEQUENCE: 396

Phe Gly Leu Gly Thr Lys Val Glu Ile Lys
1 5 10

<210> SEQ ID NO 397
<211> LENGTH: 440
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid

<400> SEQUENCE: 397

Glu Ser Gly Gly Glu Val Val Gln Pro Gly Gly Ser Leu Arg Leu Ser
1 5 10 15

Cys Val Ala Ser Gly Phe Ile Phe Asp Asp Tyr Ser Met His Trp Val
20 25 30

Arg Gln Val Pro Gly Lys Gly Leu Glu Trp Val Ser Leu Ile Ser Trp
35 40 45

Asp Gly Gly Arg Thr Ser Tyr Gly Asp Ser Val Lys Gly Arg Phe Thr
50 55 60

Ile Ser Arg Asp Asn Asn Lys Lys Thr Leu Phe Leu Gln Met Asn Ser
65 70 75 80

Leu Arg Pro Glu Asp Thr Ala Leu Tyr Tyr Cys Val Lys Asp Thr Gly
85 90 95

Leu Arg Ser Phe Asp Ser Trp Gly Gln Gly Ile Leu Val Thr Val Ser
100 105 110

Ser Lys Gly Pro Ser Val Phe Pro Leu Ala Pro Ser Ser Lys Ser Thr
115 120 125

Ser Gly Gly Thr Ala Ala Leu Gly Xaa Leu Val Lys Asp Tyr Phe Pro
130 135 140

Glu Pro Val Thr Val Ser Trp Asn Ser Gly Ala Leu Thr Ser Gly Val
145 150 155 160

His Thr Phe Pro Ala Val Leu Gln Ser Ser Gly Leu Tyr Ser Leu Ser
165 170 175

Ser Val Val Thr Val Pro Ser Ser Ser Leu Gly Thr Gln Thr Tyr Ile
180 185 190

Cys Asn Val Asn His Lys Pro Ser Asn Thr Lys Val Asp Lys Xaa Val
195 200 205

Glu Pro Lys Ser Cys Asp Lys Thr His Thr Cys Pro Pro Cys Pro Ala
210 215 220

Pro Glu Leu Leu Gly Gly Pro Ser Val Phe Leu Phe Pro Pro Lys Pro
225 230 235 240

Lys Asp Thr Leu Met Ile Ser Arg Thr Pro Glu Val Thr Cys Val Val
245 250 255

Val Asp Val Ser His Glu Asp Pro Glu Val Lys Phe Asn Trp Tyr Val
260 265 270

Asp Gly Val Glu Val His Asn Ala Lys Thr Lys Pro Arg Glu Glu Gln
275 280 285

Tyr Asn Ser Thr Tyr Arg Val Val Ser Val Leu Thr Val Leu His Gln
290 295 300

Asp Trp Leu Asn Gly Lys Glu Tyr Lys Cys Lys Val Ser Asn Lys Ala
305 310 315 320

Leu Pro Ala Pro Ile Glu Lys Thr Ile Ser Lys Ala Lys Gly Gln Pro
325 330 335

Arg Glu Pro Gln Val Tyr Thr Leu Pro Pro Ser Arg Asp Glu Xaa Thr
340 345 350

Lys Asn Gln Val Ser Leu Thr Cys Leu Val Lys Gly Phe Tyr Pro Ser
355 360 365

Asp Ile Ala Val Glu Trp Glu Ser Asn Gly Gln Pro Glu Asn Asn Tyr
370 375 380

Lys Thr Thr Pro Pro Val Leu Asp Ser Asp Gly Ser Phe Phe Leu Tyr
385 390 395 400

Ser Lys Leu Thr Val Asp Lys Ser Arg Trp Gln Gln Gly Asn Val Phe
405 410 415

Ser Cys Ser Val Met His Glu Ala Leu His Asn His Tyr Thr Gln Lys
420 425 430

Ser Leu Ser Leu Ser Pro Gly Lys
435 440

<210> SEQ ID NO 398
<211> LENGTH: 215
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 398

Asp Val Xaa Glu Thr Gln Ser Pro Leu Ser Leu Pro Val Thr Pro Gly
1 5 10 15

```
Glu Pro Ala Ser Ile Ser Cys Arg Ser Ser Gln Ser Leu Val His Ser
            20                  25                  30

Asn Gly Tyr Thr Tyr Leu Asp Trp Tyr Leu Gln Arg Pro Gly Gln Ser
        35                  40                  45

Pro Gln Leu Leu Ile Tyr Met Gly Ser Lys Arg Ala Ser Gly Val Pro
    50                  55                  60

Asp Arg Phe Ser Gly Ser Phe Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Leu Gly Thr Lys Val Glu Ile Lys Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Lys
    210                 215
```

<210> SEQ ID NO 399
<211> LENGTH: 341
<212> TYPE: DNA
<213> ORGANISM: Artificial Sequence
<220> FEATURE:
<223> OTHER INFORMATION: Synthetic Construct

<400> SEQUENCE: 399

```
ggagtctggc ggagaggtcg tacagcctgg ggggtccctg agactctctt gtgtagcctc     60

tggattcatc tttgatgatt attccatgca ctgggtccgt caagtcccgg ggaagggtct    120

tgagtgggtc tctctaatta gttgggatgg tggtcgcaca tcctatggag actctgtgaa    180

gggtcgattc accatctcca gagacaacaa caagaagacc ctgtttctgc aaatgaacag    240

tctgagacct gaggacaccg ccctgtatta ttgtgtaaaa gatactggac ttcgaagctt    300

tgactcttgg ggccagggaa ttctggtcac cgtctcctca g                         341
```

<210> SEQ ID NO 400
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(9)
<223> OTHER INFORMATION: n is a, c, g, or t

<400> SEQUENCE: 400

```
gatgttgnng agactcagtc tccactctcc ctgcccgtca cccctggaga gccggcctcc     60

atctcctgca ggtctagtca gagcctcgtt catagtaatg gatacaccta tttggattgg    120
```

tacctgcaga ggccagggca gtctccgcaa ctcctgatct atatgggttc taagcgggcc 180
tccggggtcc ctgacaggtt cagtggcagt ttctcaggca cagattttac actgaaaatc 240
agcagagtgg aggctgaaga tgttggggtt tattactgca tgcaagctct ccaaagttgg 300
acgttcggcc tagggaccaa ggtggaaatc aaac 334

<210> SEQ ID NO 401
<211> LENGTH: 8
<212> TYPE: PRT
<213> ORGANISM: Artificial Sequence
<220> FEATURE:
<223> OTHER INFORMATION: Synthetic Construct

<400> SEQUENCE: 401

Gly Phe Thr Phe Asp Asp Tyr Ser
1 5

<210> SEQ ID NO 402
<211> LENGTH: 8
<212> TYPE: PRT
<213> ORGANISM: Artificial Sequence
<220> FEATURE:
<223> OTHER INFORMATION: Synthetic Construct

<400> SEQUENCE: 402

Ile Ser Trp Asp Gly Gly Arg Thr
1 5

<210> SEQ ID NO 403
<211> LENGTH: 11
<212> TYPE: PRT
<213> ORGANISM: Artificial Sequence
<220> FEATURE:
<223> OTHER INFORMATION: Synthetic Construct

<400> SEQUENCE: 403

Val Lys Asp Thr Gly Leu Arg Ser Phe Asp Ser
1 5 10

<210> SEQ ID NO 404
<211> LENGTH: 12
<212> TYPE: PRT
<213> ORGANISM: Artificial Sequence
<220> FEATURE:
<223> OTHER INFORMATION: Synthetic Construct

<400> SEQUENCE: 404

Gln Ser Val Phe Asp Asp Ser Ser Asn Lys Asn Tyr
1 5 10

<210> SEQ ID NO 405
<211> LENGTH: 3
<212> TYPE: PRT
<213> ORGANISM: Artificial Sequence
<220> FEATURE:
<223> OTHER INFORMATION: Synthetic Construct

<400> SEQUENCE: 405

Trp Ala Ser
1

<210> SEQ ID NO 406
<211> LENGTH: 9
<212> TYPE: PRT
<213> ORGANISM: Artificial Sequence
<220> FEATURE:
<223> OTHER INFORMATION: Synthetic Construct

<400> SEQUENCE: 406

His Gln Tyr Tyr Ser Thr Pro His Ser
1 5

<210> SEQ ID NO 407
<211> LENGTH: 113
<212> TYPE: PRT
<213> ORGANISM: Artificial Sequence
<220> FEATURE:
<223> OTHER INFORMATION: Synthetic Construct

<400> SEQUENCE: 407

Glu Ser Gly Gly Val Val Val Gln Pro Gly Gly Ser Leu Arg Leu Ser
1 5 10 15

Cys Ala Ala Ser Gly Phe Thr Phe Asp Asp Tyr Ser Met His Trp Val
20 25 30

Arg Gln Val Pro Gly Lys Gly Leu Glu Trp Val Ser Leu Ile Ser Trp
35 40 45

Asp Gly Gly Arg Thr Ser Tyr Gly Asp Ser Val Lys Gly Arg Phe Thr
50 55 60

Ile Ser Arg Asp Asn Ser Lys Arg Ser Leu Phe Leu Gln Met Thr Asn
65 70 75 80

Leu Arg Pro Glu Asp Thr Ala Phe Tyr Tyr Cys Val Lys Asp Thr Gly
85 90 95

Leu Arg Ser Phe Asp Ser Trp Gly Gln Gly Thr Leu Val Thr Val Ser
100 105 110

Ser

<210> SEQ ID NO 408
<211> LENGTH: 113
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 408

Asp Xaa Xaa Xaa Thr Gln Ser Pro Asp Ser Val Ala Val Ser Leu Gly
1 5 10 15

Gln Arg Ala Thr Ile Asn Cys Glu Ser Ser Gln Ser Val Phe Asp Asp
20 25 30

Ser Ser Asn Lys Asn Tyr Leu Ala Trp Tyr Gln His Lys Pro Gly Gln
35 40 45

Pro Pro Lys Leu Leu Ile Tyr Trp Ala Ser Ser Arg Glu Ser Gly Val
50 55 60

Pro Asp Arg Phe Ile Gly Ser Gly Ser Gly Thr Asp Phe Thr Leu Thr
65 70 75 80

Ile Ser Ser Leu Gln Ala Ala Asp Val Ala Val Tyr Tyr Cys His Gln
85 90 95

Tyr Tyr Ser Thr Pro His Ser Phe Gly Gln Gly Thr Lys Val Ala Ile
100 105 110

Lys

<210> SEQ ID NO 409
<211> LENGTH: 20
<212> TYPE: PRT
<213> ORGANISM: Artificial Sequence
<220> FEATURE:
<223> OTHER INFORMATION: Synthetic Construct

<400> SEQUENCE: 409

Glu Ser Gly Gly Val Val Val Gln Pro Gly Gly Ser Leu Arg Leu Ser
1 5 10 15

Cys Ala Ala Ser
20

<210> SEQ ID NO 410
<211> LENGTH: 17
<212> TYPE: PRT
<213> ORGANISM: Artificial Sequence
<220> FEATURE:
<223> OTHER INFORMATION: Synthetic Construct

<400> SEQUENCE: 410

Met His Trp Val Arg Gln Val Pro Gly Lys Gly Leu Glu Trp Val Ser
1 5 10 15

Leu

<210> SEQ ID NO 411
<211> LENGTH: 38
<212> TYPE: PRT
<213> ORGANISM: Artificial Sequence
<220> FEATURE:
<223> OTHER INFORMATION: Synthetic Construct

<400> SEQUENCE: 411

Ser Tyr Gly Asp Ser Val Lys Gly Arg Phe Thr Ile Ser Arg Asp Asn
1 5 10 15

Ser Lys Arg Ser Leu Phe Leu Gln Met Thr Asn Leu Arg Pro Glu Asp
20 25 30

Thr Ala Phe Tyr Tyr Cys
35

<210> SEQ ID NO 412
<211> LENGTH: 11
<212> TYPE: PRT
<213> ORGANISM: Artificial Sequence
<220> FEATURE:
<223> OTHER INFORMATION: Synthetic Construct

<400> SEQUENCE: 412

Trp Gly Gln Gly Thr Leu Val Thr Val Ser Ser
1 5 10

<210> SEQ ID NO 413
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 413

Asp Xaa Xaa Xaa Thr Gln Ser Pro Asp Ser Val Ala Val Ser Leu Gly
1 5 10 15

Gln Arg Ala Thr Ile Asn Cys Glu Ser Ser
20 25

<210> SEQ ID NO 414
<211> LENGTH: 17
<212> TYPE: PRT
<213> ORGANISM: Artificial Sequence
<220> FEATURE:
<223> OTHER INFORMATION: Synthetic Construct

<400> SEQUENCE: 414

Leu Ala Trp Tyr Gln His Lys Pro Gly Gln Pro Pro Lys Leu Leu Ile
1 5 10 15

Tyr

<210> SEQ ID NO 415
<211> LENGTH: 36
<212> TYPE: PRT
<213> ORGANISM: Artificial Sequence
<220> FEATURE:
<223> OTHER INFORMATION: Synthetic Construct

<400> SEQUENCE: 415

Ser Arg Glu Ser Gly Val Pro Asp Arg Phe Ile Gly Ser Gly Ser Gly
1 5 10 15

Thr Asp Phe Thr Leu Thr Ile Ser Ser Leu Gln Ala Ala Asp Val Ala
20 25 30

Val Tyr Tyr Cys
35

<210> SEQ ID NO 416
<211> LENGTH: 10
<212> TYPE: PRT
<213> ORGANISM: Artificial Sequence
<220> FEATURE:
<223> OTHER INFORMATION: Synthetic Construct

<400> SEQUENCE: 416

Phe Gly Gln Gly Thr Lys Val Ala Ile Lys
1 5 10

<210> SEQ ID NO 417
<211> LENGTH: 440
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid

<400> SEQUENCE: 417

Glu Ser Gly Gly Val Val Val Gln Pro Gly Gly Ser Leu Arg Leu Ser
1 5 10 15

Cys Ala Ala Ser Gly Phe Thr Phe Asp Asp Tyr Ser Met His Trp Val
20 25 30

Arg Gln Val Pro Gly Lys Gly Leu Glu Trp Val Ser Leu Ile Ser Trp

```
        35                  40                  45

Asp Gly Gly Arg Thr Ser Tyr Gly Asp Ser Val Lys Gly Arg Phe Thr
    50                  55                  60

Ile Ser Arg Asp Asn Ser Lys Arg Ser Leu Phe Leu Gln Met Thr Asn
65                  70                  75                  80

Leu Arg Pro Glu Asp Thr Ala Phe Tyr Tyr Cys Val Lys Asp Thr Gly
                85                  90                  95

Leu Arg Ser Phe Asp Ser Trp Gly Gln Gly Thr Leu Val Thr Val Ser
            100                 105                 110

Ser Lys Gly Pro Ser Val Phe Pro Leu Ala Pro Ser Ser Lys Ser Thr
        115                 120                 125

Ser Gly Gly Thr Ala Ala Leu Gly Xaa Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Xaa Val
        195                 200                 205

Glu Pro Lys Ser Cys Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Xaa Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440
```

<210> SEQ ID NO 418

<211> LENGTH: 217
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 418

```
Asp Xaa Xaa Xaa Thr Gln Ser Pro Asp Ser Val Ala Val Ser Leu Gly
1               5                   10                  15

Gln Arg Ala Thr Ile Asn Cys Glu Ser Ser Gln Ser Val Phe Asp Asp
            20                  25                  30

Ser Ser Asn Lys Asn Tyr Leu Ala Trp Tyr Gln His Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Ala Asp Val Ala Val Tyr Tyr Cys His Gln
                85                  90                  95

Tyr Tyr Ser Thr Pro His Ser Phe Gly Gln Gly Thr Lys Val Ala Ile
            100                 105                 110

Lys Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Lys
    210                 215
```

<210> SEQ ID NO 419
<211> LENGTH: 342
<212> TYPE: DNA
<213> ORGANISM: Artificial Sequence
<220> FEATURE:
<223> OTHER INFORMATION: Synthetic Construct

<400> SEQUENCE: 419

```
tggagtctgg cggagtcgtg gtacagcctg gggggtccct gagactctcc tgtgcagcct      60

ctggattcac ctttgatgat tattccatgc actgggtccg tcaagttccg gggaagggtc     120

ttgagtgggt ctctcttatt agttgggatg gtggccggac atcctatgga gactcagtga     180

agggtcgatt caccatctcc agagacaaca gcaagaggtc cctgtttctg caaatgacca     240

atctgagacc tgaagacacc gccttctatt actgtgtaaa agatactgga ctccgaagtt     300

ttgactcttg gggccaggga accctggtca ccgtctcctc ag                        342
```

<210> SEQ ID NO 420
<211> LENGTH: 340

<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 420
gacatnngnn tgacccagtc tccagactcc gtggctgtgt ctctgggcca gagggccacc 60
atcaactgcg agtccagcca gagtgttttc gatgactcca gcaataagaa ctacttagct 120
tggtatcaac acaaaccagg acagcctcct aaactactca tttactgggc atctagccgg 180
gaatccgggg tccctgaccg attcattggc agcgggtctg ggacagactt cactctcacc 240
atcagcagcc tgcaggctgc tgatgtggca gtttattact gtcatcaata ttatagtact 300
cctcactctt ttggccaggg gaccaaggtg gcgattaaac 340

<210> SEQ ID NO 421
<211> LENGTH: 8
<212> TYPE: PRT
<213> ORGANISM: Artificial Sequence
<220> FEATURE:
<223> OTHER INFORMATION: Synthetic Construct

<400> SEQUENCE: 421

Gly Phe Thr Phe Asp Asp Tyr Ser
1 5

<210> SEQ ID NO 422
<211> LENGTH: 8
<212> TYPE: PRT
<213> ORGANISM: Artificial Sequence
<220> FEATURE:
<223> OTHER INFORMATION: Synthetic Construct

<400> SEQUENCE: 422

Ile Ser Trp Asp Gly Gly Arg Thr
1 5

<210> SEQ ID NO 423
<211> LENGTH: 11
<212> TYPE: PRT
<213> ORGANISM: Artificial Sequence
<220> FEATURE:
<223> OTHER INFORMATION: Synthetic Construct

<400> SEQUENCE: 423

Val Lys Asp Thr Gly Leu Arg Ser Phe Asp Tyr
1 5 10

<210> SEQ ID NO 424
<211> LENGTH: 11
<212> TYPE: PRT
<213> ORGANISM: Artificial Sequence
<220> FEATURE:
<223> OTHER INFORMATION: Synthetic Construct

<400> SEQUENCE: 424

Gln Gly Leu Gln His Ser Asn Gly Tyr Asn Tyr
1 5 10

<210> SEQ ID NO 425
<211> LENGTH: 3
<212> TYPE: PRT
<213> ORGANISM: Artificial Sequence
<220> FEATURE:
<223> OTHER INFORMATION: Synthetic Construct

<400> SEQUENCE: 425

Met Gly Ser
1

<210> SEQ ID NO 426
<211> LENGTH: 8
<212> TYPE: PRT
<213> ORGANISM: Artificial Sequence
<220> FEATURE:
<223> OTHER INFORMATION: Synthetic Construct

<400> SEQUENCE: 426

Met Gln Ala Leu Gln Ser Trp Thr
1 5

<210> SEQ ID NO 427
<211> LENGTH: 113
<212> TYPE: PRT
<213> ORGANISM: Artificial Sequence
<220> FEATURE:
<223> OTHER INFORMATION: Synthetic Construct

<400> SEQUENCE: 427

Glu Ser Gly Gly Val Val Val Gln Pro Gly Gly Ser Leu Arg Leu Ser
1 5 10 15

Cys Ala Ala Ser Gly Phe Thr Phe Asp Asp Tyr Ser Met His Trp Val
20 25 30

Arg Gln Leu Pro Gly Lys Gly Leu Glu Trp Val Ser Leu Ile Ser Trp
35 40 45

Asp Gly Gly Arg Thr Asp Tyr Ala Asp Ser Val Lys Gly Arg Phe Thr
50 55 60

Ile Ser Arg Asp Asn Ser Lys Ser Ser Leu Leu Leu Gln Met Asn Ser
65 70 75 80

Leu Arg Leu Glu Asp Thr Ala Leu Tyr Tyr Cys Val Lys Asp Thr Gly
85 90 95

Leu Arg Ser Phe Asp Tyr Trp Gly Gln Gly Thr Leu Val Thr Val Ser
100 105 110

Ser

<210> SEQ ID NO 428
<211> LENGTH: 111
<212> TYPE: PRT
<213> ORGANISM: Artificial Sequence
<220> FEATURE:
<223> OTHER INFORMATION: Synthetic Construct

<400> SEQUENCE: 428

Asp Val Gly Glu Thr Gln Ser Pro Leu Ser Leu Pro Val Thr Pro Gly
1 5 10 15

Glu Pro Ala Ser Met Ser Cys Arg Ser Ser Gln Gly Leu Gln His Ser
20 25 30

Asn Gly Tyr Asn Tyr Val Asp Trp Tyr Leu Gln Lys Pro Gly Gln Ser
35 40 45

Pro Gln Leu Leu Ile Tyr Met Gly Ser Lys Arg Ala Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Gln Gly Thr Lys Val Glu Ile Lys
            100                 105                 110


<210> SEQ ID NO 429
<211> LENGTH: 20
<212> TYPE: PRT
<213> ORGANISM: Artificial Sequence
<220> FEATURE:
<223> OTHER INFORMATION: Synthetic Construct

<400> SEQUENCE: 429

Glu Ser Gly Gly Val Val Val Gln Pro Gly Gly Ser Leu Arg Leu Ser
1               5                   10                  15

Cys Ala Ala Ser
            20


<210> SEQ ID NO 430
<211> LENGTH: 17
<212> TYPE: PRT
<213> ORGANISM: Artificial Sequence
<220> FEATURE:
<223> OTHER INFORMATION: Synthetic Construct

<400> SEQUENCE: 430

Met His Trp Val Arg Gln Leu Pro Gly Lys Gly Leu Glu Trp Val Ser
1               5                   10                  15

Leu


<210> SEQ ID NO 431
<211> LENGTH: 38
<212> TYPE: PRT
<213> ORGANISM: Artificial Sequence
<220> FEATURE:
<223> OTHER INFORMATION: Synthetic Construct

<400> SEQUENCE: 431

Asp Tyr Ala Asp Ser Val Lys Gly Arg Phe Thr Ile Ser Arg Asp Asn
1               5                   10                  15

Ser Lys Ser Ser Leu Leu Leu Gln Met Asn Ser Leu Arg Leu Glu Asp
            20                  25                  30

Thr Ala Leu Tyr Tyr Cys
        35


<210> SEQ ID NO 432
<211> LENGTH: 11
<212> TYPE: PRT
<213> ORGANISM: Artificial Sequence
<220> FEATURE:
<223> OTHER INFORMATION: Synthetic Construct

<400> SEQUENCE: 432

Trp Gly Gln Gly Thr Leu Val Thr Val Ser Ser
1               5                   10


<210> SEQ ID NO 433
<211> LENGTH: 26
<212> TYPE: PRT
<213> ORGANISM: Artificial Sequence
```

<220> FEATURE:
<223> OTHER INFORMATION: Synthetic Construct

<400> SEQUENCE: 433

Asp Val Gly Glu Thr Gln Ser Pro Leu Ser Leu Pro Val Thr Pro Gly
1 5 10 15

Glu Pro Ala Ser Met Ser Cys Arg Ser Ser
20 25

<210> SEQ ID NO 434
<211> LENGTH: 17
<212> TYPE: PRT
<213> ORGANISM: Artificial Sequence
<220> FEATURE:
<223> OTHER INFORMATION: Synthetic Construct

<400> SEQUENCE: 434

Val Asp Trp Tyr Leu Gln Lys Pro Gly Gln Ser Pro Gln Leu Leu Ile
1 5 10 15

Tyr

<210> SEQ ID NO 435
<211> LENGTH: 36
<212> TYPE: PRT
<213> ORGANISM: Artificial Sequence
<220> FEATURE:
<223> OTHER INFORMATION: Synthetic Construct

<400> SEQUENCE: 435

Lys Arg Ala Ser Gly Val Pro Asp Arg Phe Ser Gly Ser Gly Ser Gly
1 5 10 15

Thr Asp Phe Thr Leu Lys Ile Ser Arg Val Glu Ala Glu Asp Val Gly
20 25 30

Val Tyr Tyr Cys
35

<210> SEQ ID NO 436
<211> LENGTH: 10
<212> TYPE: PRT
<213> ORGANISM: Artificial Sequence
<220> FEATURE:
<223> OTHER INFORMATION: Synthetic Construct

<400> SEQUENCE: 436

Phe Gly Gln Gly Thr Lys Val Glu Ile Lys
1 5 10

<210> SEQ ID NO 437
<211> LENGTH: 440
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid

<400> SEQUENCE: 437

```
Glu Ser Gly Gly Val Val Val Gln Pro Gly Gly Ser Leu Arg Leu Ser
1               5                   10                  15

Cys Ala Ala Ser Gly Phe Thr Phe Asp Asp Tyr Ser Met His Trp Val
            20                  25                  30

Arg Gln Leu Pro Gly Lys Gly Leu Glu Trp Val Ser Leu Ile Ser Trp
        35                  40                  45

Asp Gly Gly Arg Thr Asp Tyr Ala Asp Ser Val Lys Gly Arg Phe Thr
    50                  55                  60

Ile Ser Arg Asp Asn Ser Lys Ser Ser Leu Leu Leu Gln Met Asn Ser
65                  70                  75                  80

Leu Arg Leu Glu Asp Thr Ala Leu Tyr Tyr Cys Val Lys Asp Thr Gly
                85                  90                  95

Leu Arg Ser Phe Asp Tyr Trp Gly Gln Gly Thr Leu Val Thr Val Ser
            100                 105                 110

Ser Lys Gly Pro Ser Val Phe Pro Leu Ala Pro Ser Ser Lys Ser Thr
        115                 120                 125

Ser Gly Gly Thr Ala Ala Leu Gly Xaa Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Xaa Val
        195                 200                 205

Glu Pro Lys Ser Cys Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Xaa Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415
```

```
Ser Cys Ser Val Met His Glu Ala Leu His Asn His Tyr Thr Gln Lys
            420                 425                 430

Ser Leu Ser Leu Ser Pro Gly Lys
        435                 440


<210> SEQ ID NO 438
<211> LENGTH: 215
<212> TYPE: PRT
<213> ORGANISM: Artificial Sequence
<220> FEATURE:
<223> OTHER INFORMATION: Synthetic Construct

<400> SEQUENCE: 438

Asp Val Gly Glu Thr Gln Ser Pro Leu Ser Leu Pro Val Thr Pro Gly
1               5                   10                  15

Glu Pro Ala Ser Met Ser Cys Arg Ser Ser Gln Gly Leu Gln His Ser
            20                  25                  30

Asn Gly Tyr Asn Tyr Val Asp Trp Tyr Leu Gln Lys Pro Gly Gln Ser
        35                  40                  45

Pro Gln Leu Leu Ile Tyr Met Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Trp Thr Phe Gly Gln Gly Thr Lys Val Glu Ile Lys Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Lys
    210                 215


<210> SEQ ID NO 439
<211> LENGTH: 341
<212> TYPE: DNA
<213> ORGANISM: Artificial Sequence
<220> FEATURE:
<223> OTHER INFORMATION: Synthetic Construct

<400> SEQUENCE: 439

ggagtctggc ggagtcgtgg tacagcctgg gggatccctg agactctcct gtgcagcctc      60

tggattcact tttgatgatt actccatgca ctgggtccgt caacttccgg ggaaaggtct     120

ggagtgggtc tctcttatta gttgggatgg aggtcgcaca gactatgcag actctgtgaa     180

gggtcgattc accatctcca gagacaatag caagagctcc ctgcttctgc aaatgaacag     240

tctgagactt gaagacaccg ccttgtatta ctgtgtaaaa gatacagggc ttcgaagctt     300

tgactactgg ggccagggaa ccctggtcac cgtctcctca g                         341
```

<210> SEQ ID NO 440
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: n is a, c, g, or t

<400> SEQUENCE: 440
gatgttggng agactcagtc tccactctcc ctgcccgtca cccctggaga gccggcctcc 60
atgtcctgca ggtctagtca gggcctccag catagtaatg gatacaacta tgtggattgg 120
tacctgcaga agccagggca gtctccacag ctcctgatct atatgggctc taagcgggcc 180
tccggggtcc ctgacaggtt cagtggcagt ggatcaggca cagattttac actgaaaatc 240
agcagagtgg aggctgagga tgttggggtt tattactgca tgcaagctct acaaagttgg 300
acgttcggcc aagggaccaa ggtggaaatc aaac 334

<210> SEQ ID NO 441
<211> LENGTH: 8
<212> TYPE: PRT
<213> ORGANISM: Artificial Sequence
<220> FEATURE:
<223> OTHER INFORMATION: Synthetic Construct

<400> SEQUENCE: 441

Gly Phe Thr Phe Asn Tyr Ala Val
1 5

<210> SEQ ID NO 442
<211> LENGTH: 10
<212> TYPE: PRT
<213> ORGANISM: Artificial Sequence
<220> FEATURE:
<223> OTHER INFORMATION: Synthetic Construct

<400> SEQUENCE: 442

Ile Asp Ser Glu Ser Asp Gly Gly Thr Thr
1 5 10

<210> SEQ ID NO 443
<211> LENGTH: 15
<212> TYPE: PRT
<213> ORGANISM: Artificial Sequence
<220> FEATURE:
<223> OTHER INFORMATION: Synthetic Construct

<400> SEQUENCE: 443

Asn Thr His Phe Tyr Cys Thr Thr Thr Ser Cys Tyr Gly Asp His
1 5 10 15

<210> SEQ ID NO 444
<211> LENGTH: 12
<212> TYPE: PRT
<213> ORGANISM: Artificial Sequence
<220> FEATURE:
<223> OTHER INFORMATION: Synthetic Construct

<400> SEQUENCE: 444

Gln Ser Val Leu Tyr Ser Pro Lys Asn Lys His Tyr
1 5 10

<210> SEQ ID NO 445
<211> LENGTH: 3
<212> TYPE: PRT
<213> ORGANISM: Artificial Sequence
<220> FEATURE:
<223> OTHER INFORMATION: Synthetic Construct

<400> SEQUENCE: 445

Trp Ala Ser
1

<210> SEQ ID NO 446
<211> LENGTH: 8
<212> TYPE: PRT
<213> ORGANISM: Artificial Sequence
<220> FEATURE:
<223> OTHER INFORMATION: Synthetic Construct

<400> SEQUENCE: 446

Gln Gln Tyr Tyr Ser Gly Arg Thr
1 5

<210> SEQ ID NO 447
<211> LENGTH: 119
<212> TYPE: PRT
<213> ORGANISM: Artificial Sequence
<220> FEATURE:
<223> OTHER INFORMATION: Synthetic Construct

<400> SEQUENCE: 447

Glu Ser Gly Gly Gly Leu Val Lys Pro Gly Glu Ser Leu Arg Leu Ser
1 5 10 15

Cys Glu Gly Ser Gly Phe Thr Phe Asn Tyr Ala Val Met Ser Trp Val
20 25 30

Arg Gln Ala Pro Gly Lys Gly Leu Glu Trp Val Gly Arg Ile Asp Ser
35 40 45

Glu Ser Asp Gly Gly Thr Thr Asp Tyr Ala Ala Pro Val Lys Gly Arg
50 55 60

Phe Thr Ile Ser Arg Asp Asp Ser Arg Asn Thr Leu His Leu Gln Met
65 70 75 80

Asn Ser Leu Glu Ile Gly Asp Thr Ala Val Tyr Tyr Cys Asn Thr His
85 90 95

Phe Tyr Cys Thr Thr Thr Ser Cys Tyr Gly Asp His Trp Gly Gln Gly
100 105 110

Thr Leu Val Thr Val Ser Ser
115

<210> SEQ ID NO 448
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 448

Thr Xaa Xaa Val Thr Gln Ser Pro Glu Phe Leu Ser Leu Ser Leu Gly
1 5 10 15

Glu Arg Ala Ser Ile Asn Cys Lys Ala Ser Gln Ser Val Leu Tyr Ser
20 25 30

```
Pro Lys Asn Lys His Tyr Leu Ala Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Thr Phe Gln Ala Glu Asp Val Ala Val Tyr Tyr Cys Gln Gln
                85                  90                  95

Tyr Tyr Ser Gly Arg Thr Phe Gly Pro Gly Thr Lys Val Asp Ile Lys
            100                 105                 110


<210> SEQ ID NO 449
<211> LENGTH: 20
<212> TYPE: PRT
<213> ORGANISM: Artificial Sequence
<220> FEATURE:
<223> OTHER INFORMATION: Synthetic Construct

<400> SEQUENCE: 449

Glu Ser Gly Gly Gly Leu Val Lys Pro Gly Glu Ser Leu Arg Leu Ser
1               5                   10                  15

Cys Glu Gly Ser
            20


<210> SEQ ID NO 450
<211> LENGTH: 17
<212> TYPE: PRT
<213> ORGANISM: Artificial Sequence
<220> FEATURE:
<223> OTHER INFORMATION: Synthetic Construct

<400> SEQUENCE: 450

Met Ser Trp Val Arg Gln Ala Pro Gly Lys Gly Leu Glu Trp Val Gly
1               5                   10                  15

Arg


<210> SEQ ID NO 451
<211> LENGTH: 38
<212> TYPE: PRT
<213> ORGANISM: Artificial Sequence
<220> FEATURE:
<223> OTHER INFORMATION: Synthetic Construct

<400> SEQUENCE: 451

Asp Tyr Ala Ala Pro Val Lys Gly Arg Phe Thr Ile Ser Arg Asp Asp
1               5                   10                  15

Ser Arg Asn Thr Leu His Leu Gln Met Asn Ser Leu Glu Ile Gly Asp
            20                  25                  30

Thr Ala Val Tyr Tyr Cys
        35


<210> SEQ ID NO 452
<211> LENGTH: 11
<212> TYPE: PRT
<213> ORGANISM: Artificial Sequence
<220> FEATURE:
<223> OTHER INFORMATION: Synthetic Construct

<400> SEQUENCE: 452

Trp Gly Gln Gly Thr Leu Val Thr Val Ser Ser
1               5                   10
```

<210> SEQ ID NO 453
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 453

Thr Xaa Xaa Val Thr Gln Ser Pro Glu Phe Leu Ser Leu Ser Leu Gly
1               5                   10                  15

Glu Arg Ala Ser Ile Asn Cys Lys Ala Ser
            20                  25

<210> SEQ ID NO 454
<211> LENGTH: 17
<212> TYPE: PRT
<213> ORGANISM: Artificial Sequence
<220> FEATURE:
<223> OTHER INFORMATION: Synthetic Construct

<400> SEQUENCE: 454

Leu Ala Trp Tyr Gln Gln Lys Pro Gly Gln Pro Pro Lys Leu Leu Met
1               5                   10                  15

Tyr

<210> SEQ ID NO 455
<211> LENGTH: 36
<212> TYPE: PRT
<213> ORGANISM: Artificial Sequence
<220> FEATURE:
<223> OTHER INFORMATION: Synthetic Construct

<400> SEQUENCE: 455

Thr Arg Glu Ser Gly Val Pro Asp Arg Phe Ser Gly Ser Gly Ser Gly
1               5                   10                  15

Thr Asp Phe Thr Leu Thr Ile Asn Thr Phe Gln Ala Glu Asp Val Ala
            20                  25                  30

Val Tyr Tyr Cys
        35

<210> SEQ ID NO 456
<211> LENGTH: 10
<212> TYPE: PRT
<213> ORGANISM: Artificial Sequence
<220> FEATURE:
<223> OTHER INFORMATION: Synthetic Construct

<400> SEQUENCE: 456

Phe Gly Pro Gly Thr Lys Val Asp Ile Lys
1               5                   10

<210> SEQ ID NO 457
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:

<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 457

```
Glu Ser Gly Gly Gly Leu Val Lys Pro Gly Glu Ser Leu Arg Leu Ser
1               5                   10                  15

Cys Glu Gly Ser Gly Phe Thr Phe Asn Tyr Ala Val Met Ser Trp Val
            20                  25                  30

Arg Gln Ala Pro Gly Lys Gly Leu Glu Trp Val Gly Arg Ile Asp Ser
        35                  40                  45

Glu Ser Asp Gly Gly Thr Thr Asp Tyr Ala Ala Pro Val Lys Gly Arg
    50                  55                  60

Phe Thr Ile Ser Arg Asp Asp Ser Arg Asn Thr Leu His Leu Gln Met
65                  70                  75                  80

Asn Ser Leu Glu Ile Gly Asp Thr Ala Val Tyr Tyr Cys Asn Thr His
                85                  90                  95

Phe Tyr Cys Thr Thr Thr Ser Cys Tyr Gly Asp His Trp Gly Gln Gly
            100                 105                 110

Thr Leu Val Thr Val Ser Ser Lys Gly Pro Ser Val Phe Pro Leu Ala
        115                 120                 125

Pro Ser Ser Lys Ser Thr Ser Gly Gly Thr Ala Ala Leu Gly Xaa Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Xaa Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Xaa Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 458
<211> LENGTH: 216
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 458

Thr Xaa Xaa Val Thr Gln Ser Pro Glu Phe Leu Ser Leu Ser Leu Gly
1               5                   10                  15

Glu Arg Ala Ser Ile Asn Cys Lys Ala Ser Gln Ser Val Leu Tyr Ser
            20                  25                  30

Pro Lys Asn Lys His Tyr Leu Ala Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Thr Phe Gln Ala Glu Asp Val Ala Val Tyr Tyr Cys Gln Gln
                85                  90                  95

Tyr Tyr Ser Gly Arg Thr Phe Gly Pro Gly Thr Lys Val Asp Ile Lys
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Lys
    210                 215

<210> SEQ ID NO 459
<211> LENGTH: 358
<212> TYPE: DNA
<213> ORGANISM: Artificial Sequence
<220> FEATURE:
<223> OTHER INFORMATION: Synthetic Construct

<400> SEQUENCE: 459
gagtctgggg gaggcttggt aaagcctggg gagtcccttc gactctcctg tgaaggctct 60
ggattcactt tcaattacgc cgtgatgagc tgggtccgcc aggctccagg gaaggggctg 120
gagtgggttg gccgtattga tagcgaaagt gacggtggga caacagacta cgctgcaccc 180
gtgaaaggca gattcaccat ctcaagagac gattcaagaa acacgctgca tctgcagatg 240
aacagcctgg aaatcggcga cacagccgtt tattattgta acacccactt ctactgtacg 300
acaaccagct gctatggaga ccattggggc caggggaccc tggtcaccgt ctcctcag 358

<210> SEQ ID NO 460
<211> LENGTH: 337
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 460
acatnggnng tgacccagtc tccagagttc ctgagtctgt ctctgggcga gagggcctcc 60
atcaactgca aggccagcca gagtgtttta tacagcccca aaaataagca ctacttggct 120
tggtatcagc agaaacctgg acagcctcct aagctgctca tgtattgggc ttctacccgg 180
gaatccgggg tccctgaccg attcagtggc agcgggtctg gtacagattt cactctcacc 240
atcaacacct tccaggctga ggatgtggca gtctattact gtcagcaata ctatagtggt 300
cgcactttcg gccctgggac caaagtggat atcaaac 337

<210> SEQ ID NO 461
<211> LENGTH: 8
<212> TYPE: PRT
<213> ORGANISM: Artificial Sequence
<220> FEATURE:
<223> OTHER INFORMATION: Synthetic Construct

<400> SEQUENCE: 461

Gly Tyr Ser Phe Thr Arg Phe Asp
1 5

<210> SEQ ID NO 462
<211> LENGTH: 8
<212> TYPE: PRT
<213> ORGANISM: Artificial Sequence
<220> FEATURE:
<223> OTHER INFORMATION: Synthetic Construct

<400> SEQUENCE: 462

Met Asn Pro Lys Ser Gly His Ser
1 5

<210> SEQ ID NO 463
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 463

Ala Arg Gly Val Asp Asn Arg Xaa
1               5

<210> SEQ ID NO 464
<211> LENGTH: 12
<212> TYPE: PRT
<213> ORGANISM: Artificial Sequence
<220> FEATURE:
<223> OTHER INFORMATION: Synthetic Construct

<400> SEQUENCE: 464

Gln Ser Val Phe Asp Asp Ser Ser Asn Lys Asn Tyr
1               5                   10

<210> SEQ ID NO 465
<211> LENGTH: 3
<212> TYPE: PRT
<213> ORGANISM: Artificial Sequence
<220> FEATURE:
<223> OTHER INFORMATION: Synthetic Construct

<400> SEQUENCE: 465

Trp Ala Ser
1

<210> SEQ ID NO 466
<211> LENGTH: 9
<212> TYPE: PRT
<213> ORGANISM: Artificial Sequence
<220> FEATURE:
<223> OTHER INFORMATION: Synthetic Construct

<400> SEQUENCE: 466

Leu Gln Tyr Tyr Ser Thr Pro His Ser
1               5

<210> SEQ ID NO 467
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (98)..(98)
<223> OTHER INFORMATION: Xaa can be any naturally occurring amino acid

<400> SEQUENCE: 467

Ser Gly Ala Glu Val Lys Lys Pro Gly Ala Ser Val Lys Val Ser Cys
1               5                   10                  15

Lys Thr Ser Gly Tyr Ser Phe Thr Arg Phe Asp Ile Asn Trp Val Arg
            20                  25                  30

Gln Ala Thr Gly Gln Gly Leu Glu Trp Met Gly Trp Met Asn Pro Lys
        35                  40                  45

Ser Gly His Ser Gly Pro Ala Gln Lys Phe Gln Gly Arg Ile Thr Met
    50                  55                  60

Thr Val Asn Thr Ser Ile Ser Thr Ala Tyr Met Glu Leu Ser Ser Leu
65                  70                  75                  80

Arg Phe Glu Asp Thr Ala Val Tyr Tyr Cys Ala Arg Gly Val Asp Asn
                85                  90                  95

```
Arg Xaa Trp Gly Gln Gly Thr Leu Ile Thr Val Ser Ser
            100                 105


<210> SEQ ID NO 468
<211> LENGTH: 113
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 468

Asp Ile Xaa Xaa Thr Gln Ser Pro Asp Ser Val Ala Val Ser Leu Gly
1               5                   10                  15

Gln Arg Ala Thr Ile Asn Cys Glu Ser Ser Gln Ser Val Phe Asp Asp
            20                  25                  30

Ser Ser Asn Lys Asn Tyr Leu Ala Trp Tyr Gln His Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Ala Asp Val Ala Val Tyr Tyr Cys Leu Gln
                85                  90                  95

Tyr Tyr Ser Thr Pro His Ser Phe Gly Gln Gly Thr Lys Val Ala Ile
            100                 105                 110

Asn


<210> SEQ ID NO 469
<211> LENGTH: 19
<212> TYPE: PRT
<213> ORGANISM: Artificial Sequence
<220> FEATURE:
<223> OTHER INFORMATION: Synthetic Construct

<400> SEQUENCE: 469

Ser Gly Ala Glu Val Lys Lys Pro Gly Ala Ser Val Lys Val Ser Cys
1               5                   10                  15

Lys Thr Ser


<210> SEQ ID NO 470
<211> LENGTH: 17
<212> TYPE: PRT
<213> ORGANISM: Artificial Sequence
<220> FEATURE:
<223> OTHER INFORMATION: Synthetic Construct

<400> SEQUENCE: 470

Ile Asn Trp Val Arg Gln Ala Thr Gly Gln Gly Leu Glu Trp Met Gly
1               5                   10                  15

Trp


<210> SEQ ID NO 471
<211> LENGTH: 38
<212> TYPE: PRT
<213> ORGANISM: Artificial Sequence
<220> FEATURE:
<223> OTHER INFORMATION: Synthetic Construct

<400> SEQUENCE: 471
```

Gly Pro Ala Gln Lys Phe Gln Gly Arg Ile Thr Met Thr Val Asn Thr
1 5 10 15

Ser Ile Ser Thr Ala Tyr Met Glu Leu Ser Ser Leu Arg Phe Glu Asp
20 25 30

Thr Ala Val Tyr Tyr Cys
35

<210> SEQ ID NO 472
<211> LENGTH: 11
<212> TYPE: PRT
<213> ORGANISM: Artificial Sequence
<220> FEATURE:
<223> OTHER INFORMATION: Synthetic Construct

<400> SEQUENCE: 472

Trp Gly Gln Gly Thr Leu Ile Thr Val Ser Ser
1 5 10

<210> SEQ ID NO 473
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 473

Asp Ile Xaa Xaa Thr Gln Ser Pro Asp Ser Val Ala Val Ser Leu Gly
1 5 10 15

Gln Arg Ala Thr Ile Asn Cys Glu Ser Ser
20 25

<210> SEQ ID NO 474
<211> LENGTH: 17
<212> TYPE: PRT
<213> ORGANISM: Artificial Sequence
<220> FEATURE:
<223> OTHER INFORMATION: Synthetic Construct

<400> SEQUENCE: 474

Leu Ala Trp Tyr Gln His Lys Pro Gly Gln Pro Pro Lys Leu Leu Ile
1 5 10 15

Tyr

<210> SEQ ID NO 475
<211> LENGTH: 36
<212> TYPE: PRT
<213> ORGANISM: Artificial Sequence
<220> FEATURE:
<223> OTHER INFORMATION: Synthetic Construct

<400> SEQUENCE: 475

Ser Arg Glu Ser Gly Val Pro Asp Arg Phe Ile Gly Ser Gly Ser Gly
1 5 10 15

Thr Asp Phe Thr Leu Thr Ile Ser Ser Leu Gln Ala Ala Asp Val Ala
20 25 30

Val Tyr Tyr Cys
35

<210> SEQ ID NO 476

<211> LENGTH: 10
<212> TYPE: PRT
<213> ORGANISM: Artificial Sequence
<220> FEATURE:
<223> OTHER INFORMATION: Synthetic Construct

<400> SEQUENCE: 476

Phe Gly Gln Gly Thr Lys Val Ala Ile Asn
1               5                   10

<210> SEQ ID NO 477
<211> LENGTH: 436
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid

<400> SEQUENCE: 477

Ser Gly Ala Glu Val Lys Lys Pro Gly Ala Ser Val Lys Val Ser Cys
1               5                   10                  15

Lys Thr Ser Gly Tyr Ser Phe Thr Arg Phe Asp Ile Asn Trp Val Arg
            20                  25                  30

Gln Ala Thr Gly Gln Gly Leu Glu Trp Met Gly Trp Met Asn Pro Lys
        35                  40                  45

Ser Gly His Ser Gly Pro Ala Gln Lys Phe Gln Gly Arg Ile Thr Met
    50                  55                  60

Thr Val Asn Thr Ser Ile Ser Thr Ala Tyr Met Glu Leu Ser Ser Leu
65                  70                  75                  80

Arg Phe Glu Asp Thr Ala Val Tyr Tyr Cys Ala Arg Gly Val Asp Asn
                85                  90                  95

Arg Xaa Trp Gly Gln Gly Thr Leu Ile Thr Val Ser Ser Lys Gly Pro
            100                 105                 110

Ser Val Phe Pro Leu Ala Pro Ser Ser Lys Ser Thr Ser Gly Gly Thr
        115                 120                 125

Ala Ala Leu Gly Xaa Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Xaa Val Glu Pro Lys Ser
        195                 200                 205

Cys Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225 230 235 240

Met Ile Ser Arg Thr Pro Glu Val Thr Cys Val Val Val Asp Val Ser
245 250 255

His Glu Asp Pro Glu Val Lys Phe Asn Trp Tyr Val Asp Gly Val Glu
260 265 270

Val His Asn Ala Lys Thr Lys Pro Arg Glu Glu Gln Tyr Asn Ser Thr
275 280 285

Tyr Arg Val Val Ser Val Leu Thr Val Leu His Gln Asp Trp Leu Asn
290 295 300

Gly Lys Glu Tyr Lys Cys Lys Val Ser Asn Lys Ala Leu Pro Ala Pro
305 310 315 320

Ile Glu Lys Thr Ile Ser Lys Ala Lys Gly Gln Pro Arg Glu Pro Gln
325 330 335

Val Tyr Thr Leu Pro Pro Ser Arg Asp Glu Xaa Thr Lys Asn Gln Val
340 345 350

Ser Leu Thr Cys Leu Val Lys Gly Phe Tyr Pro Ser Asp Ile Ala Val
355 360 365

Glu Trp Glu Ser Asn Gly Gln Pro Glu Asn Asn Tyr Lys Thr Thr Pro
370 375 380

Pro Val Leu Asp Ser Asp Gly Ser Phe Phe Leu Tyr Ser Lys Leu Thr
385 390 395 400

Val Asp Lys Ser Arg Trp Gln Gln Gly Asn Val Phe Ser Cys Ser Val
405 410 415

Met His Glu Ala Leu His Asn His Tyr Thr Gln Lys Ser Leu Ser Leu
420 425 430

Ser Pro Gly Lys
435

<210> SEQ ID NO 478
<211> LENGTH: 217
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 478

Asp Ile Xaa Xaa Thr Gln Ser Pro Asp Ser Val Ala Val Ser Leu Gly
1 5 10 15

Gln Arg Ala Thr Ile Asn Cys Glu Ser Ser Gln Ser Val Phe Asp Asp
20 25 30

Ser Ser Asn Lys Asn Tyr Leu Ala Trp Tyr Gln His Lys Pro Gly Gln
35 40 45

Pro Pro Lys Leu Leu Ile Tyr Trp Ala Ser Ser Arg Glu Ser Gly Val
50 55 60

Pro Asp Arg Phe Ile Gly Ser Gly Ser Gly Thr Asp Phe Thr Leu Thr
65 70 75 80

Ile Ser Ser Leu Gln Ala Ala Asp Val Ala Val Tyr Tyr Cys Leu Gln
85 90 95

Tyr Tyr Ser Thr Pro His Ser Phe Gly Gln Gly Thr Lys Val Ala Ile
100 105 110

Asn Ala Pro Ser Val Phe Ile Phe Pro Pro Ser Asp Glu Gln Leu Lys
115 120 125

```
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Lys
    210                 215
```

```
<210> SEQ ID NO 479
<211> LENGTH: 330
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (294)..(295)
<223> OTHER INFORMATION: n is a, c, g, or t

<400> SEQUENCE: 479

agtctggggc tgaggtgaag aagcctgggg cctcagtgaa ggtctcctgc aagacttctg     60

gatacagctt cacccgtttt gatatcaact gggtgcgaca ggccactgga caagggcttg    120

agtggatggg atggatgaac cctaagagtg gtcactcagg ccctgcacag aagttccagg    180

gcagaatcac catgaccgtt aacacctcca taagtacagc ctacatggag ctgagcagcc    240

tgagatttga ggacacggcc gtttattatt gtgcgcgagg cgtggataat cgtnnctggg    300

gccagggaac cctaatcacc gtctcctcag                                     330


<210> SEQ ID NO 480
<211> LENGTH: 340
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(12)
<223> OTHER INFORMATION: n is a, c, g, or t

<400> SEQUENCE: 480

gacatcgnnn nnacccagtc tccagactcc gtggctgtgt ctctgggcca gagggccacc     60

atcaactgcg agtccagcca gagtgttttc gatgactcca gcaataagaa ctacttagct    120

tggtatcaac acaaaccagg acagcctcct aaactactca tttactgggc atctagccgg    180

gaatccgggg tccctgaccg attcattggc agcgggtctg ggacagactt cactctcacc    240

atcagcagcc tgcaggctgc tgatgtggca gtttattact gtcttcaata ttatagtact    300

cctcactctt ttggccaggg gaccaaggtg gcgattaacc                          340


<210> SEQ ID NO 481
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 481

Gly Phe Thr Phe Asp Asp Tyr Ser
1               5

<210> SEQ ID NO 482
<211> LENGTH: 8
<212> TYPE: PRT
<213> ORGANISM: Artificial Sequence
<220> FEATURE:
<223> OTHER INFORMATION: Synthetic Construct

<400> SEQUENCE: 482

Ile Ser Trp Asp Gly Ala Arg Thr
1               5

<210> SEQ ID NO 483
<211> LENGTH: 11
<212> TYPE: PRT
<213> ORGANISM: Artificial Sequence
<220> FEATURE:
<223> OTHER INFORMATION: Synthetic Construct

<400> SEQUENCE: 483

Val Lys Asp Thr Gly Leu Arg Ser Phe Asp Ser
1               5                   10

<210> SEQ ID NO 484
<211> LENGTH: 11
<212> TYPE: PRT
<213> ORGANISM: Artificial Sequence
<220> FEATURE:
<223> OTHER INFORMATION: Synthetic Construct

<400> SEQUENCE: 484

Gln Ser Leu Leu His Ser Asn Gly Tyr Asn Tyr
1               5                   10

<210> SEQ ID NO 485
<211> LENGTH: 3
<212> TYPE: PRT
<213> ORGANISM: Artificial Sequence
<220> FEATURE:
<223> OTHER INFORMATION: Synthetic Construct

<400> SEQUENCE: 485

Met Gly Ser
1

<210> SEQ ID NO 486
<211> LENGTH: 8
<212> TYPE: PRT
<213> ORGANISM: Artificial Sequence
<220> FEATURE:
<223> OTHER INFORMATION: Synthetic Construct

<400> SEQUENCE: 486

Met Gln Ala Leu Gln Thr Trp Thr
1               5

<210> SEQ ID NO 487
<211> LENGTH: 114
<212> TYPE: PRT
<213> ORGANISM: Artificial Sequence
<220> FEATURE:
<223> OTHER INFORMATION: Synthetic Construct

<400> SEQUENCE: 487

```
Val Glu Ser Gly Gly Val Val Val Gln Pro Gly Gly Ser Leu Arg Leu
1               5                   10                  15

Ser Cys Ala Ala Ser Gly Phe Thr Phe Asp Asp Tyr Ser Met His Trp
            20                  25                  30

Val Arg Gln Val Pro Gly Lys Gly Leu Glu Trp Val Ser Leu Ile Ser
        35                  40                  45

Trp Asp Gly Ala Arg Thr Ser Tyr Gly Asp Ser Val Lys Gly Arg Phe
    50                  55                  60

Thr Ile Ser Arg Asp Asn Ser Lys Arg Ser Leu Phe Leu Gln Met Thr
65                  70                  75                  80

Asn Leu Arg Pro Glu Asp Thr Ala Phe Tyr Tyr Cys Val Lys Asp Thr
                85                  90                  95

Gly Leu Arg Ser Phe Asp Ser Trp Gly Gln Gly Thr Leu Val Thr Val
            100                 105                 110

Ser Ser


<210> SEQ ID NO 488
<211> LENGTH: 111
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 488

Asp Val Xaa Glu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Met Gly Ser Lys Arg Ala Ser Gly Val Pro
    50                  55                  60

Asp Arg Phe Ser Gly Ser Val Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Trp Thr Phe Gly Gln Gly Thr Lys Val Glu Ile Lys
            100                 105                 110


<210> SEQ ID NO 489
<211> LENGTH: 21
<212> TYPE: PRT
<213> ORGANISM: Artificial Sequence
<220> FEATURE:
<223> OTHER INFORMATION: Synthetic Construct

<400> SEQUENCE: 489

Val Glu Ser Gly Gly Val Val Val Gln Pro Gly Gly Ser Leu Arg Leu
1               5                   10                  15

Ser Cys Ala Ala Ser
            20


<210> SEQ ID NO 490
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 490

Met His Trp Val Arg Gln Val Pro Gly Lys Gly Leu Glu Trp Val Ser
1 5 10 15

Leu

<210> SEQ ID NO 491
<211> LENGTH: 38
<212> TYPE: PRT
<213> ORGANISM: Artificial Sequence
<220> FEATURE:
<223> OTHER INFORMATION: Synthetic Construct

<400> SEQUENCE: 491

Ser Tyr Gly Asp Ser Val Lys Gly Arg Phe Thr Ile Ser Arg Asp Asn
1 5 10 15

Ser Lys Arg Ser Leu Phe Leu Gln Met Thr Asn Leu Arg Pro Glu Asp
20 25 30

Thr Ala Phe Tyr Tyr Cys
35

<210> SEQ ID NO 492
<211> LENGTH: 11
<212> TYPE: PRT
<213> ORGANISM: Artificial Sequence
<220> FEATURE:
<223> OTHER INFORMATION: Synthetic Construct

<400> SEQUENCE: 492

Trp Gly Gln Gly Thr Leu Val Thr Val Ser Ser
1 5 10

<210> SEQ ID NO 493
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 493

Asp Val Xaa Glu Thr Gln Ser Pro Leu Ser Leu Pro Val Thr Pro Gly
1 5 10 15

Glu Pro Ala Ser Ile Ser Cys Arg Ser Ser
20 25

<210> SEQ ID NO 494
<211> LENGTH: 17
<212> TYPE: PRT
<213> ORGANISM: Artificial Sequence
<220> FEATURE:
<223> OTHER INFORMATION: Synthetic Construct

<400> SEQUENCE: 494

Leu Asp Trp Tyr Leu Gln Lys Pro Gly Gln Ser Pro Gln Leu Leu Ile
1 5 10 15

Tyr

<210> SEQ ID NO 495
<211> LENGTH: 36
<212> TYPE: PRT
<213> ORGANISM: Artificial Sequence
<220> FEATURE:
<223> OTHER INFORMATION: Synthetic Construct

<400> SEQUENCE: 495

Lys Arg Ala Ser Gly Val Pro Asp Arg Phe Ser Gly Ser Val Ser Gly
1 5 10 15

Thr Asp Phe Thr Leu Lys Ile Ser Arg Val Glu Ala Glu Asp Val Gly
20 25 30

Val Tyr Tyr Cys
35

<210> SEQ ID NO 496
<211> LENGTH: 10
<212> TYPE: PRT
<213> ORGANISM: Artificial Sequence
<220> FEATURE:
<223> OTHER INFORMATION: Synthetic Construct

<400> SEQUENCE: 496

Phe Gly Gln Gly Thr Lys Val Glu Ile Lys
1 5 10

<210> SEQ ID NO 497
<211> LENGTH: 441
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid

<400> SEQUENCE: 497

Val Glu Ser Gly Gly Val Val Val Gln Pro Gly Gly Ser Leu Arg Leu
1 5 10 15

Ser Cys Ala Ala Ser Gly Phe Thr Phe Asp Asp Tyr Ser Met His Trp
20 25 30

Val Arg Gln Val Pro Gly Lys Gly Leu Glu Trp Val Ser Leu Ile Ser
35 40 45

Trp Asp Gly Ala Arg Thr Ser Tyr Gly Asp Ser Val Lys Gly Arg Phe
50 55 60

Thr Ile Ser Arg Asp Asn Ser Lys Arg Ser Leu Phe Leu Gln Met Thr
65 70 75 80

Asn Leu Arg Pro Glu Asp Thr Ala Phe Tyr Tyr Cys Val Lys Asp Thr
85 90 95

Gly Leu Arg Ser Phe Asp Ser Trp Gly Gln Gly Thr Leu Val Thr Val
100 105 110

Ser Ser Lys Gly Pro Ser Val Phe Pro Leu Ala Pro Ser Ser Lys Ser
115 120 125

Thr Ser Gly Gly Thr Ala Ala Leu Gly Xaa Leu Val Lys Asp Tyr Phe
130 135 140

```
Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Xaa
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Xaa
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 498
<211> LENGTH: 215
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 498

```
Asp Val Xaa Glu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
```

```
        35                  40                  45

Pro Gln Leu Leu Ile Tyr Met Gly Ser Lys Arg Ala Ser Gly Val Pro
    50                  55                  60

Asp Arg Phe Ser Gly Ser Val Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Trp Thr Phe Gly Gln Gly Thr Lys Val Glu Ile Lys Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Lys
    210                 215


<210> SEQ ID NO 499
<211> LENGTH: 343
<212> TYPE: DNA
<213> ORGANISM: Artificial Sequence
<220> FEATURE:
<223> OTHER INFORMATION: Synthetic Construct

<400> SEQUENCE: 499

gtggagtctg gcggagtcgt ggtacagcct gggggtccc tgagactctc ctgtgcagcc      60

tctggattca cctttgatga ttattccatg cactgggtcc gtcaagttcc ggggaagggt     120

cttgagtggg tctctcttat tagttgggat ggtgcccgga catcctatgg agactctgtg     180

aagggtcgat tcaccatctc cagagacaac agcaagaggt ccctgtttct gcaaatgacc     240

aatctgagac ctgaagacac cgccttctat tactgtgtaa aagatactgg acttcgaagt     300

tttgactctt ggggccaggg aaccctggtc accgtctcct cag                       343


<210> SEQ ID NO 500
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(9)
<223> OTHER INFORMATION: n is a, c, g, or t

<400> SEQUENCE: 500

gatgttnnng agactcagtc tccactctcc ctgcccgtca cccctggaga gccggcctcc      60

atctcctgca ggtctagtca gagcctcctg catagtaatg gatacaacta tttggattgg     120

tacctccaga agccagggca gtctccacag ctcctgatct atatgggttc taagcgggcc     180

tccggggtcc ctgacaggtt cagtggcagt gtctcaggca cagattttac actgaaaatc     240
```

agcagagtgg aggctgagga tgttggggtt tattactgca tgcaagctct acaaacttgg 300
acgttcggcc aagggaccaa ggtggaaatc aaac 334

<210> SEQ ID NO 501
<211> LENGTH: 8
<212> TYPE: PRT
<213> ORGANISM: Artificial Sequence
<220> FEATURE:
<223> OTHER INFORMATION: Synthetic Construct

<400> SEQUENCE: 501

Gly Phe Thr Phe Gly Asp Tyr Thr
1 5

<210> SEQ ID NO 502
<211> LENGTH: 8
<212> TYPE: PRT
<213> ORGANISM: Artificial Sequence
<220> FEATURE:
<223> OTHER INFORMATION: Synthetic Construct

<400> SEQUENCE: 502

Ile Lys Trp Asn Gly Gly Gly Ile
1 5

<210> SEQ ID NO 503
<211> LENGTH: 11
<212> TYPE: PRT
<213> ORGANISM: Artificial Sequence
<220> FEATURE:
<223> OTHER INFORMATION: Synthetic Construct

<400> SEQUENCE: 503

Ala Lys Asp Ile Gly Leu Arg Ser Leu Asp Ser
1 5 10

<210> SEQ ID NO 504
<211> LENGTH: 11
<212> TYPE: PRT
<213> ORGANISM: Artificial Sequence
<220> FEATURE:
<223> OTHER INFORMATION: Synthetic Construct

<400> SEQUENCE: 504

Gln Ser Leu Leu His Ser Asn Gly Tyr Thr Tyr
1 5 10

<210> SEQ ID NO 505
<211> LENGTH: 3
<212> TYPE: PRT
<213> ORGANISM: Artificial Sequence
<220> FEATURE:
<223> OTHER INFORMATION: Synthetic Construct

<400> SEQUENCE: 505

Met Gly Ser
1

<210> SEQ ID NO 506
<211> LENGTH: 8
<212> TYPE: PRT
<213> ORGANISM: Artificial Sequence
<220> FEATURE:
<223> OTHER INFORMATION: Synthetic Construct

<400> SEQUENCE: 506

Met Gln Ala Leu Gln Gly Trp Thr
1 5

<210> SEQ ID NO 507
<211> LENGTH: 117
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid

<400> SEQUENCE: 507

Cys Xaa Xaa Val Glu Ser Gly Gly Gly Leu Val Gln Pro Gly Arg Ser
1 5 10 15

Leu Arg Leu Ser Cys Thr Ala Ser Gly Phe Thr Phe Gly Asp Tyr Thr
20 25 30

Met His Trp Val Arg Gln Ala Pro Gly Lys Gly Leu Glu Trp Val Ser
35 40 45

Asn Ile Lys Trp Asn Gly Gly Gly Ile Gly Tyr Ala Asp Ser Xaa Lys
50 55 60

Gly Arg Phe Thr Ile Ser Arg Asp Asn Ala Gly Asn Ser Leu Tyr Leu
65 70 75 80

Gln Met Asn Ser Leu Arg Pro Glu Asp Thr Ala Phe Tyr Tyr Cys Ala
85 90 95

Lys Asp Ile Gly Leu Arg Ser Leu Asp Ser Trp Gly Gln Gly Thr Leu
100 105 110

Val Ile Val Ser Ser
115

<210> SEQ ID NO 508
<211> LENGTH: 111
<212> TYPE: PRT
<213> ORGANISM: Artificial Sequence
<220> FEATURE:
<223> OTHER INFORMATION: Synthetic Construct

<400> SEQUENCE: 508

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Thr Tyr Leu Asp Trp Tyr Leu Gln Lys Pro Gly Gln Ser
35 40 45

Pro Gln Leu Leu Ile Tyr Met Gly Ser Lys Arg Ala Ser Gly Val Pro
50 55 60

Asp Arg Phe Ser Gly Ser Phe Ser Asp Thr Asp Phe Thr Leu Thr Ile
65 70 75 80

Ser Arg Val Glu Ala Glu Asp Val Gly Val Tyr Tyr Cys Met Gln Ala
85 90 95

Leu Gln Gly Trp Thr Phe Gly Gln Gly Thr Lys Val Glu Ile Lys
100 105 110

<210> SEQ ID NO 509
<211> LENGTH: 24

<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 509

Cys Xaa Xaa Val Glu Ser Gly Gly Gly Leu Val Gln Pro Gly Arg Ser
1 5 10 15

Leu Arg Leu Ser Cys Thr Ala Ser
20

<210> SEQ ID NO 510
<211> LENGTH: 17
<212> TYPE: PRT
<213> ORGANISM: Artificial Sequence
<220> FEATURE:
<223> OTHER INFORMATION: Synthetic Construct

<400> SEQUENCE: 510

Met His Trp Val Arg Gln Ala Pro Gly Lys Gly Leu Glu Trp Val Ser
1 5 10 15

Asn

<210> SEQ ID NO 511
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 511

Gly Tyr Ala Asp Ser Xaa Lys Gly Arg Phe Thr Ile Ser Arg Asp Asn
1 5 10 15

Ala Gly Asn Ser Leu Tyr Leu Gln Met Asn Ser Leu Arg Pro Glu Asp
20 25 30

Thr Ala Phe Tyr Tyr Cys
35

<210> SEQ ID NO 512
<211> LENGTH: 11
<212> TYPE: PRT
<213> ORGANISM: Artificial Sequence
<220> FEATURE:
<223> OTHER INFORMATION: Synthetic Construct

<400> SEQUENCE: 512

Trp Gly Gln Gly Thr Leu Val Ile Val Ser Ser
1 5 10

<210> SEQ ID NO 513
<211> LENGTH: 26
<212> TYPE: PRT
<213> ORGANISM: Artificial Sequence
<220> FEATURE:
<223> OTHER INFORMATION: Synthetic Construct

<400> SEQUENCE: 513

Asp Val Val Met Thr Gln Ser Pro Leu Ser Leu Pro Val Thr Pro Gly

```
1               5                   10                  15

Glu Pro Ala Ser Ile Ser Cys Arg Ser Ser
            20                  25


<210> SEQ ID NO 514
<211> LENGTH: 17
<212> TYPE: PRT
<213> ORGANISM: Artificial Sequence
<220> FEATURE:
<223> OTHER INFORMATION: Synthetic Construct

<400> SEQUENCE: 514

Leu Asp Trp Tyr Leu Gln Lys Pro Gly Gln Ser Pro Gln Leu Leu Ile
1               5                   10                  15

Tyr


<210> SEQ ID NO 515
<211> LENGTH: 36
<212> TYPE: PRT
<213> ORGANISM: Artificial Sequence
<220> FEATURE:
<223> OTHER INFORMATION: Synthetic Construct

<400> SEQUENCE: 515

Lys Arg Ala Ser Gly Val Pro Asp Arg Phe Ser Gly Ser Phe Ser Asp
1               5                   10                  15

Thr Asp Phe Thr Leu Thr Ile Ser Arg Val Glu Ala Glu Asp Val Gly
            20                  25                  30

Val Tyr Tyr Cys
        35


<210> SEQ ID NO 516
<211> LENGTH: 10
<212> TYPE: PRT
<213> ORGANISM: Artificial Sequence
<220> FEATURE:
<223> OTHER INFORMATION: Synthetic Construct

<400> SEQUENCE: 516

Phe Gly Gln Gly Thr Lys Val Glu Ile Lys
1               5                   10


<210> SEQ ID NO 517
<211> LENGTH: 444
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
```

<400> SEQUENCE: 517

Cys Xaa Xaa Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Thr
            20                  25                  30

Met His Trp Val Arg Gln Ala Pro Gly Lys Gly Leu Glu Trp Val Ser
        35                  40                  45

Asn Ile Lys Trp Asn Gly Gly Gly Ile Gly Tyr Ala Asp Ser Xaa Lys
    50                  55                  60

Gly Arg Phe Thr Ile Ser Arg Asp Asn Ala Gly Asn Ser Leu Tyr Leu
65                  70                  75                  80

Gln Met Asn Ser Leu Arg Pro Glu Asp Thr Ala Phe Tyr Tyr Cys Ala
                85                  90                  95

Lys Asp Ile Gly Leu Arg Ser Leu Asp Ser Trp Gly Gln Gly Thr Leu
            100                 105                 110

Val Ile Val Ser Ser Lys Gly Pro Ser Val Phe Pro Leu Ala Pro Ser
        115                 120                 125

Ser Lys Ser Thr Ser Gly Gly Thr Ala Ala Leu Gly Xaa Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Xaa Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Xaa Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln

```
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 518
<211> LENGTH: 215
<212> TYPE: PRT
<213> ORGANISM: Artificial Sequence
<220> FEATURE:
<223> OTHER INFORMATION: Synthetic Construct

<400> SEQUENCE: 518

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Asp Trp Tyr Leu Gln Lys Pro Gly Gln Ser
        35                  40                  45

Pro Gln Leu Leu Ile Tyr Met Gly Ser Lys Arg Ala Ser Gly Val Pro
    50                  55                  60

Asp Arg Phe Ser Gly Ser Phe Ser Asp Thr Asp Phe Thr Leu Thr Ile
65                  70                  75                  80

Ser Arg Val Glu Ala Glu Asp Val Gly Val Tyr Tyr Cys Met Gln Ala
                85                  90                  95

Leu Gln Gly Trp Thr Phe Gly Gln Gly Thr Lys Val Glu Ile Lys Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Lys
    210                 215


<210> SEQ ID NO 519
<211> LENGTH: 353
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
```

<400> SEQUENCE: 519
gtgcnannnn gtggaatctg ggggaggctt ggtacagcct ggcaggtccc tgagactctc 60
ctgtacagcc tctggtttca cctttggtga ttataccatg cattgggtcc ggcaagctcc 120
agggaagggc ctggagtggg tctcaaatat taagtggaat ggtggtggca taggctatgc 180
ggactctgnt aagggccgat tcaccatctc cagagacaac gccgggaact ccctctatct 240
acaaatgaac agtctgagac ctgaggatac ggccttttat tactgtgcaa aagatattgg 300
actacgttcc cttgactcct ggggccaggg gaccctggtc atcgtctcct cag 353

<210> SEQ ID NO 520
<211> LENGTH: 334
<212> TYPE: DNA
<213> ORGANISM: Artificial Sequence
<220> FEATURE:
<223> OTHER INFORMATION: Synthetic Construct

<400> SEQUENCE: 520
gatgttgtga tgactcagtc tccactctcc ctgcccgtca cccctggaga gccggcctcc 60
atctcctgca ggtctagtca gagcctcctg catagtaatg gatacaccta tttggattgg 120
tacctgcaga agccagggca gtctccacag ctcctgatct atatgggttc taagcgggcc 180
tccggggtcc ctgacaggtt cagtggcagt ttctcagaca cagatttcac actgacaatc 240
agcagagtgg aggctgagga tgttggggtt tattactgca tgcaggctct acaaggttgg 300
acgttcggcc aagggaccaa ggtggaaatc aaac 334

<210> SEQ ID NO 521
<211> LENGTH: 8
<212> TYPE: PRT
<213> ORGANISM: Artificial Sequence
<220> FEATURE:
<223> OTHER INFORMATION: Synthetic Construct

<400> SEQUENCE: 521

Gly Phe Thr Phe Pro Arg Ala Trp
1 5

<210> SEQ ID NO 522
<211> LENGTH: 10
<212> TYPE: PRT
<213> ORGANISM: Artificial Sequence
<220> FEATURE:
<223> OTHER INFORMATION: Synthetic Construct

<400> SEQUENCE: 522

Leu Lys Ser Glu Asn Asp Gly Gly Thr Ala
1 5 10

<210> SEQ ID NO 523
<211> LENGTH: 15
<212> TYPE: PRT
<213> ORGANISM: Artificial Sequence
<220> FEATURE:
<223> OTHER INFORMATION: Synthetic Construct

<400> SEQUENCE: 523

Ser Thr Val Pro Tyr Cys Pro Gly Asp Ser Cys Tyr Gly Asn Phe
1 5 10 15

<210> SEQ ID NO 524
<211> LENGTH: 12

<212> TYPE: PRT
<213> ORGANISM: Artificial Sequence
<220> FEATURE:
<223> OTHER INFORMATION: Synthetic Construct

<400> SEQUENCE: 524

Gln Ser Leu Leu Tyr Ser Ser Asn Asn Arg Asn Tyr
1 5 10

<210> SEQ ID NO 525
<211> LENGTH: 3
<212> TYPE: PRT
<213> ORGANISM: Artificial Sequence
<220> FEATURE:
<223> OTHER INFORMATION: Synthetic Construct

<400> SEQUENCE: 525

Trp Ala Ser
1

<210> SEQ ID NO 526
<211> LENGTH: 6
<212> TYPE: PRT
<213> ORGANISM: Artificial Sequence
<220> FEATURE:
<223> OTHER INFORMATION: Synthetic Construct

<400> SEQUENCE: 526

Gln Gln Tyr Trp Gly Pro
1 5

<210> SEQ ID NO 527
<211> LENGTH: 123
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 527

Cys Xaa Xaa Val Glu Ser Gly Gly Gly Phe Val Lys Pro Gly Gly Ser
1 5 10 15

Leu Arg Leu Ser Cys Ala Ala Ser Gly Phe Thr Phe Pro Arg Ala Trp
20 25 30

Met Thr Trp Val Arg Gln Ala Pro Gly Lys Gly Leu Glu Trp Val Gly
35 40 45

Arg Leu Lys Ser Glu Asn Asp Gly Gly Thr Ala Asp Tyr Ala Glu Val
50 55 60

Val Lys Asp Arg Phe Val Ile Thr Arg Asp Asp Ser Lys Asn Thr Leu
65 70 75 80

Tyr Leu Glu Met Thr Asn Val Lys Thr Glu Asp Thr Gly Val Tyr Phe
85 90 95

Cys Ser Thr Val Pro Tyr Cys Pro Gly Asp Ser Cys Tyr Gly Asn Phe
100 105 110

Trp Gly Gln Gly Thr His Val Ile Val Ser Ser
115 120

<210> SEQ ID NO 528
<211> LENGTH: 110
<212> TYPE: PRT
<213> ORGANISM: Artificial Sequence
<220> FEATURE:
<223> OTHER INFORMATION: Synthetic Construct

<400> SEQUENCE: 528

```
Asp Ile Val Met Thr Gln Ser Pro Asp Ser Leu Ala Leu Ser Leu Gly
1               5                   10                  15

Glu Arg Ala Ala Ile Asn Cys Lys Ser Ser Gln Ser Leu Leu Tyr Ser
            20                  25                  30

Ser Asn Asn Arg Asn Tyr Leu Ser Trp Tyr Gln Gln Lys Pro Gly Gln
        35                  40                  45

Pro Pro Lys Leu Leu Ile Tyr Trp Ala Ser Thr Arg Val Ser Gly Val
    50                  55                  60

Pro Asp Arg Phe Ser Gly Ser Gly Ser Gly Thr His Phe Thr Leu Thr
65                  70                  75                  80

Ile Ser Ser Leu Gln Ala Glu Asp Val Ala Val Tyr Tyr Cys Gln Gln
                85                  90                  95

Tyr Trp Gly Pro Phe Gly Gln Gly Thr Lys Val Glu Ile Lys
            100                 105                 110
```

<210> SEQ ID NO 529
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 529

```
Cys Xaa Xaa Val Glu Ser Gly Gly Gly Phe Val Lys Pro Gly Gly Ser
1               5                   10                  15

Leu Arg Leu Ser Cys Ala Ala Ser
            20
```

<210> SEQ ID NO 530
<211> LENGTH: 17
<212> TYPE: PRT
<213> ORGANISM: Artificial Sequence
<220> FEATURE:
<223> OTHER INFORMATION: Synthetic Construct

<400> SEQUENCE: 530

```
Met Thr Trp Val Arg Gln Ala Pro Gly Lys Gly Leu Glu Trp Val Gly
1               5                   10                  15

Arg
```

<210> SEQ ID NO 531
<211> LENGTH: 38
<212> TYPE: PRT
<213> ORGANISM: Artificial Sequence
<220> FEATURE:
<223> OTHER INFORMATION: Synthetic Construct

<400> SEQUENCE: 531

```
Asp Tyr Ala Glu Val Val Lys Asp Arg Phe Val Ile Thr Arg Asp Asp
1               5                   10                  15

Ser Lys Asn Thr Leu Tyr Leu Glu Met Thr Asn Val Lys Thr Glu Asp
            20                  25                  30

Thr Gly Val Tyr Phe Cys
        35
```

<210> SEQ ID NO 532
<211> LENGTH: 11
<212> TYPE: PRT
<213> ORGANISM: Artificial Sequence
<220> FEATURE:
<223> OTHER INFORMATION: Synthetic Construct

<400> SEQUENCE: 532

Trp Gly Gln Gly Thr His Val Ile Val Ser Ser
1               5                   10

<210> SEQ ID NO 533
<211> LENGTH: 26
<212> TYPE: PRT
<213> ORGANISM: Artificial Sequence
<220> FEATURE:
<223> OTHER INFORMATION: Synthetic Construct

<400> SEQUENCE: 533

Asp Ile Val Met Thr Gln Ser Pro Asp Ser Leu Ala Leu Ser Leu Gly
1               5                   10                  15

Glu Arg Ala Ala Ile Asn Cys Lys Ser Ser
            20                  25

<210> SEQ ID NO 534
<211> LENGTH: 17
<212> TYPE: PRT
<213> ORGANISM: Artificial Sequence
<220> FEATURE:
<223> OTHER INFORMATION: Synthetic Construct

<400> SEQUENCE: 534

Leu Ser Trp Tyr Gln Gln Lys Pro Gly Gln Pro Pro Lys Leu Leu Ile
1               5                   10                  15

Tyr

<210> SEQ ID NO 535
<211> LENGTH: 36
<212> TYPE: PRT
<213> ORGANISM: Artificial Sequence
<220> FEATURE:
<223> OTHER INFORMATION: Synthetic Construct

<400> SEQUENCE: 535

Thr Arg Val Ser Gly Val Pro Asp Arg Phe Ser Gly Ser Gly Ser Gly
1               5                   10                  15

Thr His Phe Thr Leu Thr Ile Ser Ser Leu Gln Ala Glu Asp Val Ala
            20                  25                  30

Val Tyr Tyr Cys
        35

<210> SEQ ID NO 536
<211> LENGTH: 10
<212> TYPE: PRT
<213> ORGANISM: Artificial Sequence
<220> FEATURE:
<223> OTHER INFORMATION: Synthetic Construct

<400> SEQUENCE: 536

Phe Gly Gln Gly Thr Lys Val Glu Ile Lys
1               5                   10

<210> SEQ ID NO 537

```
<211> LENGTH: 450
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 537

Cys Xaa Xaa Val Glu Ser Gly Gly Gly Phe Val Lys Pro Gly Gly Ser
1               5                   10                  15

Leu Arg Leu Ser Cys Ala Ala Ser Gly Phe Thr Phe Pro Arg Ala Trp
            20                  25                  30

Met Thr Trp Val Arg Gln Ala Pro Gly Lys Gly Leu Glu Trp Val Gly
        35                  40                  45

Arg Leu Lys Ser Glu Asn Asp Gly Gly Thr Ala Asp Tyr Ala Glu Val
    50                  55                  60

Val Lys Asp Arg Phe Val Ile Thr Arg Asp Asp Ser Lys Asn Thr Leu
65                  70                  75                  80

Tyr Leu Glu Met Thr Asn Val Lys Thr Glu Asp Thr Gly Val Tyr Phe
                85                  90                  95

Cys Ser Thr Val Pro Tyr Cys Pro Gly Asp Ser Cys Tyr Gly Asn Phe
            100                 105                 110

Trp Gly Gln Gly Thr His Val Ile Val Ser Ser Lys Gly Pro Ser Val
        115                 120                 125

Phe Pro Leu Ala Pro Ser Ser Lys Ser Thr Ser Gly Gly Thr Ala Ala
    130                 135                 140

Leu Gly Xaa Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Xaa Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Xaa Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 538
<211> LENGTH: 214
<212> TYPE: PRT
<213> ORGANISM: Artificial Sequence
<220> FEATURE:
<223> OTHER INFORMATION: Synthetic Construct

<400> SEQUENCE: 538

Asp Ile Val Met Thr Gln Ser Pro Asp Ser Leu Ala Leu Ser Leu Gly
1               5                   10                  15

Glu Arg Ala Ala Ile Asn Cys Lys Ser Ser Gln Ser Leu Leu Tyr Ser
            20                  25                  30

Ser Asn Asn Arg Asn Tyr Leu Ser Trp Tyr Gln Gln Lys Pro Gly Gln
        35                  40                  45

Pro Pro Lys Leu Leu Ile Tyr Trp Ala Ser Thr Arg Val Ser Gly Val
    50                  55                  60

Pro Asp Arg Phe Ser Gly Ser Gly Ser Gly Thr His Phe Thr Leu Thr
65                  70                  75                  80

Ile Ser Ser Leu Gln Ala Glu Asp Val Ala Val Tyr Tyr Cys Gln Gln
                85                  90                  95

Tyr Trp Gly Pro Phe Gly Gln Gly Thr Lys Val Glu Ile Lys Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

```
        195                 200                 205

Asn Arg Gly Glu Cys Lys
    210
```

<210> SEQ ID NO 539
<211> LENGTH: 371
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 539

```
gtgccngntg gtggagtctg ggggaggctt cgtaaagcct ggggggtccc tcagactctc     60

ctgtgcagcc tctggattca ctttccctcg ggcctggatg acttgggtcc gccaggcgcc    120

agggaagggg ctggagtggg ttggccgtct taaaagtgag aatgacggtg gaacagcaga    180

ctacgctgaa gtcgttaaag acagatttgt catcacgaga gacgactcaa aaaatacact    240

ctacttggaa atgactaatg tgaagaccga agacacgggc gtctatttct gtagcaccgt    300

gccatattgt cctggtgact cctgctacgg aaatttctgg ggccagggaa cccacgtcat    360

tgtctcctca g                                                          371
```

<210> SEQ ID NO 540
<211> LENGTH: 331
<212> TYPE: DNA
<213> ORGANISM: Artificial Sequence
<220> FEATURE:
<223> OTHER INFORMATION: Synthetic Construct

<400> SEQUENCE: 540

```
gacatcgtga tgacccagtc tccagactcg ctggctctgt cactgggcga gagggccgcc     60

atcaactgca agtccagcca gagtcttttg tacagctcca ataataggaa ttatttatct    120

tggtatcagc agaaaccggg acagcctcct aaattgctca tttactgggc atctacccga    180

gtatccgggg tccctgaccg attcagtggc agcgggtctg ggacacattt cactctcact    240

ataagcagcc tgcaggctga agatgtggca gtttattatt gtcaacaata ttgggggccg    300

ttcggccaag ggaccaaagt ggaaatcaaa c                                   331
```

<210> SEQ ID NO 541
<211> LENGTH: 8
<212> TYPE: PRT
<213> ORGANISM: Artificial Sequence
<220> FEATURE:
<223> OTHER INFORMATION: Synthetic Construct

<400> SEQUENCE: 541

```
Gly Phe Thr Phe Asn Asn Tyr Ala
1               5
```

<210> SEQ ID NO 542
<211> LENGTH: 8
<212> TYPE: PRT
<213> ORGANISM: Artificial Sequence
<220> FEATURE:
<223> OTHER INFORMATION: Synthetic Construct

<400> SEQUENCE: 542

Ile Ser Ala Ser Gly Gly Ser Arg
1               5

<210> SEQ ID NO 543
<211> LENGTH: 18
<212> TYPE: PRT
<213> ORGANISM: Artificial Sequence
<220> FEATURE:
<223> OTHER INFORMATION: Synthetic Construct

<400> SEQUENCE: 543

Ala Lys Asp Arg Val Glu Asp Gly Asn Tyr Glu Lys Asp Trp His Phe
1               5                   10                  15

Asp Leu

<210> SEQ ID NO 544
<211> LENGTH: 7
<212> TYPE: PRT
<213> ORGANISM: Artificial Sequence
<220> FEATURE:
<223> OTHER INFORMATION: Synthetic Construct

<400> SEQUENCE: 544

Pro Ile Val Ser Gly Asn Tyr
1               5

<210> SEQ ID NO 545
<211> LENGTH: 3
<212> TYPE: PRT
<213> ORGANISM: Artificial Sequence
<220> FEATURE:
<223> OTHER INFORMATION: Synthetic Construct

<400> SEQUENCE: 545

Asp Ala Ser
1

<210> SEQ ID NO 546
<211> LENGTH: 9
<212> TYPE: PRT
<213> ORGANISM: Artificial Sequence
<220> FEATURE:
<223> OTHER INFORMATION: Synthetic Construct

<400> SEQUENCE: 546

Gln Gln Tyr Ala Lys Ser Pro Val Thr
1               5

<210> SEQ ID NO 547
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 547

Ala Xaa Xaa Val Glu Ser Gly Gly Gly Leu Gly Gln Pro Gly Gly Ser
1               5                   10                  15

Leu Arg Leu Ser Cys Pro Ala Ser Gly Phe Thr Phe Asn Asn Tyr Ala
            20                  25                  30

```
Met Ser Trp Ile Arg Gln Ala Pro Gly Lys Gly Leu Glu Trp Val Ser
        35                  40                  45

Ala Ile Ser Ala Ser Gly Gly Ser Arg Phe Tyr Ala Asp Ser Val Arg
    50                  55                  60

Gly Arg Phe Thr Ile Ser Arg Asp Asn Ala Lys Asn Thr Leu Tyr Leu
65                  70                  75                  80

Gln Leu Asn Ser Leu Arg Ala Glu Asp Thr Ala Val Tyr Phe Cys Ala
                85                  90                  95

Lys Asp Arg Val Glu Asp Gly Asn Tyr Glu Lys Asp Trp His Phe Asp
            100                 105                 110

Leu Trp Gly Arg Gly Thr Leu Val Thr Val Ser Ser
        115                 120


<210> SEQ ID NO 548
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 548

Glu Ile Val Xaa Thr Gln Ser Pro Gly Thr Leu Ser Leu Ser Pro Gly
1               5                   10                  15

Glu Arg Ala Thr Leu Ser Cys Arg Ala Ser Pro Ile Val Ser Gly Asn
            20                  25                  30

Tyr Leu Ala Trp Tyr Gln Gln Arg Pro Gly Gln Ser Pro Arg Leu Leu
        35                  40                  45

Ile Tyr Asp Ala Ser Ser Arg Ala Ser Gly Val Pro Asp Arg Phe Ser
    50                  55                  60

Gly Gly Gly Ser Ala Thr Asp Phe Thr Leu Thr Ile Ser Arg Leu Glu
65                  70                  75                  80

Pro Glu Asp Phe Ala Val Tyr Tyr Cys Gln Gln Tyr Ala Lys Ser Pro
                85                  90                  95

Val Thr Phe Gly Gly Gly Thr Lys Val Glu Ile Lys
            100                 105


<210> SEQ ID NO 549
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 549

Ala Xaa Xaa Val Glu Ser Gly Gly Gly Leu Gly Gln Pro Gly Gly Ser
1               5                   10                  15

Leu Arg Leu Ser Cys Pro Ala Ser
            20


<210> SEQ ID NO 550
<211> LENGTH: 17
<212> TYPE: PRT
<213> ORGANISM: Artificial Sequence
```

<220> FEATURE:
<223> OTHER INFORMATION: Synthetic Construct

<400> SEQUENCE: 550

Met Ser Trp Ile Arg Gln Ala Pro Gly Lys Gly Leu Glu Trp Val Ser
1 5 10 15

Ala

<210> SEQ ID NO 551
<211> LENGTH: 38
<212> TYPE: PRT
<213> ORGANISM: Artificial Sequence
<220> FEATURE:
<223> OTHER INFORMATION: Synthetic Construct

<400> SEQUENCE: 551

Phe Tyr Ala Asp Ser Val Arg Gly Arg Phe Thr Ile Ser Arg Asp Asn
1 5 10 15

Ala Lys Asn Thr Leu Tyr Leu Gln Leu Asn Ser Leu Arg Ala Glu Asp
20 25 30

Thr Ala Val Tyr Phe Cys
35

<210> SEQ ID NO 552
<211> LENGTH: 11
<212> TYPE: PRT
<213> ORGANISM: Artificial Sequence
<220> FEATURE:
<223> OTHER INFORMATION: Synthetic Construct

<400> SEQUENCE: 552

Trp Gly Arg Gly Thr Leu Val Thr Val Ser Ser
1 5 10

<210> SEQ ID NO 553
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 553

Glu Ile Val Xaa Thr Gln Ser Pro Gly Thr Leu Ser Leu Ser Pro Gly
1 5 10 15

Glu Arg Ala Thr Leu Ser Cys Arg Ala Ser
20 25

<210> SEQ ID NO 554
<211> LENGTH: 17
<212> TYPE: PRT
<213> ORGANISM: Artificial Sequence
<220> FEATURE:
<223> OTHER INFORMATION: Synthetic Construct

<400> SEQUENCE: 554

Leu Ala Trp Tyr Gln Gln Arg Pro Gly Gln Ser Pro Arg Leu Leu Ile
1 5 10 15

Tyr

<210> SEQ ID NO 555

<211> LENGTH: 36
<212> TYPE: PRT
<213> ORGANISM: Artificial Sequence
<220> FEATURE:
<223> OTHER INFORMATION: Synthetic Construct

<400> SEQUENCE: 555

Ser Arg Ala Ser Gly Val Pro Asp Arg Phe Ser Gly Gly Gly Ser Ala
1 5 10 15

Thr Asp Phe Thr Leu Thr Ile Ser Arg Leu Glu Pro Glu Asp Phe Ala
20 25 30

Val Tyr Tyr Cys
35

<210> SEQ ID NO 556
<211> LENGTH: 10
<212> TYPE: PRT
<213> ORGANISM: Artificial Sequence
<220> FEATURE:
<223> OTHER INFORMATION: Synthetic Construct

<400> SEQUENCE: 556

Phe Gly Gly Gly Thr Lys Val Glu Ile Lys
1 5 10

<210> SEQ ID NO 557
<211> LENGTH: 451
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid

<400> SEQUENCE: 557

Ala Xaa Xaa Val Glu Ser Gly Gly Gly Leu Gly Gln Pro Gly Gly Ser
1 5 10 15

Leu Arg Leu Ser Cys Pro Ala Ser Gly Phe Thr Phe Asn Asn Tyr Ala
20 25 30

Met Ser Trp Ile Arg Gln Ala Pro Gly Lys Gly Leu Glu Trp Val Ser
35 40 45

Ala Ile Ser Ala Ser Gly Gly Ser Arg Phe Tyr Ala Asp Ser Val Arg
50 55 60

Gly Arg Phe Thr Ile Ser Arg Asp Asn Ala Lys Asn Thr Leu Tyr Leu
65 70 75 80

Gln Leu Asn Ser Leu Arg Ala Glu Asp Thr Ala Val Tyr Phe Cys Ala
85 90 95

Lys Asp Arg Val Glu Asp Gly Asn Tyr Glu Lys Asp Trp His Phe Asp
100 105 110

Leu Trp Gly Arg Gly Thr Leu Val Thr Val Ser Ser Lys Gly Pro Ser
115 120 125

Val Phe Pro Leu Ala Pro Ser Ser Lys Ser Thr Ser Gly Gly Thr Ala
130 135 140

Ala Leu Gly Xaa Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Xaa Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Xaa Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 558
<211> LENGTH: 212
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 558

Glu Ile Val Xaa Thr Gln Ser Pro Gly Thr Leu Ser Leu Ser Pro Gly 1 5 10 15

Glu Arg Ala Thr Leu Ser Cys Arg Ala Ser Pro Ile Val Ser Gly Asn
20 25 30

Tyr Leu Ala Trp Tyr Gln Gln Arg Pro Gly Gln Ser Pro Arg Leu Leu
35 40 45

Ile Tyr Asp Ala Ser Ser Arg Ala Ser Gly Val Pro Asp Arg Phe Ser
50 55 60

Gly Gly Gly Ser Ala Thr Asp Phe Thr Leu Thr Ile Ser Arg Leu Glu
65 70 75 80

Pro Glu Asp Phe Ala Val Tyr Tyr Cys Gln Gln Tyr Ala Lys Ser Pro
85 90 95

Val Thr Phe Gly Gly Gly Thr Lys Val Glu Ile Lys Ala Pro Ser Val
100 105 110

Phe Ile Phe Pro Pro Ser Asp Glu Gln Leu Lys Ser Gly Thr Ala Ser
115 120 125

Val Val Cys Leu Leu Asn Asn Phe Tyr Pro Arg Glu Ala Lys Val Gln
130 135 140

Trp Lys Val Asp Asn Ala Leu Gln Ser Gly Asn Ser Gln Glu Ser Val
145 150 155 160

Thr Glu Gln Asp Ser Lys Asp Ser Thr Tyr Ser Leu Ser Ser Thr Leu
165 170 175

Thr Leu Ser Lys Ala Asp Tyr Glu Lys His Lys Val Tyr Ala Cys Glu
180 185 190

Val Thr His Gln Gly Leu Ser Ser Pro Val Thr Lys Ser Phe Asn Arg
195 200 205

Gly Glu Cys Lys
210

<210> SEQ ID NO 559
<211> LENGTH: 375
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(11)
<223> OTHER INFORMATION: n is a, c, g, or t

<400> SEQUENCE: 559
gtgccaannn ngtggagtcg gggggaggct tggggcagcc ggggggggtcc ctgagactct 60 cctgtccagc ctctggattc acctttaaca actatgccat gagttggatc cgccaggctc 120
cagggaaggg gctggagtgg gtctcagcta ttagcgccag tggcggtagc agattctacg 180
cagactccgt gaggggccga ttcaccatct ccagagacaa tgccaagaac accctatatc 240
tccaactgaa cagcctgaga gccgaggaca cggccgtata tttctgtgcg aaagatcggg 300
tggaggacgg taactacgag aaagactggc acttcgatct ctggggccgt ggcaccctgg 360
tcactgtctc gtcag 375

<210> SEQ ID NO 560
<211> LENGTH: 325
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(11)

<223> OTHER INFORMATION: n is a, c, g, or t

<400> SEQUENCE: 560
gaaattgtnn ngacgcagtc tccaggcacc ctgtctttgt ctccagggga gagagccacc 60
ctctcctgca gggccagtcc gattgttagc ggcaattact tagcctggta tcagcagaga 120
cctggccagt ctccccggct cctcatctat gatgcatcca gcagggccag tggcgtccca 180
gacaggttca gtggcggtgg gtctgcgaca gacttcactc tcaccatcag cagactggag 240
cctgaagact ttgcagtgta ttactgtcag cagtatgcta agtcacccgt cactttcggc 300
ggagggacca aggtggagat caaac 325

<210> SEQ ID NO 561
<211> LENGTH: 8
<212> TYPE: PRT
<213> ORGANISM: Artificial Sequence
<220> FEATURE:
<223> OTHER INFORMATION: Synthetic Construct

<400> SEQUENCE: 561

Gly Phe Thr Phe Gly Asp Tyr Thr
1 5

<210> SEQ ID NO 562
<211> LENGTH: 8
<212> TYPE: PRT
<213> ORGANISM: Artificial Sequence
<220> FEATURE:
<223> OTHER INFORMATION: Synthetic Construct

<400> SEQUENCE: 562

Ile Lys Trp Asn Ser Ala Asp Ile
1 5

<210> SEQ ID NO 563
<211> LENGTH: 11
<212> TYPE: PRT
<213> ORGANISM: Artificial Sequence
<220> FEATURE:
<223> OTHER INFORMATION: Synthetic Construct

<400> SEQUENCE: 563

Val Lys Asp Thr Gly Leu Arg Ser Phe Asp Ser
1 5 10

<210> SEQ ID NO 564
<211> LENGTH: 11
<212> TYPE: PRT
<213> ORGANISM: Artificial Sequence
<220> FEATURE:
<223> OTHER INFORMATION: Synthetic Construct

<400> SEQUENCE: 564

Gln Ser Leu Leu His Thr Asn Gly Tyr Asn Tyr
1 5 10

<210> SEQ ID NO 565
<211> LENGTH: 3
<212> TYPE: PRT
<213> ORGANISM: Artificial Sequence
<220> FEATURE:
<223> OTHER INFORMATION: Synthetic Construct

<400> SEQUENCE: 565

Leu Gly Ser

1

<210> SEQ ID NO 566
<211> LENGTH: 8
<212> TYPE: PRT
<213> ORGANISM: Artificial Sequence
<220> FEATURE:
<223> OTHER INFORMATION: Synthetic Construct

<400> SEQUENCE: 566

Met Gln Ala Leu Gln Thr Trp Thr
1 5

<210> SEQ ID NO 567
<211> LENGTH: 114
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid

<400> SEQUENCE: 567

Xaa Glu Ser Gly Gly Gly Leu Val Lys Pro Gly Arg Ser Leu Arg Leu
1 5 10 15

Ser Cys Ala Ala Ser Gly Phe Thr Phe Gly Asp Tyr Thr Met His Trp
20 25 30

Val Arg Gln Ala Pro Gly Lys Gly Leu Glu Trp Val Ser Asn Ile Lys
35 40 45

Trp Asn Ser Ala Asp Ile Gly Tyr Ala Gly Xaa Xaa Lys Gly Arg Phe
50 55 60

Ile Ile Ser Arg Asp Asn Ala Glu Asn Phe Met Tyr Leu Gln Met Asn
65 70 75 80

Ser Leu Arg Val Glu Asp Thr Ala Thr Tyr Phe Cys Val Lys Asp Thr
85 90 95

Gly Leu Arg Ser Phe Asp Ser Trp Gly Arg Gly Thr Leu Val Ile Val
100 105 110

Ser Ser

<210> SEQ ID NO 568
<211> LENGTH: 111
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 568

Gln Xaa Xaa Leu Thr Gln Ser Pro Leu Ser Leu Pro Val Thr Pro Gly
1 5 10 15

Glu Pro Ala Ser Ile Ser Cys Arg Ser Ser Gln Ser Leu Leu His Thr
20 25 30

Asn Gly Tyr Asn Tyr Met Asp Trp Tyr Leu Gln Lys Pro Gly Gln Ser
35 40 45

Pro Gln Leu Leu Ile Tyr Leu Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Trp Thr Phe Gly Gln Gly Thr Lys Val Glu Ile Lys
            100                 105                 110

<210> SEQ ID NO 569
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 569

Xaa Glu Ser Gly Gly Gly Leu Val Lys Pro Gly Arg Ser Leu Arg Leu
1               5                   10                  15

Ser Cys Ala Ala Ser
            20

<210> SEQ ID NO 570
<211> LENGTH: 17
<212> TYPE: PRT
<213> ORGANISM: Artificial Sequence
<220> FEATURE:
<223> OTHER INFORMATION: Synthetic Construct

<400> SEQUENCE: 570

Met His Trp Val Arg Gln Ala Pro Gly Lys Gly Leu Glu Trp Val Ser
1               5                   10                  15

Asn

<210> SEQ ID NO 571
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: Xaa can be any naturally occurring amino acid

<400> SEQUENCE: 571

Gly Tyr Ala Gly Xaa Xaa Lys Gly Arg Phe Ile Ile Ser Arg Asp Asn
1               5                   10                  15

Ala Glu Asn Phe Met Tyr Leu Gln Met Asn Ser Leu Arg Val Glu Asp
            20                  25                  30

Thr Ala Thr Tyr Phe Cys
        35

<210> SEQ ID NO 572
<211> LENGTH: 11
<212> TYPE: PRT
<213> ORGANISM: Artificial Sequence
<220> FEATURE:
<223> OTHER INFORMATION: Synthetic Construct

<400> SEQUENCE: 572

Trp Gly Arg Gly Thr Leu Val Ile Val Ser Ser
1 5 10

<210> SEQ ID NO 573
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 573

Gln Xaa Xaa Leu Thr Gln Ser Pro Leu Ser Leu Pro Val Thr Pro Gly
1 5 10 15

Glu Pro Ala Ser Ile Ser Cys Arg Ser Ser
20 25

<210> SEQ ID NO 574
<211> LENGTH: 17
<212> TYPE: PRT
<213> ORGANISM: Artificial Sequence
<220> FEATURE:
<223> OTHER INFORMATION: Synthetic Construct

<400> SEQUENCE: 574

Met Asp Trp Tyr Leu Gln Lys Pro Gly Gln Ser Pro Gln Leu Leu Ile
1 5 10 15

Tyr

<210> SEQ ID NO 575
<211> LENGTH: 36
<212> TYPE: PRT
<213> ORGANISM: Artificial Sequence
<220> FEATURE:
<223> OTHER INFORMATION: Synthetic Construct

<400> SEQUENCE: 575

Lys Arg Ala Ser Gly Val Pro Asp Arg Phe Ser Gly Ser Gly Ser Gly
1 5 10 15

Thr Asp Phe Thr Leu Lys Ile Ser Arg Val Glu Ala Glu Asp Val Gly
20 25 30

Val Tyr Tyr Cys
35

<210> SEQ ID NO 576
<211> LENGTH: 10
<212> TYPE: PRT
<213> ORGANISM: Artificial Sequence
<220> FEATURE:
<223> OTHER INFORMATION: Synthetic Construct

<400> SEQUENCE: 576

Phe Gly Gln Gly Thr Lys Val Glu Ile Lys
1 5 10

<210> SEQ ID NO 577
<211> LENGTH: 441
<212> TYPE: PRT
<213> ORGANISM: Artificial Sequence
<220> FEATURE:
<223> OTHER INFORMATION: Synthetic Construct
<220> FEATURE:

<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid

<400> SEQUENCE: 577

```
Xaa Glu Ser Gly Gly Gly Leu Val Lys Pro Gly Arg Ser Leu Arg Leu
1               5                   10                  15

Ser Cys Ala Ala Ser Gly Phe Thr Phe Gly Asp Tyr Thr Met His Trp
            20                  25                  30

Val Arg Gln Ala Pro Gly Lys Gly Leu Glu Trp Val Ser Asn Ile Lys
        35                  40                  45

Trp Asn Ser Ala Asp Ile Gly Tyr Ala Gly Xaa Xaa Lys Gly Arg Phe
    50                  55                  60

Ile Ile Ser Arg Asp Asn Ala Glu Asn Phe Met Tyr Leu Gln Met Asn
65                  70                  75                  80

Ser Leu Arg Val Glu Asp Thr Ala Thr Tyr Phe Cys Val Lys Asp Thr
                85                  90                  95

Gly Leu Arg Ser Phe Asp Ser Trp Gly Arg Gly Thr Leu Val Ile Val
            100                 105                 110

Ser Ser Lys Gly Pro Ser Val Phe Pro Leu Ala Pro Ser Ser Lys Ser
        115                 120                 125

Thr Ser Gly Gly Thr Ala Ala Leu Gly Xaa Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Xaa
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300
```

```
Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Xaa
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 578
<211> LENGTH: 215
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 578

Gln Xaa Xaa Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Met Asp Trp Tyr Leu Gln Lys Pro Gly Gln Ser
        35                  40                  45

Pro Gln Leu Leu Ile Tyr Leu Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Trp Thr Phe Gly Gln Gly Thr Lys Val Glu Ile Lys Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys Lys
210 215

<210> SEQ ID NO 579
<211> LENGTH: 343
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t

<400> SEQUENCE: 579
gnngaatctg ggggaggctt ggtaaagcct ggcaggtccc tgagactctc ctgtgcagcc 60
tctggtttca ccttcggtga ttacaccatg cattgggtcc ggcaagctcc agggaagggc 120
ctggagtggg tctcaaatat taagtggaat agcgccgaca tagggtacgc gggctntkck 180
aagggccgat tcatcatctc cagagacaac gccgagaact tcatgtattt acagatgaac 240
agtctgagag ttgaggacac ggccacttat ttctgtgtaa aagatactgg actccgttcc 300
tttgactcct ggggccgggg aaccctggtc atcgtctctt cag 343

<210> SEQ ID NO 580
<211> LENGTH: 334
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 580
cagtntgnnc tgactcagtc tccactctcc ctgcccgtca cccctggaga gccggcctcc 60
atctcctgca ggtcgagtca gagcctcctt catactaacg gctacaacta tatggattgg 120
tacctgcaga agccagggca gtcaccacaa ctcctgatct atttgggttc taagcgggcc 180
tccggggtcc ctgacaggtt cagtggcagt ggatcaggaa cagattttac actgaaaatc 240
agcagagtgg aggctgagga tgttggggtg tattactgca tgcaagctct acaaacttgg 300
acgttcggcc aagggaccaa ggtggaaatc aagc 334

<210> SEQ ID NO 581
<211> LENGTH: 8
<212> TYPE: PRT
<213> ORGANISM: Artificial Sequence
<220> FEATURE:
<223> OTHER INFORMATION: Synthetic Construct

<400> SEQUENCE: 581

Gly Tyr Thr Phe Ser Ser Tyr Asp
1 5

<210> SEQ ID NO 582

<211> LENGTH: 8
<212> TYPE: PRT
<213> ORGANISM: Artificial Sequence
<220> FEATURE:
<223> OTHER INFORMATION: Synthetic Construct

<400> SEQUENCE: 582

Met Asn Pro Lys Asn Gly Tyr Ser
1               5

<210> SEQ ID NO 583
<211> LENGTH: 16
<212> TYPE: PRT
<213> ORGANISM: Artificial Sequence
<220> FEATURE:
<223> OTHER INFORMATION: Synthetic Construct

<400> SEQUENCE: 583

Val Arg Val Arg Thr Ile Ser Gln Gly Asp Ser Trp Tyr Phe Asp Leu
1               5                   10                  15

<210> SEQ ID NO 584
<211> LENGTH: 6
<212> TYPE: PRT
<213> ORGANISM: Artificial Sequence
<220> FEATURE:
<223> OTHER INFORMATION: Synthetic Construct

<400> SEQUENCE: 584

Gln Gly Leu Thr Val Ser
1               5

<210> SEQ ID NO 585
<211> LENGTH: 3
<212> TYPE: PRT
<213> ORGANISM: Artificial Sequence
<220> FEATURE:
<223> OTHER INFORMATION: Synthetic Construct

<400> SEQUENCE: 585

Ala Ala Ser
1

<210> SEQ ID NO 586
<211> LENGTH: 9
<212> TYPE: PRT
<213> ORGANISM: Artificial Sequence
<220> FEATURE:
<223> OTHER INFORMATION: Synthetic Construct

<400> SEQUENCE: 586

Met His Thr Leu Gln Pro Pro Tyr Thr
1               5

<210> SEQ ID NO 587
<211> LENGTH: 119
<212> TYPE: PRT
<213> ORGANISM: Artificial Sequence
<220> FEATURE:
<223> OTHER INFORMATION: Synthetic Construct

<400> SEQUENCE: 587

Val Gln Ser Gly Pro Glu Val Lys Lys Pro Gly Ala Ser Val Lys Val
1               5                   10                  15

Ser Cys Lys Ala Ser Gly Tyr Thr Phe Ser Ser Tyr Asp Phe Asn Trp
            20                  25                  30

```
Val Arg Gln Ala Pro Gly Gln Gly Leu Glu Trp Met Gly Trp Met Asn
        35                  40                  45

Pro Lys Asn Gly Tyr Ser Gly Phe Ala Gln Asn Phe Arg Gly Arg Ile
    50                  55                  60

Ser Met Thr Arg Asn Ser Ser Ile Thr Thr Ala Tyr Met Glu Leu Thr
65                  70                  75                  80

Ser Leu Thr Ser Asp Asp Thr Ala Val Tyr Tyr Cys Val Arg Val Arg
                85                  90                  95

Thr Ile Ser Gln Gly Asp Ser Trp Tyr Phe Asp Leu Trp Gly Arg Gly
            100                 105                 110

Thr Leu Val Thr Val Ser Ser
        115


<210> SEQ ID NO 588
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (62)..(62)
<223> OTHER INFORMATION: Xaa can be any naturally occurring amino acid

<400> SEQUENCE: 588

Asp Met Ala Thr Thr Gln Ser Pro Ser Ser Val Ser Ala Ser Glu Gly
1               5                   10                  15

Asp Arg Ala Val Ile Ser Cys Arg Ala Ser Gln Gly Leu Thr Val Ser
            20                  25                  30

Leu Ala Arg Asn His Pro Glu Thr Gly Glu Ala Pro Asn Leu Leu Ile
        35                  40                  45

Ser Ala Ala Ser Ser Leu Arg Gly Thr Val Ala Ala Pro Xaa Ser Gly
    50                  55                  60

Ser Gly Ser Gly Thr Asp Phe Thr Leu Lys Ile Thr Arg Val Glu Ala
65                  70                  75                  80

Glu Asp Val Gly Val Tyr Tyr Cys Met His Thr Leu Gln Pro Pro Tyr
                85                  90                  95

Thr Phe Gly Arg Gly Thr Lys Leu Glu Ile Lys
            100                 105


<210> SEQ ID NO 589
<211> LENGTH: 21
<212> TYPE: PRT
<213> ORGANISM: Artificial Sequence
<220> FEATURE:
<223> OTHER INFORMATION: Synthetic Construct

<400> SEQUENCE: 589

Val Gln Ser Gly Pro Glu Val Lys Lys Pro Gly Ala Ser Val Lys Val
1               5                   10                  15

Ser Cys Lys Ala Ser
            20


<210> SEQ ID NO 590
<211> LENGTH: 17
<212> TYPE: PRT
<213> ORGANISM: Artificial Sequence
<220> FEATURE:
<223> OTHER INFORMATION: Synthetic Construct

<400> SEQUENCE: 590
```

Phe Asn Trp Val Arg Gln Ala Pro Gly Gln Gly Leu Glu Trp Met Gly
1 5 10 15

Trp

<210> SEQ ID NO 591
<211> LENGTH: 38
<212> TYPE: PRT
<213> ORGANISM: Artificial Sequence
<220> FEATURE:
<223> OTHER INFORMATION: Synthetic Construct

<400> SEQUENCE: 591

Gly Phe Ala Gln Asn Phe Arg Gly Arg Ile Ser Met Thr Arg Asn Ser
1 5 10 15

Ser Ile Thr Thr Ala Tyr Met Glu Leu Thr Ser Leu Thr Ser Asp Asp
20 25 30

Thr Ala Val Tyr Tyr Cys
35

<210> SEQ ID NO 592
<211> LENGTH: 11
<212> TYPE: PRT
<213> ORGANISM: Artificial Sequence
<220> FEATURE:
<223> OTHER INFORMATION: Synthetic Construct

<400> SEQUENCE: 592

Trp Gly Arg Gly Thr Leu Val Thr Val Ser Ser
1 5 10

<210> SEQ ID NO 593
<211> LENGTH: 26
<212> TYPE: PRT
<213> ORGANISM: Artificial Sequence
<220> FEATURE:
<223> OTHER INFORMATION: Synthetic Construct

<400> SEQUENCE: 593

Asp Met Ala Thr Thr Gln Ser Pro Ser Ser Val Ser Ala Ser Glu Gly
1 5 10 15

Asp Arg Ala Val Ile Ser Cys Arg Ala Ser
20 25

<210> SEQ ID NO 594
<211> LENGTH: 17
<212> TYPE: PRT
<213> ORGANISM: Artificial Sequence
<220> FEATURE:
<223> OTHER INFORMATION: Synthetic Construct

<400> SEQUENCE: 594

Leu Ala Arg Asn His Pro Glu Thr Gly Glu Ala Pro Asn Leu Leu Ile
1 5 10 15

Ser

<210> SEQ ID NO 595
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: Xaa can be any naturally occurring amino acid

<400> SEQUENCE: 595

Ser Leu Arg Gly Thr Val Ala Ala Pro Xaa Ser Gly Ser Gly Ser Gly
1 5 10 15

Thr Asp Phe Thr Leu Lys Ile Thr Arg Val Glu Ala Glu Asp Val Gly
20 25 30

Val Tyr Tyr Cys
35

<210> SEQ ID NO 596
<211> LENGTH: 10
<212> TYPE: PRT
<213> ORGANISM: Artificial Sequence
<220> FEATURE:
<223> OTHER INFORMATION: Synthetic Construct

<400> SEQUENCE: 596

Phe Gly Arg Gly Thr Lys Leu Glu Ile Lys
1 5 10

<210> SEQ ID NO 597
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 597

Val Gln Ser Gly Pro Glu Val Lys Lys Pro Gly Ala Ser Val Lys Val
1 5 10 15

Ser Cys Lys Ala Ser Gly Tyr Thr Phe Ser Ser Tyr Asp Phe Asn Trp
20 25 30

Val Arg Gln Ala Pro Gly Gln Gly Leu Glu Trp Met Gly Trp Met Asn
35 40 45

Pro Lys Asn Gly Tyr Ser Gly Phe Ala Gln Asn Phe Arg Gly Arg Ile
50 55 60

Ser Met Thr Arg Asn Ser Ser Ile Thr Thr Ala Tyr Met Glu Leu Thr
65 70 75 80

Ser Leu Thr Ser Asp Asp Thr Ala Val Tyr Tyr Cys Val Arg Val Arg
85 90 95

Thr Ile Ser Gln Gly Asp Ser Trp Tyr Phe Asp Leu Trp Gly Arg Gly
100 105 110

Thr Leu Val Thr Val Ser Ser Lys Gly Pro Ser Val Phe Pro Leu Ala
115 120 125

Pro Ser Ser Lys Ser Thr Ser Gly Gly Thr Ala Ala Leu Gly Xaa Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Xaa Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Xaa Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 598
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (62)..(62)
<223> OTHER INFORMATION: Xaa can be any naturally occurring amino acid

<400> SEQUENCE: 598

```
Asp Met Ala Thr Thr Gln Ser Pro Ser Ser Val Ser Ala Ser Glu Gly
1               5                   10                  15

Asp Arg Ala Val Ile Ser Cys Arg Ala Ser Gln Gly Leu Thr Val Ser
            20                  25                  30

Leu Ala Arg Asn His Pro Glu Thr Gly Glu Ala Pro Asn Leu Leu Ile
        35                  40                  45

Ser Ala Ala Ser Ser Leu Arg Gly Thr Val Ala Ala Pro Xaa Ser Gly
    50                  55                  60

Ser Gly Ser Gly Thr Asp Phe Thr Leu Lys Ile Thr Arg Val Glu Ala
```

```
65                  70                  75                  80

Glu Asp Val Gly Val Tyr Tyr Cys Met His Thr Leu Gln Pro Pro Tyr
                85                  90                  95

Thr Phe Gly Arg Gly Thr Lys Leu Glu Ile Lys Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210
```

<210> SEQ ID NO 599
<211> LENGTH: 359
<212> TYPE: DNA
<213> ORGANISM: Artificial Sequence
<220> FEATURE:
<223> OTHER INFORMATION: Synthetic Construct

<400> SEQUENCE: 599

```
ggtgcagtct gggcctgagg tgaagaagcc tggggcctca gtgaaggtct cctgcaaggc     60

ttctggatat accttcagta gttatgactt caactgggtg cgacaggccc ctggacaagg    120

gcttgagtgg atgggatgga tgaaccctaa aaatggttac tcaggcttcg cacagaattt    180

ccggggccgg atatccatga ccaggaactc ctccataacc acagcctaca tggagctgac    240

cagcctgaca tctgatgaca cggccgttta ttattgtgtg agagtgagga caatttctca    300

gggcgacagc tggtacttcg atctctgggg ccgtggcacc ctggtcactg tctcctcag     359
```

<210> SEQ ID NO 600
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (185)..(185)
<223> OTHER INFORMATION: n is a, c, g, or t

<400> SEQUENCE: 600

```
gacatggcga cgacccagtc tccatcttcc gtgtctgcat ctgaagggga cagagccgtc     60

atctcttgtc gggcgagtca gggtcttacc gtgtcgttag ccaggaatca cccggagaca    120

ggggaagccc ctaacctcct aatctctgct gcatcgagtt tgcgaggaac tgtggctgca    180

ccatncagtg gcagtggatc aggcacagat tttacactga aaatcaccag agtggaggct    240

gaggatgttg ggtttatta ctgtatgcat actctacaac ccccgtacac ttttggccgg    300

gggaccaagc tggagatcaa ac                                              322
```

<210> SEQ ID NO 601

<211> LENGTH: 8
<212> TYPE: PRT
<213> ORGANISM: Artificial Sequence
<220> FEATURE:
<223> OTHER INFORMATION: Synthetic Construct

<400> SEQUENCE: 601

Gly Tyr Thr Phe Ser Asn Tyr Asp
1               5

<210> SEQ ID NO 602
<211> LENGTH: 8
<212> TYPE: PRT
<213> ORGANISM: Artificial Sequence
<220> FEATURE:
<223> OTHER INFORMATION: Synthetic Construct

<400> SEQUENCE: 602

Met Asn Pro Lys Asn Gly Tyr Ser
1               5

<210> SEQ ID NO 603
<211> LENGTH: 16
<212> TYPE: PRT
<213> ORGANISM: Artificial Sequence
<220> FEATURE:
<223> OTHER INFORMATION: Synthetic Construct

<400> SEQUENCE: 603

Val Arg Val Arg Thr Ile Ser Lys Gly Asp Ser Trp Tyr Phe Asp Leu
1               5                   10                  15

<210> SEQ ID NO 604
<211> LENGTH: 11
<212> TYPE: PRT
<213> ORGANISM: Artificial Sequence
<220> FEATURE:
<223> OTHER INFORMATION: Synthetic Construct

<400> SEQUENCE: 604

Gln Ser Leu Leu His Asn Asn Gly Tyr Asn Tyr
1               5                   10

<210> SEQ ID NO 605
<211> LENGTH: 3
<212> TYPE: PRT
<213> ORGANISM: Artificial Sequence
<220> FEATURE:
<223> OTHER INFORMATION: Synthetic Construct

<400> SEQUENCE: 605

Leu Val Ser
1

<210> SEQ ID NO 606
<211> LENGTH: 9
<212> TYPE: PRT
<213> ORGANISM: Artificial Sequence
<220> FEATURE:
<223> OTHER INFORMATION: Synthetic Construct

<400> SEQUENCE: 606

Met His Thr Leu Gln Pro Pro Tyr Thr
1               5

<210> SEQ ID NO 607
<211> LENGTH: 118

<212> TYPE: PRT
<213> ORGANISM: Artificial Sequence
<220> FEATURE:
<223> OTHER INFORMATION: Synthetic Construct

<400> SEQUENCE: 607

Gln Ser Gly Pro Glu Val Lys Lys Pro Gly Ala Ser Val Lys Val Ser
1 5 10 15

Cys Lys Ser Ser Gly Tyr Thr Phe Ser Asn Tyr Asp Phe Asn Trp Val
20 25 30

Arg Gln Ala Pro Gly Gln Gly Leu Glu Trp Met Gly Trp Met Asn Pro
35 40 45

Lys Asn Gly Tyr Ser Gly Phe Ala Gln Asn Phe Arg Gly Arg Ile Ser
50 55 60

Met Thr Arg Asn Ser Ser Ile Thr Thr Ala Tyr Met Glu Leu Thr Ser
65 70 75 80

Leu Thr Ser Asp Asp Thr Ala Leu Tyr Tyr Cys Val Arg Val Arg Thr
85 90 95

Ile Ser Lys Gly Asp Ser Trp Tyr Phe Asp Leu Trp Gly Arg Gly Thr
100 105 110

Leu Val Thr Val Ser Ser
115

<210> SEQ ID NO 608
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid

<400> SEQUENCE: 608

Arg Cys Xaa Xaa Thr Gln Ser Gln Val Ser Leu Pro Val Thr Pro Gly
1 5 10 15

Glu Pro Ala Ser Ile Ser Cys Arg Ser Ser Gln Ser Leu Leu His Asn
20 25 30

Asn Gly Tyr Asn Tyr Val Asp Trp Tyr Leu Gln Lys Pro Gly Gln Ser
35 40 45

Pro Gln Leu Leu Ile Tyr Leu Val Ser Asn Pro Val Ser Ile Phe Arg
50 55 60

Val Cys Ile Xaa Gly Ser Gly Ser Gly Thr Asp Phe Thr Leu Lys Ile
65 70 75 80

Thr Arg Val Glu Ala Glu Asp Val Gly Val Tyr Tyr Cys Met His Thr
85 90 95

Leu Gln Pro Pro Tyr Thr Phe Gly Gln Gly Thr Lys Leu Xaa Ile Lys
100 105 110

<210> SEQ ID NO 609
<211> LENGTH: 20
<212> TYPE: PRT
<213> ORGANISM: Artificial Sequence
<220> FEATURE:
<223> OTHER INFORMATION: Synthetic Construct

<400> SEQUENCE: 609

Gln Ser Gly Pro Glu Val Lys Lys Pro Gly Ala Ser Val Lys Val Ser
1 5 10 15

Cys Lys Ser Ser
20

<210> SEQ ID NO 610
<211> LENGTH: 17
<212> TYPE: PRT
<213> ORGANISM: Artificial Sequence
<220> FEATURE:
<223> OTHER INFORMATION: Synthetic Construct

<400> SEQUENCE: 610

Phe Asn Trp Val Arg Gln Ala Pro Gly Gln Gly Leu Glu Trp Met Gly
1 5 10 15

Trp

<210> SEQ ID NO 611
<211> LENGTH: 38
<212> TYPE: PRT
<213> ORGANISM: Artificial Sequence
<220> FEATURE:
<223> OTHER INFORMATION: Synthetic Construct

<400> SEQUENCE: 611

Gly Phe Ala Gln Asn Phe Arg Gly Arg Ile Ser Met Thr Arg Asn Ser
1 5 10 15

Ser Ile Thr Thr Ala Tyr Met Glu Leu Thr Ser Leu Thr Ser Asp Asp
20 25 30

Thr Ala Leu Tyr Tyr Cys
35

<210> SEQ ID NO 612
<211> LENGTH: 11
<212> TYPE: PRT
<213> ORGANISM: Artificial Sequence
<220> FEATURE:
<223> OTHER INFORMATION: Synthetic Construct

<400> SEQUENCE: 612

Trp Gly Arg Gly Thr Leu Val Thr Val Ser Ser
1 5 10

<210> SEQ ID NO 613
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 613

Arg Cys Xaa Xaa Thr Gln Ser Gln Val Ser Leu Pro Val Thr Pro Gly
1 5 10 15

Glu Pro Ala Ser Ile Ser Cys Arg Ser Ser
20 25

<210> SEQ ID NO 614
<211> LENGTH: 17
<212> TYPE: PRT
<213> ORGANISM: Artificial Sequence
<220> FEATURE:
<223> OTHER INFORMATION: Synthetic Construct

<400> SEQUENCE: 614

Val Asp Trp Tyr Leu Gln Lys Pro Gly Gln Ser Pro Gln Leu Leu Ile
1 5 10 15

Tyr

<210> SEQ ID NO 615
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: Xaa can be any naturally occurring amino acid

<400> SEQUENCE: 615

Asn Pro Val Ser Ile Phe Arg Val Cys Ile Xaa Gly Ser Gly Ser Gly
1 5 10 15

Thr Asp Phe Thr Leu Lys Ile Thr Arg Val Glu Ala Glu Asp Val Gly
20 25 30

Val Tyr Tyr Cys
35

<210> SEQ ID NO 616
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 616

Phe Gly Gln Gly Thr Lys Leu Xaa Ile Lys
1 5 10

<210> SEQ ID NO 617
<211> LENGTH: 445
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid

<400> SEQUENCE: 617

Gln Ser Gly Pro Glu Val Lys Lys Pro Gly Ala Ser Val Lys Val Ser
1 5 10 15

```
Cys Lys Ser Ser Gly Tyr Thr Phe Ser Asn Tyr Asp Phe Asn Trp Val
            20                  25                  30

Arg Gln Ala Pro Gly Gln Gly Leu Glu Trp Met Gly Trp Met Asn Pro
        35                  40                  45

Lys Asn Gly Tyr Ser Gly Phe Ala Gln Asn Phe Arg Gly Arg Ile Ser
    50                  55                  60

Met Thr Arg Asn Ser Ser Ile Thr Thr Ala Tyr Met Glu Leu Thr Ser
65                  70                  75                  80

Leu Thr Ser Asp Asp Thr Ala Leu Tyr Tyr Cys Val Arg Val Arg Thr
                85                  90                  95

Ile Ser Lys Gly Asp Ser Trp Tyr Phe Asp Leu Trp Gly Arg Gly Thr
            100                 105                 110

Leu Val Thr Val Ser Ser Lys Gly Pro Ser Val Phe Pro Leu Ala Pro
        115                 120                 125

Ser Ser Lys Ser Thr Ser Gly Gly Thr Ala Ala Leu Gly Xaa Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Xaa Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Xaa Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
```

435 440 445

<210> SEQ ID NO 618
<211> LENGTH: 216
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid

<400> SEQUENCE: 618

Arg Cys Xaa Xaa Thr Gln Ser Gln Val Ser Leu Pro Val Thr Pro Gly
1 5 10 15

Glu Pro Ala Ser Ile Ser Cys Arg Ser Ser Gln Ser Leu Leu His Asn
20 25 30

Asn Gly Tyr Asn Tyr Val Asp Trp Tyr Leu Gln Lys Pro Gly Gln Ser
35 40 45

Pro Gln Leu Leu Ile Tyr Leu Val Ser Asn Pro Val Ser Ile Phe Arg
50 55 60

Val Cys Ile Xaa Gly Ser Gly Ser Gly Thr Asp Phe Thr Leu Lys Ile
65 70 75 80

Thr Arg Val Glu Ala Glu Asp Val Gly Val Tyr Tyr Cys Met His Thr
85 90 95

Leu Gln Pro Pro Tyr Thr Phe Gly Gln Gly Thr Lys Leu Xaa Ile Lys
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys Lys
210 215

<210> SEQ ID NO 619
<211> LENGTH: 356
<212> TYPE: DNA
<213> ORGANISM: Artificial Sequence
<220> FEATURE:
<223> OTHER INFORMATION: Synthetic Construct

<400> SEQUENCE: 619
gcagtctggg cctgaggtga agaagcctgg ggcctcagtg aaggtctcct gcaagtcttc 60
tggatatacc ttcagtaatt atgacttcaa ctgggtgcga caggcccctg gacaagggct 120
tgagtggatg ggatggatga accctaaaaa tggctactca ggcttcgcac agaatttccg 180
gggccggata tccatgacca ggaactcctc cataaccaca gcctacatgg agctgaccag 240
cctgacatct gatgacacgg ccctttatta ttgtgtgaga gtgaggacaa tttctaaggg 300
cgacagctgg tacttcgatc tctggggccg tggcaccctg gtcactgtct cctcag 356

<210> SEQ ID NO 620
<211> LENGTH: 337
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t

<400> SEQUENCE: 620
cgatgttgnn agactcagtc tcaagtctcc ctgcccgtca cccctggaga gccggcctcc 60
atctcctgca ggtctagtca gagcctcctg cataacaatg gatacaacta tgtggattgg 120
tacctgcaga agccagggca gtctccacaa ctcctgatct atttggtttc gaacccagtc 180
tccatcttcc gtgtctgcat cngtggcagt ggatcaggca cagattttac actgaagatc 240
accagagtgg aggctgagga tgttggggtt tattactgta tgcatactct acaacccccg 300
tacacttttg gccaggggac caagctggan atcaaac 337

<210> SEQ ID NO 621
<211> LENGTH: 8
<212> TYPE: PRT
<213> ORGANISM: Artificial Sequence
<220> FEATURE:
<223> OTHER INFORMATION: Synthetic Construct

<400> SEQUENCE: 621

Gly Phe Thr Phe Asn Asn Tyr Ala
1 5

<210> SEQ ID NO 622
<211> LENGTH: 8
<212> TYPE: PRT
<213> ORGANISM: Artificial Sequence
<220> FEATURE:
<223> OTHER INFORMATION: Synthetic Construct

<400> SEQUENCE: 622

Ile Ser Gly Arg Thr Gly Ser Ala
1 5

<210> SEQ ID NO 623
<211> LENGTH: 17
<212> TYPE: PRT
<213> ORGANISM: Artificial Sequence
<220> FEATURE:
<223> OTHER INFORMATION: Synthetic Construct

<400> SEQUENCE: 623

```
Ala Arg Asp Gly Gln Glu Gly Gly Asn Tyr Ala Ala Glu Tyr Phe Gln
1               5                   10                  15

Asn


<210> SEQ ID NO 624
<211> LENGTH: 6
<212> TYPE: PRT
<213> ORGANISM: Artificial Sequence
<220> FEATURE:
<223> OTHER INFORMATION: Synthetic Construct

<400> SEQUENCE: 624

Gln Ser Ile Ser Lys Trp
1               5


<210> SEQ ID NO 625
<211> LENGTH: 3
<212> TYPE: PRT
<213> ORGANISM: Artificial Sequence
<220> FEATURE:
<223> OTHER INFORMATION: Synthetic Construct

<400> SEQUENCE: 625

Lys Ala Ser
1


<210> SEQ ID NO 626
<211> LENGTH: 9
<212> TYPE: PRT
<213> ORGANISM: Artificial Sequence
<220> FEATURE:
<223> OTHER INFORMATION: Synthetic Construct

<400> SEQUENCE: 626

Gln His Phe Asn Thr Glu Leu Leu Thr
1               5


<210> SEQ ID NO 627
<211> LENGTH: 120
<212> TYPE: PRT
<213> ORGANISM: Artificial Sequence
<220> FEATURE:
<223> OTHER INFORMATION: Synthetic Construct

<400> SEQUENCE: 627

Val Glu Ser Gly Gly Gly Leu Ala Gln Pro Gly Gly Ser Leu Thr Leu
1               5                   10                  15

Ser Cys Ala Ala Ser Gly Phe Thr Phe Asn Asn Tyr Ala Met Ser Trp
            20                  25                  30

Val Arg Gln Ala Pro Gly Lys Gly Leu Glu Trp Val Ser Gly Ile Ser
        35                  40                  45

Gly Arg Thr Gly Ser Ala His Tyr Ala Asp Ala Val Arg Gly Arg Phe
    50                  55                  60

Thr Ile Ser Arg Asp Asn Ala Lys Asn Thr Leu Tyr Leu Gln Met Ser
65                  70                  75                  80

Ser Leu Arg Ala Asp Asp Thr Ala Thr Tyr Tyr Cys Ala Arg Asp Gly
                85                  90                  95

Gln Glu Gly Gly Asn Tyr Ala Ala Glu Tyr Phe Gln Asn Trp Gly Gln
            100                 105                 110

Gly Thr Leu Val Thr Val Ser Ser
        115                 120
```

<210> SEQ ID NO 628
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 628

```
Arg His Xaa Xaa Thr Gln Ser Pro Ser Thr Leu Ala Ala Ser Val Gly
1               5                   10                  15

Asp Arg Val Thr Ile Thr Cys Arg Ala Ser Gln Ser Ile Ser Lys Trp
            20                  25                  30

Leu Ala Trp Tyr Gln Gln Lys Pro Gly Lys Ala Pro Lys Leu Leu Ile
        35                  40                  45

Tyr Lys Ala Ser Arg Leu Gln Ser Gly Ala Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln His Phe Asn Thr Glu Leu Leu
                85                  90                  95

Thr Phe Gly Gly Gly Thr Lys Val Glu Ile Lys
            100                 105
```

<210> SEQ ID NO 629
<211> LENGTH: 21
<212> TYPE: PRT
<213> ORGANISM: Artificial Sequence
<220> FEATURE:
<223> OTHER INFORMATION: Synthetic Construct

<400> SEQUENCE: 629

```
Val Glu Ser Gly Gly Gly Leu Ala Gln Pro Gly Gly Ser Leu Thr Leu
1               5                   10                  15

Ser Cys Ala Ala Ser
            20
```

<210> SEQ ID NO 630
<211> LENGTH: 17
<212> TYPE: PRT
<213> ORGANISM: Artificial Sequence
<220> FEATURE:
<223> OTHER INFORMATION: Synthetic Construct

<400> SEQUENCE: 630

```
Met Ser Trp Val Arg Gln Ala Pro Gly Lys Gly Leu Glu Trp Val Ser
1               5                   10                  15

Gly
```

<210> SEQ ID NO 631
<211> LENGTH: 38
<212> TYPE: PRT
<213> ORGANISM: Artificial Sequence
<220> FEATURE:
<223> OTHER INFORMATION: Synthetic Construct

<400> SEQUENCE: 631

```
His Tyr Ala Asp Ala Val Arg Gly Arg Phe Thr Ile Ser Arg Asp Asn
1               5                   10                  15

Ala Lys Asn Thr Leu Tyr Leu Gln Met Ser Ser Leu Arg Ala Asp Asp
```

20 25 30

Thr Ala Thr Tyr Tyr Cys
35

<210> SEQ ID NO 632
<211> LENGTH: 11
<212> TYPE: PRT
<213> ORGANISM: Artificial Sequence
<220> FEATURE:
<223> OTHER INFORMATION: Synthetic Construct

<400> SEQUENCE: 632

Trp Gly Gln Gly Thr Leu Val Thr Val Ser Ser
1 5 10

<210> SEQ ID NO 633
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 633

Arg His Xaa Xaa Thr Gln Ser Pro Ser Thr Leu Ala Ala Ser Val Gly
1 5 10 15

Asp Arg Val Thr Ile Thr Cys Arg Ala Ser
20 25

<210> SEQ ID NO 634
<211> LENGTH: 17
<212> TYPE: PRT
<213> ORGANISM: Artificial Sequence
<220> FEATURE:
<223> OTHER INFORMATION: Synthetic Construct

<400> SEQUENCE: 634

Leu Ala Trp Tyr Gln Gln Lys Pro Gly Lys Ala Pro Lys Leu Leu Ile
1 5 10 15

Tyr

<210> SEQ ID NO 635
<211> LENGTH: 36
<212> TYPE: PRT
<213> ORGANISM: Artificial Sequence
<220> FEATURE:
<223> OTHER INFORMATION: Synthetic Construct

<400> SEQUENCE: 635

Arg Leu Gln Ser Gly Ala Pro Ser Arg Phe Ser Gly Ser Gly Ser Gly
1 5 10 15

Thr Glu Phe Thr Leu Thr Ile Asn Ser Leu Gln Pro Asp Asp Phe Ala
20 25 30

Thr Tyr Tyr Cys
35

<210> SEQ ID NO 636
<211> LENGTH: 10
<212> TYPE: PRT
<213> ORGANISM: Artificial Sequence
<220> FEATURE:
<223> OTHER INFORMATION: Synthetic Construct

<400> SEQUENCE: 636

Phe Gly Gly Gly Thr Lys Val Glu Ile Lys
1               5                   10

<210> SEQ ID NO 637
<211> LENGTH: 447
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid

<400> SEQUENCE: 637

Val Glu Ser Gly Gly Gly Leu Ala Gln Pro Gly Gly Ser Leu Thr Leu
1               5                   10                  15

Ser Cys Ala Ala Ser Gly Phe Thr Phe Asn Asn Tyr Ala Met Ser Trp
            20                  25                  30

Val Arg Gln Ala Pro Gly Lys Gly Leu Glu Trp Val Ser Gly Ile Ser
        35                  40                  45

Gly Arg Thr Gly Ser Ala His Tyr Ala Asp Ala Val Arg Gly Arg Phe
    50                  55                  60

Thr Ile Ser Arg Asp Asn Ala Lys Asn Thr Leu Tyr Leu Gln Met Ser
65                  70                  75                  80

Ser Leu Arg Ala Asp Asp Thr Ala Thr Tyr Tyr Cys Ala Arg Asp Gly
                85                  90                  95

Gln Glu Gly Gly Asn Tyr Ala Ala Glu Tyr Phe Gln Asn Trp Gly Gln
            100                 105                 110

Gly Thr Leu Val Thr Val Ser Ser Lys Gly Pro Ser Val Phe Pro Leu
        115                 120                 125

Ala Pro Ser Ser Lys Ser Thr Ser Gly Gly Thr Ala Ala Leu Gly Xaa
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Xaa Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Xaa Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 638
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 638

Arg His Xaa Xaa Thr Gln Ser Pro Ser Thr Leu Ala Ala Ser Val Gly
1 5 10 15

Asp Arg Val Thr Ile Thr Cys Arg Ala Ser Gln Ser Ile Ser Lys Trp
20 25 30

Leu Ala Trp Tyr Gln Gln Lys Pro Gly Lys Ala Pro Lys Leu Leu Ile
35 40 45

Tyr Lys Ala Ser Arg Leu Gln Ser Gly Ala Pro Ser Arg Phe Ser Gly
50 55 60

Ser Gly Ser Gly Thr Glu Phe Thr Leu Thr Ile Asn Ser Leu Gln Pro
65 70 75 80

Asp Asp Phe Ala Thr Tyr Tyr Cys Gln His Phe Asn Thr Glu Leu Leu
85 90 95

Thr Phe Gly Gly Gly Thr Lys Val Glu Ile Lys Ala Pro Ser Val Phe
100 105 110

Ile Phe Pro Pro Ser Asp Glu Gln Leu Lys Ser Gly Thr Ala Ser Val
115 120 125

Val Cys Leu Leu Asn Asn Phe Tyr Pro Arg Glu Ala Lys Val Gln Trp
130 135 140

Lys Val Asp Asn Ala Leu Gln Ser Gly Asn Ser Gln Glu Ser Val Thr
145 150 155 160

Glu Gln Asp Ser Lys Asp Ser Thr Tyr Ser Leu Ser Ser Thr Leu Thr
165 170 175

```
Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210


<210> SEQ ID NO 639
<211> LENGTH: 361
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: n is a, c, g, or t

<400> SEQUENCE: 639

gtngagtcgg ggggaggcct cgcacagcct gggggatccc tgacactctc ctgtgcagcg      60

tctgggttca cattcaacaa ttatgccatg agctgggtcc gccaggctcc agggaagggg     120

ctggagtggg tctcaggaat aagtgggaga actggtagcg cacactacgc agacgccgtg     180

aggggccggt tcaccatctc cagagacaat gccaagaaca cactgtatct ccaaatgagc     240

agcctgagag ccgatgacac ggccacatat tactgtgcga gagatggtca agagggtgga     300

aactacgccg ctgaatactt tcagaactgg ggccagggca ccctggtcac cgtctcctca     360

g                                                                      361


<210> SEQ ID NO 640
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(10)
<223> OTHER INFORMATION: n is a, c, g, or t

<400> SEQUENCE: 640

cgacatcnnn agacccagtc tccttccacc ctggctgcat ctgtaggaga cagagtcacc      60

atcacttgcc gggccagtca gagtattagt aagtggttgg cctggtatca gcagaaacca     120

gggaaagccc ctaagctgct gatctataag gcatctcgtt tacaaagtgg ggccccatca     180

aggttcagcg gcagtggatc tgggacagag ttcactctca ccataaacag cctgcagcct     240

gatgattttg caacttatta ctgccaacac tttaatactg aacttctcac tttcggcggc     300

gggaccaagg tggagatcaa ac                                              322


<210> SEQ ID NO 641
<211> LENGTH: 8
<212> TYPE: PRT
<213> ORGANISM: Artificial Sequence
<220> FEATURE:
<223> OTHER INFORMATION: Synthetic Construct

<400> SEQUENCE: 641

Gly Phe Thr Phe Arg Ser Tyr Ala
1               5


<210> SEQ ID NO 642
```

<211> LENGTH: 8
<212> TYPE: PRT
<213> ORGANISM: Artificial Sequence
<220> FEATURE:
<223> OTHER INFORMATION: Synthetic Construct

<400> SEQUENCE: 642

Ile Ser Gly Ser Gly Gly Ser Thr
1               5

<210> SEQ ID NO 643
<211> LENGTH: 17
<212> TYPE: PRT
<213> ORGANISM: Artificial Sequence
<220> FEATURE:
<223> OTHER INFORMATION: Synthetic Construct

<400> SEQUENCE: 643

Ala Lys Asp Gly Gln Thr Gly Gly Asn Tyr Ala Ala Glu Tyr Phe Gln
1               5                   10                  15

His

<210> SEQ ID NO 644
<211> LENGTH: 6
<212> TYPE: PRT
<213> ORGANISM: Artificial Sequence
<220> FEATURE:
<223> OTHER INFORMATION: Synthetic Construct

<400> SEQUENCE: 644

Gln Ser Val Ser Lys Trp
1               5

<210> SEQ ID NO 645
<211> LENGTH: 3
<212> TYPE: PRT
<213> ORGANISM: Artificial Sequence
<220> FEATURE:
<223> OTHER INFORMATION: Synthetic Construct

<400> SEQUENCE: 645

Lys Ala Ser
1

<210> SEQ ID NO 646
<211> LENGTH: 9
<212> TYPE: PRT
<213> ORGANISM: Artificial Sequence
<220> FEATURE:
<223> OTHER INFORMATION: Synthetic Construct

<400> SEQUENCE: 646

Gln His Phe Asn Thr Glu Gln Leu Thr
1               5

<210> SEQ ID NO 647
<211> LENGTH: 119
<212> TYPE: PRT
<213> ORGANISM: Artificial Sequence
<220> FEATURE:
<223> OTHER INFORMATION: Synthetic Construct

<400> SEQUENCE: 647

Glu Ser Gly Gly Gly Leu Val Gln Pro Gly Gly Ser Leu Arg Leu Ser
1               5                   10                  15

Cys Ala Ala Ser Gly Phe Thr Phe Arg Ser Tyr Ala Met Ser Trp Val

```
            20                  25                  30

Arg Gln Ala Pro Gly Lys Gly Leu Glu Trp Val Ser Gly Ile Ser Gly
        35                  40                  45

Ser Gly Gly Ser Thr His Tyr Ala Asp Ser Val Glu Gly Arg Phe Ala
    50                  55                  60

Val Ser Arg Asp Asn Ser Lys Asn Thr Val Tyr Leu Glu Met Asn Ser
65                  70                  75                  80

Leu Arg Ala Glu Asp Thr Ala Val Tyr Tyr Cys Ala Lys Asp Gly Gln
                85                  90                  95

Thr Gly Gly Asn Tyr Ala Ala Glu Tyr Phe Gln His Trp Gly Gln Gly
            100                 105                 110

Ser Leu Val Thr Val Ser Ser
        115
```

<210> SEQ ID NO 648
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 648

```
Arg His Arg Xaa Thr Gln Ser Pro Ser Thr Leu Ser Ala Ser Val Gly
1               5                   10                  15

Asp Arg Val Thr Ile Thr Cys Arg Ala Ser Gln Ser Val Ser Lys Trp
            20                  25                  30

Leu Ala Trp Tyr Gln Gln Lys Ala Gly Lys Ala Pro Arg Leu Leu Ile
        35                  40                  45

Tyr Lys Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Phe Asn Thr Glu Gln Leu
                85                  90                  95

Thr Phe Gly Gly Gly Thr Lys Val Glu Ile Lys
            100                 105
```

<210> SEQ ID NO 649
<211> LENGTH: 20
<212> TYPE: PRT
<213> ORGANISM: Artificial Sequence
<220> FEATURE:
<223> OTHER INFORMATION: Synthetic Construct

<400> SEQUENCE: 649

```
Glu Ser Gly Gly Gly Leu Val Gln Pro Gly Gly Ser Leu Arg Leu Ser
1               5                   10                  15

Cys Ala Ala Ser
            20
```

<210> SEQ ID NO 650
<211> LENGTH: 17
<212> TYPE: PRT
<213> ORGANISM: Artificial Sequence
<220> FEATURE:
<223> OTHER INFORMATION: Synthetic Construct

<400> SEQUENCE: 650

Met Ser Trp Val Arg Gln Ala Pro Gly Lys Gly Leu Glu Trp Val Ser
1 5 10 15

Gly

<210> SEQ ID NO 651
<211> LENGTH: 38
<212> TYPE: PRT
<213> ORGANISM: Artificial Sequence
<220> FEATURE:
<223> OTHER INFORMATION: Synthetic Construct

<400> SEQUENCE: 651

His Tyr Ala Asp Ser Val Glu Gly Arg Phe Ala Val Ser Arg Asp Asn
1 5 10 15

Ser Lys Asn Thr Val Tyr Leu Glu Met Asn Ser Leu Arg Ala Glu Asp
20 25 30

Thr Ala Val Tyr Tyr Cys
35

<210> SEQ ID NO 652
<211> LENGTH: 11
<212> TYPE: PRT
<213> ORGANISM: Artificial Sequence
<220> FEATURE:
<223> OTHER INFORMATION: Synthetic Construct

<400> SEQUENCE: 652

Trp Gly Gln Gly Ser Leu Val Thr Val Ser Ser
1 5 10

<210> SEQ ID NO 653
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 653

Arg His Arg Xaa Thr Gln Ser Pro Ser Thr Leu Ser Ala Ser Val Gly
1 5 10 15

Asp Arg Val Thr Ile Thr Cys Arg Ala Ser
20 25

<210> SEQ ID NO 654
<211> LENGTH: 17
<212> TYPE: PRT
<213> ORGANISM: Artificial Sequence
<220> FEATURE:
<223> OTHER INFORMATION: Synthetic Construct

<400> SEQUENCE: 654

Leu Ala Trp Tyr Gln Gln Lys Ala Gly Lys Ala Pro Arg Leu Leu Ile
1 5 10 15

Tyr

<210> SEQ ID NO 655
<211> LENGTH: 36
<212> TYPE: PRT
<213> ORGANISM: Artificial Sequence
<220> FEATURE:
<223> OTHER INFORMATION: Synthetic Construct

<400> SEQUENCE: 655

Thr Leu Asp Ser Gly Val Pro Ser Arg Phe Ser Gly Ser Gly Ser Gly
1 5 10 15

Thr Glu Phe Thr Leu Thr Ile Ser Ser Leu Gln Pro Asp Asp Phe Ala
20 25 30

Thr Tyr Tyr Cys
35

<210> SEQ ID NO 656
<211> LENGTH: 10
<212> TYPE: PRT
<213> ORGANISM: Artificial Sequence
<220> FEATURE:
<223> OTHER INFORMATION: Synthetic Construct

<400> SEQUENCE: 656

Phe Gly Gly Gly Thr Lys Val Glu Ile Lys
1 5 10

<210> SEQ ID NO 657
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 657

Glu Ser Gly Gly Gly Leu Val Gln Pro Gly Gly Ser Leu Arg Leu Ser
1 5 10 15

Cys Ala Ala Ser Gly Phe Thr Phe Arg Ser Tyr Ala Met Ser Trp Val
20 25 30

Arg Gln Ala Pro Gly Lys Gly Leu Glu Trp Val Ser Gly Ile Ser Gly
35 40 45

Ser Gly Gly Ser Thr His Tyr Ala Asp Ser Val Glu Gly Arg Phe Ala
50 55 60

Val Ser Arg Asp Asn Ser Lys Asn Thr Val Tyr Leu Glu Met Asn Ser
65 70 75 80

Leu Arg Ala Glu Asp Thr Ala Val Tyr Tyr Cys Ala Lys Asp Gly Gln
85 90 95

Thr Gly Gly Asn Tyr Ala Ala Glu Tyr Phe Gln His Trp Gly Gln Gly
100 105 110

Ser Leu Val Thr Val Ser Ser Lys Gly Pro Ser Val Phe Pro Leu Ala
115 120 125

Pro Ser Ser Lys Ser Thr Ser Gly Gly Thr Ala Ala Leu Gly Xaa Leu
130 135 140

Val Lys Asp Tyr Phe Pro Glu Pro Val Thr Val Ser Trp Asn Ser Gly
145 150 155 160

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Xaa Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Xaa Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 658
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 658

```
Arg His Arg Xaa Thr Gln Ser Pro Ser Thr Leu Ser Ala Ser Val Gly
1               5                   10                  15

Asp Arg Val Thr Ile Thr Cys Arg Ala Ser Gln Ser Val Ser Lys Trp
            20                  25                  30

Leu Ala Trp Tyr Gln Gln Lys Ala Gly Lys Ala Pro Arg Leu Leu Ile
        35                  40                  45

Tyr Lys Ala Ser Thr Leu Asp Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Phe Asn Thr Glu Gln Leu
                85                  90                  95

Thr Phe Gly Gly Gly Thr Lys Val Glu Ile Lys Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210
```

<210> SEQ ID NO 659
<211> LENGTH: 358
<212> TYPE: DNA
<213> ORGANISM: Artificial Sequence
<220> FEATURE:
<223> OTHER INFORMATION: Synthetic Construct

<400> SEQUENCE: 659

```
gagtctgggg gaggcttggt gcagcctggg gggtccctga gactctcgtg tgcagcctct      60

ggattcacct ttagaagtta tgccatgagt tgggtccgac aggctccagg gaagggactg     120

gagtgggtct ctggtattag tggtagtggc ggcagcacac actatgcaga ctccgtggag     180

ggccggttcg ccgtctccag agacaattcc aagaacacgg tgtatctgga aatgaacagc     240

ctgagagccg aggacacggc cgtatattac tgtgcgaaag atggtcaaac gggtgggaac     300

tatgccgctg agtacttcca acactggggc cagggctccc tggtcaccgt ctcctcag       358
```

<210> SEQ ID NO 660
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(11)
<223> OTHER INFORMATION: n is a, c, g, or t

<400> SEQUENCE: 660

```
cgacatcgnn ngacccagtc tccttccacc ctgtctgcat ctgtgggaga cagagtcacc      60

atcacttgcc gggccagtca gagtgttagt aagtggttgg cctggtatca gcagaaagca     120

gggaaagccc ctaggctcct gatctacaag gcgtccactt tagatagtgg ggtcccatca     180

aggttcagcg gcagtggatc tgggacagaa ttcactctta ccatcagcag cctgcagcct     240

gatgattttg caacttatta ctgccaacac tttaatactg aacaactcac tttcggcgga     300

gggaccaagg tggagatcaa ac                                              322
```

<210> SEQ ID NO 661
<211> LENGTH: 8
<212> TYPE: PRT
<213> ORGANISM: Artificial Sequence
<220> FEATURE:
<223> OTHER INFORMATION: Synthetic Construct

<400> SEQUENCE: 661

Gly Tyr Thr Leu Thr Asn Tyr Ile
1               5

<210> SEQ ID NO 662
<211> LENGTH: 8
<212> TYPE: PRT
<213> ORGANISM: Artificial Sequence
<220> FEATURE:
<223> OTHER INFORMATION: Synthetic Construct

<400> SEQUENCE: 662

Leu Asn Pro Ser Gly Gly Gln Ser
1               5

<210> SEQ ID NO 663
<211> LENGTH: 20
<212> TYPE: PRT
<213> ORGANISM: Artificial Sequence
<220> FEATURE:
<223> OTHER INFORMATION: Synthetic Construct

<400> SEQUENCE: 663

Ala Arg Val His Cys Thr Ser Thr Ser Cys Pro Tyr Tyr Tyr Tyr Tyr
1               5                   10                  15

Gly Leu Asp Val
            20

<210> SEQ ID NO 664
<211> LENGTH: 6
<212> TYPE: PRT
<213> ORGANISM: Artificial Sequence
<220> FEATURE:
<223> OTHER INFORMATION: Synthetic Construct

<400> SEQUENCE: 664

Gln Gly Leu Asn Ser Trp
1               5

<210> SEQ ID NO 665
<211> LENGTH: 3
<212> TYPE: PRT
<213> ORGANISM: Artificial Sequence
<220> FEATURE:
<223> OTHER INFORMATION: Synthetic Construct

<400> SEQUENCE: 665

Ser Val Ser
1

<210> SEQ ID NO 666
<211> LENGTH: 9
<212> TYPE: PRT
<213> ORGANISM: Artificial Sequence
<220> FEATURE:
<223> OTHER INFORMATION: Synthetic Construct

<400> SEQUENCE: 666

Gln Gln Ala Asn Ser Phe Pro Phe Thr 1 5

<210> SEQ ID NO 667
<211> LENGTH: 123
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid

<400> SEQUENCE: 667

Val Gln Ser Gly Thr Glu Val Lys Gln Pro Gly Ala Ser Val Arg Val
1 5 10 15

Ser Cys Arg Ala Ser Gly Tyr Thr Leu Thr Asn Tyr Ile Ile His Trp
20 25 30

Val Arg Gln Ala Pro Gly Gln Gly Leu Glu Trp Met Gly Thr Leu Asn
35 40 45

Pro Ser Gly Gly Gln Ser Asn Tyr Ala Gln Lys Phe Gln Gly Arg Ile
50 55 60

Thr Ile Xaa Arg Asp Thr Ser Xaa Xaa Xaa Val Tyr Xaa Asp Ile Ser
65 70 75 80

Ser Leu Thr Xaa Xaa Asp Thr Ala Val Tyr Tyr Cys Ala Arg Val His
85 90 95

Cys Thr Ser Thr Ser Cys Pro Tyr Tyr Tyr Tyr Tyr Gly Leu Asp Val
100 105 110

Trp Gly Gln Gly Thr Thr Val Thr Val Ser Ser
115 120

<210> SEQ ID NO 668
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 668

Asp Xaa Xaa Xaa Thr Gln Ser Pro Ser Ser Val Ser Ala Ser Val Gly
1 5 10 15

Asp Arg Val Thr Ile Thr Cys Arg Ala Ser Gln Gly Leu Asn Ser Trp
20 25 30

Leu Ala Trp Tyr Gln Gln Lys Pro Gly Arg Ala Pro Lys Leu Leu Ile
35 40 45

His Ser Val Ser Ala Leu Gln Ser Gly Val Pro Ser Arg Phe Ser Gly
50 55 60

Ser Arg Ser Gly Thr Asp Phe Thr Leu Thr Ile Ser Ser Leu Gln Pro

```
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Arg Val Asp Val Asn
            100                 105


<210> SEQ ID NO 669
<211> LENGTH: 21
<212> TYPE: PRT
<213> ORGANISM: Artificial Sequence
<220> FEATURE:
<223> OTHER INFORMATION: Synthetic Construct

<400> SEQUENCE: 669

Val Gln Ser Gly Thr Glu Val Lys Gln Pro Gly Ala Ser Val Arg Val
1               5                   10                  15

Ser Cys Arg Ala Ser
            20


<210> SEQ ID NO 670
<211> LENGTH: 17
<212> TYPE: PRT
<213> ORGANISM: Artificial Sequence
<220> FEATURE:
<223> OTHER INFORMATION: Synthetic Construct

<400> SEQUENCE: 670

Ile His Trp Val Arg Gln Ala Pro Gly Gln Gly Leu Glu Trp Met Gly
1               5                   10                  15

Thr


<210> SEQ ID NO 671
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid

<400> SEQUENCE: 671

Asn Tyr Ala Gln Lys Phe Gln Gly Arg Ile Thr Ile Xaa Arg Asp Thr
1               5                   10                  15

Ser Xaa Xaa Xaa Val Tyr Xaa Asp Ile Ser Ser Leu Thr Xaa Xaa Asp
            20                  25                  30

Thr Ala Val Tyr Tyr Cys
        35


<210> SEQ ID NO 672
<211> LENGTH: 11
<212> TYPE: PRT
<213> ORGANISM: Artificial Sequence
```

<220> FEATURE:
<223> OTHER INFORMATION: Synthetic Construct

<400> SEQUENCE: 672

Trp Gly Gln Gly Thr Thr Val Thr Val Ser Ser
1 5 10

<210> SEQ ID NO 673
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 673

Asp Xaa Xaa Xaa Thr Gln Ser Pro Ser Ser Val Ser Ala Ser Val Gly
1 5 10 15

Asp Arg Val Thr Ile Thr Cys Arg Ala Ser
20 25

<210> SEQ ID NO 674
<211> LENGTH: 17
<212> TYPE: PRT
<213> ORGANISM: Artificial Sequence
<220> FEATURE:
<223> OTHER INFORMATION: Synthetic Construct

<400> SEQUENCE: 674

Leu Ala Trp Tyr Gln Gln Lys Pro Gly Arg Ala Pro Lys Leu Leu Ile
1 5 10 15

His

<210> SEQ ID NO 675
<211> LENGTH: 36
<212> TYPE: PRT
<213> ORGANISM: Artificial Sequence
<220> FEATURE:
<223> OTHER INFORMATION: Synthetic Construct

<400> SEQUENCE: 675

Ala Leu Gln Ser Gly Val Pro Ser Arg Phe Ser Gly Ser Arg Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 676
<211> LENGTH: 10
<212> TYPE: PRT
<213> ORGANISM: Artificial Sequence
<220> FEATURE:
<223> OTHER INFORMATION: Synthetic Construct

<400> SEQUENCE: 676

Phe Gly Pro Gly Thr Arg Val Asp Val Asn
1 5 10

<210> SEQ ID NO 677
<211> LENGTH: 450
<212> TYPE: PRT

<213> ORGANISM: Artificial Sequence
<220> FEATURE:
<223> OTHER INFORMATION: Synthetic Construct
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 677

Val Gln Ser Gly Thr Glu Val Lys Gln Pro Gly Ala Ser Val Arg Val
1 5 10 15

Ser Cys Arg Ala Ser Gly Tyr Thr Leu Thr Asn Tyr Ile Ile His Trp
20 25 30

Val Arg Gln Ala Pro Gly Gln Gly Leu Glu Trp Met Gly Thr Leu Asn
35 40 45

Pro Ser Gly Gly Gln Ser Asn Tyr Ala Gln Lys Phe Gln Gly Arg Ile
50 55 60

Thr Ile Xaa Arg Asp Thr Ser Xaa Xaa Xaa Val Tyr Xaa Asp Ile Ser
65 70 75 80

Ser Leu Thr Xaa Xaa Asp Thr Ala Val Tyr Tyr Cys Ala Arg Val His
85 90 95

Cys Thr Ser Thr Ser Cys Pro Tyr Tyr Tyr Tyr Tyr Gly Leu Asp Val
100 105 110

Trp Gly Gln Gly Thr Thr Val Thr Val Ser Ser Lys Gly Pro Ser Val
115 120 125

Phe Pro Leu Ala Pro Ser Ser Lys Ser Thr Ser Gly Gly Thr Ala Ala
130 135 140

Leu Gly Xaa Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Xaa Val Glu Pro Lys Ser Cys Asp
210 215 220

Lys Thr His Thr Cys Pro Pro Cys Pro Ala Pro Glu Leu Leu Gly Gly
225 230 235 240

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Xaa Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 678
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 678

```
Asp Xaa Xaa Xaa Thr Gln Ser Pro Ser Ser Val Ser Ala Ser Val Gly
1               5                   10                  15

Asp Arg Val Thr Ile Thr Cys Arg Ala Ser Gln Gly Leu Asn Ser Trp
            20                  25                  30

Leu Ala Trp Tyr Gln Gln Lys Pro Gly Arg Ala Pro Lys Leu Leu Ile
        35                  40                  45

His Ser Val Ser Ala Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Arg Val Asp Val Asn Ala Pro Ser Val Phe
            100                 105                 110

Ile Phe Pro Pro Ser Asp Glu Gln Leu Lys Ser Gly Thr Ala Ser Val
        115                 120                 125
```

```
Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210
```

<210> SEQ ID NO 679
<211> LENGTH: 369
<212> TYPE: DNA
<213> ORGANISM: Artificial Sequence
<220> FEATURE:
<223> OTHER INFORMATION: Synthetic Construct

<400> SEQUENCE: 679

```
gtgcagtctg ggactgaagt gaagcagccc ggggcctcag tgagggtttc ctgcagggca     60

tccggataca ccttaaccaa ctacataata cactgggtgc gacaggcccc tggacaaggg    120

cttgagtgga tgggaacact caaccctagt ggtggtcagt caaattacgc acagaagttc    180

cagggaagaa tcaccatcwc cagrgacacs tccmygarsw cagtgtacmt ggacatcagc    240

agcctgacat rtgrggacac ggctgtgtat tactgtgcga gagtccattg tactagtacc    300

agctgcccct attactacta ctacggtttg gacgtctggg gccaagggac cacggtcacc    360

gtctcctca                                                            369
```

<210> SEQ ID NO 680
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 680

```
gacatnnntn agacccagtc tccatcttcc gtgtctgcat ctgttggaga cagagtcacc     60

atcacttgtc gggcgagcca gggtcttaac agctggttag cctggtatca gcaaaaacca    120

gggagagccc ctaagctcct gattcattct gtttcggctt tgcaaagtgg agtcccatcc    180

aggttcagcg gcagtagatc tgggacagat ttcactctca ccatcagcag cctgcagcct    240

gaagattttg ccacttacta ttgtcagcag gctaacagtt tcccattcac tttcggccct    300

gggaccagag tggatgtcaa cc                                             322
```

<210> SEQ ID NO 681
<211> LENGTH: 8
<212> TYPE: PRT
<213> ORGANISM: Artificial Sequence
<220> FEATURE:

<223> OTHER INFORMATION: Synthetic Construct

<400> SEQUENCE: 681

Gly Tyr Thr Phe Ile Asp Tyr Tyr
1               5

<210> SEQ ID NO 682
<211> LENGTH: 8
<212> TYPE: PRT
<213> ORGANISM: Artificial Sequence
<220> FEATURE:
<223> OTHER INFORMATION: Synthetic Construct

<400> SEQUENCE: 682

Ile Asn Pro Lys Ser Gly Gly Thr
1               5

<210> SEQ ID NO 683
<211> LENGTH: 15
<212> TYPE: PRT
<213> ORGANISM: Artificial Sequence
<220> FEATURE:
<223> OTHER INFORMATION: Synthetic Construct

<400> SEQUENCE: 683

Ala Arg Pro Arg Arg Arg Gly Asn Tyr Ser Tyr Gly Met Asp Val
1               5                   10                  15

<210> SEQ ID NO 684
<211> LENGTH: 6
<212> TYPE: PRT
<213> ORGANISM: Artificial Sequence
<220> FEATURE:
<223> OTHER INFORMATION: Synthetic Construct

<400> SEQUENCE: 684

Gln Asn Ile Asp Asp Tyr
1               5

<210> SEQ ID NO 685
<211> LENGTH: 3
<212> TYPE: PRT
<213> ORGANISM: Artificial Sequence
<220> FEATURE:
<223> OTHER INFORMATION: Synthetic Construct

<400> SEQUENCE: 685

Gly Ala Ser
1

<210> SEQ ID NO 686
<211> LENGTH: 9
<212> TYPE: PRT
<213> ORGANISM: Artificial Sequence
<220> FEATURE:
<223> OTHER INFORMATION: Synthetic Construct

<400> SEQUENCE: 686

Gln Glu Thr Tyr Thr Phe Pro Tyr Thr
1               5

<210> SEQ ID NO 687
<211> LENGTH: 115
<212> TYPE: PRT
<213> ORGANISM: Artificial Sequence
<220> FEATURE:
<223> OTHER INFORMATION: Synthetic Construct

<400> SEQUENCE: 687

Gly Ala Glu Val Ala Lys Pro Gly Ala Ser Val Lys Val Ser Cys Lys
1               5                   10                  15

Ala Ser Gly Tyr Thr Phe Ile Asp Tyr Tyr Ile Tyr Trp Val Arg Gln
            20                  25                  30

Ala Pro Gly Gln Gly Leu Lys Ser Val Ala Trp Ile Asn Pro Lys Ser
        35                  40                  45

Gly Gly Thr Asn Tyr Ala Gln Asp Phe Gln Gly Arg Val Thr Leu Thr
    50                  55                  60

Arg Asp Thr Ser Ile Thr Thr Ala Tyr Met Glu Leu Asn Gly Leu Arg
65                  70                  75                  80

Ser Asp Asp Thr Ala Val Tyr Tyr Cys Ala Arg Pro Arg Arg Arg Gly
                85                  90                  95

Asn Tyr Ser Tyr Gly Met Asp Val Trp Gly Gln Gly Thr Ala Val Ile
            100                 105                 110

Val Ser Ser
        115

<210> SEQ ID NO 688
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 688

Arg His Xaa Val Thr Gln Ser Pro Ser Ser Leu Ser Ala Ser Val Gly
1               5                   10                  15

Asp Arg Val Thr Ile Thr Cys Arg Ala Ser Gln Asn Ile Asp Asp Tyr
            20                  25                  30

Leu Asn Trp Tyr Gln Gln Thr Glu Gly Lys Ala Pro Gln Leu Leu Ile
        35                  40                  45

Phe Gly Ala Ser Ser Leu His Asn Gly Val Pro Thr Arg Phe Ser Gly
    50                  55                  60

Ser Gly Ser Gly Arg Asp Phe Thr Leu Thr Ile Thr Ser Leu Gln Arg
65                  70                  75                  80

Asp Asp Phe Ala Thr Tyr Tyr Cys Gln Glu Thr Tyr Thr Phe Pro Tyr
                85                  90                  95

Thr Phe Gly Gln Gly Thr Lys Leu Glu Ile Lys
            100                 105

<210> SEQ ID NO 689
<211> LENGTH: 18
<212> TYPE: PRT
<213> ORGANISM: Artificial Sequence
<220> FEATURE:
<223> OTHER INFORMATION: Synthetic Construct

<400> SEQUENCE: 689

Gly Ala Glu Val Ala Lys Pro Gly Ala Ser Val Lys Val Ser Cys Lys
1               5                   10                  15

Ala Ser

<210> SEQ ID NO 690

<211> LENGTH: 17
<212> TYPE: PRT
<213> ORGANISM: Artificial Sequence
<220> FEATURE:
<223> OTHER INFORMATION: Synthetic Construct

<400> SEQUENCE: 690

Ile Tyr Trp Val Arg Gln Ala Pro Gly Gln Gly Leu Lys Ser Val Ala
1 5 10 15

Trp

<210> SEQ ID NO 691
<211> LENGTH: 38
<212> TYPE: PRT
<213> ORGANISM: Artificial Sequence
<220> FEATURE:
<223> OTHER INFORMATION: Synthetic Construct

<400> SEQUENCE: 691

Asn Tyr Ala Gln Asp Phe Gln Gly Arg Val Thr Leu Thr Arg Asp Thr
1 5 10 15

Ser Ile Thr Thr Ala Tyr Met Glu Leu Asn Gly Leu Arg Ser Asp Asp
20 25 30

Thr Ala Val Tyr Tyr Cys
35

<210> SEQ ID NO 692
<211> LENGTH: 11
<212> TYPE: PRT
<213> ORGANISM: Artificial Sequence
<220> FEATURE:
<223> OTHER INFORMATION: Synthetic Construct

<400> SEQUENCE: 692

Trp Gly Gln Gly Thr Ala Val Ile Val Ser Ser
1 5 10

<210> SEQ ID NO 693
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 693

Arg His Xaa Val Thr Gln Ser Pro Ser Ser Leu Ser Ala Ser Val Gly
1 5 10 15

Asp Arg Val Thr Ile Thr Cys Arg Ala Ser
20 25

<210> SEQ ID NO 694
<211> LENGTH: 17
<212> TYPE: PRT
<213> ORGANISM: Artificial Sequence
<220> FEATURE:
<223> OTHER INFORMATION: Synthetic Construct

<400> SEQUENCE: 694

Leu Asn Trp Tyr Gln Gln Thr Glu Gly Lys Ala Pro Gln Leu Leu Ile
1 5 10 15

Phe

<210> SEQ ID NO 695
<211> LENGTH: 36
<212> TYPE: PRT
<213> ORGANISM: Artificial Sequence
<220> FEATURE:
<223> OTHER INFORMATION: Synthetic Construct

<400> SEQUENCE: 695

Ser Leu His Asn Gly Val Pro Thr Arg Phe Ser Gly Ser Gly Ser Gly
1 5 10 15

Arg Asp Phe Thr Leu Thr Ile Thr Ser Leu Gln Arg Asp Asp Phe Ala
20 25 30

Thr Tyr Tyr Cys
35

<210> SEQ ID NO 696
<211> LENGTH: 10
<212> TYPE: PRT
<213> ORGANISM: Artificial Sequence
<220> FEATURE:
<223> OTHER INFORMATION: Synthetic Construct

<400> SEQUENCE: 696

Phe Gly Gln Gly Thr Lys Leu Glu Ile Lys
1 5 10

<210> SEQ ID NO 697
<211> LENGTH: 442
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid

<400> SEQUENCE: 697

Gly Ala Glu Val Ala Lys Pro Gly Ala Ser Val Lys Val Ser Cys Lys
1 5 10 15

Ala Ser Gly Tyr Thr Phe Ile Asp Tyr Tyr Ile Tyr Trp Val Arg Gln
20 25 30

Ala Pro Gly Gln Gly Leu Lys Ser Val Ala Trp Ile Asn Pro Lys Ser
35 40 45

Gly Gly Thr Asn Tyr Ala Gln Asp Phe Gln Gly Arg Val Thr Leu Thr
50 55 60

Arg Asp Thr Ser Ile Thr Thr Ala Tyr Met Glu Leu Asn Gly Leu Arg
65 70 75 80

Ser Asp Asp Thr Ala Val Tyr Tyr Cys Ala Arg Pro Arg Arg Arg Gly
85 90 95

Asn Tyr Ser Tyr Gly Met Asp Val Trp Gly Gln Gly Thr Ala Val Ile
100 105 110

Val Ser Ser Lys Gly Pro Ser Val Phe Pro Leu Ala Pro Ser Ser Lys
115 120 125

```
Ser Thr Ser Gly Gly Thr Ala Ala Leu Gly Xaa Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Xaa Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Xaa Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 698
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 698

```
Arg His Xaa Val Thr Gln Ser Pro Ser Ser Leu Ser Ala Ser Val Gly
1               5                   10                  15

Asp Arg Val Thr Ile Thr Cys Arg Ala Ser Gln Asn Ile Asp Asp Tyr
            20                  25                  30
```

```
Leu Asn Trp Tyr Gln Gln Thr Glu Gly Lys Ala Pro Gln Leu Leu Ile
        35                  40                  45

Phe Gly Ala Ser Ser Leu His Asn Gly Val Pro Thr Arg Phe Ser Gly
    50                  55                  60

Ser Gly Ser Gly Arg Asp Phe Thr Leu Thr Ile Thr Ser Leu Gln Arg
65                  70                  75                  80

Asp Asp Phe Ala Thr Tyr Tyr Cys Gln Glu Thr Tyr Thr Phe Pro Tyr
                85                  90                  95

Thr Phe Gly Gln Gly Thr Lys Leu Glu Ile Lys Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210
```

<210> SEQ ID NO 699
<211> LENGTH: 347
<212> TYPE: DNA
<213> ORGANISM: Artificial Sequence
<220> FEATURE:
<223> OTHER INFORMATION: Synthetic Construct

<400> SEQUENCE: 699

```
ctggggctga ggtggcgaag cctggggcct cagtgaaggt ctcctgcaag gcgtctggat     60

acaccttcat cgactactat atatactggg tgcgacaggc ccctggacaa ggtcttaaat    120

cggtggcatg gatcaaccct aagagtggtg gcacaaacta cgcacaggac tttcagggca    180

gggtcaccct taccagggac acgtccatca ccacagccta catggagctg aacggtctga    240

gatctgacga cacggccgtt tattactgtg cgagaccgag acgacgggga aattattcct    300

acggcatgga cgtctggggc caagggaccg ctgtcattgt ctcctca                 347
```

<210> SEQ ID NO 700
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is a, c, g, or t

<400> SEQUENCE: 700

```
cgacatngtg tgacccagtc tccatcctcc ctgtctgcat ctgtaggaga cagagtcacc     60

atcacttgcc gggcaagtca gaacattgac gactatttaa actggtatca gcagacagaa    120

gggaaagccc ctcagctcct gatctttggt gcatcgagtt tgcacaatgg ggtcccaaca    180
```

aggttcagtg gcagtggatc tgggagagac ttcactctca ccatcaccag tctgcaacgt 240
gacgattttg caacttacta ctgtcaagag acttacactt tcccatacac ttttggccag 300
gggaccaagc tggagatcaa ac 322

<210> SEQ ID NO 701
<211> LENGTH: 8
<212> TYPE: PRT
<213> ORGANISM: Artificial Sequence
<220> FEATURE:
<223> OTHER INFORMATION: Synthetic Construct

<400> SEQUENCE: 701

Gly Phe Thr Phe Ser Lys Ala Trp
1 5

<210> SEQ ID NO 702
<211> LENGTH: 10
<212> TYPE: PRT
<213> ORGANISM: Artificial Sequence
<220> FEATURE:
<223> OTHER INFORMATION: Synthetic Construct

<400> SEQUENCE: 702

Ile Lys Ser Asn Ile Asp Asp Gly Thr Ile
1 5 10

<210> SEQ ID NO 703
<211> LENGTH: 15
<212> TYPE: PRT
<213> ORGANISM: Artificial Sequence
<220> FEATURE:
<223> OTHER INFORMATION: Synthetic Construct

<400> SEQUENCE: 703

Phe Thr Val Pro Tyr Cys Asn Gly Thr His Cys Tyr Gly Thr Ala
1 5 10 15

<210> SEQ ID NO 704
<211> LENGTH: 12
<212> TYPE: PRT
<213> ORGANISM: Artificial Sequence
<220> FEATURE:
<223> OTHER INFORMATION: Synthetic Construct

<400> SEQUENCE: 704

Gln Ser Leu Phe Tyr Ser Gly Thr Asn Lys Asn Tyr
1 5 10

<210> SEQ ID NO 705
<211> LENGTH: 3
<212> TYPE: PRT
<213> ORGANISM: Artificial Sequence
<220> FEATURE:
<223> OTHER INFORMATION: Synthetic Construct

<400> SEQUENCE: 705

Trp Ala Ser
1

<210> SEQ ID NO 706
<211> LENGTH: 6
<212> TYPE: PRT
<213> ORGANISM: Artificial Sequence
<220> FEATURE:
<223> OTHER INFORMATION: Synthetic Construct
<220> FEATURE:

<221> NAME/KEY: misc_feature
<222> LOCATION: (4)..(4)
<223> OTHER INFORMATION: Xaa can be any naturally occurring amino acid

<400> SEQUENCE: 706

Gln Arg His Xaa Glu Thr
1 5

<210> SEQ ID NO 707
<211> LENGTH: 124
<212> TYPE: PRT
<213> ORGANISM: Artificial Sequence
<220> FEATURE:
<223> OTHER INFORMATION: Synthetic Construct

<400> SEQUENCE: 707

Arg Cys Gln Leu Val Glu Ser Gly Gly Ser Leu Val Lys Pro Gly Gly
1 5 10 15

Ser Leu Arg Leu Ser Cys Ala Ala Ser Gly Phe Thr Phe Ser Lys Ala
20 25 30

Trp Met Ser Trp Ala Arg Gln Ala Pro Gly Lys Gly Leu Glu Trp Val
35 40 45

Gly Arg Ile Lys Ser Asn Ile Asp Asp Gly Thr Ile Asp Tyr Ala Ala
50 55 60

Ser Val Lys Gly Arg Phe Thr Ile Ala Arg Asp Asp Ser Glu Asn Thr
65 70 75 80

Leu His Leu Gln Met Asn Ser Leu Arg Thr Glu Asp Thr Ala Val Tyr
85 90 95

Tyr Cys Phe Thr Val Pro Tyr Cys Asn Gly Thr His Cys Tyr Gly Thr
100 105 110

Ala Trp Gly Gln Gly Thr Leu Val Ile Val Ser Ser
115 120

<210> SEQ ID NO 708
<211> LENGTH: 110
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(92)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 708

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Tyr Ser
20 25 30

Gly Thr Asn Lys Asn Tyr Leu Glu Leu Trp Leu His His Leu Xaa Xaa
35 40 45

Pro Pro Lys Leu Leu Ile Tyr Trp Ala Ser Ile Arg Glu Ser Gly Val
50 55 60

Pro Asp Arg Phe Ser Gly Cys Gly Asp Xaa Xaa Xaa Ser Arg Leu Pro
65 70 75 80

Ile Ser Ser Leu Arg Ala Xaa Asp Xaa Xaa Xaa Xaa Tyr Cys Gln Arg
85 90 95

His Xaa Glu Thr Phe Xaa Gln Gly Thr Arg Val Glu Ile Lys
100 105 110

<210> SEQ ID NO 709
<211> LENGTH: 25
<212> TYPE: PRT
<213> ORGANISM: Artificial Sequence
<220> FEATURE:
<223> OTHER INFORMATION: Synthetic Construct

<400> SEQUENCE: 709

Arg Cys Gln Leu Val Glu Ser Gly Gly Ser Leu Val Lys Pro Gly Gly
1 5 10 15

Ser Leu Arg Leu Ser Cys Ala Ala Ser
20 25

<210> SEQ ID NO 710
<211> LENGTH: 17
<212> TYPE: PRT
<213> ORGANISM: Artificial Sequence
<220> FEATURE:
<223> OTHER INFORMATION: Synthetic Construct

<400> SEQUENCE: 710

Met Ser Trp Ala Arg Gln Ala Pro Gly Lys Gly Leu Glu Trp Val Gly
1 5 10 15

Arg

<210> SEQ ID NO 711
<211> LENGTH: 38
<212> TYPE: PRT
<213> ORGANISM: Artificial Sequence
<220> FEATURE:
<223> OTHER INFORMATION: Synthetic Construct

<400> SEQUENCE: 711

Asp Tyr Ala Ala Ser Val Lys Gly Arg Phe Thr Ile Ala Arg Asp Asp
1 5 10 15

Ser Glu Asn Thr Leu His Leu Gln Met Asn Ser Leu Arg Thr Glu Asp
20 25 30

Thr Ala Val Tyr Tyr Cys
35

<210> SEQ ID NO 712
<211> LENGTH: 11
<212> TYPE: PRT
<213> ORGANISM: Artificial Sequence
<220> FEATURE:
<223> OTHER INFORMATION: Synthetic Construct

<400> SEQUENCE: 712

Trp Gly Gln Gly Thr Leu Val Ile Val Ser Ser
1 5 10

<210> SEQ ID NO 713
<211> LENGTH: 26
<212> TYPE: PRT
<213> ORGANISM: Artificial Sequence
<220> FEATURE:
<223> OTHER INFORMATION: Synthetic Construct

<400> SEQUENCE: 713

Asp Ile Val Met Thr Gln Ser Pro Asp Ser Leu Ala Val Ser Leu Gly
1 5 10 15

Glu Arg Ala Thr Ile Asn Cys Lys Ser Ser
20 25

<210> SEQ ID NO 714
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(10)
<223> OTHER INFORMATION: Xaa can be any naturally occurring amino acid

<400> SEQUENCE: 714

Leu Glu Leu Trp Leu His His Leu Xaa Xaa Pro Pro Lys Leu Leu Ile
1 5 10 15

Tyr

<210> SEQ ID NO 715
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid

<400> SEQUENCE: 715

Ile Arg Glu Ser Gly Val Pro Asp Arg Phe Ser Gly Cys Gly Asp Xaa
1 5 10 15

Xaa Xaa Ser Arg Leu Pro Ile Ser Ser Leu Arg Ala Xaa Asp Xaa Xaa
20 25 30

Xaa Xaa Tyr Cys
35

<210> SEQ ID NO 716
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)

<223> OTHER INFORMATION: Xaa can be any naturally occurring amino acid

<400> SEQUENCE: 716

Phe Xaa Gln Gly Thr Arg Val Glu Ile Lys
1 5 10

<210> SEQ ID NO 717
<211> LENGTH: 451
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid

<400> SEQUENCE: 717

Arg Cys Gln Leu Val Glu Ser Gly Gly Ser Leu Val Lys Pro Gly Gly
1 5 10 15

Ser Leu Arg Leu Ser Cys Ala Ala Ser Gly Phe Thr Phe Ser Lys Ala
20 25 30

Trp Met Ser Trp Ala Arg Gln Ala Pro Gly Lys Gly Leu Glu Trp Val
35 40 45

Gly Arg Ile Lys Ser Asn Ile Asp Asp Gly Thr Ile Asp Tyr Ala Ala
50 55 60

Ser Val Lys Gly Arg Phe Thr Ile Ala Arg Asp Asp Ser Glu Asn Thr
65 70 75 80

Leu His Leu Gln Met Asn Ser Leu Arg Thr Glu Asp Thr Ala Val Tyr
85 90 95

Tyr Cys Phe Thr Val Pro Tyr Cys Asn Gly Thr His Cys Tyr Gly Thr
100 105 110

Ala Trp Gly Gln Gly Thr Leu Val Ile Val Ser Ser Lys Gly Pro Ser
115 120 125

Val Phe Pro Leu Ala Pro Ser Ser Lys Ser Thr Ser Gly Gly Thr Ala
130 135 140

Ala Leu Gly Xaa Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Xaa Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Xaa Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 718
<211> LENGTH: 214
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(92)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 718

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Gly Thr Asn Lys Asn Tyr Leu Glu Leu Trp Leu His His Leu Xaa Xaa
        35                  40                  45

```
Pro Pro Lys Leu Leu Ile Tyr Trp Ala Ser Ile Arg Glu Ser Gly Val
    50                  55                  60

Pro Asp Arg Phe Ser Gly Cys Gly Asp Xaa Xaa Xaa Ser Arg Leu Pro
65                  70                  75                  80

Ile Ser Ser Leu Arg Ala Xaa Asp Xaa Xaa Xaa Xaa Tyr Cys Gln Arg
                85                  90                  95

His Xaa Glu Thr Phe Xaa Gln Gly Thr Arg Val Glu Ile Lys Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Lys
    210
```

<210> SEQ ID NO 719
<211> LENGTH: 373
<212> TYPE: DNA
<213> ORGANISM: Artificial Sequence
<220> FEATURE:
<223> OTHER INFORMATION: Synthetic Construct

<400> SEQUENCE: 719

```
aggtgccagc tggtggagtc tgggggatcc ttggtgaagc ctgggggtc cctcagactc      60

tcctgtgcag cctctggatt cactttcagt aaggcctgga tgagttgggc ccgccaggct    120

ccagggaagg gtctggagtg ggtcggccgt attaaaagta atattgatga tgggactata    180

gactacgctg catccgtgaa aggaagattc accatcgcaa gagatgattc cgaaaacaca    240

ctccacctcc aaatgaatag cctgagaacc gaggacacag ccgtttatta ctgtttcaca    300

gttccctatt gtaatgggac tcactgttat ggaactgcgt ggggccaggg aaccctggtc    360

atcgtctcgt cag                                                       373
```

<210> SEQ ID NO 720
<211> LENGTH: 331
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (138)..(139)
<223> OTHER INFORMATION: n is a, c, g, or t

<400> SEQUENCE: 720

```
gacatcgtga tgacccagtc tccagactcc ctggctgtgt ctctgggcga gagggccacc     60

atcaactgca agtccagcca gagtcttttc tacagcggca ccaataaaaa ctacttagaa    120

ctgtggctgc accatctnng tcwgcctcct aagttgctca tttactgggc ttctatccgg    180

gagtccgggg tccctgaccg attcagtggc tgcggtgatg rsmcagwytc cagactccct    240
```

atcagcagcc tgcgggctgr agatgkgsca stttmwtact gtcarcggca ttgrgagacg 300
ttckgccaag ggaccagggt tgagatcaaa c 331

<210> SEQ ID NO 721
<211> LENGTH: 8
<212> TYPE: PRT
<213> ORGANISM: Artificial Sequence
<220> FEATURE:
<223> OTHER INFORMATION: Synthetic Construct

<400> SEQUENCE: 721

Gly Phe Thr Phe Ser Asp Tyr Tyr
1 5

<210> SEQ ID NO 722
<211> LENGTH: 10
<212> TYPE: PRT
<213> ORGANISM: Artificial Sequence
<220> FEATURE:
<223> OTHER INFORMATION: Synthetic Construct

<400> SEQUENCE: 722

Ser Arg Asn Lys Ala Asn Ser Tyr Thr Thr
1 5 10

<210> SEQ ID NO 723
<211> LENGTH: 13
<212> TYPE: PRT
<213> ORGANISM: Artificial Sequence
<220> FEATURE:
<223> OTHER INFORMATION: Synthetic Construct

<400> SEQUENCE: 723

Ala Arg Ala Phe Ser Gly Gly Ser Tyr Cys Ser Asp Tyr
1 5 10

<210> SEQ ID NO 724
<211> LENGTH: 6
<212> TYPE: PRT
<213> ORGANISM: Artificial Sequence
<220> FEATURE:
<223> OTHER INFORMATION: Synthetic Construct

<400> SEQUENCE: 724

Gln Gly Ile Ser Ser Tyr
1 5

<210> SEQ ID NO 725
<211> LENGTH: 3
<212> TYPE: PRT
<213> ORGANISM: Artificial Sequence
<220> FEATURE:
<223> OTHER INFORMATION: Synthetic Construct

<400> SEQUENCE: 725

Ala Ala Ser
1

<210> SEQ ID NO 726
<211> LENGTH: 9
<212> TYPE: PRT
<213> ORGANISM: Artificial Sequence
<220> FEATURE:
<223> OTHER INFORMATION: Synthetic Construct

<400> SEQUENCE: 726

```
Gln Gln Leu Asn Ser Tyr Pro Ser Thr
1               5


<210> SEQ ID NO 727
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 727

Cys Xaa Xaa Val Glu Ser Gly Gly Gly Leu Val Gln Pro Gly Gly Ser
1               5                   10                  15

Leu Arg Leu Ser Cys Ala Ala Ser Gly Phe Thr Phe Ser Asp Tyr Tyr
            20                  25                  30

Met Asp Trp Val Arg Gln Ala Pro Gly Lys Gly Leu Glu Trp Val Gly
        35                  40                  45

Arg Ser Arg Asn Lys Ala Asn Ser Tyr Thr Thr Glu Tyr Ala Ala Ser
    50                  55                  60

Val Lys Gly Arg Phe Thr Ile Ser Arg Asp Asp Ser Lys Asn Ser Val
65                  70                  75                  80

Tyr Leu Gln Met Asn Ser Leu Lys Thr Glu Asp Thr Ala Val Tyr Tyr
                85                  90                  95

Cys Ala Arg Ala Phe Ser Gly Gly Ser Tyr Cys Ser Asp Tyr Trp Gly
            100                 105                 110

Gln Gly Thr Leu Val Thr Val Ser Ser
        115                 120


<210> SEQ ID NO 728
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 728

Asp Ile Pro Xaa Thr Gln Ser Pro Ser Phe Leu Ser Ala Ser Val Gly
1               5                   10                  15

Asp Arg Val Thr Ile Thr Cys Arg Thr Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Ser
                85                  90                  95

Thr Phe Gly Gln Gly Thr Arg Leu Glu Ile Lys
            100                 105


<210> SEQ ID NO 729
```

<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 729

Cys Xaa Xaa Val Glu Ser Gly Gly Gly Leu Val Gln Pro Gly Gly Ser
1               5                   10                  15

Leu Arg Leu Ser Cys Ala Ala Ser
            20

<210> SEQ ID NO 730
<211> LENGTH: 17
<212> TYPE: PRT
<213> ORGANISM: Artificial Sequence
<220> FEATURE:
<223> OTHER INFORMATION: Synthetic Construct

<400> SEQUENCE: 730

Met Asp Trp Val Arg Gln Ala Pro Gly Lys Gly Leu Glu Trp Val Gly
1               5                   10                  15

Arg

<210> SEQ ID NO 731
<211> LENGTH: 38
<212> TYPE: PRT
<213> ORGANISM: Artificial Sequence
<220> FEATURE:
<223> OTHER INFORMATION: Synthetic Construct

<400> SEQUENCE: 731

Glu Tyr Ala Ala Ser Val Lys Gly Arg Phe Thr Ile Ser Arg Asp Asp
1               5                   10                  15

Ser Lys Asn Ser Val Tyr Leu Gln Met Asn Ser Leu Lys Thr Glu Asp
            20                  25                  30

Thr Ala Val Tyr Tyr Cys
        35

<210> SEQ ID NO 732
<211> LENGTH: 11
<212> TYPE: PRT
<213> ORGANISM: Artificial Sequence
<220> FEATURE:
<223> OTHER INFORMATION: Synthetic Construct

<400> SEQUENCE: 732

Trp Gly Gln Gly Thr Leu Val Thr Val Ser Ser
1               5                   10

<210> SEQ ID NO 733
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 733

Asp Ile Pro Xaa Thr Gln Ser Pro Ser Phe Leu Ser Ala Ser Val Gly
1 5 10 15

Asp Arg Val Thr Ile Thr Cys Arg Thr Ser
20 25

<210> SEQ ID NO 734
<211> LENGTH: 17
<212> TYPE: PRT
<213> ORGANISM: Artificial Sequence
<220> FEATURE:
<223> OTHER INFORMATION: Synthetic Construct

<400> SEQUENCE: 734

Leu Ala Trp Tyr Gln Gln Lys Pro Gly Lys Ala Pro Lys Leu Leu Ile
1 5 10 15

Tyr

<210> SEQ ID NO 735
<211> LENGTH: 36
<212> TYPE: PRT
<213> ORGANISM: Artificial Sequence
<220> FEATURE:
<223> OTHER INFORMATION: Synthetic Construct

<400> SEQUENCE: 735

Thr Leu Gln Ser Gly Val Pro Ser Arg Phe Ser Gly Ser Gly Ser Gly
1 5 10 15

Thr Glu Phe Thr Leu Thr Ile Ser Ser Leu Gln Pro Glu Asp Phe Ala
20 25 30

Thr Tyr Tyr Cys
35

<210> SEQ ID NO 736
<211> LENGTH: 10
<212> TYPE: PRT
<213> ORGANISM: Artificial Sequence
<220> FEATURE:
<223> OTHER INFORMATION: Synthetic Construct

<400> SEQUENCE: 736

Phe Gly Gln Gly Thr Arg Leu Glu Ile Lys
1 5 10

<210> SEQ ID NO 737
<211> LENGTH: 448
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 737

```
Cys Xaa Xaa Val Glu Ser Gly Gly Gly Leu Val Gln Pro Gly Gly Ser
1               5                   10                  15

Leu Arg Leu Ser Cys Ala Ala Ser Gly Phe Thr Phe Ser Asp Tyr Tyr
            20                  25                  30

Met Asp Trp Val Arg Gln Ala Pro Gly Lys Gly Leu Glu Trp Val Gly
        35                  40                  45

Arg Ser Arg Asn Lys Ala Asn Ser Tyr Thr Thr Glu Tyr Ala Ala Ser
    50                  55                  60

Val Lys Gly Arg Phe Thr Ile Ser Arg Asp Asp Ser Lys Asn Ser Val
65                  70                  75                  80

Tyr Leu Gln Met Asn Ser Leu Lys Thr Glu Asp Thr Ala Val Tyr Tyr
                85                  90                  95

Cys Ala Arg Ala Phe Ser Gly Gly Ser Tyr Cys Ser Asp Tyr Trp Gly
            100                 105                 110

Gln Gly Thr Leu Val Thr Val Ser Ser Lys Gly Pro Ser Val Phe Pro
        115                 120                 125

Leu Ala Pro Ser Ser Lys Ser Thr Ser Gly Gly Thr Ala Ala Leu Gly
    130                 135                 140

Xaa Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Xaa Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Xaa Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
        420                 425                 430

Leu His Asn His Tyr Thr Gln Lys Ser Leu Ser Leu Ser Pro Gly Lys
    435                 440                 445


<210> SEQ ID NO 738
<211> LENGTH: 211
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 738

Asp Ile Pro Xaa Thr Gln Ser Pro Ser Phe Leu Ser Ala Ser Val Gly
1               5                   10                  15

Asp Arg Val Thr Ile Thr Cys Arg Thr Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Ser
                85                  90                  95

Thr Phe Gly Gln Gly Thr Arg Leu Glu Ile Lys Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys Lys
    210


<210> SEQ ID NO 739
<211> LENGTH: 365
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 739
```

gtgccnnnng gtngagtctg ggggaggctt ggtccagcct ggagggtccc tgagactctc 60
ctgtgcagcc tctggattca ccttcagtga ctactacatg gactgggtcc gccaggctcc 120
agggaagggg ctggagtggg taggccgttc tagaaacaaa gctaacagtt acaccacaga 180
atacgccgcg tctgtgaaag gcagattcac catctcaaga gatgattcaa agaactcagt 240
atatctgcaa atgaacagcc tgaaaaccga ggacacggcc gtgtattact gtgcaagggc 300
tttctcgggt gggagctact gttccgacta ctggggccag ggaaccctgg tcaccgtctc 360
ctcag 365

<210> SEQ ID NO 740
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(11)
<223> OTHER INFORMATION: n is a, c, g, or t

<400> SEQUENCE: 740
gacatcccnn ngacccagtc tccatccttc ctgtctgcat ctgtaggaga cagagtcacc 60
atcacttgcc gtaccagtca gggcattagc agttatttag cctggtatca gcaaaaacca 120
gggaaagccc ctaagctcct gatctatgct gcatccactt tgcaaagtgg ggtcccatca 180
aggttcagcg gcagtggatc tgggacagaa ttcactctca caatcagcag cctgcagcct 240
gaagattttg caacttatta ctgtcaacaa cttaatagtt acccgtccac cttcggccaa 300
gggacacgac tggagattaa ac 322

<210> SEQ ID NO 741
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 741

Gly Phe Thr Phe Xaa Ser Xaa Ala
1               5

<210> SEQ ID NO 742
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 742

Ile Xaa Xaa Xaa Gly Gly Xaa Thr
1 5

<210> SEQ ID NO 743
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 743

Xaa Xaa Xaa Xaa Xaa Xaa Xaa Gly Xaa Xaa Xaa Xaa Xaa Thr Xaa
1 5 10 15

<210> SEQ ID NO 744
<211> LENGTH: 7
<212> TYPE: PRT
<213> ORGANISM: Artificial Sequence
<220> FEATURE:
<223> OTHER INFORMATION: Synthetic Construct

<400> SEQUENCE: 744

Gln Pro Ile Ser Ser Thr Tyr
1 5

<210> SEQ ID NO 745
<211> LENGTH: 3
<212> TYPE: PRT
<213> ORGANISM: Artificial Sequence
<220> FEATURE:
<223> OTHER INFORMATION: Synthetic Construct

<400> SEQUENCE: 745

Ala Thr Ser
1

<210> SEQ ID NO 746
<211> LENGTH: 10
<212> TYPE: PRT
<213> ORGANISM: Artificial Sequence
<220> FEATURE:
<223> OTHER INFORMATION: Synthetic Construct

<400> SEQUENCE: 746

Gln His Tyr Ser Asn Ser Pro Pro Tyr Thr
1 5 10

<210> SEQ ID NO 747
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:

<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(88)
<223> OTHER INFORMATION: Xaa can be any naturally occurring amino acid
<220> FEATURE:
<221> NAME/KEY: misc_feature
<222> LOCATION: (90)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 747

Gly Xaa Leu Arg Xaa Ser Cys Ala Ala Ser Gly Phe Thr Phe Xaa Ser
1 5 10 15

Xaa Ala Met Xaa Trp Val Arg Gln Xaa Pro Gly Lys Gly Leu Glu Trp
20 25 30

Val Xaa Xaa Ile Xaa Xaa Xaa Gly Gly Xaa Thr Xaa Tyr Xaa Xaa Xaa
35 40 45

Val Lys Gly Arg Phe Xaa Ile Ser Arg Asp Xaa Ser Lys Xaa Thr Leu
50 55 60

Tyr Leu Gln Met Asn Ser Leu Xaa Xaa Glu Asp Thr Ala Xaa Tyr Xaa
65 70 75 80

Cys Xaa Xaa Xaa Xaa Xaa Xaa Xaa Gly Xaa Xaa Xaa Xaa Xaa Thr Xaa
85 90 95

Trp Gly Gln Gly Thr Xaa Val Thr Val Ser Ser
100 105

<210> SEQ ID NO 748
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 748

Glu Ile Xaa Xaa Thr Gln Ser Pro Gly Thr Leu Ser Leu Ser Leu Gly
1 5 10 15

Glu Gly Ala Thr Leu Ser Cys Arg Ala Ser Gln Pro Ile Ser Ser Thr
20 25 30

Tyr Leu Thr Trp Tyr Gln Gln Arg Pro Gly Gln Ala Pro Arg Leu Leu
35 40 45

Ile Tyr Ala Thr Ser Thr Arg Ala Thr Asp Ile Pro Asp Arg Phe Ser
50 55 60

Gly Ser Gly Ser Gly Thr Asp Phe Thr Leu Thr Ile Ser Arg Leu Glu
65 70 75 80

Thr Glu Asp Phe Ala Val Tyr Tyr Cys Gln His Tyr Ser Asn Ser Pro
85 90 95

Pro Tyr Thr Phe Gly Gln Gly Thr Lys Leu Glu Ile Lys
100 105

<210> SEQ ID NO 749
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 749

Gly Xaa Leu Arg Xaa Ser Cys Ala Ala Ser
1 5 10

<210> SEQ ID NO 750
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 750

```
Met Xaa Trp Val Arg Gln Xaa Pro Gly Lys Gly Leu Glu Trp Val Xaa
1               5                   10                  15

Xaa
```

<210> SEQ ID NO 751
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 751

```
Xaa Tyr Xaa Xaa Xaa Val Lys Gly Arg Phe Xaa Ile Ser Arg Asp Xaa
1               5                   10                  15

Ser Lys Xaa Thr Leu Tyr Leu Gln Met Asn Ser Leu Xaa Xaa Glu Asp
            20                  25                  30

Thr Ala Xaa Tyr Xaa Cys
        35
```

<210> SEQ ID NO 752
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 752

```
Trp Gly Gln Gly Thr Xaa Val Thr Val Ser Ser
1               5                   10
```

<210> SEQ ID NO 753
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 753

```
Glu Ile Xaa Xaa Thr Gln Ser Pro Gly Thr Leu Ser Leu Ser Leu Gly
1               5                   10                  15

Glu Gly Ala Thr Leu Ser Cys Arg Ala Ser
            20                  25
```

<210> SEQ ID NO 754
<211> LENGTH: 17
<212> TYPE: PRT
<213> ORGANISM: Artificial Sequence
<220> FEATURE:
<223> OTHER INFORMATION: Synthetic Construct

<400> SEQUENCE: 754

```
Leu Thr Trp Tyr Gln Gln Arg Pro Gly Gln Ala Pro Arg Leu Leu Ile
1               5                   10                  15

Tyr
```

<210> SEQ ID NO 755
<211> LENGTH: 36
<212> TYPE: PRT
<213> ORGANISM: Artificial Sequence
<220> FEATURE:
<223> OTHER INFORMATION: Synthetic Construct

<400> SEQUENCE: 755

```
Thr Arg Ala Thr Asp Ile Pro Asp Arg Phe Ser Gly Ser Gly Ser Gly
1               5                   10                  15

Thr Asp Phe Thr Leu Thr Ile Ser Arg Leu Glu Thr Glu Asp Phe Ala
            20                  25                  30

Val Tyr Tyr Cys
        35
```

<210> SEQ ID NO 756
<211> LENGTH: 10
<212> TYPE: PRT
<213> ORGANISM: Artificial Sequence
<220> FEATURE:
<223> OTHER INFORMATION: Synthetic Construct

<400> SEQUENCE: 756

Phe Gly Gln Gly Thr Lys Leu Glu Ile Lys
1 5 10

<210> SEQ ID NO 757
<211> LENGTH: 434
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(80)

<223> OTHER INFORMATION: Xaa can be any naturally occurring amino acid
<220> FEATURE:
<221> NAME/KEY: misc_feature
<222> LOCATION: (82)..(88)
<223> OTHER INFORMATION: Xaa can be any naturally occurring amino acid
<220> FEATURE:
<221> NAME/KEY: misc_feature
<222> LOCATION: (90)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (345)..(345)
<223> OTHER INFORMATION: Xaa can be any naturally occurring amino acid

<400> SEQUENCE: 757

```
Gly Xaa Leu Arg Xaa Ser Cys Ala Ala Ser Gly Phe Thr Phe Xaa Ser
1               5                   10                  15

Xaa Ala Met Xaa Trp Val Arg Gln Xaa Pro Gly Lys Gly Leu Glu Trp
            20                  25                  30

Val Xaa Xaa Ile Xaa Xaa Xaa Gly Gly Xaa Thr Xaa Tyr Xaa Xaa Xaa
        35                  40                  45

Val Lys Gly Arg Phe Xaa Ile Ser Arg Asp Xaa Ser Lys Xaa Thr Leu
    50                  55                  60

Tyr Leu Gln Met Asn Ser Leu Xaa Xaa Glu Asp Thr Ala Xaa Tyr Xaa
65                  70                  75                  80

Cys Xaa Xaa Xaa Xaa Xaa Xaa Xaa Gly Xaa Xaa Xaa Xaa Xaa Thr Xaa
                85                  90                  95

Trp Gly Gln Gly Thr Xaa Val Thr Val Ser Ser Lys Gly Pro Ser Val
            100                 105                 110

Phe Pro Leu Ala Pro Ser Ser Lys Ser Thr Ser Gly Gly Thr Ala Ala
        115                 120                 125

Leu Gly Xaa Leu Val Lys Asp Tyr Phe Pro Glu Pro Val Thr Val Ser
    130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
                165                 170                 175

Ser Ser Ser Leu Gly Thr Gln Thr Tyr Ile Cys Asn Val Asn His Lys
            180                 185                 190

Pro Ser Asn Thr Lys Val Asp Lys Xaa Val Glu Pro Lys Ser Cys Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255
```

Asp Pro Glu Val Lys Phe Asn Trp Tyr Val Asp Gly Val Glu Val His
260 265 270

Asn Ala Lys Thr Lys Pro Arg Glu Glu Gln Tyr Asn Ser Thr Tyr Arg
275 280 285

Val Val Ser Val Leu Thr Val Leu His Gln Asp Trp Leu Asn Gly Lys
290 295 300

Glu Tyr Lys Cys Lys Val Ser Asn Lys Ala Leu Pro Ala Pro Ile Glu
305 310 315 320

Lys Thr Ile Ser Lys Ala Lys Gly Gln Pro Arg Glu Pro Gln Val Tyr
325 330 335

Thr Leu Pro Pro Ser Arg Asp Glu Xaa Thr Lys Asn Gln Val Ser Leu
340 345 350

Thr Cys Leu Val Lys Gly Phe Tyr Pro Ser Asp Ile Ala Val Glu Trp
355 360 365

Glu Ser Asn Gly Gln Pro Glu Asn Asn Tyr Lys Thr Thr Pro Pro Val
370 375 380

Leu Asp Ser Asp Gly Ser Phe Phe Leu Tyr Ser Lys Leu Thr Val Asp
385 390 395 400

Lys Ser Arg Trp Gln Gln Gly Asn Val Phe Ser Cys Ser Val Met His
405 410 415

Glu Ala Leu His Asn His Tyr Thr Gln Lys Ser Leu Ser Leu Ser Pro
420 425 430

Gly Lys

<210> SEQ ID NO 758
<211> LENGTH: 213
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 758

Glu Ile Xaa Xaa Thr Gln Ser Pro Gly Thr Leu Ser Leu Ser Leu Gly
1 5 10 15

Glu Gly Ala Thr Leu Ser Cys Arg Ala Ser Gln Pro Ile Ser Ser Thr
20 25 30

Tyr Leu Thr Trp Tyr Gln Gln Arg Pro Gly Gln Ala Pro Arg Leu Leu
35 40 45

Ile Tyr Ala Thr Ser Thr Arg Ala Thr Asp Ile Pro Asp Arg Phe Ser
50 55 60

Gly Ser Gly Ser Gly Thr Asp Phe Thr Leu Thr Ile Ser Arg Leu Glu
65 70 75 80

Thr Glu Asp Phe Ala Val Tyr Tyr Cys Gln His Tyr Ser Asn Ser Pro
85 90 95

Pro Tyr Thr Phe Gly Gln Gly Thr Lys Leu Glu Ile Lys Ala Pro Ser
100 105 110

Val Phe Ile Phe Pro Pro Ser Asp Glu Gln Leu Lys Ser Gly Thr Ala
115 120 125

Ser Val Val Cys Leu Leu Asn Asn Phe Tyr Pro Arg Glu Ala Lys Val
130 135 140

Gln Trp Lys Val Asp Asn Ala Leu Gln Ser Gly Asn Ser Gln Glu Ser
145 150 155 160

```
Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys Lys
    210
```

```
<210> SEQ ID NO 759
<211> LENGTH: 322
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 759

ggggncctga gantctcctg tgcagcctct ggattcacct ttnncagywa kgccatgasc     60

tgggtccgcc agrctccagg gaagggrctg gagtgggtyk smsstattar wrgnrrtggt    120

ggkasmacak actacrcwgm myccgtgaar ggcmgrttca ycatytcmag agayrattcm    180

aarracacgy tgtatctrca ratgaayagy ctgararccg aggacacrgc cstmtattwc    240

tgtrcsanaa kaysanaykg wrrtggsnct yaytrctwyn ngactwcntg gggccaggga    300

acccwggtca ccgtctcctc an                                             322
```

```
<210> SEQ ID NO 760
<211> LENGTH: 328
<212> TYPE: DNA
```

<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(10)
<223> OTHER INFORMATION: n is a, c, g, or t

<400> SEQUENCE: 760
gaaattgnnn tgacgcagtc tccaggcacc ctgtctttgt ctctaggtga aggagccacc 60
ctctcctgca gggccagtca gcctattagt agcacctact taacctggta ccagcagaga 120
cctggccagg ctccccggct cctcatctac gctacgtcca ccagggccac tgacatccca 180
gacaggttca gtggcagtgg ctctgggaca gacttcactc tcaccatcag tagactggag 240
actgaagatt ttgcagtgta ctactgtcaa cattattcta actcacctcc gtacactttt 300
ggccagggga ccaagctgga gatcaaac 328

<210> SEQ ID NO 761
<211> LENGTH: 8
<212> TYPE: PRT
<213> ORGANISM: Artificial Sequence
<220> FEATURE:
<223> OTHER INFORMATION: Synthetic Construct

<400> SEQUENCE: 761

Gly Phe Pro Phe Asp Ser His Ala
1 5

<210> SEQ ID NO 762
<211> LENGTH: 8
<212> TYPE: PRT
<213> ORGANISM: Artificial Sequence
<220> FEATURE:
<223> OTHER INFORMATION: Synthetic Construct

<400> SEQUENCE: 762

Ile Ser Asn Asn Gly Ala Ser Ala
1 5

<210> SEQ ID NO 763
<211> LENGTH: 17
<212> TYPE: PRT
<213> ORGANISM: Artificial Sequence
<220> FEATURE:
<223> OTHER INFORMATION: Synthetic Construct

<400> SEQUENCE: 763

Ala Arg Thr Gln Tyr Tyr Asp Ser Arg Gly Phe Tyr Phe Ser Leu Asp
1 5 10 15

Ala

<210> SEQ ID NO 764
<211> LENGTH: 7
<212> TYPE: PRT
<213> ORGANISM: Artificial Sequence
<220> FEATURE:
<223> OTHER INFORMATION: Synthetic Construct

<400> SEQUENCE: 764

Gln Pro Ile Ser Ser Thr Tyr
1 5

<210> SEQ ID NO 765
<211> LENGTH: 3

<212> TYPE: PRT
<213> ORGANISM: Artificial Sequence
<220> FEATURE:
<223> OTHER INFORMATION: Synthetic Construct

<400> SEQUENCE: 765

Ala Thr Ser
1

<210> SEQ ID NO 766
<211> LENGTH: 10
<212> TYPE: PRT
<213> ORGANISM: Artificial Sequence
<220> FEATURE:
<223> OTHER INFORMATION: Synthetic Construct

<400> SEQUENCE: 766

Gln His Tyr Ser Asn Ser Pro Pro Tyr Thr
1 5 10

<210> SEQ ID NO 767
<211> LENGTH: 119
<212> TYPE: PRT
<213> ORGANISM: Artificial Sequence
<220> FEATURE:
<223> OTHER INFORMATION: Synthetic Construct

<400> SEQUENCE: 767

Glu Ser Gly Gly Gly Val Val Gln Pro Gly Arg Ser Val Arg Leu Ser
1 5 10 15

Cys Val Gly Ser Gly Phe Pro Phe Asp Ser His Ala Ile His Trp Val
20 25 30

Arg Gln Ala Pro Gly Trp Gly Leu Glu Trp Val Ala Val Ile Ser Asn
35 40 45

Asn Gly Ala Ser Ala His Tyr Thr Asp Ser Val Lys Gly Arg Phe Thr
50 55 60

Val Ser Arg Asp Asn Ser Lys His Thr Val Tyr Leu Leu Leu Asn Ser
65 70 75 80

Leu Thr Lys Glu Asp Thr Ala Val Tyr Tyr Cys Ala Arg Thr Gln Tyr
85 90 95

Tyr Asp Ser Arg Gly Phe Tyr Phe Ser Leu Asp Ala Trp Gly Gln Gly
100 105 110

Thr Leu Val Thr Val Ser Ser
115

<210> SEQ ID NO 768
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 768

Glu Ile Xaa Xaa Thr Gln Ser Pro Gly Thr Leu Ser Leu Ser Leu Gly
1 5 10 15

Glu Gly Ala Thr Leu Ser Cys Arg Ala Ser Gln Pro Ile Ser Ser Thr
20 25 30

Tyr Leu Thr Trp Tyr Gln Gln Arg Pro Gly Gln Ala Pro Arg Leu Leu
35 40 45

```
Ile Tyr Ala Thr Ser Thr Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Thr Glu Asp Phe Ala Val Tyr Tyr Cys Gln His Tyr Ser Asn Ser Pro
                85                  90                  95

Pro Tyr Thr Phe Gly Gln Gly Thr Lys Leu Glu Ile Lys
            100                 105


<210> SEQ ID NO 769
<211> LENGTH: 20
<212> TYPE: PRT
<213> ORGANISM: Artificial Sequence
<220> FEATURE:
<223> OTHER INFORMATION: Synthetic Construct

<400> SEQUENCE: 769

Glu Ser Gly Gly Gly Val Val Gln Pro Gly Arg Ser Val Arg Leu Ser
1               5                   10                  15

Cys Val Gly Ser
            20


<210> SEQ ID NO 770
<211> LENGTH: 17
<212> TYPE: PRT
<213> ORGANISM: Artificial Sequence
<220> FEATURE:
<223> OTHER INFORMATION: Synthetic Construct

<400> SEQUENCE: 770

Ile His Trp Val Arg Gln Ala Pro Gly Trp Gly Leu Glu Trp Val Ala
1               5                   10                  15

Val


<210> SEQ ID NO 771
<211> LENGTH: 38
<212> TYPE: PRT
<213> ORGANISM: Artificial Sequence
<220> FEATURE:
<223> OTHER INFORMATION: Synthetic Construct

<400> SEQUENCE: 771

His Tyr Thr Asp Ser Val Lys Gly Arg Phe Thr Val Ser Arg Asp Asn
1               5                   10                  15

Ser Lys His Thr Val Tyr Leu Leu Leu Asn Ser Leu Thr Lys Glu Asp
            20                  25                  30

Thr Ala Val Tyr Tyr Cys
        35


<210> SEQ ID NO 772
<211> LENGTH: 11
<212> TYPE: PRT
<213> ORGANISM: Artificial Sequence
<220> FEATURE:
<223> OTHER INFORMATION: Synthetic Construct

<400> SEQUENCE: 772

Trp Gly Gln Gly Thr Leu Val Thr Val Ser Ser
1               5                   10


<210> SEQ ID NO 773
<211> LENGTH: 26
```

<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 773

Glu Ile Xaa Xaa Thr Gln Ser Pro Gly Thr Leu Ser Leu Ser Leu Gly
1 5 10 15

Glu Gly Ala Thr Leu Ser Cys Arg Ala Ser
20 25

<210> SEQ ID NO 774
<211> LENGTH: 17
<212> TYPE: PRT
<213> ORGANISM: Artificial Sequence
<220> FEATURE:
<223> OTHER INFORMATION: Synthetic Construct

<400> SEQUENCE: 774

Leu Thr Trp Tyr Gln Gln Arg Pro Gly Gln Ala Pro Arg Leu Leu Ile
1 5 10 15

Tyr

<210> SEQ ID NO 775
<211> LENGTH: 36
<212> TYPE: PRT
<213> ORGANISM: Artificial Sequence
<220> FEATURE:
<223> OTHER INFORMATION: Synthetic Construct

<400> SEQUENCE: 775

Thr Arg Ala Thr Asp Ile Pro Asp Arg Phe Ser Gly Ser Gly Ser Gly
1 5 10 15

Thr Asp Phe Thr Leu Thr Ile Ser Arg Leu Glu Thr Glu Asp Phe Ala
20 25 30

Val Tyr Tyr Cys
35

<210> SEQ ID NO 776
<211> LENGTH: 10
<212> TYPE: PRT
<213> ORGANISM: Artificial Sequence
<220> FEATURE:
<223> OTHER INFORMATION: Synthetic Construct

<400> SEQUENCE: 776

Phe Gly Gln Gly Thr Lys Leu Glu Ile Lys
1 5 10

<210> SEQ ID NO 777
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 777

Glu Ser Gly Gly Gly Val Val Gln Pro Gly Arg Ser Val Arg Leu Ser
1 5 10 15

Cys Val Gly Ser Gly Phe Pro Phe Asp Ser His Ala Ile His Trp Val
20 25 30

Arg Gln Ala Pro Gly Trp Gly Leu Glu Trp Val Ala Val Ile Ser Asn
35 40 45

Asn Gly Ala Ser Ala His Tyr Thr Asp Ser Val Lys Gly Arg Phe Thr
50 55 60

Val Ser Arg Asp Asn Ser Lys His Thr Val Tyr Leu Leu Leu Asn Ser
65 70 75 80

Leu Thr Lys Glu Asp Thr Ala Val Tyr Tyr Cys Ala Arg Thr Gln Tyr
85 90 95

Tyr Asp Ser Arg Gly Phe Tyr Phe Ser Leu Asp Ala Trp Gly Gln Gly
100 105 110

Thr Leu Val Thr Val Ser Ser Lys Gly Pro Ser Val Phe Pro Leu Ala
115 120 125

Pro Ser Ser Lys Ser Thr Ser Gly Gly Thr Ala Ala Leu Gly Xaa Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Xaa Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Xaa Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 778
<211> LENGTH: 213
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 778

Glu Ile Xaa Xaa Thr Gln Ser Pro Gly Thr Leu Ser Leu Ser Leu Gly
1 5 10 15

Glu Gly Ala Thr Leu Ser Cys Arg Ala Ser Gln Pro Ile Ser Ser Thr
20 25 30

Tyr Leu Thr Trp Tyr Gln Gln Arg Pro Gly Gln Ala Pro Arg Leu Leu
35 40 45

Ile Tyr Ala Thr Ser Thr Arg Ala Thr Asp Ile Pro Asp Arg Phe Ser
50 55 60

Gly Ser Gly Ser Gly Thr Asp Phe Thr Leu Thr Ile Ser Arg Leu Glu
65 70 75 80

Thr Glu Asp Phe Ala Val Tyr Tyr Cys Gln His Tyr Ser Asn Ser Pro
85 90 95

Pro Tyr Thr Phe Gly Gln Gly Thr Lys Leu Glu Ile Lys Ala Pro Ser
100 105 110

Val Phe Ile Phe Pro Pro Ser Asp Glu Gln Leu Lys Ser Gly Thr Ala
115 120 125

Ser Val Val Cys Leu Leu Asn Asn Phe Tyr Pro Arg Glu Ala Lys Val
130 135 140

Gln Trp Lys Val Asp Asn Ala Leu Gln Ser Gly Asn Ser Gln Glu Ser
145 150 155 160

Val Thr Glu Gln Asp Ser Lys Asp Ser Thr Tyr Ser Leu Ser Ser Thr
165 170 175

Leu Thr Leu Ser Lys Ala Asp Tyr Glu Lys His Lys Val Tyr Ala Cys
180 185 190

Glu Val Thr His Gln Gly Leu Ser Ser Pro Val Thr Lys Ser Phe Asn
195 200 205

Arg Gly Glu Cys Lys
210

<210> SEQ ID NO 779
<211> LENGTH: 358
<212> TYPE: DNA
<213> ORGANISM: Artificial Sequence
<220> FEATURE:
<223> OTHER INFORMATION: Synthetic Construct

<400> SEQUENCE: 779
gagtctgggg gaggcgttgt ccagcctggg aggtccgtga gactctcctg tgtaggctct 60

```
ggattcccat tcgatagtca tgccatacac tgggtccgcc aggctccagg ctggggcctg    120

gagtgggtgg cagttatctc aaacaatggc gccagtgcac attacacaga ctccgtgaag    180

ggccgattca ccgtctccag agacaattcc aagcacaccg tctatctact tctgaacagt    240

ctgacaaaag aagacacggc tgtctactac tgtgcgagga cacaatatta tgatagtcgt    300

ggtttttact tttctctcga cgcctggggc cagggaaccc tcgtcaccgt ctcctcag      358
```

<210> SEQ ID NO 780
<211> LENGTH: 328
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(10)
<223> OTHER INFORMATION: n is a, c, g, or t

<400> SEQUENCE: 780

```
gaaattgnnn tgacgcagtc tccaggcacc ctgtctttgt ctctaggtga aggagccacc     60

ctctcctgca gggccagtca gcctattagt agcacctact taacctggta ccagcagaga    120

cctggccagg ctcccccggct cctcatctac gctacgtcca ccagggccac tgacatccca    180

gacaggttca gtggcagtgg ctctgggaca gacttcactc tcaccatcag tagactggag    240

actgaagatt ttgcagtgta ctactgtcaa cattattcta actcacctcc gtacactttt    300

ggccagggga ccaagctgga gatcaaac                                       328
```

<210> SEQ ID NO 781
<211> LENGTH: 8
<212> TYPE: PRT
<213> ORGANISM: Artificial Sequence
<220> FEATURE:
<223> OTHER INFORMATION: Synthetic Construct

<400> SEQUENCE: 781

```
Gly Phe Thr Phe Ser Lys Ala Trp
1               5
```

<210> SEQ ID NO 782
<211> LENGTH: 10
<212> TYPE: PRT
<213> ORGANISM: Artificial Sequence
<220> FEATURE:
<223> OTHER INFORMATION: Synthetic Construct

<400> SEQUENCE: 782

```
Ile Lys Ser Lys Ile Asp Asp Gly Thr Val
1               5                   10
```

<210> SEQ ID NO 783
<211> LENGTH: 15
<212> TYPE: PRT
<213> ORGANISM: Artificial Sequence
<220> FEATURE:
<223> OTHER INFORMATION: Synthetic Construct

<400> SEQUENCE: 783

```
Thr Thr Val Pro Tyr Cys Asn Gly Thr His Cys Tyr Gly Thr Ala
1               5                   10                  15
```

<210> SEQ ID NO 784
<211> LENGTH: 12

<212> TYPE: PRT
<213> ORGANISM: Artificial Sequence
<220> FEATURE:
<223> OTHER INFORMATION: Synthetic Construct

<400> SEQUENCE: 784

Gln Ser Leu Leu Tyr Ser Gly Asn Asn Lys Asn Tyr
1 5 10

<210> SEQ ID NO 785
<211> LENGTH: 3
<212> TYPE: PRT
<213> ORGANISM: Artificial Sequence
<220> FEATURE:
<223> OTHER INFORMATION: Synthetic Construct

<400> SEQUENCE: 785

Trp Ala Ser
1

<210> SEQ ID NO 786
<211> LENGTH: 6
<212> TYPE: PRT
<213> ORGANISM: Artificial Sequence
<220> FEATURE:
<223> OTHER INFORMATION: Synthetic Construct

<400> SEQUENCE: 786

Gln Arg His Trp Glu Thr
1 5

<210> SEQ ID NO 787
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid

<400> SEQUENCE: 787

Val Pro Xaa Xaa Xaa Glu Ser Gly Gly Ala Leu Val Lys Pro Gly Gly
1 5 10 15

Ser Leu Arg Leu Ser Cys Glu Ala Ser Gly Phe Thr Phe Ser Lys Ala
20 25 30

Trp Met Ser Trp Val Arg Gln Ala Pro Gly Lys Gly Leu Glu Trp Val
35 40 45

Gly Arg Ile Lys Ser Lys Ile Asp Asp Gly Thr Val Asp Tyr Asp Ala
50 55 60

Pro Val Lys Gly Arg Phe Thr Ile Ala Arg Asp Asp Ala Lys Asn Thr
65 70 75 80

Leu Tyr Leu Gln Met Asn Ser Leu Arg Thr Asp Asp Thr Ala Val Tyr
85 90 95

Tyr Cys Thr Thr Val Pro Tyr Cys Asn Gly Thr His Cys Tyr Gly Thr
100 105 110

Ala Trp Gly Gln Gly Thr Leu Val Thr Val Ser Ser
115 120

<210> SEQ ID NO 788
<211> LENGTH: 110
<212> TYPE: PRT
<213> ORGANISM: Artificial Sequence
<220> FEATURE:
<223> OTHER INFORMATION: Synthetic Construct

<400> SEQUENCE: 788

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Tyr Ser
20 25 30

Gly Asn Asn Lys Asn Tyr Leu Thr Trp Tyr Gln Gln Lys Pro Gly Gln
35 40 45

Pro Pro Lys Leu Leu Ile Tyr Trp Ala Ser Ile Arg Glu Ser Gly Val
50 55 60

Pro Asp Arg Phe Ser Gly Gly Gly Ser Gly Thr Asp Phe Thr Leu Thr
65 70 75 80

Ile Ser Ser Leu Gln Ala Glu Asp Val Ala Ile Tyr Tyr Cys Gln Arg
85 90 95

His Trp Glu Thr Phe Gly Gln Gly Thr Arg Val Glu Ile Lys
100 105 110

<210> SEQ ID NO 789
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid

<400> SEQUENCE: 789

Val Pro Xaa Xaa Xaa Glu Ser Gly Gly Ala Leu Val Lys Pro Gly Gly
1 5 10 15

Ser Leu Arg Leu Ser Cys Glu Ala Ser
20 25

<210> SEQ ID NO 790
<211> LENGTH: 17
<212> TYPE: PRT
<213> ORGANISM: Artificial Sequence
<220> FEATURE:
<223> OTHER INFORMATION: Synthetic Construct

<400> SEQUENCE: 790

Met Ser Trp Val Arg Gln Ala Pro Gly Lys Gly Leu Glu Trp Val Gly
1 5 10 15

Arg

<210> SEQ ID NO 791
<211> LENGTH: 38
<212> TYPE: PRT
<213> ORGANISM: Artificial Sequence
<220> FEATURE:
<223> OTHER INFORMATION: Synthetic Construct

<400> SEQUENCE: 791

Asp Tyr Asp Ala Pro Val Lys Gly Arg Phe Thr Ile Ala Arg Asp Asp
1 5 10 15

Ala Lys Asn Thr Leu Tyr Leu Gln Met Asn Ser Leu Arg Thr Asp Asp
20 25 30

Thr Ala Val Tyr Tyr Cys
35

<210> SEQ ID NO 792
<211> LENGTH: 11
<212> TYPE: PRT
<213> ORGANISM: Artificial Sequence
<220> FEATURE:
<223> OTHER INFORMATION: Synthetic Construct

<400> SEQUENCE: 792

Trp Gly Gln Gly Thr Leu Val Thr Val Ser Ser
1               5                   10

<210> SEQ ID NO 793
<211> LENGTH: 26
<212> TYPE: PRT
<213> ORGANISM: Artificial Sequence
<220> FEATURE:
<223> OTHER INFORMATION: Synthetic Construct

<400> SEQUENCE: 793

Asp Ile Val Met Thr Gln Ser Pro Asp Ser Leu Ala Val Ser Leu Gly
1               5                   10                  15

Glu Arg Ala Thr Ile Asn Cys Lys Ser Ser
            20                  25

<210> SEQ ID NO 794
<211> LENGTH: 17
<212> TYPE: PRT
<213> ORGANISM: Artificial Sequence
<220> FEATURE:
<223> OTHER INFORMATION: Synthetic Construct

<400> SEQUENCE: 794

Leu Thr Trp Tyr Gln Gln Lys Pro Gly Gln Pro Pro Lys Leu Leu Ile
1               5                   10                  15

Tyr

<210> SEQ ID NO 795
<211> LENGTH: 36
<212> TYPE: PRT
<213> ORGANISM: Artificial Sequence
<220> FEATURE:
<223> OTHER INFORMATION: Synthetic Construct

<400> SEQUENCE: 795

Ile Arg Glu Ser Gly Val Pro Asp Arg Phe Ser Gly Gly Gly Ser Gly
1               5                   10                  15

Thr Asp Phe Thr Leu Thr Ile Ser Ser Leu Gln Ala Glu Asp Val Ala
            20                  25                  30

Ile Tyr Tyr Cys
        35

<210> SEQ ID NO 796
<211> LENGTH: 10
<212> TYPE: PRT
<213> ORGANISM: Artificial Sequence
<220> FEATURE:
<223> OTHER INFORMATION: Synthetic Construct

<400> SEQUENCE: 796

Phe Gly Gln Gly Thr Arg Val Glu Ile Lys
1               5                   10

<210> SEQ ID NO 797

```
<211> LENGTH: 451
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid

<400> SEQUENCE: 797

Val Pro Xaa Xaa Xaa Glu Ser Gly Gly Ala Leu Val Lys Pro Gly Gly
1               5                   10                  15

Ser Leu Arg Leu Ser Cys Glu Ala Ser Gly Phe Thr Phe Ser Lys Ala
            20                  25                  30

Trp Met Ser Trp Val Arg Gln Ala Pro Gly Lys Gly Leu Glu Trp Val
        35                  40                  45

Gly Arg Ile Lys Ser Lys Ile Asp Asp Gly Thr Val Asp Tyr Asp Ala
    50                  55                  60

Pro Val Lys Gly Arg Phe Thr Ile Ala Arg Asp Asp Ala Lys Asn Thr
65                  70                  75                  80

Leu Tyr Leu Gln Met Asn Ser Leu Arg Thr Asp Asp Thr Ala Val Tyr
                85                  90                  95

Tyr Cys Thr Thr Val Pro Tyr Cys Asn Gly Thr His Cys Tyr Gly Thr
            100                 105                 110

Ala Trp Gly Gln Gly Thr Leu Val Thr Val Ser Ser Lys Gly Pro Ser
        115                 120                 125

Val Phe Pro Leu Ala Pro Ser Ser Lys Ser Thr Ser Gly Gly Thr Ala
    130                 135                 140

Ala Leu Gly Xaa Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Xaa Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Xaa Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 798
<211> LENGTH: 214
<212> TYPE: PRT
<213> ORGANISM: Artificial Sequence
<220> FEATURE:
<223> OTHER INFORMATION: Synthetic Construct

<400> SEQUENCE: 798

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Asn Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Gly Gly Ser Gly Thr Asp Phe Thr Leu Thr
65                  70                  75                  80

Ile Ser Ser Leu Gln Ala Glu Asp Val Ala Ile Tyr Tyr Cys Gln Arg
                85                  90                  95

His Trp Glu Thr Phe Gly Gln Gly Thr Arg Val Glu Ile Lys Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

195 200 205

Asn Arg Gly Glu Cys Lys
210

<210> SEQ ID NO 799
<211> LENGTH: 373
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(15)
<223> OTHER INFORMATION: n is a, c, g, or t

<400> SEQUENCE: 799
gtgccannnn nnnnngagtc tgggggagcc ttggtaaagc cggggggggtc ccttagactc 60 tcctgtgaag cctctggatt cactttcagt aaggcctgga tgagttgggt ccgtcaggcc 120
ccagggaagg gtctggaatg ggtcggccgt attaaaagta agattgatga tgggactgtc 180
gactacgatg cacccgtgaa aggcagattc accatcgcaa gagatgatgc caaaaataca 240
ctctatctgc aaatgaatag cctgagaacc gacgacacag ccgtgtatta ctgtaccaca 300
gttccctatt gtaatgggac tcactgttat gggactgcgt ggggccaggg aaccctggtc 360
accgtctcct cag 373

<210> SEQ ID NO 800
<211> LENGTH: 331
<212> TYPE: DNA
<213> ORGANISM: Artificial Sequence
<220> FEATURE:
<223> OTHER INFORMATION: Synthetic Construct

<400> SEQUENCE: 800
gacatcgtga tgacccagtc tccagactcc ctggctgtgt ctctgggcga gagggccacc 60
atcaactgca agtccagcca gagtcttttg tacagcggca acaataagaa ctacttaact 120
tggtaccagc agaaaccagg acagcctcct aagttgctca tttactgggc atctatccgg 180
gagtccgggg tccctgaccg attcagtggc ggcgggtctg ggacagattt cactctcacc 240
atcagcagcc tgcaggctga agatgtggct atttattact gtcagcgaca ttgggagacg 300
ttcggccaag ggaccagggt tgagatcaaa c 331

<210> SEQ ID NO 801
<211> LENGTH: 8
<212> TYPE: PRT
<213> ORGANISM: Artificial Sequence
<220> FEATURE:
<223> OTHER INFORMATION: Synthetic Construct

<400> SEQUENCE: 801

Gly Phe Thr Phe Ser Thr Phe Ala
1 5

<210> SEQ ID NO 802
<211> LENGTH: 8
<212> TYPE: PRT
<213> ORGANISM: Artificial Sequence
<220> FEATURE:
<223> OTHER INFORMATION: Synthetic Construct

<400> SEQUENCE: 802

Ile Ser Asp Asn Gly Asn Arg Lys 1 5

<210> SEQ ID NO 803
<211> LENGTH: 17
<212> TYPE: PRT
<213> ORGANISM: Artificial Sequence
<220> FEATURE:
<223> OTHER INFORMATION: Synthetic Construct

<400> SEQUENCE: 803

Ala Lys Thr Arg Asp Tyr Asp Ser Arg Gly Tyr Tyr Phe Gly Leu Asp
1 5 10 15

His

<210> SEQ ID NO 804
<211> LENGTH: 7
<212> TYPE: PRT
<213> ORGANISM: Artificial Sequence
<220> FEATURE:
<223> OTHER INFORMATION: Synthetic Construct

<400> SEQUENCE: 804

Gln Ser Val Ile Ser Asn Tyr
1 5

<210> SEQ ID NO 805
<211> LENGTH: 3
<212> TYPE: PRT
<213> ORGANISM: Artificial Sequence
<220> FEATURE:
<223> OTHER INFORMATION: Synthetic Construct

<400> SEQUENCE: 805

Ala Ala Ser
1

<210> SEQ ID NO 806
<211> LENGTH: 10
<212> TYPE: PRT
<213> ORGANISM: Artificial Sequence
<220> FEATURE:
<223> OTHER INFORMATION: Synthetic Construct

<400> SEQUENCE: 806

Gln His Tyr Gly Asn Ser Pro Pro Tyr Thr
1 5 10

<210> SEQ ID NO 807
<211> LENGTH: 123
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid

<400> SEQUENCE: 807

Cys Xaa Leu Val Glu Ser Gly Gly Gly Val Val Gln Pro Gly Arg Ser
1 5 10 15

Leu Arg Leu Ser Cys Ala Ala Ser Gly Phe Thr Phe Ser Thr Phe Ala
20 25 30

```
Leu His Trp Val Arg Gln Ala Pro Gly Lys Gly Leu Glu Trp Met Ala
        35                  40                  45

Val Ile Ser Asp Asn Gly Asn Arg Lys Asp Tyr Ala Asp Ser Val Lys
    50                  55                  60

Gly Arg Phe Thr Ile Ser Arg Asp Asn Ser Glu Asn Thr Leu Tyr Leu
65                  70                  75                  80

Glu Met Asn Ser Leu Arg Pro Glu Asp Thr Xaa Val Tyr Tyr Cys Ala
                85                  90                  95

Lys Thr Arg Asp Tyr Asp Ser Arg Gly Tyr Tyr Phe Gly Leu Asp His
            100                 105                 110

Trp Gly Gln Gly Thr Leu Val Thr Val Ser Ser
        115                 120


<210> SEQ ID NO 808
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 808

Glu Ile Gly Xaa Thr Gln Ser Pro Gly Thr Leu Ser Leu Ser Pro Gly
1               5                   10                  15

Glu Arg Ala Thr Leu Ser Cys Arg Ala Ser Gln Ser Val Ile Ser Asn
            20                  25                  30

Tyr Leu Ala Trp Tyr Gln His Lys Pro Gly Gln Ala Pro Arg Leu Leu
        35                  40                  45

Ile Tyr Ala Ala Ser Ser Arg Ala Thr Asp Ile Pro Asp Arg Phe Ser
    50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln His Tyr Gly Asn Ser Pro
                85                  90                  95

Pro Tyr Thr Phe Gly Gln Gly Thr Lys Val Glu Ile Lys
            100                 105


<210> SEQ ID NO 809
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 809

Cys Xaa Leu Val Glu Ser Gly Gly Gly Val Val Gln Pro Gly Arg Ser
1               5                   10                  15

Leu Arg Leu Ser Cys Ala Ala Ser
            20


<210> SEQ ID NO 810
<211> LENGTH: 17
<212> TYPE: PRT
<213> ORGANISM: Artificial Sequence
```

<220> FEATURE:
<223> OTHER INFORMATION: Synthetic Construct

<400> SEQUENCE: 810

Leu His Trp Val Arg Gln Ala Pro Gly Lys Gly Leu Glu Trp Met Ala
1 5 10 15

Val

<210> SEQ ID NO 811
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (34)..(34)
<223> OTHER INFORMATION: Xaa can be any naturally occurring amino acid

<400> SEQUENCE: 811

Asp Tyr Ala Asp Ser Val Lys Gly Arg Phe Thr Ile Ser Arg Asp Asn
1 5 10 15

Ser Glu Asn Thr Leu Tyr Leu Glu Met Asn Ser Leu Arg Pro Glu Asp
20 25 30

Thr Xaa Val Tyr Tyr Cys
35

<210> SEQ ID NO 812
<211> LENGTH: 11
<212> TYPE: PRT
<213> ORGANISM: Artificial Sequence
<220> FEATURE:
<223> OTHER INFORMATION: Synthetic Construct

<400> SEQUENCE: 812

Trp Gly Gln Gly Thr Leu Val Thr Val Ser Ser
1 5 10

<210> SEQ ID NO 813
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 813

Glu Ile Gly Xaa Thr Gln Ser Pro Gly Thr Leu Ser Leu Ser Pro Gly
1 5 10 15

Glu Arg Ala Thr Leu Ser Cys Arg Ala Ser
20 25

<210> SEQ ID NO 814
<211> LENGTH: 17
<212> TYPE: PRT
<213> ORGANISM: Artificial Sequence
<220> FEATURE:
<223> OTHER INFORMATION: Synthetic Construct

<400> SEQUENCE: 814

Leu Ala Trp Tyr Gln His Lys Pro Gly Gln Ala Pro Arg Leu Leu Ile
1 5 10 15

Tyr

<210> SEQ ID NO 815
<211> LENGTH: 36
<212> TYPE: PRT
<213> ORGANISM: Artificial Sequence
<220> FEATURE:
<223> OTHER INFORMATION: Synthetic Construct

<400> SEQUENCE: 815

Ser Arg Ala Thr Asp Ile Pro Asp Arg Phe Ser Gly Ser Gly Ser Gly
1 5 10 15

Thr Asp Phe Ile Leu Thr Ile Ser Arg Leu Glu Pro Glu Asp Phe Ala
20 25 30

Val Tyr Tyr Cys
35

<210> SEQ ID NO 816
<211> LENGTH: 10
<212> TYPE: PRT
<213> ORGANISM: Artificial Sequence
<220> FEATURE:
<223> OTHER INFORMATION: Synthetic Construct

<400> SEQUENCE: 816

Phe Gly Gln Gly Thr Lys Val Glu Ile Lys
1 5 10

<210> SEQ ID NO 817
<211> LENGTH: 450
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 817

Cys Xaa Leu Val Glu Ser Gly Gly Gly Val Val Gln Pro Gly Arg Ser
1 5 10 15

Leu Arg Leu Ser Cys Ala Ala Ser Gly Phe Thr Phe Ser Thr Phe Ala
20 25 30

Leu His Trp Val Arg Gln Ala Pro Gly Lys Gly Leu Glu Trp Met Ala
35 40 45

Val Ile Ser Asp Asn Gly Asn Arg Lys Asp Tyr Ala Asp Ser Val Lys
50 55 60

Gly Arg Phe Thr Ile Ser Arg Asp Asn Ser Glu Asn Thr Leu Tyr Leu
65 70 75 80

```
Glu Met Asn Ser Leu Arg Pro Glu Asp Thr Xaa Val Tyr Tyr Cys Ala
                85                  90                  95

Lys Thr Arg Asp Tyr Asp Ser Arg Gly Tyr Tyr Phe Gly Leu Asp His
            100                 105                 110

Trp Gly Gln Gly Thr Leu Val Thr Val Ser Ser Lys Gly Pro Ser Val
        115                 120                 125

Phe Pro Leu Ala Pro Ser Ser Lys Ser Thr Ser Gly Gly Thr Ala Ala
    130                 135                 140

Leu Gly Xaa Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Xaa Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Xaa Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 818
<211> LENGTH: 213
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 818

```
Glu Ile Gly Xaa Thr Gln Ser Pro Gly Thr Leu Ser Leu Ser Pro Gly
1               5                   10                  15

Glu Arg Ala Thr Leu Ser Cys Arg Ala Ser Gln Ser Val Ile Ser Asn
            20                  25                  30

Tyr Leu Ala Trp Tyr Gln His Lys Pro Gly Gln Ala Pro Arg Leu Leu
        35                  40                  45

Ile Tyr Ala Ala Ser Ser Arg Ala Thr Asp Ile Pro Asp Arg Phe Ser
    50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln His Tyr Gly Asn Ser Pro
                85                  90                  95

Pro Tyr Thr Phe Gly Gln Gly Thr Lys Val Glu Ile Lys Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys Lys
    210
```

<210> SEQ ID NO 819
<211> LENGTH: 372
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: n is a, c, g, or t

<400> SEQUENCE: 819

```
ggtgccnnct ggtggagtct gggggaggcg tggtccagcc tgggaggtcc ctgagactct     60

cctgtgcagc ctctggattc acatttagta cctttgctct acattgggtc cgccaggctc    120

caggcaaggg gctggagtgg atggccgtta tatcagataa tgggaataga aaagactacg    180

cagactccgt gaagggccga ttcaccatct cccgagacaa ctccgagaac acactgtatc    240

tggaaatgaa cagcctgaga cctgaggaca cggmtgtcta ttactgtgcg aaaacaaggg    300

actatgatag ccgtggttat tacttcggtc ttgaccactg gggccaggga accctggtca    360

ccgtctcctc ag                                                        372
```

<210> SEQ ID NO 820

<211> LENGTH: 328
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(12)
<223> OTHER INFORMATION: n is a, c, g, or t

<400> SEQUENCE: 820
gaaataggnn nnacgcagtc tccaggcacc ctgtctttgt ctccagggga aagagccacc 60
ctctcctgca gggccagtca gagtgttatc agcaactact tagcctggta tcagcacaaa 120
cctggccagg ctcccaggct cctcatctat gctgcctcca gcagggccac tgacatccca 180
gacaggttca gtggcagtgg gtctgggaca gacttcattc tcaccatcag cagactggag 240
cctgaagatt ttgcggtata ctactgtcag cactatggta actcacctcc gtacactttt 300
ggccagggaa ccaaggtgga gattaaac 328

<210> SEQ ID NO 821
<211> LENGTH: 172
<212> TYPE: PRT
<213> ORGANISM: Arachis hypogaea

<400> SEQUENCE: 821

Met Ala Lys Leu Thr Ile Leu Val Ala Leu Ala Leu Phe Leu Leu Ala
1 5 10 15

Ala His Ala Ser Ala Arg Gln Gln Trp Glu Leu Gln Gly Asp Arg Arg
20 25 30

Cys Gln Ser Gln Leu Glu Arg Ala Asn Leu Arg Pro Cys Glu Gln His
35 40 45

Leu Met Gln Lys Ile Gln Arg Asp Glu Asp Ser Tyr Gly Arg Asp Pro
50 55 60

Tyr Ser Pro Ser Gln Asp Pro Tyr Ser Pro Ser Gln Asp Pro Asp Arg
65 70 75 80

Arg Asp Pro Tyr Ser Pro Ser Pro Tyr Asp Arg Arg Gly Ala Gly Ser
85 90 95

Ser Gln His Gln Glu Arg Cys Cys Asn Glu Leu Asn Glu Phe Glu Asn
100 105 110

Asn Gln Arg Cys Met Cys Glu Ala Leu Gln Gln Ile Met Glu Asn Gln
115 120 125

Ser Asp Arg Leu Gln Gly Arg Gln Gln Glu Gln Gln Phe Lys Arg Glu
130 135 140

Leu Arg Asn Leu Pro Gln Gln Cys Gly Leu Arg Ala Pro Gln Arg Cys
145 150 155 160

Asp Leu Glu Val Glu Ser Gly Gly Arg Asp Arg Tyr
165 170

<210> SEQ ID NO 822
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Val or Ala

<400> SEQUENCE: 822

Xaa Lys Asp Asn Gly Trp Arg Ala Phe Asp His
1 5 10

<210> SEQ ID NO 823
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Ser or Ala
<220> FEATURE:
<221> NAME/KEY: MISC_FEATURE
<222> LOCATION: (6)..(6)
<223> OTHER INFORMATION: Xaa is Asn or Thr

<400> SEQUENCE: 823

Met Gln Xaa Leu Glu Xaa Pro Trp Thr
1 5

<210> SEQ ID NO 824
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Asp or Gly
<220> FEATURE:
<221> NAME/KEY: MISC_FEATURE
<222> LOCATION: (4)..(4)
<223> OTHER INFORMATION: Xaa is Ile or Met

<400> SEQUENCE: 824

Gly Xaa Ser Xaa Ser Ser Tyr Tyr
1 5

<210> SEQ ID NO 825
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ser or Thr

<400> SEQUENCE: 825

Ile Phe Thr Xaa Gly Ser Thr
1 5

<210> SEQ ID NO 826
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ala or Val
<220> FEATURE:
<221> NAME/KEY: MISC_FEATURE
<222> LOCATION: (6)..(6)
<223> OTHER INFORMATION: Xaa is Ala or Gly
<220> FEATURE:
<221> NAME/KEY: MISC_FEATURE -continued

```
<222> LOCATION: (7)..(7)
<223> OTHER INFORMATION: Xaa is Leu or Arg
<220> FEATURE:
<221> NAME/KEY: MISC_FEATURE
<222> LOCATION: (9)..(9)
<223> OTHER INFORMATION: Xaa is Ser or His
<220> FEATURE:
<221> NAME/KEY: MISC_FEATURE
<222> LOCATION: (11)..(11)
<223> OTHER INFORMATION: Xaa is Gly or Ser

<400> SEQUENCE: 826

Xaa Arg Asp Arg Arg Xaa Xaa Ser Xaa Asp Xaa Asn Trp Tyr Trp Tyr
1               5                   10                  15

Phe Asp Leu


<210> SEQ ID NO 827
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Ile or Leu
<220> FEATURE:
<221> NAME/KEY: MISC_FEATURE
<222> LOCATION: (4)..(4)
<223> OTHER INFORMATION: Xaa is Thr or Ser

<400> SEQUENCE: 827

Gln Thr Xaa Xaa Arg Asn
1               5
```